(12) United States Patent
Lohray et al.

(10) Patent No.: US 7,041,837 B2
(45) Date of Patent: May 9, 2006

(54) HETEROCYCLIC COMPOUNDS HAVING HYPOLIPIDEMIC, HYPOCHOLESTEREMIC ACTIVITIES PROCESS FOR THEIR PREPARATION AND PHARMACEUTICAL COMPOSITIONS CONTAINING THEM AND THEIR USE IN MEDICINE

(75) Inventors: Braj Bhushan Lohray, Gujarat (IN); Vidya Bhushan Lohray, Gujarat (IN); Vijay Kumar Gajubhai Barot, Gujarat (IN); Saurin Khimshanker Raval, Gujarat (IN); Preeti Saurin Raval, Gujarat (IN); Sujay Basu, Gujarat (IN)

(73) Assignee: Cadilla Healthcare Limited, Gujarat (IN)

( * ) Notice: Subject to any disclaimer, the term of this patent is extended or adjusted under 35 U.S.C. 154(b) by 211 days.

(21) Appl. No.: 10/200,107

(22) Filed: Jul. 19, 2002

(65) Prior Publication Data

US 2003/0236254 A1 Dec. 25, 2003

Related U.S. Application Data

(63) Continuation-in-part of application No. 09/928,242, filed on Aug. 10, 2001, now abandoned.

(30) Foreign Application Priority Data

Jul. 26, 2001 (IN) .................. 711/MUM/2001

(51) Int. Cl.
C07D 207/30 (2006.01)
(52) U.S. Cl. .................................... 548/562
(58) Field of Classification Search ............... 548/562; 514/427, 428
See application file for complete search history.

(56) References Cited

U.S. PATENT DOCUMENTS

| 5,089,514 | A | 2/1992 | Hulin |
| 5,306,726 | A | 4/1994 | Hulin |
| 5,861,173 | A | 1/1999 | Nishioka et al. |
| 5,885,997 | A | 3/1999 | Lohray et al. |
| 5,889,025 | A | 3/1999 | Lohray et al. |
| 5,889,032 | A | 3/1999 | Lohray et al. |
| 5,985,884 | A | 11/1999 | Lohray et al. |
| 6,048,883 | A | 4/2000 | Haigh et al. |
| 6,054,453 | A | 4/2000 | Lohray et al. |
| 6,130,214 | A | 10/2000 | Lohray et al. |
| 6,159,966 | A | 12/2000 | Lohray et al. |
| 6,166,049 | A | 12/2000 | Smith |
| 6,265,401 | B1 | 7/2001 | Lohray et al. |
| 6,294,586 | B1 | 9/2001 | Yelle et al. |
| 6,313,113 | B1 | 11/2001 | Lohray et al. |
| 6,362,360 | B1 | 3/2002 | Andersson et al. |
| 6,369,067 | B1 | 4/2002 | Gurram et al. |
| 6,440,961 | B1 | 8/2002 | Lohray et al. |
| 6,444,816 | B1 | 9/2002 | Das et al. |
| 6,521,622 | B1 | 2/2003 | Ricks et al. |
| 6,525,083 | B1 | 2/2003 | Acton, III et al. |
| 6,569,901 | B1 | 5/2003 | Mogensen et al. |
| 6,573,628 | B1 | 6/2003 | Sloupensky et al. |
| 6,589,969 | B1 | 7/2003 | Tajima et al. |
| 6,602,901 | B1 | 8/2003 | Jeppesen et al. |

FOREIGN PATENT DOCUMENTS

| EP | 0753 298 | 1/1997 |
| EP | 90 3343 | 3/1999 |
| WO | WO 91/19702 | 12/1991 |
| WO | WO 94/01420 | 1/1994 |
| WO | WO 94/13650 | 6/1994 |
| WO | WO 94/29302 | 12/1994 |
| WO | WO 95/03038 | 2/1995 |
| WO | WO 95/17394 | 6/1995 |
| WO | WO 96/04260 | 2/1996 |
| WO | WO 96/04261 | 2/1996 |
| WO | WO 96/33998 | 10/1996 |
| WO | WO 97/25042 | 7/1997 |
| WO | WO 97/31970 | 9/1997 |
| WO | WO 97/36579 | 10/1997 |
| WO | WO 98/02159 | 1/1998 |
| WO | WO 98/28534 | 7/1998 |
| WO | WO 99/08501 | 2/1999 |
| WO | WO 99/16758 | 4/1999 |
| WO | WO 99/19313 | 4/1999 |
| WO | WO 99/20614 | 4/1999 |
| WO | WO 99/38850 | 8/1999 |
| WO | WO 00/23417 | 4/2000 |
| WO | WO 00/23445 | 4/2000 |
| WO | WO 00/23451 | 4/2000 |
| WO | WO 01/53257 | 7/2001 |

OTHER PUBLICATIONS

A. N. Collins, G. N. Sheldrake and J. Crosby, in "Chirality in Industry II", John Wiley & Sons, Inc., 1997, 81-98 and references therein.
Cancer Research, 58, 3344-3352 (1998).
Carcinogenesis, vol. 19 No. 11, 1949-1953 (1998).

(Continued)

Primary Examiner—Johann Richter
Assistant Examiner—Ebenezer Sackey
(74) Attorney, Agent, or Firm—Kelley Drye & Warren LLP

(57) ABSTRACT

Novel β-aryl-α-substituted propanoic acids having hypolipidemic and hypocholesteremic activities.

2 Claims, No Drawings

OTHER PUBLICATIONS

Cell, 87, 377-389 (1996).
Cell, 55, 932-943 (1999).
Cell, 79, 1147-1156 (1994).
Cell, 83, 803-812 (1995).
Cell, 99, 239-242 (1999).
Cell Biology, 95, 14751-14756 (1998).
Current Biol., 5, 618-621 (1995).
E. L. Eliel and S. H. Wilen, in "Stereochemistry of Organic Compound", John Wiley & Sons, Inc., 1994, 297-464 and references therein.
Endocrine Reviews, 20(5), 649-688 (1999).
Endocrinology 135, 798-800 (1994).
Exp. Clin. Endocrinol. Diabetes: 109(4), S548-559 (2001).
T. W. Greene and P. G. M. Wuts "Protective Groups in Organic Synthesis", John Wiley & Sons, Inc., 1999, 3$^{rd}$ Ed., 201-245 along with references therein.
J. Clin. Invest., 85, 962-967, 1990.
J. Medicinal Chemistry, 43(4), 527-550 (2000).
Jaques et al. "Enantiomers, Racemates and Resolution", Wiley Interscience, 1981.
Knorr, L., Ber., 1885, 18, 299-311.
Macikinnon et al., J. Biol. Chem. 261, 2548-2552 (1986).
Med. Res. Rev., 20(5), 350-366 (2000).
Miller et al., Br. Med. J. 282, 1741-1744 (1981).
Molecular Cell, 465-470 (1998).
Nature Reviews: Drug Discovery: 1(4), 276-86 (2002).
Nature, 405, 421-424 (2000).
Paal C. Ber., 1885, 18, 367-371.
Petit D., Bonnefis M. T., Rey C. and Infante R., Effects of ciprofibrate on liver lipids and lipoprotein synthesis in normal and hyperlipidemic rats, Atherosclerosis, 74, 215-225 (1988).
Picardo et al., Arteriosclerosis, 6, 434-441 (1986).
Principles of Asymmetric Synthesis J E Baldwin Ed. Tetrahedron series, vol. 14, p. No. 311-316.
Proc. Natl. Acad. Sci. 93, 5793-5796 (1996).
Proc. Natl. Acad. Sci., 94, 237-241 (1997).
Remington: the Science and Practice of Pharmacy, 19$^{th}$ Ed., 1995.
Ross and Glomset, New Engl. J. Med., 295, 369-377 (1976).
Science, 269, 543-46 (1995).
R. A. Sheldon, in "Chirotechnology", Marcel Dekker, Inc. NY, Basel, 1993, 173-204 and references therein.
Stampfer et al., N. Eng. J. Med., 325, 373-381 (1991).
Trends Endocrine. Metabolism, 4, 291-296 (1993).
Trends in Pharmacological Sci., 469-473 (2000).
Trinder, P. Ann. Clin. Biochem. 1969. 6: 24-27.
Wieland, O. Methods of Enzymatic Analysis. Bergermeyer, H., O., Ed., 1963. 211-214.
*DDT*, vol. 6, No. 13, 2001, p. 654-55, "Unravelling metabolic syndrome X."
*Diabetes Mellitus—A Fundamental Text book*, pp. 326-329, 611-613, "Definition and Classification of Diabetes Mellitus and the New Criteria for Diagnosis."
*Am Heart J.* Dec. 1988; 116(6 Pt 2): 1713-24, "The Prospective Cardiovascular Munster (PROCAM) study: prevalence of hyperlipidemia in persons with hypertension and/or diabetes mellitus and the relationship to coronary heart disease."
3$^{rd}$ Report of the National Cholesterol Education Program (NCEP), Expert Panel on 'Detection, Evaluation and Treatment of High Blood Cholesterol in Adults (Adult Treatment Panel III)'—NIH, USA.
*Diabetes Mellitus—A Fundamental Text book*, pp. 326-329, 611-613, "Fatty Acids and Insulin Resistance."
*Ann NY Acad Sci.* Nov. 18, 1999; 892:25-44, "Etiology of the metabolic syndrome : potential role of insulin resistance, leptin resistance, and other players."
*Horm Metab Res.* Feb. 2003; 35(2); 92-96, "Leptin levels in type 2 diabetes: associations with measures of insulin resistance and insulin secretion."
*Metabolism.* Jun. 2003; 52(6):713-9, "Relative impact of insulin resistance and obesity on cardiovascular risk factors in polycystic ovary syndrome."
*The Journal of Clinical Endocrinology & Metabolism 2003*, 88(5):2031-2036, "Glucose Intolerance, Insulin Resistance, and Hyperandrogenemia in First Degree Relatives of Women with Polycystic Ovary Syndrome."
*Diabetes Care.* Jun. 2003; 26(6): 1752-8, "Type 2 Diabetes and Subsequent Incidence of Breast Cancer in the Nurses' Health Study."
*Exp Biol Med (Maywood).* Apr. 2003; 228(4): 396-405, "Insulin resistance and its contribution to colon carcinogenesis."
*Cancer Epidemiology, Biomarkers & Prevention.* Dec. 2000; 9:1271-79. "Possible Mechanisms Relating Diet and Risk of Colon Cancer."
*Pol Arch Med Wewn.* Aug. 1998; 100(2):125-32, "Bone density in type 2 diabetes as related to obesity and adrenal f unction."
*FEBS Lett.* Apr. 7, 2000;471(1):119-24, "Peroxisome proliferator-activated receptor activators modulate the osteoblastic maturation of MC3T3-E1 preosteoblasts."
*Endocrinology* 1999; 140(11): 5060-65, "Thiazolidinediones inhibit osteoclast-like cell formation and bone absorption in vitro."
*Am J Surg.* Jan. 1995; 169(1): 105-9, "Alterations in hepatocyte insulin binding in chronic pancreatitis : effects of pancreatic polypeptide."
*J Clin. Endocrinol. Metab.* May 2001; 86(5): 2289-95, "Dyslipidemia in familial partial lipodystrophy caused by an R482W mutation in the LMNA gene."
*Clin Nephrol.* Nov. 2000; 54(5): 366-73, "Mild renal dysfunction is associated with insulin resistance in chronic glomerulonephritis."
*J Am Soc Nephrol.* Jul. 2002; 13(7): 1894-900, "Insulin Resistance as an Independent Predictor of Cardiovascular Mortality in Patients with End-Stage Renal Disease."
*Kidney Int.* Sep. 2002; 62(3): 963-70, "Nephropathy in type 1 diabetes: a manifestation of insulin resistance and multiple genetic susceptibilities? Further evidence from the Pittsburgh Epidemiology of Diabetes Complication Study."
*Aliment Pharmacol Ther.* Feb. 1999; 13(2): 209-17, "Glucose metabolism and insulin sensitivity in inactive inflammatory bowel disease."
*J Am Acad Dermatol.* Jul. 1985; 13(1): 1-30, "Xanthomas and hyperlipidemias."
*The Journal of Clinical Endocrinology & Metabolism* 2003; 88(6):2422-2429, "The Potential Influence of Inflammation and Insulin Resistance on the Pathogenesis and Treatment of Atherosclerosis-Related Complications in Type 2 Diabetes."
*J Clin Endocrinol Metab* 2003; 88: 2412-2421, "The Metabolic Syndrome : Peroxisome Proliferator-Activated Receptor Y and Its Therapeutic Modulation."
*J Clin Pract Suppl.* Mar. 2003; (134):10-7, "Inflammation, the metabolic syndrome and cardiovascular risk."

*Cuff Drug Targets Cardiovasc Haematol Disord.* Dec. 2001; 1(2): 107-20, "Reduction and prevention of the cardiovascular sequelae of the insulin resistance syndrome."

*The Journal of Clinical Endocrinology & Metabolism* 88 (6):2399-2403, "Insulin Resistance/Compensatory Hyperinsulinemia, Essential Hypertension, and Cardiovascular Disease."

*Endocrinology* 2003; 144(6) 2201-2207, "Minireview : Lipid Metabolism, Metabolic Diseases, and Peroxisome Proliferator-Activated Receptors."

*Am J Manag Care.* Dec. 2002; 8(20 Suppl):S635-53, "The metabolic syndrome, type 2 diabetes and cardiovascular disease : understanding the role of insulin resistance."

*Am J Health Syst Pharm.* Dec. 1, 2002; 59 Suppl 9:S9-13, "Treating dual defects in diabetes: insulin resistance and insulin secretion."

*Endocrinol Metab Clin North Am.* Dec. 2001;30(4):935-82, "Insulin therapy in type 2 diabetes."

*J Hypertens Suppl.* Sep. 2001;19 Suppl 3:S17-21, "The choice of first-line therapy: rationale for low-dose combinations of an angiotensin converting enzyme inhibitor and a diuretic."

*Diabetes Obes Metab.* May 1999; 1 Suppl 1:S41-8, "Promising new approaches."

*J Hypertens Suppl.* Jan. 1998;16(1):S35-7, "Obesity in hypertension: effects on prognosis and treatment."

*Nurse Pract.* Jun. 1996;21(6):74-5, 79-80, 83-6, "Syndrome X. Recognition and management of this metabolic disorder in primary care."

*Postgrad Med.* May 2003;Spec No:27-34, "Insulin resistance syndrome. Description, pathogenesis , and management."

*Am J Cardiol.* Apr. 3, 2003;91(7A):18E-39E, "Effects of Nonstatin Lipid Drug Therapy on High-Density Lipoprotein Metabolism."

*Am J Cardiol.* Apr. 3, 2003;91(7A):18E-39E, "Management of Patients with diabetic hyperlipidemia."

*Am J Cardiol.* Apr. 3, 2003;91(7A):18E-39E, "Treatment of patients with Metabolic Syndrome."

*Cardiovasc Drugs Ther.* Sep. 2002;16(5):457-70, "Beta-blockers and diabetes: the bad guys come good."

*Curr Drug Targets.* Jun. 2002; 3(3): 203-21, "Multiple drug targets in the management of type 2 diabetes."

*Annals of Internal Medicine*, Aug. 1999; 131(4): 281-303, "Pharmacologic Therapy for Type 2 Diabetes Mellitus."

*Diabetes Mellitus—A Fundamental Text book*, p. 769-811, "Insulin Secretogogues Sulfonylureas and Meglitinides."

*Detection Evaluation and Treatment of High Blood Cholesterol in Adults* (Adult Treatment Panel 111)-"Drug Therapy."

*Int J Clin Pract Suppl.* Oct. 2000; (113): 54-62, "Current treatment of insulin resistance in type 2 diabetes mellitus."

*Diabet Med.* 1998; 15 Suppl 4:S13-9, "Improving glycaemic control with current therapies."

*Am J Manag Care.* Oct. 2000; 8(16 Suppl): S460-71, "Current treatment approaches to type 2 diabetes mellitus: successes and shortcomings."

HETEROCYCLIC COMPOUNDS HAVING HYPOLIPIDEMIC, HYPOCHOLESTEREMIC ACTIVITIES PROCESS FOR THEIR PREPARATION AND PHARMACEUTICAL COMPOSITIONS CONTAINING THEM AND THEIR USE IN MEDICINE

CROSS-REFERENCE TO RELATED APPLICATION(S)

This application is a continuation-in-part patent application of U.S. patent application Ser. No. 09/928,242, filed on Aug. 10, 2001 now abandoned.

FIELD OF INVENTION

The present invention relates to novel hypolipidaemic and hypocholesterolemic compounds, their derivatives, their analogs, their tautomeric forms, their stereoisomers, their polymorphs, their pharmaceutically acceptable salts, their pharmaceutically acceptable solvates and pharmaceutically acceptable compositions containing them. More particularly, the present invention relates to novel β-aryl-α-substituted propanoic acids of the general formula (I), their derivatives, their analogs, their tautomeric forms, their stereoisomers, their pharmaceutically acceptable salts, their pharmaceutically acceptable solvates, pharmaceutical compositions containing them, use of these compounds in medicine and the intermediates involved in their preparation.

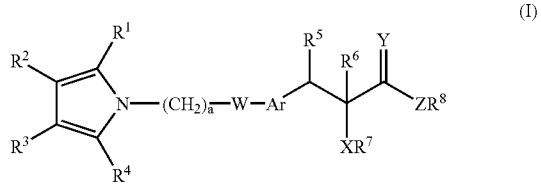

The present invention also relates to a process for the preparation of the above said novel compounds, their derivatives, their analogs, their tautomeric forms, their stereoisomers, their pharmaceutically acceptable salts, their pharmaceutically acceptable solvates, and pharmaceutical compositions containing them.

The compounds of the general formula (I) lower or modulate triglyceride levels and/or cholesterol levels and/or low-density lipoproteins (LDL) and raise HDL plasma levels and hence are useful in combating different medical conditions, where such lowering (and raising) is beneficial. Thus, it could be used in the treatment and/or prophylaxis of obesity, hyperlipidaemia, hypercholesteremia, hypertension, atherosclerotic disease events, vascular restenosis, diabetes and many other related conditions.

The compounds of general formula (I) are useful to prevent or reduce the risk of developing atherosclerosis, which leads to diseases and conditions such as artereosclerotic cardiovascular diseases, stroke, coronary heart diseases, cerebrovascular diseases, peripheral vessel diseases and related disorders. These compounds of general formula (I) are useful for the treatment and/or prophylaxis of metabolic disorders loosely defined as Syndrome X. The characteristic features of Syndrome X include initial insulin resistance followed by hyperinsulinemia, dyslipidemia and impaired glucose tolerance. The glucose intolerance can lead to non-insulin dependent diabetes mellitus (NIDDM, Type 2 diabetes), which is characterized by hyperglycemia, which if not controlled may lead to diabetic complications or metabolic disorders caused by insulin resistance. Diabetes is no longer considered to be associated only with glucose metabolism, but it affects anatomical and physiological parameters, the intensity of which vary depending upon stages/duration and severity of the diabetic state. The compounds of this invention are also useful in prevention, halting or slowing progression or reducing the risk of the above mentioned disorders along with the resulting secondary diseases such as cardiovascular diseases, like arteriosclerosis, atherosclerosis; diabetic retinopathy, diabetic neuropathy and renal disease including diabetic nephropathy, glomerulonephritis, glomerular sclerosis, nephrotic syndrome, hypertensive nephrosclerosis and end stage renal diseases, like microalbuminuria and albuminuria, which may be result of hyperglycemia or hyperinsulinemia.

The compounds of the present invention can be useful as aldose reductase inhibitors; for improving cognitive functions in dementia, and in the treatment and/or prophylaxis of disorders such as psoriasis, polycystic ovarian syndrome (PCOS), cancer, osteoporosis, leptin resistance, inflammation and inflammatory bowel diseases, xanthoma, pancreatitis, myotonic dystrophy, endothelial cell dysfunction and hyperlipidemia.

The compounds of the present invention are useful in the treatment of the diseases mentioned herein, alone or in combination one or more hypoglycemic, antihyperglycemic, hypolipidaemic, hypolipoproteinemic agents, antioxidants, antihypertensives, such as HMG CoA reductase inhibitor, fibrate, statins, glitazones, sulfonyl ureas, insulin, α-glycosidase inhibitors, nicotinic acid, cholestyramine, cholestipol or probucol, and the like.

BACKGROUND OF THE INVENTION

Hyperlipidaemia has been recognized as the major risk factor in causing cardiovascular diseases due to atherosclerosis. Atherosclerosis and other such peripheral vascular diseases affect the quality of life of a large population in the world. The therapy aims to lower the elevated plasma LDL cholesterol, low-density lipoprotein and plasma triglycerides in order to prevent or reduce the risk of occurrence of cardiovascular diseases. The detailed etiology of atherosclerosis and coronary artery diseases is discussed by Ross and Glomset [New Engl. J. Med., 295, 369–377 (1976)]. Plasma cholesterol is generally found esterified with various serum lipoproteins and numerous studies have suggested an inverse relationship between serum HDL-cholesterol level and risk for occurrence of cardiovascular disease. Many studies have suggested an increased risk of coronary artery diseases (CAD) due to elevated LDL and VLDL-cholesterol levels [Stampfer et al., *N. Engl. J. Med.*, 325, 373–381(1991)]. The other studies illustrate protective effects of HDL against progression of atherosclerosis. Thus, HDL has become a crucial factor in treating diseases with increased levels of cholesterol [Miller et. al., *Br. Med. J.* 282, 1741–1744 (1981); Picardo et al., *Arteriosclerosis*, 6, 434–441 (1986); Macikinnon et al., *J. Biol. Chem.* 261, 2548–2552 (1986)].

Diabetes is associated with a number of complications and also affect a large population. This disease is usually associated with other diseases such as obesity, hyperlipidemia, hypertension and angina. It is well established that improper treatment can aggravate impaired glucose tolerance and insulin resistance, thereby leading to frank diabetes. Further, patients with insulin resistance and type 2 diabetes often have raised triglycerides and low HDL-cholesterol concentrations and therefore, have greater risk of cardiovascular diseases. The present therapy for these diseases includes sulfonylureas and biguanides along with insulin. This type of drug therapy may lead to mild to severe hypoglycemia, which may lead to coma or in some cases may lead to death, as a result of unsatisfactory glycaemic control by these drugs. Recent addition of drugs in the treatment of diabetes are the thiazolidinediones, drugs having insulin-sensitizing action. Thiazolidinediones are prescribed alone or in combination with other anti-diabetic agents like troglitazone, rosiglitazone and pioglitazone. These are useful in treating diabetes, lipid metabolism but are suspected to have tumor-inducing potential and cause hepatic dysfunction, which may lead to liver failure. Further, serious undesirable side-effects have occurred in animal and/or human studies which include cardiac hypertrophy, hema dilution and liver toxicity in a few glitazones progressing to advanced human trials. The drawback is considered to be idiosyncratic. Presently, there is a need for a safe and an effective drug, to treat insulin resistance, diabetes and hyperlipidemia. [*Exp. Clin. Endocrinol. Diabetes:* 109(4), S548–9 (2001)]

Obesity is another major health problem being associated with increased morbidity and mortality. It is a metabolic disorder, in which excess of fat is accumulated in the body. Although, its etiology is unclear, the general feature includes excess of calorie intake than it is consumed. Various therapies such as dieting, exercise, appetite suppression, inhibition of fat absorption etc. have been used to combat obesity. However, more efficient therapies to treat this abnormality is essential as obesity is closely related to several diseases such as coronary heart disease, stroke, diabetes, gout, osteoarthritis, hyperlipidaemia and reduced fertility. It also leads to social and psychological problems [*Nature Reviews: Drug Discovery:* 1(4), 276–86 (2002)].

Peroxisome Proliferator Activated Receptor (PPAR) is a member of the steroid/retinoid/thyroid hormone receptor family. PPAR$\alpha$, PPAR$\gamma$ and PPAR$\delta$ have been identified as subtypes of PPARs. Extensive reviews regarding PPAR, their role in different diseased conditions are widely published [*Endocrine Reviews,* 20(5), 649–688 (1999); *J. Medicinal Chemistry,* 43(4), 58–550 (2000); *Cell,* 55, 932–943 (1999); *Nature,* 405, 421–424 (2000); *Trends in Pharmacological Sci.,* 469–473 (2000)]. PPAR$\gamma$ activation has been found to play a central role in initiating and regulating adipocyte differentiation [Endocrinology 135, 798–800, (1994)] and energy homeostasis, [*Cell,* 83, 803–812 (1995); *Cell,* 99, 239–242 (1999)]. PPAR$\gamma$ agonists would stimulate the terminal differentiation of adipocyte precursors and cause morphological and molecular changes characteristic of a more differentiated, less malignant state. During adipocyte differentiation, several highly specialized proteins are induced, which are being involved in lipid storage and metabolism. It is accepted that PPAR$\gamma$ activation leads to expression of CAP gene [Cell biology, 95, 14751–14756, (1998)], however, the exact link from PPAR$\gamma$ activation to changes in glucose metabolism and decrease in insulin resistance in muscle has not been clear. PPAR$\alpha$ is involved in stimulating $\beta$-oxidation of fatty acids [*Trends Endocrine. Metabolism,* 4, 291–296 (1993)] resulting in plasma circulating free fatty acid reduction [*Current Biol.,* 5, 618–621 (1995)]. Recently, role of PPAR$\gamma$ activation in the terminal differentiation of adipocyte precursors has been implicated in the treatment of cancer. [*Cell,* 79, 1147–1156 (1994); *Cell,* 377–389 (1996); *Molecular Cell,* 465–470) 1998); *Carcinogenesis,* 1949–1953 (1998); *Proc. Natl. Acad. Sci.,* 94, 237–241 (1997); *Cancer Research,* 58, 3344–3352 (1998)]. Since PPAR$\gamma$ is expressed in certain cells consistently, PPAR$\gamma$ agonists would lead to nontoxic chemotherapy. There is growing evidence that PPAR agonists may also influence the cardiovascular system through PPAR receptors as well as directly by modulating vessel wall function [*Med. Res. Rev.,* 20 (5), 350–366 (2000)].

PPAR $\alpha$ agonists have been found useful in the treatment of obesity (WO 97/36579). Dual PPAR $\alpha$ and $\gamma$ agonists have been suggested to be useful for Syndrome X (WO 97/25042). PPAR $\gamma$ agonists and HMG-CoA reductase inhibitors have exhibited synergism and indicated the usefulness of the combination in the treatment of atherosclerosis and xanthoma (EP 0753 298).

Leptin is a protein when bound to leptin receptors is involved in sending satiety signal to the hypothalamus. Leptin resistance would therefore lead to excess food intake, reduced energy expenditure, obesity, impaired glucose tolerance and diabetes [*Science,* 269, 543–46(1995)]. It has been reported that insulin sensitizers lower plasma leptin concentration [*Proc. Natl. Acad. Sci.* 93, 5793–5796 (1996): WO 98/02159)].

A number of compounds belonging to $\beta$-aryl-$\alpha$-hydroxypropanoic acids and their derivatives have been reported to be useful in the treatment of hyperlipidemia, hypercholesterolemia and hyperglycemia [U.S. Pat. Nos. 5,306,726, 5,985,884, 6,054,453, 6,130,214, EP 90 3343, PCT publications Nos. WO 91/19702, WO 94/01420, WO 94/13650, WO 95/03038, WO 95/17394, WO 96/04260, WO 96/04261, WO 96/33998, WO 97/25042, WO 97/36579, WO 98/28534, WO 99/08501, WO 99/16758, WO 99/19313, WO99/20614, WO 00/23417, WO 00/23445, WO 00/23451, WO 01/53257].

A few $\beta$-aryl-$\alpha$-hydroxypropanoic acids, their derivatives, and their analogs have been reported to be useful in the treatment of hyperglycemia and hypercholesterolemia. Some of such compounds described in the prior art are outlined below:

U.S. Pat. Nos. 5,306,726 and 5,089,514 disclose several 3-aryl-2-hydroxypropionic acid derivatives of general formulae (II) and (III) as hypolipidaemic and hypoglycemic agents. Examples of these compounds are shown in the formulae (IV) and (V).

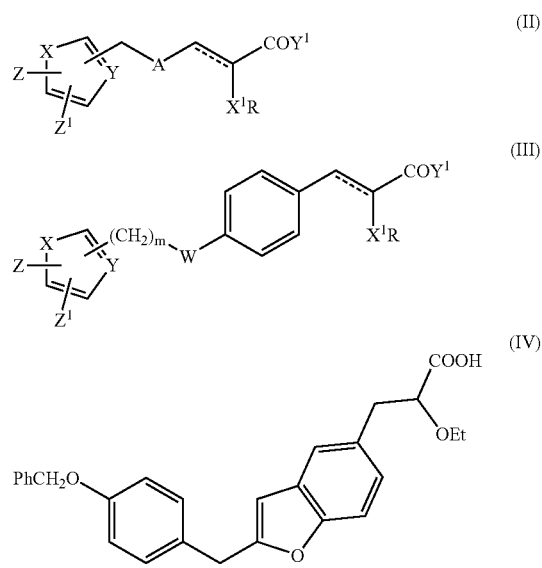

-continued

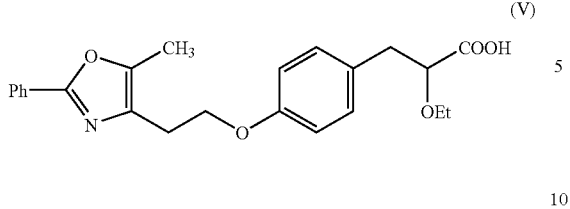
(V)

International Patent Applications, U.S. Pat. No. 6,166,049 and WO 96/04260 disclose compounds of general formula (VI) wherein, $R^a$ represents 2-benzoxazolyl or 2-pyridyl and $R^b$ represent $CF_3$, $CH_2OCH_3$ or $CH_3$. A typical example is (S)-3-[4-[2-[N-(2-benzoxazolyl)N-methylamino]ethoxy] phenyl]-2-(2,2,2,-trifluoro ethoxy)propanoic acid (VII).

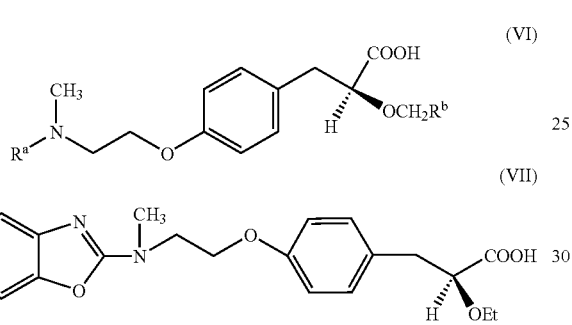
(VI)

(VII)

International patent applications, WO 94/13650, WO 94/29302, U.S. Pat. No. 6,048,883, WO 95/17394 and WO 97/31970 disclose the compounds of general formula (VIII) wherein, $$A^1\text{—}X\text{—}(CH_2)_n\text{—}O\text{—}A^2\text{—}A^3\text{—}YR^2 \quad (VIII)$$

$A^1$ represents aromatic heterocycle moiety, $A^2$ represents substituted benzene ring and $A^3$ represents moiety of formula $(CH_2)_m\text{—}CH\text{—}(OR^1)$, where $R^1$ represents alkyl groups, m is integer of the range of 1–5; X represents substituted or unsubstituted N; Y represents C=O or C=S and $R^2$ represents $OR^3$ where $R^3$ may be hydrogen, alkyl, aralkyl, or aryl group and n is integer in the range of 2–6. An example of these compounds is shown in formula (IX).

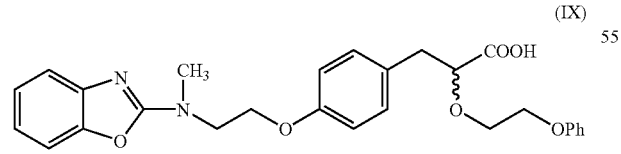
(IX)

International patent application, WO 00/23,445, WO 00/23,417 and WO 00/23,451 disclose cyclic compounds of the general formula (X) useful in treatment of diabetes and obesity. A typical example of these compounds is shown formulae (XI) and (XII).

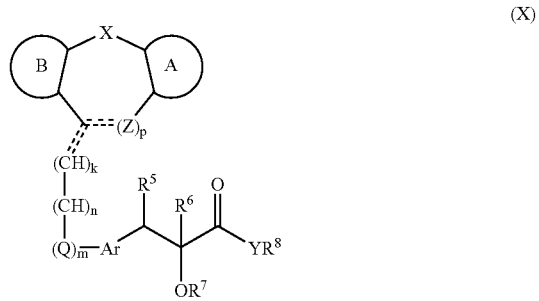
(X)

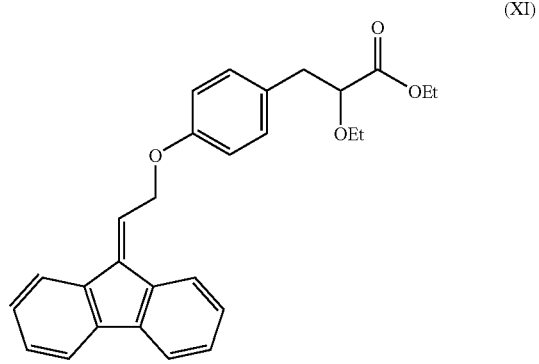
(XI)

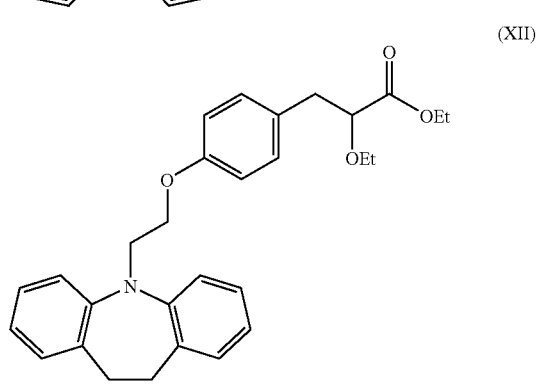
(XII)

International patent application, WO 99/08501 and WO 97/319707, disclose cyclic compounds of the formulae (XIII) and (XIV) active as PPAR-gamma agonist. A typical examples of these compounds is shown formulae (XV) and (XVI).

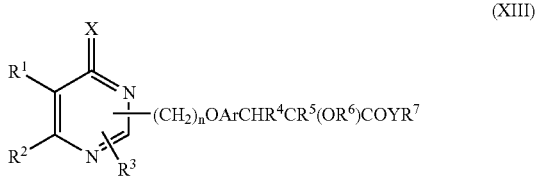
(XIII)

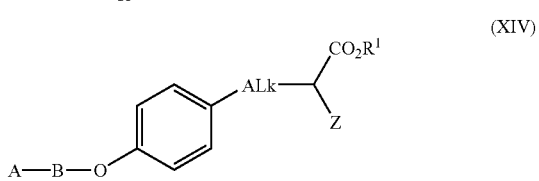
(XIV)

-continued

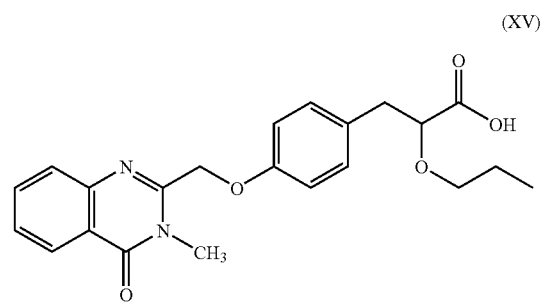
(XV)

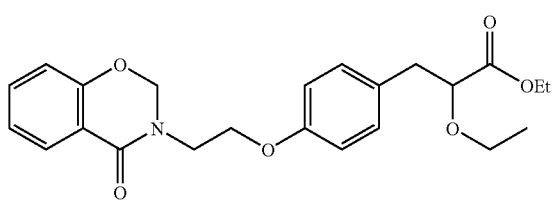
(XVI)

U.S. Pat. No. 6,054,453 and WO 99/16758 reports compounds of general formulae (XVII), (XVIII), which reduce glucose, cholesterol and triglycerides exemplified by compounds of formula (XIX).

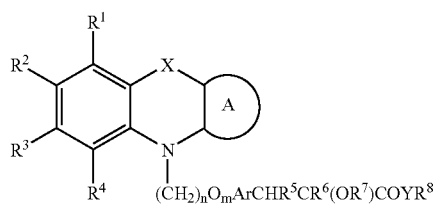
(XVII)

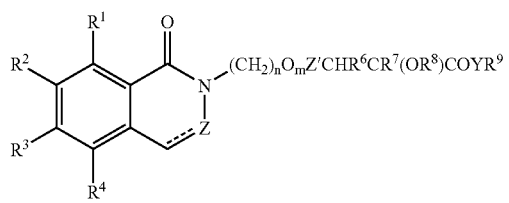
(XVIII)

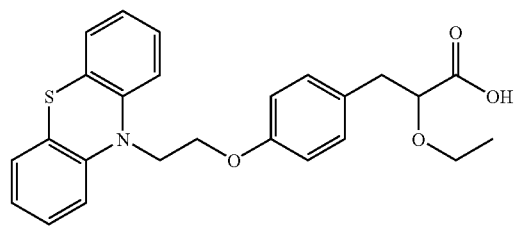
(XIX)

WO 99/19,313, U.S. Pat. No. 6,130,214 and WO 99/38850 reports compounds of general formula (XX) and (XXI) and (XXII) which reduce glucose, cholesterol and triglycerides.

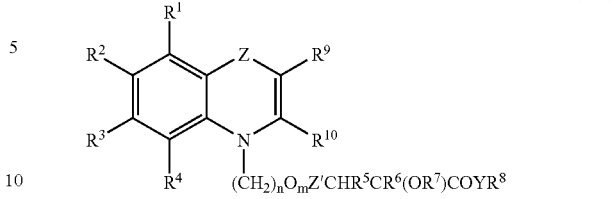
(XX)

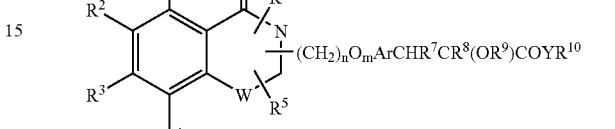
(XXI)

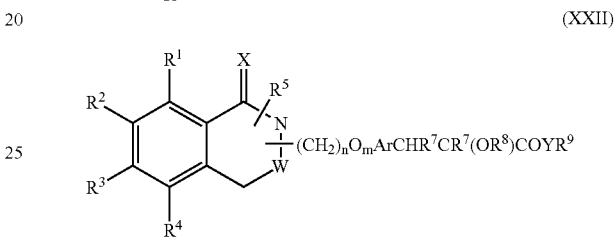
(XXII)

SUMMARY OF INVENTION

The objective of this invention is to develop novel compounds represented by the general formula (I) used as hypocholesterolemic, hypolipidaemic, hypolipoproteinemic, anti-obesity and antihyperglycemic agents which may have additional body weight lowering effect and beneficial effect in the treatment and/or prophylaxis of diseases caused by hyperlipidaemia, diseases classified under syndrome X and atherosclerosis.

The main objective of the present invention is to provide novel βaryl-α-substituted propanoic acids represented by the general formula (I), their derivatives, their analogs, their tautomeric forms, their stereoisomers, their polymorphs, their pharmaceutically acceptable salts, their pharmaceutically acceptable solvates, and pharmaceutical compositions containing them or their mixtures thereof.

Another objective of the present invention is to provide novel β-aryl-α-substituted propanoic acids represented by the general formula (I), their derivatives, their analogs, their tautomeric forms, their stereoisomers, their pharmaceutically acceptable salts, their pharmaceutically acceptable solvates, and pharmaceutical compositions containing them or their mixtures thereof having enhanced activities, without toxic effects or with reduced toxic effect.

Yet another objective of this invention is to provide a process for the preparation of novel β-aryl-α-substituted propanoic acids represented by the general formula (I), their derivatives, their analogs, their tautomeric forms, their stereoisomers, their pharmaceutically acceptable salts, their pharmaceutically acceptable solvates.

Still another objective of the present invention is to provide pharmaceutical compositions containing compounds of the general formula (I), their derivatives, their analogs, their tautomeric forms, their stereoisomers, their pharmaceutically acceptable salts, their pharmaceutically acceptable solvates or their mixtures in combination with suitable carriers, solvents, diluents and other media normally employed in preparing such compositions.

A further objective of the present invention is to provide process for preparation of intermediates involved in the process.

DETAILED DESCRIPTION OF THE INVENTION

Accordingly, the present invention relates to compounds of the general formula (I),

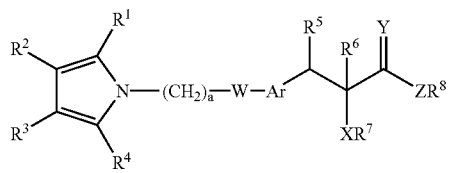

(I)

their derivatives, their analogs, their tautomeric forms, their stereoisomers, their polymorphs, their pharmaceutically acceptable salts, their pharmaceutically acceptable solvates, wherein $R^1$, $R^2$, $R^3$, $R^4$ may be same or different, and represent hydrogen, halogen, haloalkyl, perhaloalkyl, haloalkoxy, perhaloalkoxy, hydroxy, thio, amino, nitro, cyano, formyl, amidino, guanidino, or substituted or unsubstituted groups selected from linear or branched $(C_1-C_{12})$alkyl, linear or branched $(C_1-C_{12})$alkenyl, linear or branched $(C_1-C_{12})$alkynyl, $(C_3-C_7)$cycloalkyl, $(C_3-C_7)$cycloalkenyl, bicycloalkyl, bicycloalkenyl, $(C_1-C_{12})$alkoxy, $(C_1-C_{12})$alkenoxy, cyclo $(C_3-C_7)$alkoxy, aryl, aryloxy, aralkyl, ar$(C_1-C_{12})$alkoxy, heterocyclyl, heteroaryl, heterocyclyl$(C_1-C_{12})$alkyl, heteroar$(C_1-C_{12})$alkyl, heteroaryloxy, heteroar$(C_1-C_{12})$alkoxy, heterocycloxy, heterocyclylalkyloxy, acyl, acyloxy, acylamino, mono-substituted or di-substituted amino, arylamino, aralkylamino, carboxylic acid and its derivatives such as esters and amides, hydroxyalkyl, aminoalkyl, mono-substituted or di-substituted aminoalkyl, alkoxyalkyl, aryloxyalkyl, aralkoxyalkyl, $(C_1-C_{12})$alkylthio, thio$(C_1-C_{12})$alkyl, arylthio, $(C_1-C_{12})$alkoxycarbonylamino, aryloxycarbonylamino, aralkyloxycarbonylamino, aminocarbonylamino, alkylaminocarbonylamino, alkylamidino, alkylguanidino, dialkylguanidino, hydrazino, alkyl hydrazino, alkoxyamino, hydroxyl amino, derivatives of sulfenyl and sulfonyl groups, sulfonic acid and its derivatives, phosphonic acid and its derivatives;

n represents an integer varying from 1 to 8;

W represents O, S or $NR^9$, where $R^9$ represents hydrogen, $(C_1-C_{12})$alkyl or aryl groups;

Ar represents a substituted or unsubstituted divalent single or fused aromatic, heteroaromatic or a heterocyclic group;

$R^5$ and $R^6$ represent both hydrogen or together represent a bond or may also represent a hydroxy, $(C_1-C_{12})$alkyl, $(C_1-C_{12})$alkoxy, halogen, acyl, substituted or unsubstituted aralkyl group;

X represent O or S;

$R^7$ represents hydrogen, perfluoro$(C_1-C_{12})$alkyl, substituted or unsubstituted groups selected from linear or branched $(C_1-C_{12})$alkyl, cyclo$(C_1-C_{12})$alkyl, aryl, ar$(C_1-C_{12})$alkyl, heteroaryl, heteroar$(C_1-C_{1-12})$alkyl, heterocyclyl, alkoxyalkyl, aryloxyalkyl, alkoxycarbonyl, aryloxycarbonyl, cycloalkyloxycarbonyl, alkylaminocarbonyl, arylaminocarbonyl or acyl groups;

Y represents O or S;

Z represents O, S or $NR^{10}$ where $R^{10}$ represents hydrogen or substituted or unsubstituted groups selected from $(C_1-C_{12})$ alkyl, aryl, ar$(C_1-C_{12})$alkyl, hydroxy$(C_1-C_{12})$alkyl, amino$(C_1-C_{12})$alkyl, heteroaryl or heteroar $(C_1-C_{12})$alkyl groups;

$R^8$ represents hydrogen, substituted or unsubstituted groups selected from linear or branched $(C_1-C_{12})$alkyl, aryl, ar$(C_1-C_{12})$alkyl, heteroaryl, heteroar$(C_1-C_{12})$alkyl, heterocylyl, heterocyclylalkyl, hydroxyalkyl, alkoxyalkyl or alkylaminoalkyl groups;

$R^8$ and $R^8$ together may form 5 or 6 membered substituted or unsubstituted heterocyclic ring structure containing one or more heteroatoms selected from O, N or S.

The various groups, radicals and substituents used anywhere in the specification are described in the following paragraphs.

The term "alkyl" used herein, either alone or in combination with other radicals, denotes a linear or branched radical containing one to twelve carbons, such as methyl, ethyl, n-propyl, iso-propyl, n-butyl, sec-butyl, tert-butyl, amyl, t-amyl, n-pentyl, n-hexyl, iso-hexyl, heptyl, octyl and the like.

The term "alkenyl" used herein, either alone or in combination with other radicals, denotes a linear or branched radical containing one to twelve carbons; such as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl and the like. The term "alkenyl" includes dienes and trienes of straight and branched chains.

The term "alkynyl" used herein, either alone or in combination with other radicals, denotes a linear or branched radical containing one to twelve carbons, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 4-hexynyl, 5- hexynyl, and the like. The term "alkynyl" includes di- and tri-ynes.

The term "cyclo$(C_3-C_7)$alkyl" used herein, either alone or in combination with other radicals, denotes a radical containing three to seven carbons, such as cyclopropyl, cyclobutyl, cyclopentyl, cyclohexyl, cycloheptyl and the like.

The term "cyclo$(C_3-C_7)$alkenyl" used herein, either alone or in combination with other radicals, denotes a radical containing three to seven carbons, such as cyclopropenyl, 1-cyclobutenyl, 2-cylobutenyl, 1-cyclopentenyl, 2-cyclopentenyl, 3-cyclopentenyl, 1-cyclohexenyl, 2-cyclohexenyl, 3-cyclohexenyl, 1-cycloheptenyl, cycloheptadienyl, cycloheptatrienyl, and the like.

The term "alkoxy" used herein, either alone or in combination with other radicals, denotes a radical alkyl, as defined above, attached directly to an oxygen atom, such as methoxy, ethoxy, n-propoxy, iso-propoxy, n-butoxy, t-butoxy, iso-butoxy, pentyloxy, hexyloxy, and the like.

The term "alkenoxy" used herein, either alone or in combination with other radicals, denotes an alkenyl radical, as defined above, attached to an oxygen atom, such as vinyloxy, allyloxy, butenoxy, pentenoxy, hexenoxy, and the like.

The term "cyclo($C_3$–$C_7$)alkoxy" used herein, either alone or in combination with other radicals, denotes a radical containing three to seven carbon atoms, such as cyclopropyloxy, cyclobutyloxy, cyclopentyloxy, cyclohexyloxy, cycloheptyloxy and the like.

The term "halo" or "halogen" used herein, either alone or in combination with other radicals, such as "haloalkyl", "perhaloalkyl" etc refers to a fluoro, chloro, bromo or iodo group. The term "haloalkyl" denotes a radical alkyl, as defined above, substituted with one or more halogens such as perhaloalkyl, more preferably, perfluoro($C_1$–$C_6$)alkyl such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups. The term "haloalkoxy" denotes a haloalkyl, as defined above, directly attached to an oxygen atom, such as fluoromethoxy, chloromethoxy, fluoroethoxy chloroethoxy groups, and the like. The term "perhaloalkoxy" denotes a perhaloalkyl radical, as defined above, directly attached to an oxygen atom, trifluoromethoxy, trifluoroethoxy, and the like.

The term "aryl" or "aromatic" used herein, either alone or in combination with other radicals, denotes an aromatic system containing one, two or three rings wherein such rings may be attached together in a pendant manner or may be fused, such as phenyl, naphthyl, tetrahydronaphthyl, indane, biphenyl, and the like. The term 'aralkyl" denotes an alkyl group, as defined above, attached to an aryl, such as benzyl, phenethyl, naphthylmethyl, and the like. The term "aryloxy" denotes an aryl radical, as defined above, attached to an alkoxy group, such as phenoxy, naphthyloxy and the like, which may be substituted. The term "aralkoxy" denotes an arylalkyl moiety, as defined above, such as benzyloxy, phenethyloxy, naphthylmethyloxy, phenylpropyloxy, and the like, which may be substituted.

The term "heterocyclyl" or "heterocyclic" used herein. either alone or in combination with other radicals, denotes saturated, partially saturated and unsaturated ring-shaped radicals, the heteroatoms selected from nitrogen, sulfur and oxygen. Examples of saturated heterocyclic radicals include aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, and the like; examples of partially saturated heterocyclic radicals include dihydrothiophene, dihydropyran, dihydrofuran, dihydrothiazole, and the like.

The term "heteroaryl" or "heteroaromatic" used herein, either alone or in combination with other radicals, denotes unsaturated 5 to 6 membered heterocyclic radicals containing one or more hetero atoms selected from O, N or S, attached to an aryl group, such as pyridyl, thienyl, furyl, pyrrolyl, oxazolyl, thiazolyl, imidazolyl, isoxazolyl, oxadiazolyl, tetrazolyl, benzopyranyl, benzofuranyl, benzothienyl, indolinyl, indolyl, azaindolyl, azaindoliiyl, quinolinyl, pyrimidinyl, pyrazolyl, quinazolinyl, pyrimidonyl, benzoxazinyl, benzoxazinonyl, benzothiazinyl, benzothiazinonyl, benzoxazolyl, benzothiazolyl, benzimidazolyl, and the like.

The term "heterocyclyl($C_1$–$C_{12}$)alkyl" used herein, either alone or in combination with other radicals, represents a heterocyclyl group, as defined above, substituted with an alkyl group of one to twelve carbons, such as pyrrolidinealkyl, piperidinealkyl, morpholinealkyl, thiomorpholinealkyl, oxazolinealkyl, and the like, which may be substituted. The term "heteroaralkyl" used herein, either alone or in combination with other radicals, denotes a heteroaryl group, as defined above, attached to a straight or branched saturated carbon chain containing 1 to 6 carbons, such as (2-furyl)methyl, (3-furyl)methyl, (2-thienyl)methyl, (3-thienyl)methyl, (2-pyridyl)methyl, 1-methyl-1-(2-pyrimidyl) ethyl and the like. The terms "heteroaryloxy", "heteroaralkoxy", "heterocycloxy", "heterocylylalkoxy" denotes heteroaryl, heteroarylalkyl, heterocyclyl, heterocylylalkyl groups respectively, as defined above, attached to an oxygen atom.

The term "acyl" used herein, either alone or in combination with other radicals, denotes a radical containing one to eight carbons such as formyl, acetyl, propanoyl, butanoyl, iso-butanoyl, pentanoyl, hexanoyl, heptanoyl, benzoyl and the like, which may be substituted.

The term "acyloxy" used herein, either alone or in combination with other radicals, denotes a radical acyl, as defined above, directly attached to an oxygen atom, such as acetyloxy, propionyloxy, butanoyloxy, iso-butanoyloxy, benzoyloxy and the like and may be substituted.

The term "acylamino" used herein, either alone or in combination with other radicals, denotes an acyl group as defined earlier attached to one amino group and may be $CH_3CONH$, $C_2H_5CONH$, $C_3H_7CONH$, $C_4H_9CONH$, $C_6H_5CONH$ and the like, which may be substituted.

The term "mono-substituted amino" used herein, either alone or in combination with other radicals, denotes an amino group, substituted with one group selected from ($C_1$–$C_6$)alkyl, substituted alkyl, aryl, substituted aryl or arylalkyl groups. Examples of monoalkylamino group include methylamine, ethylamine, n-propylamine, n-butylamine, n-pentylamine and the like and may be substituted.

The term 'disubstituted amino" used herein, either alone or in combination with other radicals, denotes an amino group, substituted with two radicals that may be same or different selected from ($C_1$–$C_6$)alkyl, substituted alkyl, aryl, substituted aryl, or arylalkyl groups, such as dimethylamino, methylethylamino, diethylamino, phenylmethyl amino and the like and may be substituted.

The term "arylamino" used herein, either alone or in combination with other radicals, denotes an aryl group, as defined above, linked through amino having a free valence bond from the nitrogen atom, such as phenylamino, naphthylamino, N-methyl anilino and the like and may be substituted.

The term "aralkylamino" used herein, either alone or in combination with other radicals, denotes an arylalkyl group as defined above linked through amino having a free valence bond from the nitrogen atom e.g. benzylamino, phenethylamino, 3-phenylpropylamino, 1-napthylmethylamino, 2-(1-napthyl)ethylamino and the like and may be substituted.

The term "oxo" or "carbonyl" used herein, either alone (—C=O—) or in combination with other radicals, such as "alkylcarbonyl", denotes a carbonyl radical (—C=O—) substituted with an alkyl radical such as acyl or alkanoyl, as described above.

The term "carboxylic acid" used herein, alone or in combination with other radicals, denotes a —COOH group, and includes derivatives of carboxylic acid such as esters and amides. The term "ester" used herein, alone or in combination with other radicals, denotes —COO— group, and includes carboxylic acid derivatives, where the ester moieties are alkoxycarbonyl, such as methoxycarbonyl, ethoxycarbonyl, and the like, which may be substituted; aryloxycarbonyl group such as phenoxycarbonyl, napthyloxycarbonyl, and the like, which may be substituted; aralkoxycarbonyl group such as benzyloxycarbonyl, phenethyloxycarbonyl, napthylmethoxycarbonyl, and the like, which may be substituted; heteroaryloxycarbonyl, heteroaralkoxycarbonyl, wherein the heteroaryl group, is as defined above, which may be substituted; heterocyclyloxycarbonyl, where the heterocyclic group, as defined earlier, which may be substituted.

The term "amide" used herein, alone or in combination with other radicals, represents an aminocarbonyl radical ($H_2N-C=O-$), wherein the amino group is mono- or di-substituted or unsubstituted, such as methylamide, dimethylamide, ethylamide, diethylamide, and the like. The term "aminocarbonyl" used herein, either alone or in combination with other radicals, with other terms such as 'aminocarbonylalkyl", "n-alkylaminocarbonyl", "N-arylaminocarbonyl", "N,N-dialkylaminocarbonyl", "N-alkyl-N-arylaminocarbonyl", "N-alkyl-N-hydroxyaminocarbonyl", and "N-alkyl-N-hydroxyaminocarbonylalkyl", substituted or unsubstituted. The terms "N-alkylaminocabonyl" and "N,N-dialkylaminocarbonyl" denotes aminocarbonyl radicals, as defined above, which have been substituted with one alkyl radical and with two alkyl radicals, respectively. Preferred are "lower alkylaminocarbonyl" having ($C_1$-$C_6$) lower alkyl radicals as described above attached to aminocarbonyl radical. The terms "N-arylaminocarbonyl" and "N-alkyl-N-arylaminocarbonyl" denote amiocarbonyl radicals substituted, respectively with one aryl radical, or one alkyl and one aryl radical. The term "aminocarbonylalkyl" includes alkyl radicals substituted with aminocarbonyl radicals.

The term "hydroxyalkyl" used herein, either alone or in combination with other radicals, denotes an alkyl group, as defined above, substituted with one or more hydroxy radicals, such as hydroxymethyl, hydroxyethyl, hydroxypropyl, hydroxybutyl, hydroxypentyl, hydroxyhexyl and the like.

The term "aminoalkyl" used herein, alone or in combination with other radicals, denotes an amino ($-NH_2$) moiety attached to an alkyl radical, as defined above, which may be substituted, such as mono- and di-substituted aminoalkyl. The term "alkylamino" used herein, alone or in combination with other radicals, denotes an alkyl radical, as defined above, attached to an amino group, which may be substituted, such as mono- and di-substituted alkylamino.

The term "alkoxyalkyl" used herein, alone or in combination with other radicals, denotes an alkoxy group, as defined above, attached to an alkyl group, such as methoxymethyl, ethoxymethyl, methoxyethyl, ethoxyethyl and the like. The term "aryloxyalkyl" used herein, alone or in combination with other radicals, includes phenoxymethyl, napthyloxymethyl, and the like. The term "aralkoxyalkyl" used herein, alone or in combination with other radicals, includes $C_6H_5CH_2OCH_2$, $C_6H_5CH_2OCH_2CH_2$, and the like.

The term "($C_1$-$C_{12}$)alkylthio" used herein, either alone or in combination with other radicals, denotes a straight or branched or cyclic monovalent substituent comprising an alkyl group of one to twelve carbon atoms, as defined above, linked through a divalent sulfur atom having a free valence bond from the sulfur atom, such as methylthio, ethylthio, propylthio, butylthio, pentylthio and the like. Examples of cyclic alkylthio are cyclopropylthio, cyclobutylthio, cyclopentylthio, cyclohexylthio and the like, which may be substituted.

The term "thio($C_1$-$C_{12}$)alkyl" used herein, either alone or in combination with other radicals, denotes an alkyl group, as defined above, attached to a group of formula $-SR'$, where R' represents hydrogen, alkyl or aryl group, e.g. thiomethyl, methylthiomethyl, phenylthiomethyl and the like, which may be substituted.

The term "arylthio' used herein, either alone or in combination with other radicals, denotes an aryl group, as defined above, linked through a divalent sulfur atom, having a free valence bond from the sulfur atom such as phenylthio, napthylthio and the like.

The term "($C_1$-$C_{12}$)alkoxycarbonylamino" used herein, alone or in combination with other radicals, denotes an alkoxycarbonyl group, as defined above, attached to an amino group, such as methoxycarbonylamino, ethoxycarbonylamino, and the like. The term "aryloxycarbonylamino" used herein, alone or in combination with other radicals, denotes an aryloxycarbonyl group, as defined above, attached to the an amino group, such as $C_6H_5OCONH$, $C_6H_5OCONCH_3$, $C_6H_5OCONC_{H5}$, $C_6H_4(CH_3O)OCONH$, $C_6H_4(OCH_3)OCONH$, and the like. The term "aralkoxycarbonylamino" used herein, alone or in combination with other radicals, denotes an aralkoxycarbonyl group, as defined above, attached to an amino group $C_6H_5CH_2OCONH$, $C_6H_5CH_2CH_2CH_2OCONH$, $C_6H_5CH_2OCONHCH_3$, $C_6H_5CH_2OCONC_2H_5$, $C_6H_4(CH_3)CH_2OCONH$, $C_6H_4(OCH_3)CH_2OCONH$, and the like.

The term "aminocarbonylamino", "alkylaminocarbonylamino", "dialkylaminocarbonylamino" used herein, alone or in combination with other radicals, denotes a carbonylamino ($-CONH_2$) group, attached to amino($NH_2$), alkylamino group or dialkylamino group respectively, where alkyl group is as defined above.

The term "amidino" used herein, either alone or in combination with other radicals, denotes a $-C(=NH)-NH_2$ radical. The term "alkylamidino" denotes an alkyl radical, as discussed above, attached to an amidino group.

The term "guanidino" used herein, either alone or in combination with other radicals, denotes $HN=C(NH_2)NH-$, suitably substituted with other radicals, such as alkylguanidino, dialkylguanidino, where the alkyl group, as defined above is attached to a guanidino group, such as methylguanidino, ethylguanidino, dimethylguanidino, and the like.

The term "hydrazino" used herein, either alone or in combination with other radicals, denotes $-NHNH-$, suitably substituted with other radicals, such as alkyl hydrazino, where an alkyl group, as defined above is attached to a hydrazino group.

The term "alkoxyamino" used herein, alone or in combination with other radicals, denotes an alkoxy group, as defined above, attached to an amino group. The term "hydroxyamino" used herein, alone or in combination with other radicals, denotes $-NHOH$ moiety, and may be substituted.

The term "sulfenyl" or "sulfenyl and its derivatives" used herein, alone or in combination with other radicals, denotes a bivalent group, $-SO-$ or RSO, where R is substituted or unsubstituted alkyl, aryl, heteroaryl, heterocyclyl, and the like.

The term "sulfonyl" or "sulfones and its derivatives" used herein, either alone or in combination with other radicals, with other terms such as alkylsulfonyl, denotes divalent radical $-SO_2-$, or $RSO_2-$, where R is substituted or unsubstituted groups selected from alkyl, aryl, heteroaryl, heterocyclyl, and the like. "Alkylsulfonyl" denotes alkyl radicals, as defined above, attached to a sulfonyl radical, such as methylsulfonyl, ethylsulfonyl, propylsulfonyl and the like. The term "arylsulfonyl" used herein, either alone or in combination with other radicals, denotes aryl radicals, as defined above, attached to a sulfonyl radical, such as phenylsulfonyl and the like.

The term "sulfonic acid or its derivatives", used herein, either alone or in combination with other radicals, denotes —$SO_3H$ group and its derivatives such as sulfonylamino ($SO_2NH_2$); N-alkylaminosulfonyl and N,N-dialkylaminosulfonyl radicals where the sulfonylamino group is substituted with one and two alkyl groups respectively, such as N-methylaminosulfonyl, N-ethylaminosulfonyl, N,N-dimethylaminosulfonyl, N-methyl-N-ethylaminosulfonyl and the like; N-arylaminosulfonyl and N-alkyl-N-arylaminosulfonyl groups where the sulfonylamino group is substituted with one aryl radical, or one alkyl and one aryl radical; —$SO_3R$, wherein 'R' represents alkyl, aryl, aralkyl groups, as defined above, which may be substituted.

The term "phosphonic acid or its derivatives", used herein, either alone or in combination with other radicals, denotes $P(O)(OH)_2$, $P(O)(O(C_1-C_6)$ alkyl$)_2$, $P(O)(O \text{ aryl})_2$, $P(O)(OH)(O(C_1-C_6)\text{alkyl})$, and the like.

The term "substituted" used in combination with other radicals, denotes suitable substituents on that radical such as substituted alkyl, substituted alkenyl, substituted alkynyl, substituted cycloalkyl, substituted aryl, etc, mentioned anywhere in the specification. The suitable substituents include, but are not limited to the following radicals, alone or in combination with other radicals, such as, hydroxyl, oxo, halo, thio, nitro, amino, cyano, formyl, amidino, guanidino, hydrazino, alkyl, haloalkyl, perhaloalkyl, alkoxy, haloalkoxy, perhaloalkoxy, alkenyl, alkynyl, cycloalkyl, cycloalkenyl, bicycloalkyl, bicycloalkenyl, alkoxy, alkenoxy, cycloalkoxy, aryl, aryloxy, aralkyl, aralkoxy, heterocylyl, heteroaryl, heterocyclylalkyl, heteroaralkyl, heteroaryloxy, heteroaralkoxy, heterocyclyloxy, heterocyclylalkoxy, heterocyclylalkoxyacyl, acyl, acyloxy, acylamino, monosubstituted or disubstituted amino, arylamino, aralkylamino, carboxylic acid and its derivatives such as esters and amides, carbonylamino, hydroxyalkyl, aminoalkyl, alkoxyalkyl, aryloxyalkyl, aralkoxyalkyl, alkylthio, thioalkyl, arylthio, alkoxycarbonylamino, aryloxycarbonylamino, aralkyloxycarbonylamino, aminocarbonylamino, alkylaminocarbonylamino, alkoxyamino, hydroxyl amino, sulfenyl derivatives, sulfonyl derivatives, sulfonic acid and its derivatives, phosphonic acid and its derivatives.

The groups $R^1$, $R^2$, $R^3$, $R^4$, $R^5$, $R^6$, $R^7$, $R^8$, $R^9$, $R^{10}$, and Ar, may be substituted, where the term "substituted" includes radicals as defined above, or any other group mentioned in the specification.

Some of the above defined terms may occur more than once in the above defined formula (I) and upon such occurences, each such term may be defined independently of the other.

It is preferred that $R^8$ represents $(C_1-C_6)$alkyl, aralkyl or hydrogen; Z represents O or NH or $N(C_1-C_3)$alkyl; Y represents O atom; X represents O or S atom; $R^7$ represents optionally substituted groups selected from linear or branched $(C_1-C_6)$alkyl, aralkyl or aryl radical; $R^5$ and $R^6$ each represent a H atom or $R^5$ and $R^6$ together may represent a bond; Ar represents a divalent phenyl group or a naphthyl group optionally substituted; W represents O or S atom; n represents an integer 2; $R^1$, $R^2$, $R^3$, $R^4$ represent hydrogen, formyl, perhaloalkyl, substituted or unsubstituted groups selected from linear or branched $(C_1-C_6)$alkyl, aralkyl, $(C_3-C_6)$cycloalkyl, $(C_1-C_6)$alkoxy, aryl, heterocyclyl, heteroaryl, heterocyclylalkyl, heteroaralkyl, alkoxy, alkylthio, arylthio, acyl, alkoxycarbonyl, aryloxycarbonyl, carboxylic acid and its derivatives.

It is more preferred that $R^8$ represents $(C_1-C_3)$alkyl, aralkyl or hydrogen; Z represents O atom; Y represents O atom; X represents O atom; $R^7$ represents linear or branched $(C_1-C_6)$alkyl, optionally substituted with one or more halogen atoms; $R^5$ and $R^6$ represent each a hydrogen atom; Ar represents a divalent phenyl group, optionally substituted with halogen, alkyl, alkoxy groups; W represents O atom; n represents an integer 2; $R^2$, $R^3$ each represent a hydrogen atom and $R^1$, $R^4$ may be same or different and represent optionally substituted groups selected from $(C_1-C_6)$alkyl, especially, $(C_1-C_4)$alkyl such as methyl, ethyl, propyl, isopropyl, butyl, iso-butyl groups; aralkyl groups such as benzyl, phenethyl; hydroxyalkyl especially hydroxymethyl; aminoalkyl especially aminomethyl; aryl, phenyl optionally substituted with one or more groups such as halo, nitro, cyano, alkyl, alkenyl, phenyl, alkoxy, 1,2-methylenedioxy, heterocyclylalkyl, heteroaralkyl, aryloxy, aralkyl, alkylthio, thioalkyl, hydroxy, alkylcarbonyloxy, halogen, amino, acylamino alkylamino, acyl, alkylsulfinyl, alkylsulfonyl, arylthio, arylsulfenyl, arylsulfonyl, carboxylic acid and its derivatives; heterocyclyl, heteroaryl, acyl, $(C_3-C_6)$cycloalkyl groups; optionally substituted heteroaryl group such as furyl, thienyl, quinolyl, benzofuryl, benzothienyl, pyridyl groups. Alternatively, $R^1$, $R^2$, $R^3$ represent hydrogen atom and $R^4$ represent optionally substituted groups selected from aryl, 1,2-methylenedioxyphenyl, heteroaryl, such as furyl, pyridyl, thienyl, benzofuranyl, benzothiophenyl, $(C_1-C_4)$alkyl, alkylthio, alkoxy, and acyl groups.

Pharmaceutically acceptable salts forming part of this invention are intended to define but not limited to salts of the carboxylic acid moiety such as alkali metal salts like Li, Na, and K salts; alkaline earth metal salts like Ca and Mg salts; salts of organic bases such as lysine, arginine, guanidine and its derivatives, which may be optionally substituted, diethanolamine, choline, tromethamine and the like; ammonium or substituted ammonium salts and aluminium salts. Salts may be acid addition salts which defines but not limited to sulfates, bisulfates, nitrates, phosphates, perchlorates, borates, hydrohalides, acetates, tartrates, maleates, fumarates, maleiates, citrates, succinates, palmoates, methanesulfonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to the present invention includes (±) Ethyl 3-{4-[2-(pyrrol-1-yl)ethoxy]phenyl}-2-ethoxypropanoate (+) Ethyl 3-{4-[2-(pyrrol-1-yl)ethoxy]phenyl}-2-ethoxypropanoate (−) Ethyl 3-{4-[2-(pyrrol-1-yl)ethoxy]phenyl}-2-ethoxypropanoate (±) Ethyl 3-{4-[2-(2,5-dimethylpyrrol-1-yl)ethoxy]phenyl}-2-ethoxypropanoate (+) Ethyl 3-{4-[2-(2,5-dimethylpyrrol-1-yl)ethoxy]phenyl}-2-ethoxypropanoate (−) Ethyl 3-{4-[2-(2,5-dimethylpyrrol-1-yl)ethoxy]phenyl}-2-ethoxypropanoate (±) Ethyl 3-{4-[2-(2,5-diisopropyl-3-phenylpyrrol-1-yl)ethoxy]phenyl}-2-ethoxypropanoate (+) Ethyl 3-{4-[2-(2,5-diisopropyl-3-phenylpyrrol-1-yl)ethoxy]phenyl}-2-ethoxypropanoate (−) Ethyl 3-{4-[2-(2,5-diisopropyl-3-phenylpyrrol-1-yl)ethoxy]phenyl}-2-ethoxypropanoate (±) Ethyl 3-(4-{2-[2-isopropyl-5-(4-methoxyphenyl)pyrrol-1-yl]ethoxy}phenyl)-2-ethoxypropanoate (+) Ethyl 3-(4-{2-[2-isopropyl-5-(4-methoxyphenyl)pyrrol-1-yl]ethoxy}phenyl)-2-ethoxypropanoate (−) Ethyl 3-(4-{2-[2-isopropyl-5-(4-methoxyphenyl)pyrrol-1-yl]ethoxy}phenyl)-2-ethoxypropanoate (±) Ethyl 3-(4-{2-[2-(4-fluorophenyl)-5-isopropylpyrrol-1-yl]ethoxy}phenyl)-2-ethoxypropanoate (+) Ethyl 3-(4-{2-[2-(4-fluorophenyl)-5-isopropylpyrrol-1-yl]ethoxy}phenyl)-2-ethoxypropanoate (−) Ethyl 3-(4-{2-[2-(4-fluorophenyl)-5-isopropylpyrrol-1-yl]ethoxy}phenyl)-2-ethoxypropanoate (±) Ethyl 3-(4-{2-[2-(4-fluorophenyl)-5-isopropyl-3-phenylpyrrol-1-yl]ethoxy}phenyl)-2-ethoxypropanoate (+) Ethyl 3-(4-{2-[2-(4-fluorophenyl)-5-isopropyl-3-phenylpyrrol-1-yl]ethoxy}phenyl)-2-ethoxypropanoate (−) Ethyl 3-(4-{2-[2-(4-fluorophenyl)-5-isopropyl-3-phenylpyrrol-1-yl]ethoxy}phenyl)-2-ethoxypropanoate (±) Ethyl 3-(4-{2-[2-(4-fluorophenyl)-5-phenylpyrrol-1-yl]ethoxy}phenyl)-2-ethoxypropanoate (+) Ethyl 3-(4-{2-[2-(4-fluorophenyl)-5-phenylpyrrol-1-yl]ethoxy}phenyl)-2-ethoxypropanoate (−) Ethyl 3-(4-{2-[2-(4-fluorophenyl)-5-phenylpyrrol-1-yl]ethoxy}phenyl)-2-ethoxypropanoate (±) Ethyl 3-[4-[2-[2-(2-phenyl-3-carboxy-5-(4-fluorophenyl)pyrrol-1-yl]ethoxy]phenyl-2-ethoxypropanoate (+) Ethyl 3-[4-[2-[2-(2-phenyl-3-carboxy-5-(4-fluorophenyl)pyrrol-1-yl]ethoxy]phenyl-2-ethoxypropanoate (−) Ethyl 3-[4-[2-[2-(2-phenyl-3-carboxy-5-(4-fluorophenyl)pyrrol-1-yl]ethoxy]phenyl-2-ethoxypropanoate (±) Ethyl 3-(4-{2-[2-(4-fluorophenyl)-5-isopropyl-3-phenyl-4-phenylcarbamoylpyrrol-1-yl]ethoxy}phenyl)-2-ethoxypropanoate (+) Ethyl 3-(4-{2-[2-(4-fluorophenyl)-5-isopropyl-3-phenyl-4-phenylcarbamoylpyrrol-1-yl]ethoxy}phenyl)-2-ethoxypropanoate (−) Ethyl 3-(4-{2-[2-(4-fluorophenyl)-5-isopropyl-3-phenyl-4-phenylcarbamoylpyrrol-1-yl]ethoxy}phenyl)-2-ethoxypropanoate (±) Ethyl 3-(4-{3-[2-(4-fluorophenyl)-5-isopropyl-3-phenyl-4-phenylcarbamoylpyrrol-1-yl]propoxy}phenyl)-2-ethoxypropanoate (+) Ethyl 3-(4-{3-[2-(4-fluorophenyl)-5-isopropyl-3-phenyl-4-phenylcarbamoylpyrrol-1-yl]propoxy}phenyl)-2-ethoxypropanoate (−) Ethyl 3-(4-{3-[2-(4-fluorophenyl)-5-isopropyl-3-phenyl-4-phenylcarbamoylpyrrol-1-yl]propoxy}phenyl)-2-ethoxypropanoate (±) Ethyl 3-{4-[2-(2-isopropyl-5-methylpyrrol-1-yl)ethoxy]phenyl}-2-ethoxypropanoate (+) Ethyl 3-{4-[2-(2-isopropyl-5-methylpyrrol-1-yl)ethoxy]phenyl}-2-ethoxypropanoate (−) Ethyl 3-{4-[2-(2-isopropyl-5-methylpyrrol-1-yl)ethoxy]phenyl}-2-ethoxypropanoate (±) Ethyl 3-{4-[2-(2,4-dimethylpyrrol-1-yl)ethoxy]phenyl}-2-ethoxypropanoate;

(+) Ethyl 3-{4-[2-(2,4-dimethylpyrrol-1-yl)ethoxy]phenyl}-2-ethoxypropanoate;

(−) Ethyl 3-{4-[2-(2,4-dimethylpyrrol-1-yl)ethoxy]phenyl}-2-ethoxypropanoate;

(±) Ethyl 3-{4-[2-(2-formylpyrrol-1-yl)ethoxy]phenyl}-2-ethoxypropanoate;

(+) Ethyl 3-{4-[2-(2-formylpyrrol-1-yl)ethoxy]phenyl}-2-ethoxypropanoate;

(−) Ethyl 3-{4-[2-(2-formylpyrrol-1-yl)ethoxy]phenyl}-2-ethoxypropanoate;

(±) Ethyl 3-{4-[2-(2-acetylpyrrol-1-yl)ethoxy]phenyl}-2-ethoxypropanoate;

(+) Ethyl 3-{4-[2-(2-acetylpyrrol-1-yl)ethoxy]phenyl}-2-ethoxypropanoate;

(−) Ethyl 3-{4-[2-(2-acetylpyrrol-1-yl)ethoxy]phenyl}-2-ethoxypropanoate;

(±) Ethyl 3-{4-[2-(2-ethylpyrrol-1-yl)ethoxy]phenyl}-2-ethoxypropanoate;

(+) Ethyl 3-{4-[2-(2-ethylpyrrol-1-yl)ethoxy]phenyl}-2-ethoxypropanoate;

(−) Ethyl 3-{4-[2-(2-ethylpyrrol-1-yl)ethoxy]phenyl}-2-ethoxypropanoate;

(±) Ethyl 3-{4-[2-(2-ethyl-5-methylpyrrol-1-yl)ethoxy]phenyl}-2-ethoxypropanoate;

(+) Ethyl 3-{4-[2-(2-ethyl-5-methylpyrrol-1-yl)ethoxy]phenyl}-2-ethoxypropanoate;

(−) Ethyl 3-{4-[2-(2-ethyl-5-methylpyrrol-1-yl)ethoxy]phenyl}-2-ethoxypropanoate;

(±) Ethyl 3-{4-[2-(5-methyl-2-propylpyrrol-1-yl)ethoxy]phenyl}-2-ethoxypropanoate;

(+) Ethyl 3-{4-[2-(5-methyl-2-propylpyrrol-1-yl)ethoxy]phenyl}-2-ethoxypropanoate;

(−) Ethyl 3-{4-[2-(5-methyl-2-propylpyrrol-1-yl)ethoxy]phenyl}-2-ethoxypropanoate;

(±) Ethyl 3-{4-[2-(5-methyl-2-n-butylpyrrol-1-yl)ethoxy]phenyl}-2-ethoxypropanoate;

(+) Ethyl 3-{4-[2-(5-methyl-2-n-butylpyrrol-1-yl)ethoxy]phenyl}-2-ethoxypropanoate;

(−) Ethyl 3-{4-[2-(5-methyl-2-n-butylpyrrol-1-yl)ethoxy]phenyl}-2-ethoxypropanoate;

(±) Ethyl 3-{4-[2-(5-methyl-2-phenylpyrrol-1-yl)ethoxy]phenyl}-2-ethoxypropanoate;

(+) Ethyl 3-{4-[2-(5-methyl-2-phenylpyrrol-1-yl)ethoxy]phenyl}-2-ethoxypropanoate;

(−) Ethyl 3-{4-[2-(5-methyl-2-phenylpyrrol-1-yl)ethoxy]phenyl}-2-ethoxypropanoate;

(±) Ethyl 3-{4-[2-(5-methyl-3-phenylpyrrol-1-yl)ethoxy]phenyl}-2-ethoxypropanoate;

(+) Ethyl 3-{4-[2-(5-methyl-3-phenylpyrrol-1-yl)ethoxy]phenyl}-2-ethoxypropanoate;

(−) Ethyl 3-{4-[2-(5-methyl-3-phenylpyrrol-1-yl)ethoxy]phenyl}-2-ethoxypropanoate;

(±) Ethyl 3-{4-[2-(5-methyl-2-phenylpyrrol-1-yl)ethoxy]phenyl}-2-methoxypropanoate;

(+) Ethyl 3-{4-[2-(5-methyl-2-phenylpyrrol-1-yl)ethoxy]phenyl}-2-methoxypropanoate;

(−) Ethyl 3-{4-[2-(5-methyl-2-phenylpyrrol-1-yl)ethoxy]phenyl}-2-methoxypropanoate;

(±) Methyl 3-{4-[2-(5-methyl-2-phenylpyrrol-1-yl)ethoxy]phenyl}-2-methoxypropanoate;

(+) Methyl 3-{4-[2-(5-methyl-2-phenylpyrrol-1-yl)ethoxy]phenyl}-2-methoxypropanoate;

(−) Methyl 3-{4-[2-(5-methyl-2-phenylpyrrol-1-yl)ethoxy]phenyl}-2-methoxypropanoate;

(±) Ethyl 3-{4-[2-(5-methyl-2-phenylpyrrol-1-yl)ethoxy]phenyl}-2-propoxypropanoate;

(+) Ethyl 3-{4-[2-(5-methyl-2-phenylpyrrol-1-yl)ethoxy]phenyl}-2-propoxypropanoate;

(−) Ethyl 3-{4-[2-(5-methyl-2-phenyl)pyrrol-1-yl)ethoxy]phenyl}-2-propoxypropanoate;

(±) Propyl 3-{4-[2-(5-methyl-2-phenylpyrrol-1-yl)ethoxy]phenyl}-2-propoxypropanoate;

(+) Propyl 3-{4-[2-(5-methyl-2-phenylpyrrol-1-yl)ethoxy]phenyl}-2-propoxypropanoate;

(−) Propyl 3-{4-[2-(5-methyl-2-phenylpyrrol-1-yl)ethoxy]phenyl}-2-propoxypropanoate;

(±) Ethyl 3-{4-[2-(5-methyl-2-(4-methylphenyl)pyrrol-1-yl)ethoxy]phenyl}-2-ethoxypropanoate;

(+) Ethyl 3-{4-[2-(5-methyl-2-(4-methylphenyl)pyrrol-1-yl)ethoxy]phenyl}-2-ethoxypropanoate;

(−) Ethyl 3-{4-[2-(5-methyl-2-(4-methylphenyl)pyrrol-1-yl)ethoxy]phenyl}-2-ethoxypropanoate;
(±) Ethyl 3-{4-[2-(5-methyl-2-(3-methylphenyl)pyrrol-1-yl)ethoxy]phenyl}-2-ethoxypropanoate;
(+) Ethyl 3-{4-[2-(5-methyl-2-(3-methylphenyl)pyrrol-1-yl)ethoxy]phenyl}-2-ethoxypropanoate;
(−) Ethyl 3-{4-[2-(5-methyl-2-(3-methylphenyl)pyrrol-1-yl)ethoxy]phenyl}-2-ethoxypropanoate;
(±) Ethyl 3-{4-[2-(5-methyl-2-(2-methylphenyl)pyrrol-1-yl)ethoxy]phenyl}-2-ethoxypropanoate;
(+) Ethyl 3-{4-[2-(5-methyl-2-(2-methylphenyl)pyrrol-1-yl)ethoxy]phenyl}-2-ethoxypropanoate;
(−) Ethyl 3-{4-[2-(5-methyl-2-(2-methylphenyl)pyrrol-1-yl)ethoxy]phenyl}-2-ethoxypropanoate;
(±) Ethyl 3-{4-[2-(5-methyl-2-(4-methoxyphenyl)pyrrol-1-yl)ethoxy]phenyl}-2-ethoxypropanoate;
(+) Ethyl 3-{4-[2-(5-methyl-2-(4-methoxyphenyl)pyrrol-1-yl)ethoxy]phenyl}-2-ethoxypropanoate;
(−) Ethyl 3-{4-[2-(5-methyl-2-(4-methoxyphenyl)pyrrol-1-yl)ethoxy]phenyl}-2-ethoxypropanoate;
(±) Ethyl 3-{4-[2-(5-methyl-2-(4-bromophenyl)pyrrol-1-yl)ethoxy]phenyl}-2-ethoxypropanoate;
(+) Ethyl 3-{4-[2-(5-methyl-2-(4-bromophenyl)pyrrol-1-yl)ethoxy]phenyl}-2-ethoxypropanoate;
(−) Ethyl 3-{4-[2-(5-methyl-2-(4-bromophenyl)pyrrol-1-yl)ethoxy]phenyl}-2-ethoxypropanoate;
(±) Ethyl 3-{4-[2-(5-methyl-2-(4-fluorophenyl)pyrrol-1-yl)ethoxy]phenyl}-2-ethoxypropanoate;
(+) Ethyl 3-{4-[2-(5-methyl-2-(4-fluorophenyl)pyrrol-1-yl)ethoxy]phenyl}-2-ethoxypropanoate;
(−) Ethyl 3-{4-[2-(5-methyl-2-(4-fluorophenyl)pyrrol-1-yl)ethoxy]phenyl}-2-ethoxypropanoate;
(±) Ethyl 3-{4-[2-(5-methyl-2-(4-chlorophenyl)pyrrol-1-yl)ethoxy]phenyl}-2-ethoxypropanoate;
(+) Ethyl 3-{4-[2-(5-methyl-2-(4-chlorophenyl)pyrrol-1-yl)ethoxy]phenyl}-2-ethoxypropanoate;
(−) Ethyl 3-{4-[2-(5-methyl-2-(4-chlorophenyl)pyrrol-1-yl)ethoxy]phenyl}-2-ethoxypropanoate;
(±) Ethyl 3-{4-[2-(4-methyl-2-phenylpyrrol-1-yl)ethoxy]phenyl}-2-ethoxypropanoate;
(+) Ethyl 3-{4-[2-(4-methyl-2-phenylpyrrol-1-yl)ethoxy]phenyl}-2-ethoxypropanoate;
(−) Ethyl 3-{4-[2-(4-methyl-2-phenylpyrrol-1-yl)ethoxy]phenyl}-2-ethoxypropanoate;
(±) Ethyl 3-{4-[2-(5-methyl-2,3-diphenylpyrrol-1-yl)ethoxy]phenyl}-2-ethoxypropanoate;
(+) Ethyl 3-{4-[2-(5-methyl-2,3-diphenylpyrrol-1-yl)ethoxy]phenyl}-2-ethoxypropanoate;
(−) Ethyl 3-{4- [2-(5-methyl-2,3-diphenylpyrro-1-yl)ethoxy]phenyl}-2-ethoxypropanoate;
(±) Ethyl 3-{4-[2-(2,5-diisopropylpyrrol-1-yl)ethoxy]phenyl}-2-ethoxypropanoate;
(+) Ethyl 3-{4-[2-(2,5-diisopropylpyrrol-1-yl)ethoxy]phenyl}-2-ethoxypropanoate;
(−) Ethyl 3-{4-[2-(2,5-diisopropylpyrrol-1-yl)ethoxy]phenyl}-2-ethoxypropanoate;
(±) Ethyl 3-{4-[2-(5-isopropyl-2-phenylpyrrol-1-yl)ethoxy]phenyl}-2-ethoxypropanoate;
(+) Ethyl 3-{4-[2-(5-isopropyl-2-phenylpyrrol-1-yl)ethoxy]phenyl}-2-ethoxypropanoate;
(−) Ethyl 3-{4-[2-(5-isopropyl-2-phenylpyrrol-1-yl)ethoxy]phenyl}-2-ethoxypropanoate;
(±) Ethyl 3-(4-{2-[2-(4-fluorophenyl)-5-isopropyl-4-phenylcarbamoylpyrrol-1-yl]ethoxy}phenyl)-2-ethoxypropanoate;
(+) Ethyl 3-(4-{2-[2-(4-fluorophenyl)-5-isopropyl-4-phenylcarbamoylpyrrol-1-yl]ethoxy}phenyl)-2-ethoxypropanoate;
(−) Ethyl 3-(4-{2-[2-(4-fluorophenyl)-5-isopropyl-4-phenylcarbamoylpyrrol-1-yl]ethoxy}phenyl)-2-ethoxypropanoate;
(±) Ethyl 3-{4-[2-(2-methylthiopyrrol-1-yl)ethoxy]phenyl}-2-ethoxypropanoate;
(+) Ethyl 3-{4-[2-(2-methylthiopyrrol-1-yl)ethoxy]phenyl}-2-ethoxypropanoate;
(−) Ethyl 3-{4-[2-(2-methylthiopyrrol-1-yl)ethoxy]phenyl}-2-ethoxypropanoate;
(±) Ethyl 3-{4-[2-(2,5-diethylpyrrol-1-yl)ethoxy]phenyl}-2-ethoxypropanoate;
(+) Ethyl 3-{4-[2-(2,5-diethylpyrrol-1-yl)ethoxy]phenyl}-2-ethoxypropanoate;
(−) Ethyl 3-{4-[2-(2,5-diethylpyrrol-1-yl)ethoxy]phenyl}-2-ethoxypropanoate;
(±) Ethyl 3-{4-[2-(5-ethyl-2-phenylpyrrol-1-yl)ethoxy]phenyl}-2-ethoxypropanoate;
(+) Ethyl 3-{4-[2-(5-ethyl-2-phenylpyrrol-1-yl)ethoxy]phenyl}-2-ethoxypropanoate;
(−) Ethyl 3-{4-[2-(5-ethyl-2-phenylpyrrol-1-yl)ethoxy]phenyl}-2-ethoxypropanoate;
(±) Ethyl 3-{4-[2-(5-ethyl-2-(2-phenylethyl) pyrrol-1-yl)ethoxy]phenyl}-2-ethoxypropanoate;
(+) Ethyl 3-{4-[2-(5-ethyl-2-(2-phenylethyl) pyrrol-1-yl)ethoxy]phenyl}-2-ethoxypropanoate;
(−) Ethyl 3-{4-[2-(5-ethyl-2-(2-phenylethyl) pyrrol-1-yl)ethoxy]phenyl}-2-ethoxypropanoate;
(±) Ethyl 3-{4-[2-(5-methyl-2-(3-methoxyphenyl) pyrrol-1-yl)ethoxy]phenyl}-2-ethoxypropanoate;
(+) Ethyl 3-{4-[2-(5-methyl-2-(3-methoxyphenyl) pyrrol-1-yl)ethoxy]phenyl}-2-ethoxypropanoate;
(−) Ethyl 3-{4-[2-(5-methyl-2-(3-methoxyphenyl) pyrrol-1-yl)ethoxy]phenyl}-2-ethoxypropanoate;
(±) Ethyl 3-{4-[2-(5-methyl-2-cyclohexyl pyrrol-1-yl)ethoxy]phenyl}-2-ethoxypropanoate;
(+) Ethyl 3-{4-[2-(5-methyl-2-cyclohexyl pyrrol-1-yl)ethoxy]phenyl}-2-ethoxypropanoate;
(−) Ethyl 3-{4-[2-(5-methyl-2-cyclohexyl pyrrol-1-yl)ethoxy]phenyl}-2-ethoxypropanoate;
(±) Ethyl 3-{4-[2-(5-methyl-2-biphenyl pyrrol-1-yl)ethoxy]phenyl}-2-ethoxypropanoate;
(+) Ethyl 3-{4-[2-(5-methyl-2-biphenyl pyrrol-1-yl)ethoxy]phenyl}-2-ethoxypropanoate;
(−) Ethyl 3-{4-[2-(5-methyl-2-biphenyl pyrrol-1-yl)ethoxy]phenyl}-2-ethoxypropanoate;
(±) Ethyl 3-{4-[2-(5-methyl-2-furan-2-yl)pyrrol-1-yl)ethoxy]phenyl}-2-ethoxypropanoate;
(+) Ethyl 3-{4-[2-(5-methyl-2-furan-2-yl)pyrrol-1-yl)ethoxy]phenyl}-2-ethoxypropanoate;
(−) Ethyl 3-{4-[2-(5-methyl-2-furan-2-yl)pyrrol-1-yl)ethoxy]phenyl}-2-ethoxypropanoate;
(±) Ethyl 3-{4-[2-(5-methyl-2-(5-methyl furan-2-yl)pyrrol-1-yl)ethoxy]phenyl}-2-ethoxypropanoate;
(+) Ethyl 3-{4-[2-(5-methyl-2-(5-methyl furan-2-yl) pyrrol-1-yl)ethoxy]phenyl}-2-ethoxypropanoate;
(−) Ethyl 3-{4-[2-(5-methyl-2-(5-methyl furan-2-yl) pyrrol-1-yl)ethoxy]phenyl}-2-ethoxypropanoate;
(±) Ethyl 3-{4-[2-(5-methyl-2-(4-thiomethyl phenyl) pyrrol-1-yl)ethoxy]phenyl}-2-ethoxypropanoate;
(+) Ethyl 3-{4-[2-(5-methyl-2-(4-thiomethyl phenyl) pyrrol-1-yl)ethoxy]phenyl}-2-ethoxypropanoate;
(−) Ethyl 3-{4-[2-(5-methyl-2-(4-thiomethyl phenyl) pyrrol-1-yl)ethoxy]phenyl}-2-ethoxypropanoate;

(±) Ethyl 3-{4-[2-(5-methyl-2-(4-cyanophenyl) pyrrol-1-yl) ethoxy]phenyl}-2-ethoxypropanoate;
(+) Ethyl 3-{4-[2-(5-methyl-2-(4-cyanophenyl) pyrrol-1-yl) ethoxy]phenyl}-2-ethoxypropanoate;
(−) Ethyl 3-{4-[2-(5-methyl-2-(4-cyanophenyl) pyrrol-1-yl) ethoxy]phenyl}-2-ethoxypropanoate;
(±) Ethyl 3-{4-[2-(5-methyl-2-(4-phenoxyphenyl) pyrrol-1-yl)ethoxy]phenyl}-2-ethoxypropanoate;
(+) Ethyl 3-{4-[2-(5-methyl-2-(4-phenoxyphenyl) pyrrol-1-yl)ethoxy]phenyl}-2-ethoxypropanoate;
(−) Ethyl 3-{4-[2-(5-methyl-2-(4-phenoxyphenyl) pyrrol-1-yl)ethoxy]phenyl}-2-ethoxypropanoate;
(±) Ethyl 3-{4-[2-(5-methyl-1'-(toluene-4-sulfonyl)-1'H-[2,2']bipyrrolyl-1-yl])ethoxy]phenyl}-2-ethoxypropanoate;
(+) Ethyl 3-{4-[2-(5-methyl-1'-(toluene-4-sulfonyl)-1'H-[2,2']bipyrrolyl-1-yl])ethoxy]phenyl}-2-ethoxypropanoate;
(−) Ethyl 3-{4-[2-(5-methyl-1'-(toluene-4-sulfonyl)-1'H-[2,2']bipyrrolyl-1-yl])ethoxy]phenyl}-2-ethoxypropanoate;
(±) Ethyl 3-{4-[2-(5-methyl-2-(3,4-dimethoxyphenyl) pyrrol-1-yl)ethoxy]phenyl}-2-ethoxypropanoate;
(+) Ethyl 3-{4-[2-(5-methyl-2-(3,4-dimethoxyphenyl) pyrrol-1-yl)ethoxy]phenyl}-2-ethoxypropanoate;
(−) Ethyl 3-{4-[2-(5-methyl-2-(3,4-dimethoxyphenyl) pyrrol-1-yl)ethoxy]phenyl}-2-ethoxypropanoate;
(±) Ethyl 3-{4-[2-(5-methyl-2-(4-methanesulfinyl-phenyl) pyrrol-1-yl)ethoxy]phenyl}-2-ethoxypropanoate;
(+) Ethyl 3-{4-[2-(5-methyl-2-(4-methanesulfinyl-phenyl) pyrrol-1-yl)ethoxy]phenyl}-2-ethoxypropanoate;
(−) Ethyl 3-{4-[2-(5-methyl-2-(4-methanesulfinyl-phenyl) pyrrol-1-yl)ethoxy]phenyl}-2-ethoxypropanoate;
(±) Ethyl 3-{4-[2-(5-methyl-2-(4-acetylamino-phenyl) pyrrol-1-yl)ethoxy]phenyl}-2-ethoxypropanoate;
(+) Ethyl 3-{4-[2-(5-methyl-2-(4-acetylamino-phenyl) pyrrol-1-yl)ethoxy]phenyl}-2-ethoxypropanoate;
(−) Ethyl 3-{4-[2-(5-methyl-2-(4-acetylamino-phenyl) pyrrol-1-yl)ethoxy]phenyl}-2-ethoxypropanoate;
(±) Ethyl 3-{4-[2-(5-methyl-2-(4-(2-piperidin-1-yl-ethoxy)-phenyl) pyrrol-1-yl)ethoxy]phenyl}-2-ethoxypropanoate;
(+) Ethyl 3-{4-[2-(5-methyl-2-(4-(2-piperidin-1-yl-ethoxy)-phenyl) pyrrol-1-yl)ethoxy]phenyl}-2-ethoxypropanoate;
(−) Ethyl 3-{4-[2-(5-methyl-2-(4-(2-piperidin-1-yl-ethoxy)-phenyl) pyrrol-1-yl)ethoxy]phenyl}-2-ethoxypropanoate;
(±) Ethyl 3-{4-[2-(5-methyl-2-(4-vinyloxy-phenyl) pyrrol-1-yl)ethoxy]phenyl}-2-ethoxypropanoate;
(+) Ethyl 3-{4-[2-(5-methyl-2-(4-vinyloxy-phenyl) pyrrol-1-yl)ethoxy]phenyl}-2-ethoxypropanoate;
(−) Ethyl 3-{4-[2-(5-methyl-2-(4-vinyloxy-phenyl) pyrrol-1-yl)ethoxy]phenyl}-2-ethoxypropanoate;
(±) Ethyl 3-{4-[2-(5-methyl-2-(4-phenylsulfanyl-phenyl) pyrrol-1-yl)ethoxy]phenyl}-2-ethoxypropanoate;
(+) Ethyl 3-{4-[2-(5-methyl-2-(4-phenylsulfanyl-phenyl) pyrrol-1-yl)ethoxy]phenyl}-2-ethoxypropanoate;
(−) Ethyl 3-{4-[2-(5-methyl-2-(4-phenylsulfanyl-phenyl) pyrrol-1-yl)ethoxy]phenyl}-2-ethoxypropanoate;
(±) Ethyl 3-{4-[2-(5-methyl-2-(4-phenylsulfinyl-phenyl) pyrrol-1-yl)ethoxy]phenyl}-2-ethoxypropanoate;
(+) Ethyl 3-{4-[2-(5-methyl-2-(4-phenylsulfinyl-phenyl) pyrrol-1-yl)ethoxy]phenyl}-2-ethoxypropanoate;
(−) Ethyl 3-{4-[2-(5-methyl-2-(4-phenylsulfinyl-phenyl) pyrrol-1-yl)ethoxy]phenyl}-2-ethoxypropanoate;
(±) Ethyl 3-{4-[2-(5-methyl-2-(4-methanesulfonyl-phenyl) pyrrol-1-yl)ethoxy]phenyl}-2-ethoxypropanoate;
(+) Ethyl 3-{4-[2-(5-methyl-2-(4-methanesulfonyl-phenyl) pyrrol-1-yl)ethoxy]phenyl}-2-ethoxypropanoate;
(−) Ethyl 3-{4-[2-(5-methyl-2-(4-methanesulfonyl-phenyl) pyrrol-1-yl)ethoxy]phenyl}-2-ethoxypropanoate;
(±) Ethyl 3-{4-[2-(5-methyl-2-(4-cyclohexylmethoxy-phenyl) pyrrol-1-yl)ethoxy]phenyl}-2-ethoxypropanoate;
(+) Ethyl 3-{4-[2-(5-methyl-2-(4-cyclohexylmethoxy-phenyl) pyrrol-1-yl)ethoxy]phenyl}-2-ethoxypropanoate;
(−) Ethyl 3-{4-[2-(5-methyl-2-(4-cyclohexylmethoxy-phenyl) pyrrol-1-yl)ethoxy]phenyl}-2-ethoxypropanoate;
(±) Ethyl 3-{4-[2-(2-benzoyl pyrrol-1-yl)ethoxy]phenyl}-2-ethoxypropanoate;
(+) Ethyl 3-{4-[2-(2-benzoyl pyrrol-1-yl)ethoxy]phenyl}-2-ethoxypropanoate;
(−) Ethyl 3-{4-[2-(2-benzoyl pyrrol-1-yl)ethoxy]phenyl}-2-ethoxypropanoate;
(±) Ethyl 3-{4-[2-(5-methyl-2-cyclopropyl pyrrol-1-yl) ethoxy]phenyl}-2-ethoxypropanoate;
(+) Ethyl 3-{4-[2-(5-methyl-2-cyclopropyl pyrrol-1-yl) ethoxy]phenyl}-2-ethoxypropanoate;
(−) Ethyl 3-{4-[2-(5-methyl-2-cyclopropyl pyrrol-1-yl) ethoxy]phenyl}-2-ethoxypropanoate;
(±) Ethyl 3-{4-[2-(5-methyl-2-(benzofuran-2-yl) pyrrol-1-yl)ethoxy]phenyl}-2-ethoxypropanoate;
(+) Ethyl 3-{4-[2-(5-methyl-2-(benzofuran-2-yl) pyrrol-1-yl)ethoxy]phenyl}-2-ethoxypropanoate;
(−) Ethyl 3-{4-[2-(5-methyl-2-(benzofuran-2-yl) pyrrol-1-yl)ethoxy]phenyl}-2-ethoxypropanoate;
(±) Ethyl 3-{4-[2-(3-carboxymethyl-2-methyl-5-phenyl pyrrol-1-yl)ethoxy]phenyl}-2-ethoxypropanoate;
(+) Ethyl 3-{4-[2-(3-carboxymethyl-2-methyl-5-phenyl pyrrol-1-yl)ethoxy]phenyl}-2-ethoxypropanoate;
(−) Ethyl 3-{4-[2-(3-carboxymethyl-2-methyl-5-phenyl pyrrol-1-yl)ethoxy]phenyl}-2-ethoxypropanoate;
(±) Ethyl-3-{4-[2-(5-methyl-2-(Benzo[1,3]dioxol-5-yl-)pyrrol-1-yl)ethoxy]phenyl}-2-ethoxypropanoate;
(+) Ethyl-3-{4-[2-(5-methyl-2-(Benzo[1,3]dioxol-5-yl-)pyrrol-1-yl)ethoxy]phenyl}-2-ethoxypropanoate;
(−) Ethyl-3-{4-[2-(5-methyl-2-(Benzo[1,3]dioxol-5-yl-)pyrrol-1-yl)ethoxy]phenyl}-2-ethoxypropanoate;
(±) Ethyl-3-{4-[2-(5-methyl-2-(naphthalen-1-yl)-pyrrol-1-yl)ethoxy]phenyl}-2-ethoxypropanoate;
(+) Ethyl-3-{4-[2-(5-methyl-2-(naphthalen-1-yl)-pyrrol-1-yl)ethoxy]phenyl}-2-ethoxypropanoate;
(−) Ethyl-3-{4-[2-(5-methyl-2-(naphthalen-1-yl)-pyrrol-1-yl)ethoxy]phenyl}-2-ethoxypropanoate;
(±) Ethyl-3-{4-[2-(5-methyl-3-benzyloxy-phenyl-pyrrol-1-yl)ethoxy]phenyl}-2-ethoxypropanoate;
(+) Ethyl-3-{4-[2-(5-methyl-3-benzyloxy-phenyl-pyrrol-1-yl)ethoxy]phenyl}-2-ethoxypropanoate;
(−) Ethyl-3-{4-[2-(5-methyl-3-benzyloxy-phenyl-pyrrol-1-yl)ethoxy]phenyl}-2-ethoxypropanoate;
(±) Ethyl-3-{4-[2-(5-methyl-2-(5-bromo-thiophen-2-yl)-pyrrol-1-yl)ethoxy]phenyl}-2-ethoxypropanoate;
(+) Ethyl-3-{4-[2-(5-methyl-2-(5-bromo-thiophen-2-yl)-pyrrol-1-yl)ethoxy]phenyl}-2-ethoxypropanoate;
(−) Ethyl-3-{4-[2-(5-methyl-2-(5-bromo-thiophen-2-yl)-pyrrol-1-yl)ethoxy]phenyl}-2-ethoxypropanoate;
(±) Ethyl-3-{4-[2-(5-methyl-2-(4-isopropoxy-phenyl)-pyrrol-1-yl)ethoxy]phenyl}-2-ethoxypropanoate;
(+) Ethyl-3-{4-[2-(5-methyl-2-(4-isopropoxy-phenyl)-pyrrol-1-yl)ethoxy]phenyl}-2-ethoxypropanoate;
(−) Ethyl-3-{4-[2-(5-methyl-2-(4-isopropoxy-phenyl)-pyrrol-1-yl)ethoxy]phenyl}-2-ethoxypropanoate;
(±) Ethyl-3-{4-[2-(3,5-dimethyl-2-phenyl-pyrrol-1-yl) ethoxy]phenyl}-2-ethoxypropanoate;
(+) Ethyl-3-{4-[2-(3,5-dimethyl-2-phenyl-pyrrol-1-yl) ethoxy]phenyl}-2-ethoxypropanoate;
(−) Ethyl-3-{4-[2-(3,5-dimethyl-2-phenyl-pyrrol-1-yl) ethoxy]phenyl}-2-ethoxypropanoate;

(±) Ethyl-3-{4-[2-(5-methyl-2-(thiophen-2-yl)-pyrrol-1-yl) ethoxy]phenyl}-2-ethoxypropanoate;
(+) Ethyl-3-{4-[2-(5-methyl-2-(thiophen-2-yl)-pyrrol-1-yl) ethoxy]phenyl}-2-ethoxypropanoate;
(−) Ethyl-3-{4-[2-(5-methyl-2-(thiophen-2-yl)-pyrrol-1-yl) ethoxy]phenyl}-2-ethoxypropanoate;
(±) Ethyl-3-{4-[2-(5-methyl-2-(4-benzyloxy-phenyl)-pyrrol-1-yl)ethoxy]phenyl}-2-ethoxypropanoate;
(+) Ethyl-3-{4-[2-(5-methyl-2-(4-benzyloxy-phenyl)-pyrrol-1-yl)ethoxy]phenyl}-2-ethoxypropanoate;
(−) Ethyl-3-{4-[2-(5-methyl-2-(4-benzyloxy-phenyl)-pyrrol-1-yl)ethoxy]phenyl}-2-ethoxypropanoate;
(±) Ethyl-3-{4-[2-(5-methyl-2-(4-hydroxy-phenyl)-pyrrol-1-yl)ethoxy]phenyl}-2-ethoxypropanoate;
(+) Ethyl-3-{4-[2-(5-methyl-2-(4-hydroxy-phenyl)-pyrrol-1-yl)ethoxy]phenyl}-2-ethoxypropanoate;
(−) Ethyl-3-{4-[2-(5-methyl-2-(4-hydroxy-phenyl)-pyrrol-1-yl)ethoxy]phenyl}-2-ethoxypropanoate;
(±) Ethyl-3-{4-[2-(2-phenyl-pyrrol-1-yl)ethoxy]phenyl}-2-ethoxypropanoate;
(+) Ethyl-3-{4-[2-(2-phenyl-pyrrol-1-yl)ethoxy]phenyl}-2-ethoxypropanoate;
(−) Ethyl-3-{4-[2-(2-phenyl-pyrrol-1-yl)ethoxy]phenyl}-2-ethoxypropanoate;
(±) Ethyl-3-{4-[2-(5-methyl-2-(5-chloro-thiophen-2-yl)-pyrrol-1-yl)ethoxy]phenyl}-2-ethoxypropanoate;
(+) Ethyl-3-{4-[2-(5-methyl-2-(5-chloro-thiophen-2-yl)-pyrrol-1-yl)ethoxy]phenyl}-2-ethoxypropanoate;
(−) Ethyl-3-{4-[2-(5-methyl-2-(5-chloro-thiophen-2-yl)-pyrrol-1-yl)ethoxy]phenyl}-2-ethoxypropanoate;
(±) Ethyl-3-{4-[2-(5-methyl-2-(4-ethoxy-phenyl)-pyrrol-1-yl)ethoxy]phenyl}-2-ethoxypropanoate;
(+) Ethyl-3-{4-[2-(5-methyl-2-(4-ethoxy-phenyl)-pyrrol-1-yl)ethoxy]phenyl}-2-ethoxypropanoate;
(−) Ethyl-3-{4-[2-(5-methyl-2-(4-ethoxy-phenyl)-pyrrol-1-yl)ethoxy]phenyl}-2-ethoxypropanoate;
(±) Ethyl-3-{4-[2-(5-methyl-2-(5-methyl-thiophen-2-yl)-pyrrol-1-yl)ethoxy]phenyl}-2-ethoxypropanoate;
(+) Ethyl-3-{4-[2-(5-methyl-2-(5-methyl-thiophen-2-yl)-pyrrol-1-yl)ethoxy]phenyl}-2-ethoxypropanoate;
(−) Ethyl-3-{4-[2-(5-methyl-2-(5-methyl-thiophen-2-yl)-pyrrol-1-yl)ethoxy]phenyl}-2-ethoxypropanoate;
(±) Ethyl-3-{4-[2-(2,3-dimethyl-5-phenyl)-pyrrol-1-yl) ethoxy]phenyl}-2-ethoxypropanoate;
(+) Ethyl-3-{4-[2-(2,3-dimethyl-5-phenyl)-pyrrol-1-yl) ethoxy]phenyl}-2-ethoxypropanoate;
(−) Ethyl-3-{4-[2-(2,3-dimethyl-5-phenyl)-pyrrol-1-yl) ethoxy]phenyl}-2-ethoxypropanoate;
(±) Ethyl-3-{4-[2-(5-methyl-2-(quinolin-2-yl-)-pyrrol-1-yl) ethoxy]phenyl}-2-ethoxypropanoate;
(+) Ethyl-3-{4-[2-(5-methyl-2-(quinolin-2-yl-)-pyrrol-1-yl) ethoxy]phenyl}-2-ethoxypropanoate;
(−) Ethyl-3-{4-[2-(5-methyl-2-(quinolin-2-yl-)-pyrrol-1-yl) ethoxy]phenyl}-2-ethoxypropanoate;
(±) Ethyl-3-{4-[2-(5-methyl-2-(pyridin-4-yl)-pyrrol-1-yl) ethoxy]phenyl}-2-ethoxypropanoate;
(+) Ethyl-3-{4-[2-(5-methyl-2-(pyridin-4-yl)-pyrrol-1-yl) ethoxy]phenyl}-2-ethoxypropanoate;
(−) Ethyl-3-{4-[2-(5-methyl-2-(pyridin-4-yl)-pyrrol-1-yl) ethoxy]phenyl}-2-ethoxypropanoate;
(±) Ethyl-3-{4-[2-(5-methyl-2-(pyridin-2-yl)-pyrrol-1-yl) ethoxy]phenyl}-2-ethoxypropanoate;
(+) Ethyl-3-{4-[2-(5-methyl-2-(pyridin-2-yl)-pyrrol-1-yl) ethoxy]phenyl}-2-ethoxypropanoate;
(−) Ethyl-3-{4-[2-(5-methyl-2-(pyridin-2-yl)-pyrrol-1-yl) ethoxy]phenyl}-2-ethoxypropanoate;
(±) Ethyl-3-{4-[2-(5-methyl-2-(pyridin-3-yl)-pyrrol-1-yl) ethoxy]phenyl}-2-ethoxypropanoate;
(+) Ethyl-3-{4-[2-(5-methyl-2-(pyridin-3-yl)-pyrrol-1-yl) ethoxy]phenyl}-2-ethoxypropanoate;
(−) Ethyl-3-{4-[2-(5-methyl-2-(pyridin-3-yl)-pyrrol-1-yl) ethoxy]phenyl}-2-ethoxypropanoate;
Ethyl (E/Z) 3-{4-[2-(5-methyl-2-phenyl-pyrrol-1-yl)ethoxy] phenyl}-2-ethoxyprop-2-enenoate;
Ethyl (Z) 3-{4-[2-(5-methyl-2-phenyl-pyrrol-1-yl)ethoxy] phenyl}-2-ethoxyprop-2-enenoate;
Ethyl (E) 3-{4-[2-(5-methyl-2-phenyl-pyrrol-1-yl)ethoxy] phenyl}-2-ethoxyprop-2-enenoate;
[(2R)-N(1S)]-2-Ethoxy-3-{4-[2-(5-methyl-2-phenylpyrrol-1-yl)ethoxy]phenyl}-N-(2-hydroxy-1phenylethyl)propanamide
[(2S)-N(1S)]-2-Ethoxy-3-{4-[2-(5-methyl-2-phenylpyrrol-1-yl)ethoxy]phenyl}-N-(2-hydroxy-1-phenylethyl) propanamide
(±) 3-{4-[2-(pyrrol-1-yl)ethoxy]phenyl}-2-ethoxypropanoic acid and its pharmaceutically acceptable salts
(+) 3-{4-[2-(pyrrol-1-yl)ethoxy]phenyl}-2-ethoxypropanoic acid and its pharmaceutically acceptable salts
(−) 3-{4-[2-(pyrrol-1-yl)ethoxy]phenyl}-2-ethoxypropanoic acid and its pharmaceutically acceptable salts
(±) 3-{4-[2-(2,5-dimethylpyrrol-1-yl)ethoxy]phenyl}-2-ethoxypropanoic acid and its pharmaceutically acceptable salts
(+) 3-{4-[2-(2,5-dimethylpyrrol-1-yl)ethoxy]phenyl}-2-ethoxypropanoic acid and its pharmaceutically acceptable salts
(−) 3-{4-[2-(2,5-dimethylpyrrol-1-yl)ethoxy]phenyl}-2-ethoxypropanoic acid and its pharmaceutically acceptable salts
(±) 3-{4-[2-(2,5-diisopropyl-3-phenylpyrrol-1-yl)ethoxy] phenyl}-2-ethoxypropanoic acid and its pharmaceutically acceptable salts
(+) 3-{4-[2-(2,5-diisopropyl-3-phenylpyrrol-1-yl)ethoxy] phenyl}-2-ethoxypropanoic acid and its pharmaceutically acceptable salts
(−) 3-{4-[2-(2,5-diisopropyl-3-phenylpyrrol-1-yl)ethoxy] phenyl}-2-ethoxypropanoic acid and its pharmaceutically acceptable salts
(±) 3-(4-{2-[2-isopropyl-5-(4-methoxyphenyl)pyrrol-1-yl] ethoxy}phenyl)-2-ethoxypropanoic acid and its pharmaceutically acceptable salts
(+) 3-(4-{2-[2-isopropyl-5-(4-methoxyphenyl)pyrrol-1-yl] ethoxy}phenyl)-2-ethoxypropanoic acid and its pharmaceutically acceptable salts
(−) 3-(4-{2-[2-isopropyl-5-(4-methoxyphenyl)pyrrol-1-yl] ethoxy}phenyl)-2-ethoxypropanoic acid and its pharmaceutically acceptable salts
(±) 3-(4-{2-[2-(4-fluorophenyl)-5-isopropylpyrrol-1-yl] ethoxy}phenyl)-2-ethoxypropanoic acid and its pharmaceutically acceptable salts
(+) 3-(4-{2-[2-(4-fluorophenyl)-5-isopropylpyrrol-1-yl] ethoxy}phenyl)-2-ethoxypropanoic acid and its pharmaceutically acceptable salts
(−) 3-(4-{2-[2-(4-fluorophenyl)-5-isopropylpyrrol-1-yl] ethoxy}phenyl)-2-ethoxypropanoic acid and its pharmaceutically acceptable salts
(±) 3-(4-(2-[2-(4-fluorophenyl)-5-isopropyl-3-phenylpyrrol-1-yl]ethoxy)phenyl)-2-ethoxypropanoic acid and its pharmaceutically acceptable salts
(+) 3-(4-(2-[2-(4-fluorophenyl)-5-isopropyl-3-phenylpyrrol-1-yl]ethoxy)phenyl)-2-ethoxypropanoic acid and its pharmaceutically acceptable salts (−) 3-(4-(2-[2-(4-fluorophenyl)-5-isopropyl-3-phenylpyrrol-1-yl]ethoxy)phenyl)-2-ethoxypropanoic acid and its pharmaceutically acceptable salts (±) 3-(4-[2-[2-(4-fluorophenyl)-5-phenylpyrrol-1-yl]ethoxy)phenyl)-2-ethoxypropanoic acid and its pharmaceutically acceptable salts (+) 3-(4-{2-[2-(4-fluorophenyl)-5-phenylpyrrol-1-yl]ethoxy}phenyl)-2-ethoxypropanoic acid and its pharmaceutically acceptable salts (−) 3-(4-{2-[2-(4-fluorophenyl)-5-phenylpyrrol-1-yl]ethoxy}phenyl)-2-ethoxypropanoic acid and its pharmaceutically acceptable salts (±) 3-[4-[2-(2-phenyl-3-carboxy-5-(4-fluorophenyl)pyrrol-1-yl)ethoxy]phenyl]-2-ethoxypropanoic acid and its pharmaceutically acceptable salts (+) 3-[4-[2-(2-phenyl-3-carboxy-5-(4-fluorophenyl)pyrrol-1-yl)ethoxy]phenyl]-2-ethoxypropanoic acid and its pharmaceutically acceptable salts (−) 3-[4-[2-(2-phenyl-3-carboxy-5-(4-fluorophenyl)pyrrol-1-yl)ethoxy]phenyl]-2-ethoxypropanoic acid and its pharmaceutically acceptable salts (±) 3-(4-{2-[2-(4-fluorophenyl)-5-isopropyl-3-phenyl-4-phenylcarbamoylpyrrol-1-yl]ethoxy}phenyl)-2-ethoxypropanoic acid and its pharmaceutically acceptable salt thereof (+) 3-(4-{2-[2-(4-fluorophenyl)-5-isopropyl-3-phenyl-4-phenylcarbamoylpyrrol-1-yl]ethoxy}phenyl)-2-ethoxypropanoic acid and its pharmaceutically acceptable salts (−) 3-(4-{2-[2-(4-fluorophenyl)-5-isopropyl-3-phenyl-4-phenylcarbamoylpyrrol-1-yl]ethoxy}phenyl)-2-ethoxypropanoic acid and its pharmaceutically acceptable salts (±) 3-(4-{3-[2-(4-fluorophenyl)-5-isopropyl-3-phenyl-4-phenylcarbamoylpyrrol-1-yl]propoxy}phenyl)-2-ethoxypropanoic acid and its pharmaceutically acceptable salts (+) 3-(4-{3-[2-(4-fluorophenyl)-5-isopropyl-3-phenyl-4-phenylcarbamoylpyrrol-1-yl]propoxy}phenyl)-2-ethoxypropanoic acid and its pharmaceutically acceptable salts (−) 3-(4-{3-[2-(4-fluorophenyl)-5-isopropyl-3-phenyl-4-phenylcarbamoylpyrrol-1-yl]propoxy}phenyl)-2ethoxypropanoic acid and its pharmaceutically acceptable salts.

(±) 3-{4-[2-(2-isopropyl-5-methylpyrrol-1-yl)ethoxy]phenyl}-2-ethoxypropanoic acid and its pharmaceutically acceptable salts (+) 3-{4-[2-(2-isopropyl-5-methylpyrrol-1-yl)ethoxy]phenyl}-2-ethoxypropanoic acid and its pharmaceutically acceptable salts (−) 3-{4-[2-(2-isopropyl-5-methylpyrrol-1-yl)ethoxy]phenyl}-2-ethoxypropanoic acid and its pharmaceutically acceptable salts (±) 3-{4-[2-(2,4-dimethylpyrrol-1-yl)ethoxy]phenyl}-2-ethoxypropanoic acid and its pharmaceutically acceptable salts;

(+) 3-{4-[2-(2,4-dimethylpyrrol-1-yl)ethoxy]phenyl}-2-ethoxypropanoic acid and its pharmaceutically acceptable salts;

(−) 3-{4-[2-(2,4-dimethylpyrrol-1-yl)ethoxy]phenyl}-2-ethoxypropanoic acid and its pharmaceutically acceptable salts;

(±) 3-{4-[2-(2-ethylpyrrol-1-yl)ethoxy]phenyl}-2-ethoxypropanoic acid and its pharmaceutically acceptable salts;

(+) 3-{4-[2-(2-ethylpyrrol-1-yl)ethoxy]phenyl}-2-ethoxypropanoic acid and its pharmaceutically acceptable salts;

(−) 3-{4-[2-(2-ethylpyrrol-1-yl)ethoxy]phenyl}-2-ethoxypropanoic acid and its pharmaceutically acceptable salts;

(±) 3-{4-[2-(2-formylpyrrol-1-yl)ethoxy]phenyl}-2-ethoxypropanoic acid and its pharmaceutically acceptable salts;

(+) 3-{4-[2-(2-formylpyrrol-1-yl)ethoxy]phenyl}-2-ethoxypropanoic acid and its pharmaceutically acceptable salts;

(−) 3-{4-[2-(2-formylpyrrol-1-yl)ethoxy]phenyl}-2-ethoxypropanoic acid and its pharmaceutically acceptable salts;

(±) 3-{4-[2-(2-acetylpyrrol-1-yl)ethoxy]phenyl}-2-ethoxypropanoic acid and its pharmaceutically acceptable salts;

(+) 3-{4-[2-(2-acetylpyrrol-1-yl)ethoxy]phenyl}-2-ethoxypropanoic acid and its pharmaceutically acceptable salts;

(−) 3-{4-[2-(2-acetylpyrrol-1-yl)ethoxy]phenyl}-2-ethoxypropanoic acid and its pharmaceutically acceptable salts;

(±) 3-{4-[2-(2-ethyl-5-methylpyrrol-1-yl)ethoxy]phenyl}-2-ethoxypropanoic acid and its pharmaceutically acceptable salts;

(+) 3-{4-[2-(2-ethyl-5-methylpyrrol-1-yl)ethoxy]phenyl}-2-ethoxypropanoic acid and its pharmaceutically acceptable salts;

(−) 3-{4-[2-(2-ethyl-5-methylpyrrol-1-yl)ethoxy]phenyl}-2-ethoxypropanoic acid and its pharmaceutically acceptable salts;

(±) 3-{4-[2-(5-methyl-2-propylpyrrol-1-yl)ethoxy]phenyl}-2-ethoxypropanoic acid and its pharmaceutically acceptable salts;

(+) 3-{4-[2-(5-methyl-2-propylpyrrol-1-yl)ethoxy]phenyl}-2-ethoxypropanoic acid and its pharmaceutically acceptable salts;

(−) 3-{4-[2-(5-methyl-2-propylpyrrol-1-yl)ethoxy]phenyl}-2-ethoxypropanoic acid and its pharmaceutically acceptable salts;

(±) 3-{4-[2-(5-methyl-2-n-butylpyrrol-1-yl)ethoxy]phenyl}-2-ethoxypropanoic acid and its pharmaceutically acceptable salts;

(+) 3-{4-[2-(5-methyl-2-n-butylpyrrol-1-yl)ethoxy]phenyl}-2-ethoxypropanoic acid and its pharmaceutically acceptable salts;

(−) 3-{4-[2-(5-methyl-2-n-butylpyrrol-1-yl)ethoxy]phenyl}-2-ethoxypropanoic acid and its pharmaceutically acceptable salts;

(±) 3-{4-[2-(5-methyl-2-phenylpyrrol-1-yl)ethoxy]phenyl}-2-ethoxypropanoic acid and its pharmaceutically acceptable salts;

(+) 3-{4-[2-(5-methyl-2-phenylpyrrol-1-yl)ethoxy]phenyl}-2-ethoxypropanoic acid and its pharmaceutically acceptable salts;

(−) 3-{4-[2-(5-methyl-2-phenylpyrrol-1-yl)ethoxy]phenyl}-2-ethoxypropanoic acid and its pharmaceutically acceptable salts;

(±) 3-{4-[2-(5-methyl-2-phenylpyrrol-1-yl)ethoxy]phenyl}-2-methoxypropanoic acid and its pharmaceutically acceptable salts;

(+) 3-{4-[2-(5-methyl-2-phenylpyrrol-1-yl)ethoxy]phenyl}-2-methoxypropanoic acid and its pharmaceutically acceptable salts;

(−) 3-{4-[2-(5-methyl-2-phenylpyrrol-1-yl)ethoxy]phenyl}-2-methoxypropanoic acid and its pharmaceutically acceptable salts;

(±) 3-{4-[2-(5-methyl-2-(4-methylphenyl)pyrrol-1-yl)ethoxy]phenyl}-2-propoxypropanoic acid and its pharmaceutically acceptable salts;

(+) 3-{4-[2-(5-methyl-2-(4-methylphenyl)pyrrol-1-yl)ethoxy]phenyl}-2-propoxypropanoic acid and its pharmaceutically acceptable salts;

(−) 3- {4-[2-(5-methyl-2-(4-methylphenyl)pyrrol-1-yl)ethoxy]phenyl}-2-propoxypropanoic acid and its pharmaceutically acceptable salts;

(±) 3-{4-[2-(5-methyl-3-phenylpyrrol-1-yl)ethoxy]phenyl}-2-ethoxypropanoic acid and its pharmaceutically acceptable salts;

(+) 3-{4-[2-(5-methyl-3-phenylpyrrol-1-yl)ethoxy]phenyl}-2-ethoxypropanoic acid and its pharmaceutically acceptable salts;

(−) 3-{4-[2-(5-methyl-3-phenylpyrrol-1-yl)ethoxy]phenyl}-2-ethoxypropanoic acid and its pharmaceutically acceptable salts;

(±) 3-{4-[2-(5-methyl-2-(4-methylphenyl)pyrrol-1-yl)ethoxy]phenyl}-2-ethoxypropanoic acid and its pharmaceutically acceptable salts;

(+) 3-{4-[2-(5-methyl-2-(4-methylphenyl)pyrrol-1-yl)ethoxy]phenyl}-2-ethoxypropanoic acid and its pharmaceutically acceptable salts;

(−) 3-{4-[2-(5-methyl-2-(4-methylphenyl)pyrrol-1-yl)ethoxy]phenyl}-2-ethoxypropanoic acid and its pharmaceutically acceptable salts;

(±) 3-{4-[2-(5-methyl-2-(3-methylphenyl)pyrrol-1-yl)ethoxy]phenyl}-2-ethoxypropanoic acid and its pharmaceutically acceptable salts;

(+) 3-{4-[2-(5-methyl-2-(3-methylphenyl)pyrrol-1-yl)ethoxy]phenyl}-2-ethoxypropanoic acid and its pharmaceutically acceptable salts;

(−) 3-{4-[2-(5-methyl-2-(3-methylphenyl)pyrrol-1-yl)ethoxy]phenyl}-2-ethoxypropanoic acid and its pharmaceutically acceptable salts;

(±) 3-{4-[2-(5-methyl-2-(2-methylphenyl)pyrrol-1-yl)ethoxy]phenyl}-2-ethoxypropanoic acid and its pharmaceutically acceptable salts;

(+) 3-{4-[2-(5-methyl-2-(2-methylphenyl)pyrrol-1-yl)ethoxy]phenyl}-2-ethoxypropanoic acid and its pharmaceutically acceptable salts;

(−) 3-{4-[2-(5-methyl-2-(2-methylphenyl)pyrrol-1-yl)ethoxy]phenyl}-2-ethoxypropanoic acid and its pharmaceutically acceptable salts;

(±) 3-{4-[2-(5-methyl-2-(4-methoxyphenyl)pyrrol-1-yl)ethoxy]phenyl}-2-ethoxypropanoic acid and its pharmaceutically acceptable salts;

(+) 3-{4-[2-(5-methyl-2-(4-methoxyphenyl)pyrrol-1-yl)ethoxy]phenyl}-2-ethoxypropanoic acid and its pharmaceutically acceptable salts;

(−) 3-{4-[2-(5-methyl-2-(4-methoxyphenyl)pyrrol-1-yl)ethoxy]phenyl}-2-ethoxypropanoic acid and its pharmaceutically acceptable salts;

(±) 3-{4-[2-(5-methyl-2-(4-bromophenyl)pyrrol-1-yl)ethoxy]phenyl}-2-ethoxypropanoic acid and its pharmaceutically acceptable salts;

(+) 3-{4-[2-(5-methyl-2-(4-bromophenyl)pyrrol-1-yl)ethoxy]phenyl}-2-ethoxypropanoic acid and its pharmaceutically acceptable salts;

(−) 3-{4-[2-(5-methyl-2-(4-bromophenyl)pyrrol-1-yl)ethoxy]phenyl}-2-ethoxypropanoic acid and its pharmaceutically acceptable salts;

(±) 3-{4-[2-(5-methyl-2-(4-fluorophenyl)pyrrol-1-yl)ethoxy]phenyl}-2-ethoxypropanoic acid and its pharmaceutically acceptable salts;

(+) 3-{4-[2-(5-methyl-2-(4-fluorophenyl)pyrrol-1-yl)ethoxy]phenyl}-2-ethoxypropanoic acid and its pharmaceutically acceptable salts;

(−) 3-{4-[2-(5-methyl-2-(4-fluorophenyl)pyrrol-1-yl)ethoxy]phenyl}-2-ethoxypropanoic acid and its pharmaceutically acceptable salts;

(±) 3-{4-[2-(5-methyl-2-(4-chlorophenyl)pyrrol-1-yl)ethoxy]phenyl}-2-ethoxypropanoic acid and its pharmaceutically acceptable salts;

(+) 3-{4-[2-(5-methyl-2-(4-chlorophenyl)pyrrol-1-yl)ethoxy]phenyl}-2-ethoxypropanoic acid and its pharmaceutically acceptable salts;

(−) 3-{4-[2-(5-methyl-2-(4-chlorophenyl)pyrrol-1-yl)ethoxy]phenyl}-2-ethoxypropanoic acid and its pharmaceutically acceptable salts;

(±) 3-{4-[2-(4-methyl-2-phenylpyrrol-1-yl)ethoxy]phenyl}-2-ethoxypropanoic acid and its pharmaceutically acceptable salts;

(+) 3-{4-[2-(4-methyl-2-phenylpyrrol-1-yl)ethoxy]phenyl}-2-ethoxypropanoic acid and its pharmaceutically acceptable salts;

(−) 3-{4-[2-(4-methyl-2-phenylpyrrol-1-yl)ethoxy]phenyl}-2-ethoxypropanoic acid and its pharmaceutically acceptable salts;

(±) 3-{4-[2-(5-methyl-2,3-diphenylpyrrol-1-yl)ethoxy]phenyl}-2-ethoxypropanoic acid and its pharmaceutically acceptable salts;

(+) 3-{4-[2-(5-methyl-2,3-diphenylpyrrol-1-yl)ethoxy]phenyl}-2-ethoxypropanoic acid and its pharmaceutically acceptable salts;

(−) 3-{4-[2-(5-methyl-2,3-diphenylpyrrol-1-yl)ethoxy]phenyl}-2-ethoxypropanoic acid and its pharmaceutically acceptable salts;

(±) 3-{4-[2-(2,5-diisopropylpyrrol-1-yl)ethoxy]phenyl}-2-ethoxypropanoic acid and its pharmaceutically acceptable salts;

(+) 3-{4-[2-(2,5-diisopropylpyrrol-1-yl)ethoxy]phenyl}-2-ethoxypropanoic acid and its pharmaceutically acceptable salts;

(−) 3-{4-[2-(2,5-diisopropylpyrrol-1-yl)ethoxy]phenyl}-2-ethoxypropanoic acid and its pharmaceutically acceptable salts;

(−) 3-{4-[2-(5-isopropyl-2-phenylpyrrol-1-yl)ethoxy]phenyl}-2-ethoxypropanoic acid and its pharmaceutically acceptable salts;

(±) 3-(4-{2-[2-(4-fluorophenyl)-5-isopropyl-4-phenylcarbamoylpyrrol-1-yl]ethoxy}phenyl)-2-ethoxypropanoic acid and its pharmaceutically acceptable salts;

(+) 3-(4-{2-[2-(4-fluorophenyl)-5-isopropyl-4-phenylcarbamoylpyrrol-1-yl]ethoxy}phenyl)-2-ethoxypropanoic acid and its pharmaceutically acceptable salts;

(−) 3-(4-{2-[2-(4-fluorophenyl)-5-isopropyl-4-phenylcarbamoylpyrrol-1-yl]ethoxy}phenyl)-2-ethoxypropanoic acid and its pharmaceutically acceptable salts;

(±) 3-{4-[2-(2-methylthiopyrrol-1-yl)ethoxy]phenyl}-2-ethoxypropanoic acid and its pharmaceutically acceptable salts;

(+) 3-{4-[2-(2-methylthiopyrrol-1-yl)ethoxy]phenyl}-2-ethoxypropanoic acid and its pharmaceutically acceptable salts;

(−) 3-{4-[2-(2-methylthiopyrrol-1-yl)ethoxy]phenyl}-2-ethoxypropanoic acid and its pharmaceutically acceptable salts;

(±) 3-{4-[2-(2,5-diethylpyrrol-1-yl)ethoxy]phenyl}-2-ethoxypropanoic acid and its pharmaceutically acceptable salts;

(+) 3-{4-[2-(2,5-diethylpyrrol-1-yl)ethoxy]phenyl}-2-ethoxypropanoic acid and its pharmaceutically acceptable salts;

(−) 3-{4-[2-(2,5-diethylpyrrol-1-yl)ethoxy]phenyl}-2-ethoxypropanoic acid and its pharmaceutically acceptable salts;

(±) 3-{4-[2-(5-ethyl-2-phenylpyrrol-1-yl)ethoxy]phenyl}-2-ethoxypropanoic acid and its pharmaceutically acceptable salts;

(+) 3-{4-[2-(5-ethyl-2-phenylpyrrol-1-yl)ethoxy]phenyl}-2-ethoxypropanoic acid and its pharmaceutically acceptable salts;

(−) 33-{4-[2-(5-ethyl-2-phenylpyrrol-1-yl)ethoxy]phenyl}-2-ethoxypropanoic acid and its pharmaceutically acceptable salts;

(±) 3-{4-[2-(5-ethyl-2-(2-phenylethyl) pyrrol-1-yl)ethoxy]phenyl}-2-ethoxypropanoic acid and its pharmaceutically acceptable salts;

(+) 3-{4-[2-(5-ethyl-2-(2-phenylethyl) pyrrol-1-yl)ethoxy]phenyl}-2-ethoxypropanoic acid and its pharmaceutically acceptable salts;.

(−) 3-{4-[2-(5-ethyl-2-(2-phenylethyl) pyrrol-1-yl)ethoxy]phenyl}-2-ethoxypropanoic acid and its pharmaceutically acceptable salts;

(±) 3-{4-[2-(5-methyl-2-(3-methoxyphenyl) pyrrol-1-yl)ethoxy]phenyl}-2-ethoxypropanoic acid and its pharmaceutically acceptable salts;

(+) 3-{4-[2-(5-methyl-2-(3-methoxyphenyl) pyrrol-1-yl)ethoxy]phenyl}-2-ethoxypropanoic acid and its pharmaceutically acceptable salts;

(−) 3-{4-[2-(5-methyl-2-(3-methoxyphenyl) pyrrol-1-yl)ethoxy]phenyl}-2-ethoxypropanoic acid and its pharmaceutically acceptable salts;

(±) 3-{4-[2-(5-methyl-2-cyclohexyl pyrrol-1-yl)ethoxy]phenyl}-2-ethoxypropanoic acid and its pharmaceutically acceptable salts;

(+) 3-{4-[2-(5-methyl-2-cyclohexyl pyrrol-1-yl)ethoxy]phenyl}-2-ethoxypropanoic acid and its pharmaceutically acceptable salts;

(−) 3-{4-[2-(5-methyl-2-cyclohexyl pyrrol-1-yl)ethoxy]phenyl}-2-ethoxypropanoic acid and its pharmaceutically acceptable salts;

(±) 3-{4-[2-(5-methyl-2-biphenyl pyrrol-1-yl)ethoxy]phenyl}-2-ethoxypropanoic acid and its pharmaceutically acceptable salts;

(+) 3-{4-[2-(5-methyl-2-biphenyl pyrrol-1-yl)ethoxy]phenyl}-2-ethoxypropanoic acid and its pharmaceutically acceptable salts;

(−) 3-{4-[2-(5-methyl-2-biphenyl pyrrol-1-yl)ethoxy]phenyl}-2-ethoxypropanoic acid and its pharmaceutically acceptable salts;

(±) 3-{4-[2-(5-methyl-2-(furan-2-yl) pyrrol-1-yl)ethoxy]phenyl}-2-ethoxypropanoic acid and its pharmaceutically acceptable salts;

(+) 3-{4-[2-(5-methyl-2-(furan-2-yl) pyrrol-1-yl)ethoxy]phenyl}-2-ethoxypropanoic acid and its pharmaceutically acceptable salts;

(−) 3-{4-[2-(5-methyl-2-(furan-2-yl) pyrrol-1-yl)ethoxy]phenyl}-2-ethoxypropanoic acid and its pharmaceutically acceptable salts;

(±) 3-{4-[2-(5-methyl-2-(5-methyl-furan-2-yl) pyrrol-1-yl)ethoxy]phenyl}-2-ethoxypropanoic acid and its pharmaceutically acceptable salts;

(+) 3-{4-[2-(5-methyl-2-(5-methyl-furan-2-yl) pyrrol-1-yl)ethoxy]phenyl}-2-ethoxypropanoic acid and its pharmaceutically acceptable salts;

(−) 3-{4-[2-(5-methyl-2-(5-methyl-furan-2-yl) pyrrol-1-yl)ethoxy]phenyl}-2-ethoxypropanoic acid and pharmaceutically acceptable salts;

(±) 3-{4-[2-(5-methyl-2-(4-thiomethyl phenyl) pyrrol-1-yl)ethoxy]phenyl}-2-ethoxypropanoic acid and its pharmaceutically acceptable salts;

(+) 3-{4-[2-(5-methyl-2-(4-thiomethyl phenyl) pyrrol-1-yl)ethoxy]phenyl}-2-ethoxypropanoic acid and its pharmaceutically acceptable salts;

(−) 3-{4-[2-(5-methyl-2-(4-thiomethyl phenyl) pyrrol-1-yl)ethoxy]phenyl}-2-ethoxypropanoic acid and its pharmaceutically acceptable salts;

(±) 3-{4-[2-(5-methyl-2-(4-cyanophenyl) pyrrol-1-yl)ethoxy]phenyl}-2-ethoxypropanoic acid and its pharmaceutically acceptable salts;

(+) 3-{4-[2-(5-methyl-2-(4-cyanophenyl) pyrrol-1-yl)ethoxy]phenyl}-2-ethoxypropanoic acid and its pharmaceutically acceptable salts;

(−) 3-{4-[2-(5-methyl-2-(4-cyanophenyl) pyrrol-1-yl)ethoxy]phenyl}-2-ethoxypropanoic acid and its pharmaceutically acceptable salts;

(±) 3-{4-[2-(5-methyl-2-(4-phenoxyphenyl) pyrrol-1-yl)ethoxy]phenyl}-2-ethoxypropanoic acid and its pharmaceutically acceptable salts;

(+) 3-{4-[2-(5-methyl-2-(4-phenoxyphenyl) pyrrol-1-yl)ethoxy]phenyl}-2-ethoxypropanoic acid and its pharmaceutically acceptable salts;

(−) 3-{4-[2-(5-methyl-2-(4-phenoxyphenyl) pyrrol-1-yl)ethoxy]phenyl}-2-ethoxypropanoic acid and its pharmaceutically acceptable salts;

(±) 3-{4-[2-(5-methyl-1'-(toluene-4-sulfonyl)-1'H-[2,2']bipyrrolyl-1-yl])ethoxy]phenyl}-2-ethoxypropanoic acid and its pharmaceutically acceptable salts;

(+) 3-{4-[2-(5-methyl-1'-(toluene-4-sulfonyl)-1'H-[2,2']bipyrrolyl-1-yl])ethoxy]phenyl}-2-ethoxypropanoic acid and its pharmaceutically acceptable salts;

(−) 3-{4-[2-(5-methyl-1'-(toluene-4-sulfonyl)-1'H-[2,2']bipyrrolyl-1-yl])ethoxy]phenyl}-2-ethoxypropanoic acid and its pharmaceutically acceptable salts;

(±) 3-{4-[2-(5-methyl-2-(3,4-dimethoxyphenyl) pyrrol-1-yl)ethoxy]phenyl}-2-ethoxypropanoic acid and its pharmaceutically acceptable salts;

(+) 3-{4-[2-(5-methyl-2-(3,4-dimethoxyphenyl) pyrrol-1-yl)ethoxy]phenyl}-2-ethoxypropanoic acid and its pharmaceutically acceptable salts;

(−) 3-{4-[2-(5-methyl-2-(3,4-dimethoxyphenyl) pyrrol-1-yl)ethoxy]phenyl}-2-ethoxypropanoic acid and its pharmaceutically acceptable salts;

(±) 3-{4-[2-(5-methyl-2-(4-methanesulfinyl-phenyl) pyrrol-1-yl)ethoxy]phenyl}-2-ethoxypropanoic acid and its pharmaceutically acceptable salts;

(+) 3-{4-[2-(5-methyl-2-(4-methanesulfinyl-phenyl) pyrrol-1-yl)ethoxy]phenyl}-2-ethoxypropanoic acid and its pharmaceutically acceptable salts;

(−) 3-{4-[2-(5-methyl-2-(4-methanesulfinyl-phenyl) pyrrol-1-yl)ethoxy]phenyl}-2-ethoxypropanoic acid and its pharmaceutically acceptable salts;

(±) 3-{4-[2-(5-methyl-2-(4-acetylamino-phenyl) pyrrol-1-yl)ethoxy]phenyl}-2-ethoxypropanoic acid and its pharmaceutically acceptable salts;

(+) 3-{4-[2-(5-methyl-2-(4-acetylamino-phenyl) pyrrol-1-yl)ethoxy]phenyl}-2-ethoxypropanoic acid and its pharmaceutically acceptable salts;

(−) 3-{4-[2-(5-methyl-2-(4-acetylamino-phenyl) pyrrol-1-yl)ethoxy]phenyl}-2-ethoxypropanoic acid and its pharmaceutically acceptable salts;

(±) 3-{4-[2-(5-methyl-2-(4-(2-piperidin-1-yl-ethoxy)-phenyl) pyrrol-1-yl)ethoxy]phenyl}-2-ethoxypropanoic acid and its pharmaceutically acceptable salts;

(+) 3-{4-[2-(5-methyl-2-(4-(2-piperidin-1-yl-ethoxy)-phenyl) pyrrol-1-yl)ethoxy]phenyl}-2-ethoxypropanoic acid and its pharmaceutically acceptable salts;

(−) 3-{4-[2-(5-methyl-2-(4-(2-piperidin-1-yl-ethoxy)-phenyl) pyrrol-1-yl)ethoxy]phenyl}-2-ethoxypropanoic acid and its pharmaceutically acceptable salts;

(±) 3-{4-[2-(5-methyl-2-(4-vinyloxy-phenyl) pyrrol-1-yl)ethoxy]phenyl}-2-ethoxypropanoic acid and its pharmaceutically acceptable salts;

(+) 3-{4-[2-(5-methyl-2-(4-vinyloxy-phenyl) pyrrol-1-yl)ethoxy]phenyl}-2-ethoxypropanoic acid and its pharmaceutically acceptable salts;

(−) 3-{4-[2-(5-methyl-2-(4-vinyloxy-phenyl) pyrrol-1-yl)ethoxy]phenyl}-2-ethoxypropanoic acid and its pharmaceutically acceptable salts;

(±) 3-{4-[2-(5-methyl-2-(4-phenylsulfanyl-phenyl) pyrrol-1-yl)ethoxy]phenyl}-2-ethoxypropanoic acid and its pharmaceutically acceptable salts;

(+) 3-{4-[2-(5-methyl-2-(4-phenylsulfanyl-phenyl) pyrrol-1-yl)ethoxy]phenyl}-2-ethoxypropanoic acid and its pharmaceutically acceptable salts;

(−) 3-{4-[2-(5-methyl-2-(4-phenylsulfanyl-phenyl) pyrrol-1-yl)ethoxy]phenyl}-2-ethoxypropanoic acid and its pharmaceutically acceptable salts;

(±) 3-{4-[2-(5-methyl-2-(4-phenylsulfinyl-phenyl) pyrrol-1-yl)ethoxy]phenyl}-2-ethoxypropanoic acid and its pharmaceutically acceptable salts;

(+) 3-{4-[2-(5-methyl-2-(4-phenylsulfinyl-phenyl) pyrrol-1-yl)ethoxy]phenyl}-2-ethoxypropanoic acid and its pharmaceutically acceptable salts;

(−) 3-{4-[2-(5-methyl-2 (4-phenylsulfinyl-phenyl) pyrrol-1-yl)ethoxy]phenyl}-2-ethoxypropanoic acid and its pharmaceutically acceptable salts;

(±) 3-{4-[2-(5-methyl-2-(4-methanesulfonyl-phenyl) pyrrol-1-yl)ethoxy]phenyl}-2-ethoxypropanoic acid and its pharmaceutically acceptable salts;

(+) 3-{4-[2-(5-methyl-2-(4-methanesulfonyl-phenyl) pyrrol-1-yl)ethoxy]phenyl}-2-ethoxypropanoic acid and its pharmaceutically acceptable salts;

(−) 3-{4-[2-(5-methyl-2-(4-methanesulfonyl-phenyl) pyrrol-1-yl)ethoxy]phenyl}-2-ethoxypropanoic acid and its pharmaceutically acceptable salts;

(±) 3-{4-[2-(5-methyl-2-(4-cyclohexylmethoxy-phenyl) pyrrol-1-yl)ethoxy]phenyl}-2-ethoxypropanoic acid and its pharmaceutically acceptable salts;

(+) 3-{4-[2-(5-methyl-2-(4-cyclohexylmethoxy-phenyl) pyrrol-1-yl)ethoxy]phenyl}-2-ethoxypropanoic acid and its pharmaceutically acceptable salts;

(−) 3-{4-[2-(5-methyl-2-(4-cyclohexylmethoxy-phenyl) pyrrol-1-yl)ethoxy]phenyl}-2-ethoxypropanoic acid and its pharmaceutically acceptable salts;

(±) 3-{4-[2-(2-benzoyl pyrrol-1-yl)ethoxy]phenyl}-2-ethoxypropanoic acid and its pharmaceutically acceptable salts;

(+) 3-{4-[2-(2-benzoyl pyrrol-1-yl)ethoxy]phenyl}-2-ethoxypropanoic acid and its pharmaceutically acceptable salts;

(−) 3-{4-[2-(2-benzoyl pyrrol-1-yl)ethoxy]phenyl }-2-ethoxypropanoic acid and its pharmaceutically acceptable salts;

(±) 3-{4-[2-(5-methyl-2-cyclopropyl pyrrol-1-yl)ethoxy]phenyl}-2-ethoxypropanoic acid and its pharmaceutically acceptable salts;

(+) 3-{4-[2-(5-methyl-2-cyclopropyl pyrrol-1-yl)ethoxy]phenyl}-2-ethoxypropanoic acid and its pharmaceutically acceptable salts;

(−) 3-{4-[2-(5-methyl-2-cyclopropyl pyrrol-1-yl)ethoxy]phenyl}-2-ethoxypropanoic acid and its pharmaceutically acceptable salts;

(±) 3-{4-[2-(5-methyl-2-(benzofuran-2-yl) pyrrol-1-yl)ethoxy]phenyl}-2-ethoxypropanoic acid and its pharmaceutically acceptable salts;

(+) 3-{4-[2-(5-methyl-2-(benzofuran-2-yl) pyrrol-1-yl)ethoxy]phenyl}-2-ethoxypropanoic acid and its pharmaceutically acceptable salts;

(−) 3-{4-[2-(5-methyl-2-(benzofuran-2-yl) pyrrol-1-yl)ethoxy]phenyl}-2-ethoxypropanoic acid and its pharmaceutically acceptable salts;

(±) 3-{4-[2-(3-carboxymethyl-2-methyl-5-phenyl pyrrol-1-yl)ethoxy]phenyl}-2-ethoxypropanoic acid and its pharmaceutically acceptable salts;

(+) 3-{4-[2-(3-carboxymethyl-2-methyl-5-phenyl pyrrol-1-yl)ethoxy]phenyl}-2-ethoxypropanoic acid and its pharmaceutically acceptable salts;

(−) 3-{4-[2-(3-carboxymethyl-2-methyl-5-phenyl pyrrol-1-yl)ethoxy]phenyl}-2-ethoxypropanoic acid and its pharmaceutically acceptable salts;

(±) 3-{4-[2-(5-methyl-2-(Benzo[1,3]dioxol-5-yl-) pyrrol-1-yl)ethoxy]phenyl}-2-ethoxypropanoic acid and its pharmaceutically acceptable salts;

(+) 3-{4-[2-(5-methyl-2-(Benzo[1,3]dioxol-5-yl-) pyrrol-1-yl)ethoxy]phenyl}-2-ethoxypropanoic acid and its pharmaceutically acceptable salts;

(−) 3-{4-[2-(5-methyl-2-(Benzo[1,3]dioxol-5-yl-) pyrrol-1-yl)ethoxy]phenyl}-2-ethoxypropanoic acid and its pharmaceutically acceptable salts;

(±) 3-{4-[2-(5-methyl-2-(naphthalen-1-yl)-pyrrol-1-yl)ethoxy]phenyl}-2-ethoxypropanoic acid and its pharmaceutically acceptable salts;

(+) 3-{4-[2-(5-methyl-2-(naphthalen-1-yl)-pyrrol-1-yl)ethoxy]phenyl}-2-ethoxypropanoic acid and its pharmaceutically acceptable salts;

(−) 3-{4-[2-(5-methyl-2-(naphthalen-1-yl)-pyrrol-1-yl)ethoxy]phenyl}-2-ethoxypropanoic acid and its pharmaceutically acceptable salts;

(±) 3-{4-[2-(5-methyl-2-(3-benzyloxy-phenyl)-pyrrol-1-yl)ethoxy]phenyl}-2-ethoxypropanoic acid and its pharmaceutically acceptable salts;

(+) 3-{4-[2-(5-methyl-2-(3-benzyloxy-phenyl)-pyrrol-1-yl)ethoxy]phenyl}-2-ethoxypropanoic acid and its pharmaceutically acceptable salts;

(−) 3-{4-[2-(5-methyl-2-(3-benzyloxy-phenyl)-pyrrol-1-yl)ethoxy]phenyl}-2-ethoxypropanoic acid and its pharmaceutically acceptable salts;

(±) 3-{4-[2-(5-methyl-2-(5-bromo-thiophen-2-yl)-pyrrol-1-yl)ethoxy]phenyl}-2-ethoxypropanoic acid and its pharmaceutically acceptable salts;

(+) 3-{4-[2-(5-methyl-2-(5-bromo-thiophen-2-yl)-pyrrol-1-yl)ethoxy]phenyl}-2-ethoxypropanoic acid and its pharmaceutically acceptable salts;

(−) 3-{4-[2-(5-methyl-2-(5-bromo-thiophen-2-yl)-pyrrol-1-yl)ethoxy]phenyl}-2-ethoxypropanoic acid and its pharmaceutically acceptable salts;

(±) 3-{4-[2-(5-methyl-2-(4-isopropoxy-phenyl)-pyrrol-1-yl)ethoxy]phenyl}-2-ethoxypropanoic acid and its pharmaceutically acceptable salts;

(+) 3-{4-[2-(5-methyl-2-(4-isopropoxy-phenyl)-pyrrol-1-yl)ethoxy]phenyl}-2-ethoxypropanoic acid and its pharmaceutically acceptable salts;

(−) 3-{4-[2-(5-methyl-2-(4-isopropoxy-phenyl)-pyrrol-1-yl)ethoxy]phenyl}-2-ethoxypropanoic acid and its pharmaceutically acceptable salts;

(±) 3-{4-[2-(3,5-dimethyl-2-phenyl-pyrrol-1-yl)ethoxy]phenyl}-2-ethoxypropanoic acid and its pharmaceutically acceptable salts;

(+) 3-{4-[2-(3,5-dimethyl-2-phenyl-pyrrol-1-yl)ethoxy]phenyl}-2-ethoxypropanoic acid and its pharmaceutically acceptable salts;

(−) 3-{4-[2-(3,5-dimethyl-2-phenyl-pyrrol-1-yl)ethoxy]phenyl}-2-ethoxypropanoic acid and its pharmaceutically acceptable salts;

(±) 3-{4-[2-(5-methyl-2-(thiophen-2-yl)-pyrrol-1-yl)ethoxy]phenyl}-2-ethoxypropanoic acid and its pharmaceutically acceptable salts;

(+) 3-{4-[2-(5-methyl-2-(thiophen-2-yl)-pyrrol-1-yl)ethoxy]phenyl}-2-ethoxypropanoic acid and its pharmaceutically acceptable salts;

(−) 3-{4-[2-(5-methyl-2-(thiophen-2-yl)-pyrrol-1-yl)ethoxy]phenyl}-2-ethoxypropanoic acid and its pharmaceutically acceptable salts;

(±) 3-{4-[2-(5-methyl-2-(4-benzyloxy-phenyl)-pyrrol-1-yl)ethoxy]phenyl}-2-ethoxypropanoic acid and its pharmaceutically acceptable salts;

(+) 3-{4-[2-(5-methyl-2-(4-benzyloxy-phenyl)-pyrrol-1-yl)ethoxy]phenyl}-2-ethoxypropanoic aid and its pharmaceutically acceptable salts;

(−) 3-{4-[2-(5-methyl-2-(4-benzyloxy-phenyl)-pyrrol-1-yl)ethoxy]phenyl}-2-ethoxypropanoic acid and its pharmaceutically acceptable salts;

(±) 3-{4-[2-(5-methyl-2-(4-hydroxy-phenyl)-pyrrol-1-yl)ethoxy]phenyl}-2-ethoxypropanoic acid and its pharmaceutically acceptable salts;

(+) 3-{4-[2-(5-methyl-2-(4-hydroxy-phenyl)-pyrrol-1-yl)ethoxy]phenyl}-2-ethoxypropanoic acid and its pharmaceutically acceptable salts;

(−) 3-{4-[2-(5-methyl-2-(4-hydroxy-phenyl)-pyrrol-1-yl)ethoxy]phenyl}-2-ethoxypropanoic acid and its pharmaceutically acceptable salts, (±) 3-{4-[2-(2-phenyl-pyrrol-1-yl)ethoxy]phenyl}-2-ethoxypropanoic acid and its pharmaceutically acceptable salts;

(+) 3-{4-[2-(2-phenyl-pyrrol-1-yl)ethoxy]phenyl}-2-ethoxypropanoic acid and its pharmaceutically acceptable salts;

(−) 3-{4-[2-(2-phenyl-pyrrol-1-yl)ethoxy]phenyl}-2-ethoxypropanoic acid and its pharmaceutically acceptable salts;

(+) 3-{4-[2-(5-methyl-2-(5-chloro-thiophen-2-yl)-pyrrol-1-yl)ethoxy]phenyl}-2-ethoxypropanoic acid and its pharmaceutically acceptable salts;

(+) 3-{4-[2-(5-methyl-2-(5-chloro-thiophen-2-yl)-pyrrol-1-yl)ethoxy]phenyl}-2-ethoxypropanoic acid and its pharmaceutically acceptable salts;

(−) 3-{4-[2-(5-methyl-2-(5-chloro-thiophen-2-yl)-pyrrol-1-yl)ethoxy]phenyl}-2-ethoxypropanoic acid and its pharmaceutically acceptable salts;

(±) 3-{4-[2-(5-methyl-2-(4-ethoxy-phenyl)-pyrrol-1-yl)ethoxy]phenyl}-2-ethoxypropanoic acid and its pharmaceutically acceptable salts;

(+) 3-{4-[2-(5-methyl-2-(4-ethoxy-phenyl)-pyrrol-1-yl)ethoxy]phenyl}-2-ethoxypropanoic acid and its pharmaceutically acceptable salts;

(−) 3-{4-[2-(5-methyl-2-(4-ethoxy-phenyl)-pyrrol-1-yl)ethoxy]phenyl}-2-ethoxypropanoic acid and its pharmaceutically acceptable salts;

(±) 3-{4-[2-(5-methyl-2-(5-methyl-thiophen-2-yl)-pyrrol-1-yl)ethoxy]phenyl}-2-ethoxypropanoic acid and its pharmaceutically acceptable salts;

(+) 3-{4-[2-(5-methyl-2-(5-methyl-thiophen-2-yl)-pyrrol-1-yl)ethoxy]phenyl}-2-ethoxypropanoic acid and its pharmaceutically acceptable salts;

(−) 3-{4-[2-(5-methyl-2-(5-methyl-thiophen-2-yl)-pyrrol-1-yl)ethoxy]phenyl}-2-ethoxypropanoic acid and its pharmaceutically acceptable salts;

(±) 3-{4-[2-(2,3-dimethyl-5-phenyl)-pyrrol-1-yl)ethoxy]phenyl}-2-ethoxypropanoic acid and its pharmaceutically acceptable salts;

(+) 3-{4-[2-(2,3-dimethyl-5-phenyl)-pyrrol-1-yl)ethoxy]phenyl}-2-ethoxypropanoic acid and its pharmaceutically acceptable salts;

(−) 3-{4-[2-(2,3-dimethyl-5-phenyl)-pyrrol-1-yl)ethoxy]phenyl}-2-ethoxypropanoic acid and its pharmaceutically acceptable salts;

(±) 3-{4-[2-(5-methyl-2-(quinolin-2-yl-)-pyrrol-1-yl)ethoxy]phenyl}-2-ethoxypropanoic acid and its pharmaceutically acceptable salts;

(+) 3-{4-[2-(5-methyl-2-(quinolin-2-yl-)-pyrrol-1-yl)ethoxy]phenyl}-2-ethoxypropanoic acid and its pharmaceutically acceptable salts;

(−) 3-{4-[2-(5-methyl-2-(quinolin-2-yl-)-pyrrol-1-yl)ethoxy]phenyl}-2-ethoxypropanoic acid and its pharmaceutically acceptable salts;

(±) 3-{4-[2-(5-methyl-2-(pyridin-4-yl)-pyrrol-1-yl)ethoxy]phenyl}-2-ethoxypropanoic acid and its pharmaceutically acceptable salts;

(+) 3-{4-[2-(5-methyl-2-(pyridin-4-yl)-pyrrol-1-yl)ethoxy]phenyl}-2-ethoxypropanoic acid and its pharmaceutically acceptable salts;

(−) 3-{4-[2-(5-methyl-2-(pyridin-4-yl)-pyrrol-1-yl)ethoxy]phenyl}-2-ethoxypropanoic acid and its pharmaceutically acceptable salts;

(±) 3-{4-[2-(5-methyl-2-(pyridin-2-yl)-pyrrol-1-yl)ethoxy]phenyl}-2-ethoxypropanoic acid and its pharmaceutically acceptable salts;

(+) 3-{4-[2-(5-methyl-2-(pyridin-2-yl)-pyrrol-1-yl)ethoxy]phenyl}-2-ethoxypropanoic acid and its pharmaceutically acceptable salts;

(−) 3-{4-[2-(5-methyl-2-(pyridin-2-yl)-pyrrol-1-yl)ethoxy]phenyl)}-2-ethoxypropanoic acid and its pharmaceutically acceptable salts;

(±) 3-{4-[2-(5-methyl-2-(pyridin-3-yl)-pyrrol-1-yl)ethoxy]phenyl}-2-ethoxypropanoic acid and its pharmaceutically acceptable salts;

(+) 3-{4-[2-(5-methyl-2-(pyridin-3-yl)-pyrrol-1-yl)ethoxy]phenyl}-2-ethoxypropanoic acid and its pharmaceutically acceptable salts;

(−) 3-{4-[2-(5-methyl-2-(pyridin-3-yl)-pyrrol-1-yl)ethoxy]phenyl}-2-ethoxypropanoic acid and its pharmaceutically acceptable salts;

(E/Z) 3-{4-[2-(5-methyl-2-phenylpyrrol-1-yl)ethoxy]phenyl}-2-ethoxyprop-2-enoic acid and its pharmaceutically acceptable salts;

(E) 3-{4-[2-(5-methyl-2-phenylpyrrol-1-yl)ethoxy]phenyl}-2-ethoxyprop-2-enoic acid and its pharmaceutically acceptable salts; and (Z) 3-{4-[2-(5-methyl-2-phenylpyrrol-1-yl)ethoxy]phenyl}-2-ethoxyprop-2-enoic acid and its pharmaceutically acceptable salts.

The signs (+) and (−) in the beginning of the name or number of a compound intends to denote the dextrorotatory or laevorotatory isomers of the compound. They may contain only one optical isomer or varying amounts of the other optical isomer, keeping the net sign of rotation of plane polarised light (+) or (−) as the case may be. The sign (±) in the beginning of the name or number of a compound intends to indicate a racemic mixture of the two enantiomers with almost zero net rotation of the plane polarized light. The present invention encompasses the use of not only the compounds of present invention described in formula (I) but also the metabolic products of these compounds formed in vivo for the treatment of diseases mentioned anywhere in the specificaiton.

The present invention also provides methods for the preparation of novel compounds described in the general formula (I), their tautomeric forms, their derivatives, their analogs, their stereoisomers, their pharmaceutically acceptable salts and their pharmaceutically acceptable solvates, wherein $R^1$, $R^2$, $R^3$, $R^4$, $R^5$, $R^6$, $R^7$, $R^8$, W, X, Y, Z, Ar and n are as defined- earlier. These methods are described below, comprising:

Route 1:

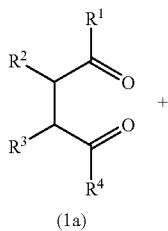
(1a)

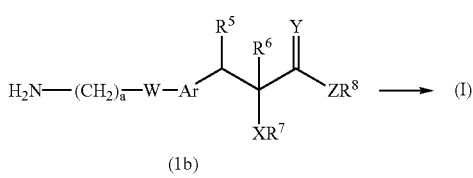
(1b)

The reaction of a compound of general formula (1a), wherein all symbols are as defined earlier with a compound of formula (1b) which may be optically active or racemic, wherein all symbols are as defined earlier to yield a compound of general formula (I) may be carried out using Paal-Knorr cyclization (Paal C. Ber., 1885, 18, 367; Knorr, L., Ber., 1885, 18, 299). The reaction may be carried out neat or in the presence of a solvent or a mixture thereof such as tetrahydrofuran, hexane, cyclohexane, toluene, methanol, ethanol, heptane, petroleum ether, xylene, benzene, ethyl acetate, tert-butyl acetate, 1,2-dichloroethane, iso-propanol, dioxane, cyclohexane, acetonitrile and the like. The reaction temperature may range from 0° C. to the reflux temperature of the solvent(s) used. The water produced may be removed by using a Dean Stark water separator or by water scavengers such as molecular sieves. The reaction may be carried out in the absence or presence of an inert atmosphere such as $N_2$, He or Ar. The reaction may be carried out under acidic condition provided by acids like acetic acid, propanoic acid, butyric acid, isobutyric acid, pivalic acid, p-toluenesulfonic acid, camphorsulfonic acid, benzenesulfonic acid, trifluoroacetic acid, chloroacetic acid, chloropropanoic acid, phenylacetic acid, phenylpropanoic acid, malonic acid, succinic acid, benzoic acid, halogenated benzoic acid, toluic acid and the like. Mineral acids such as HCl or HBr may also be used. The reaction time may range from 5 minutes to 72 hours, preferably from 1 to 48 hours.

Route 2:

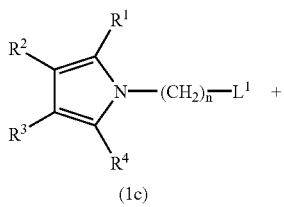
(1c)

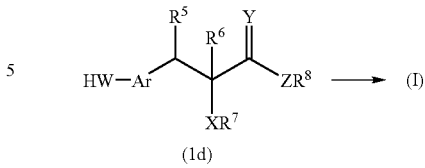
(1d)

The reaction of compound of formula (1c), where all symbols are as defined earlier and $L^1$ represents a leaving group such as halogen atom, p-toluenesulfonate, methanesulfonate, trifluoromethanesulfonate and the like with a compound of formula (1d) which may be optically active or racemic, where W is either O or S and all other symbols are as defined earlier, to produce a compound of general formula (I). This reaction may be carried out in the presence of solvents such as acetone, tetrahydrofuran, dimethylsulfoxide, dioxane, acetonitrile, dimethyl formamide, DME, benzene, toluene, pet, ether, heptane, hexane, 2-butanone, xylene, alcohols such as methanol, ethanol, propanol, butanol, iso-butanol, tert-butanol, pentanol and the like or a mixture thereof. Base such as alkali metal carbonate such as $K_2CO_3$, $Na_2CO_3$, $CsCO_3$, and the like; or alkali metal hydroxide such as NaOH, KOH and the like, may be used during this reaction. Alkali metal hydrides such as NaH, KH can be used whenever solvent employed is not protic or contain carbonyl group. The reaction may be carried out at a temperature in the range 0° C. to reflux temperature of the solvent(s) used and the reaction time may range from 1 to 48 hours.

Route 3:

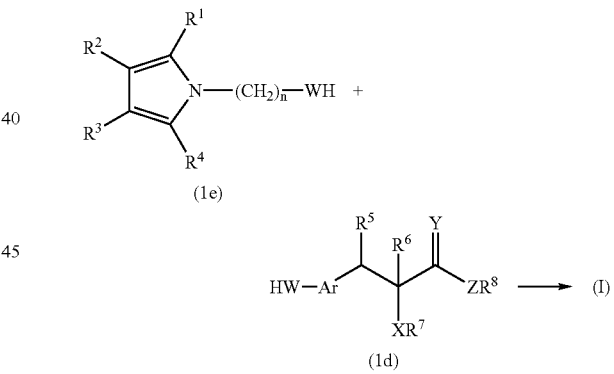

The reaction of compound of general formula (1e) where all symbols are as defined earlier and W represents oxygen atom, with a compound of general formula (1d) which may be optically active or racemic, where W is O or S and all other symbols are as defined earlier may be carried out using coupling agents such as DCC, EDC, triaryl phosphine/dialkyl azadicarboxylate such as $PPh_3/DEAD$ or $PPh_3/DIAD$ and the like. Inert atmosphere may be maintained using $N_2$, Ar or He. Solvents such as tetrahydrofuran, dioxane, DME, toluene, dichloromethane, chloroform, carbon tetrachloride, acetonitrile and the like may be used. Compounds such as 4-dimethylaminopyridine, hydroxybenzotriazole etc. may be used in the range of 0.05 to 2 equivalents. The reaction temperature in the range of 0° C. to reflux temperature of the solvent may be used, preferably, 20° C. to 80° C. The duration of the reaction may range from 0.5 to 24 h, preferably 0.5 to 12 hours.

Route 4:

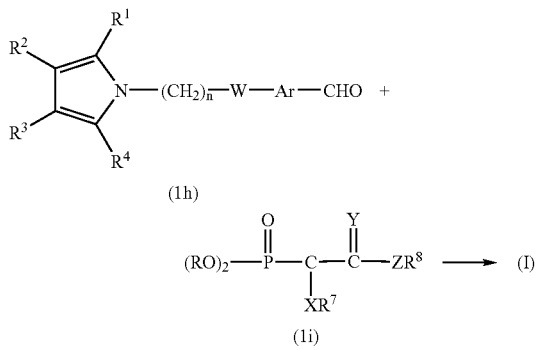

The reaction of a compound of general formula (1h) wherein all the symbols are as defined earlier, with a compound of formula (1i), where all the symbols are as defined earlier and R represents $(C_1-C_8)$ alkyl to afford a compound of formula (I) where $R^5$ and $R^6$ represent a bond and all other symbols are as defined earlier, may be carried out under Wittig Horner reaction conditions in the presence of a base such as alkali metal hydrides, like NaH or KH, alkali metal alkoxides such as NaOMe, NaOEt, $K^+$ t-BuO$^-$ or mixture thereof, organolithiums like $CH_3Li$, BuLi, sec-BuLi, LDA and the like. Aprotic solvents such as THF, dioxane, DMF, DMSO, DME and the like or mixture thereof may be employed. HMPA favours the progression of the reaction but not essential. The reaction may be carried out at a temperature ranging from $-80°$ C. to $100°$ C., preferably from $0°$ C. to $30°$ C. The reaction proceeds more effectively under anhydrous and inert conditions.

The compound of formula (I) where $R^5$ and $R^6$ represent a bond may be reduced to a compound of general formula (I) where $R^5$ and $R^6$ each represent hydrogen atom by reacting with hydrogen gas in the presence of a catalyst such as 5–10% Pd/C, Rh/C, Pt/C Raney Ni and the like, 5–100% w/w of the catalyst may be employed or the mixture thereof. The pressure of hydrogen gas may be one atmosphere to 80 psi. Suitable solvents are alcohols such as ethanol, methanol and the like, ethyl acetate, THF, dioxane, acetic acid and the like. Temperature may be in the range of $20°$ C. to $80°$ C., may be used for this reduction process. Metal-solvent such as magnesium in alcohol or sodium amalgam in alcohol may also be used, for this reduction process.

According to a feature of the present invention, there is provided an intermediate of formula (1h),

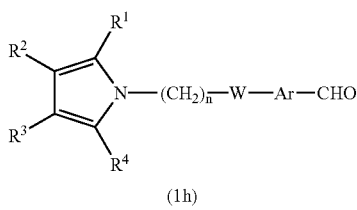

wherein $R^1$, $R^2$, $R^3$, $R^4$ may be same or different, and represent hydrogen, halogen, haloalkyl, perhaloalkyl, haloalkoxy, perhaloalkoxy, hydroxy, thio, amino, nitro, cyano, formyl, amidino, guanidino, or substituted or unsubstituted groups selected from linear or branched $(C_1-C_{12})$ alkyl, linear or branched $(C_1-C_{12})$ alkenyl, linear or branched $(C_1-C_{12})$ alkynyl, $(C_3-C_7)$ cycloalkyl, $(C_3-C_7)$ cycloalkenyl, bicycloalkyl, bicycloalkenyl, $(C_1-C_{12})$ alkoxy, $(C_1-C_{12})$ alkenoxy, cyclo$(C_3-C_7)$ alkoxy, aryl, aryloxy, aralkyl, ar$(C_1-C_{12})$ alkoxy, heterocyclyl, heteroaryl, heterocyclyl$(C_1-C_{12})$ alkyl, heteroar$(C_1-C_{12})$ alkyl, heteroaryloxy, heteroar$(C_1-C_{12})$ alkoxy, heterocycloxy, heterocyclylalkyloxy, acyl, acyloxy, acylamino, mono-substituted or di-substituted amino, arylamino, aralkylamino, carboxylic acid and its derivatives such as esters and amides, hydroxyalkyl, aminoalkyl, mono-substituted or di-substituted aminoalkyl, alkoxyalkyl, aryloxyalkyl, aralkoxyalkyl, $(C_1-C_{12})$ alkylthio, thio$(C_1-C_{12})$ alkyl, arylthio, $(C_1-C_{12})$ alkoxycarbonylamino, aryloxycarbonylamino, aralkyloxycarbonylamino, aminocarbonylamino, alkylaminocarbonylamino, alkylamidino, alkylguanidino, dialkylguanidino, hydrazino, alkyl hydrazino, alkoxyamino, hydroxyl amino, derivatives of sulfenyl and sulfonyl groups, sulfonic acid and its derivatives, phosphonic acid and its derivatives; n represents an integer varying from 1 to 8; W represents O, S or $NR^9$, where $R^9$ represents hydrogen, $(C_1-C_{12})$ alkyl or aryl groups; Ar represents a substituted or unsubstituted divalent single or fused aromatic, heteroaromatic or a heterocyclic group;

According to another feature of the present invention, there is provided a process for the preparation of intermediate of the general formula (1h) as defined earlier which comprises reacting a compound of general formula (1c),

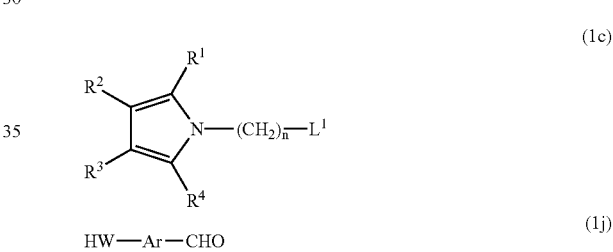

wherein, $R^1$–$R^4$, n are as defined earlier and $L^1$ is a halogen atom such as chlorine, bromine or iodine or a leaving group such as methanesulfonate, trifluoromethanesulfonate, p-toluenesulfonate and the like with the compound of the formula (1j), where Ar and W are as defined earlier.

The reaction of the compound of formula (1c) with the compound of formula (1j) to produce a compound of formula (1h) may be carried out in the presence of solvents such as acetone, THF, DMSO, dioxane, 2-butanone, acetonitrile, DMF, DME, benzene, toluene, xylene, alcohols such as methanol, ethanol, propanol, butanol, iso-butanol, tert-butanol, pentanol and the like or a mixture thereof. Bases such as alkali metal carbonates such as $K_2CO_3$, $Na_2CO_3$, $CsCO_3$ and the like may be used; alkali metal hydroxides like NaOH, KOH and the like; or mixtures thereof may be used. Alkali metal hydrides such as NaH, KH and the like, may be used in cases when the solvent used is not protic and does not contain carbonyl group. The reaction temperature may range from $20°$ C. to reflux temperature of the solvent(s) used and the reaction time may range from 1 to 48 hours. The inert atmosphere may be maintained by using inert gases such as $N_2$, Ar or He.

Alternatively, the intermediate of the general formula (1h), can also be prepared by the reaction of compound of general formula (1e),

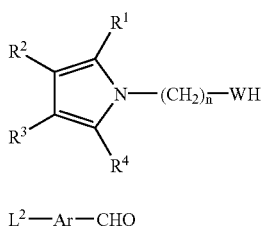

(1k)

L²—Ar—CHO wherein R¹–R⁴, n and W are as defined earlier and with a compound of the formula (1k), where Ar is as defined earlier and L² is a halogen atom such as fluorine, chlorine, bromine or iodine. The reaction of the compound of formula (1e) with the compound of formula (1k) to produce a compound of formula (1h) may be carried out in the presence of solvents such as THF, DMF, DMSO, DME and the like. Mixture of solvents may be used. The inert atmosphere may be maintained by using inert gases such as $N_2$, Ar or He. The reaction may be effected in the presence of a base such as $K_2CO_3$, $Na_2CO_3$, NaH or mixtures thereof. The reaction temperature may range from 20° C. to 150° C., preferably at a temperature in the range from 30° C. to 100° C. The duration of reaction may range from 1 to 24 hours, preferably from 2 to 6 hours.

The reaction of compound of general formula (1e) wherein W represents O and all other symbols are as defined earlier with the compound of formula (1j) may be carried out using suitable coupling agents such as dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$ toluene, acetonitrile, carbontetrachloride and the like. The inert atmosphere may be maintained by using inert gases such as $N_2$, Ar or He. The reaction may be effected in the presence of DMAP, HOBT and they must be used in the range of 0.05 to 2 equivalents, preferably 0.25 to 1 equivalents. The reaction temperature may range from 0° C. to 100° C., preferably at a temperature in the range from 20° C. to 80° C. the duration of reaction of the reaction may range from 0.5 to 24 hours, preferably from 6 to 12 hours.

In another embodiment of this invention, there is provided a process for the preparation of a compound of the general formula (1c), which comprises reacting the compound of general formula (1a) wherein R¹–R⁴ are as defined earlier,

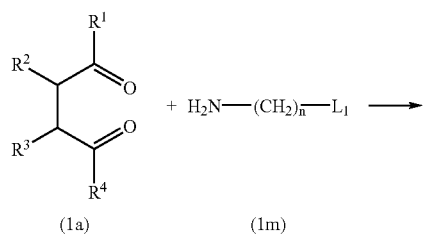

(1a)  (1m)

with either substituted amino compound (1m), where all symbols are is as defined earlier, to yield the intermediate of the general formula (1c).

In yet another embodiment of this invention, there is provided a process for the preparation of a compound of the general formula (1e), which comprises reacting the compound of general formula (1a) wherein R¹–R⁴ are as defined earlier,

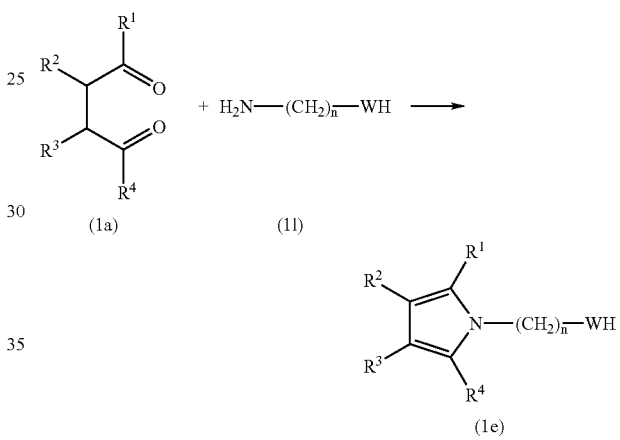

(1a)  (1l)

(1e)

with either substituted amino compound (1l), where all symbols are is as defined earlier, to yield the intermediate of the general formula (1e).

The reactions of a compound of general formula (1a) with a compound of general formula, (1l) or a compound of general formula (1m) may be carried out neat or in presence of solvents or a mixture thereof such as tetrahydrofuran, hexane, toluene, methanol, ethanol, heptane, petroleum ether, xylene, benzene, ethyl acetate, tert-butyl acetate, 1,2-dichloroethane, iso-propanol, tert-butanol, dioxane, cyclohexane, acetonitrile and the like. The reaction temperature may range from 0° C. to the reflux temperature of the solvent(s) used. The water produced may be removed by using a Dean Stark water separator or by water scavengers such as molecular sieves. The reaction may be carried out in the presence of an inert atmosphere such as $N_2$, He or Ar. The reaction may be carried out in the presence of an acid, such as acetic acid, propanoic acid, butyric acid, isobutyric acid, pivalic acid, p-toluenesulfonic acid, camphorsulfonic acid, benzenesulfonic acid, trifluoroacetic acid, chloroacetic acid, chloropropanoic acid, phenylacetic acid, phenylpropanoic acid, malonic acid, succinic acid, benzoic acid, halogenated benzoic acid, toluic acid and the like.

Yet another embodiment of this invention, there is provided an alternate process for the preparation of a compound of the general formula (1c), which comprises reacting the compound of general formula (1n) wherein $R^1$–$R^4$ are as defined earlier,

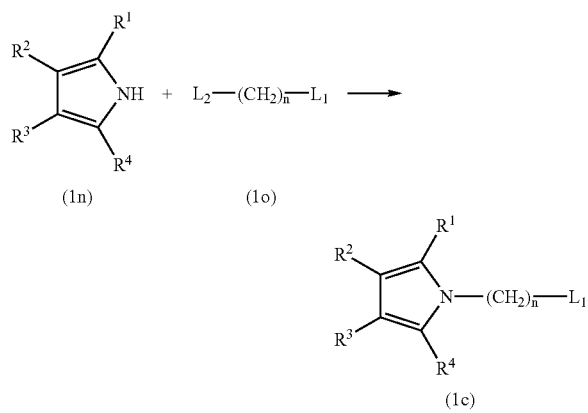

with the compound of formula (1o) where $L^1$ and $L_2$ may be same or different and represent leaving groups such as halogen atom as Cl, Br, or I, methanesulfonate, p-toluenesulfonate and the like; and n as defined earlier.

In yet another embodiment of this invention, there is provided an alternate process for the preparation of a compound of the general formula (1e), which comprises reacting the compound of general formula (1n) where $R^1$–$R^4$ are as defined earlier,

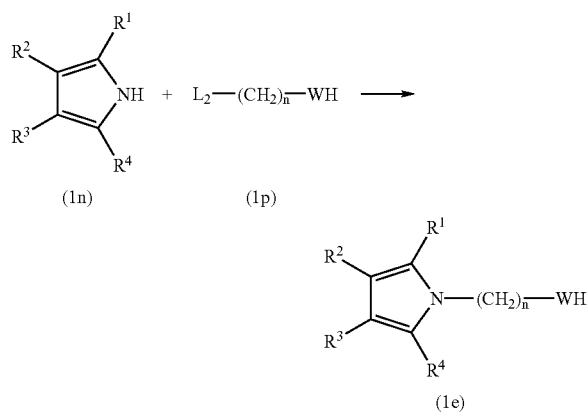

with the compound of formula (1p) where $L_2$ represent leaving groups such as halogen atom as Cl, Br, or I, methanesulfonate, p-toluenesulfonate and the like; and n as defined earlier.

The reaction of compound of general formula (1n), with either (1o) or (1p) may be carried out in solvents such as alcohol like methanol, ethanol, iso-propanol and the like; THF, dioxane, DMSO, DMF, acetonitrile, heptane, benzene, toluene, xylene and the like. The reaction may be carried out in presence of bases such as NaH, KH, $Na_2CO_3$, $K_2CO_3$, NaOH, KOH, $LiNH_2$, $NaNH_2$ and the like. Phase transfer catalyst such as tetrabutyl ammonium halide, tetrabutyl ammonium hydroxide (TBAH) and the like may be used. The reaction temperature may range from 0° C. to the reflux temperature of the solvent employed. The reaction may be carried out in the presence of an inert atmosphere such as $N_2$, He or Ar.

In another embodiment of this invention, there is provided a process for the preparation of a compound of the general formula (1e), wherein $R^1$–$R^4$ and n are as defined earlier and W represents O, which comprises reducing the corresponding acid

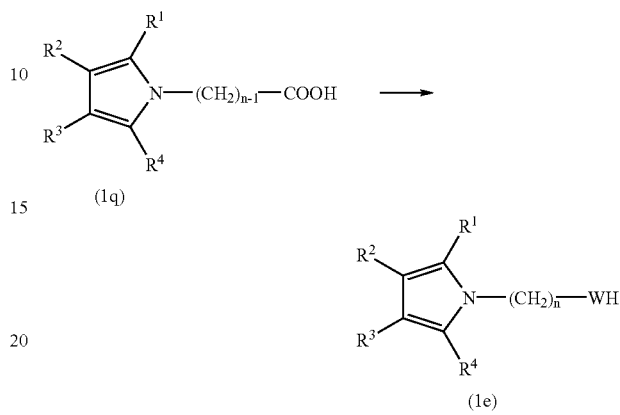

The reduction of compound of general formula (1q) may be carried out in presence of solvents or a mixture thereof such as tetrahydrofuran, dioxane, ether and the like. The reaction temperature may range from 0° C. to the reflux temperature of the solvent(s) used. The reaction may be carried out in the presence of an inert atmosphere such as $N_2$, He or Ar. Suitable reducing agent such as sodium borohydride/iodine, diborane and its derivative, $LiAlH_4$ and the like may be used.

The compound of general formula (1q) may be prepared by the reaction of compound of general formula (1n) with a compound of $L_1(CH_2)_{n-1}COOR$, where $L_1$ and R are as defined earlier, followed by hydrolysis of the ester group to acid using methods commonly used.

The compounds of the present invention have asymmetric centers and occur either as racemates or racemic mixtures as well as individual diastereomers of any of the possible isomers, including optical isomers, being included in the present invention The stereoisomers of the compounds of the present invention may be prepared by one or more ways presented below:

i. One or more of the reagents may be used in their single isomeric form. For example, compound (1b) or (1d) may be pure stereoisomers.

ii. Optically pure catalysts or chiral ligands along with metal catalysts may be employed in the reduction process. The metal catalyst may be Rhodium, Ruthenium, Indium and the like. The chiral ligands may preferably be chiral phosphines. (Principles of Asymmetric synthesis J E Baldwin Ed. Tetrahedron series, Volume 14, Page no. 311–316)

iii. Mixture of stereoisomers may be resolved by conventional methods such as microbial resolution, resolving the diastereomeric salts formed with chiral acids or chiral bases. Chiral acids may be tartaric acid, mandelic acid, lactic acid, camphorsulfonic acid, amino acids and the like. Chiral bases may be cinchona alkaloids, (+) or (−) brucine, α-methyl benzylamine, (+) or (−) phenyl glycinol, ephedrine, amino sugars such as glucosamines or a basic amino acid such as lysine, arginine and the like.

iv. Resolution of the mixture of stereoisomers may also be effected by chemical methods by derivatization of the compound with a chiral compound such as chiral amines, chiral acids, chiral amino alcohols, amino acids into a 1:1 mixture of diastereomers and the diastereomers may be separated by conventional methods of fractional crystallization, chromatography and the like followed by cleaving the derivative (Jaques et al. "Enantiomers, Racemates and Resolution", Wiley Interscience, 1981; R. A. Sheldon, in "Chirotechnology", Marcel Dekker, Inc. NY, Basel, 1993, 173–204 and references therein; A. N. Collins, G. N. Sheldrack and J Crosby, in "Chirality in Industry II", John Wiley & Sons, Inc, 1997, 81–98 and references therein; E. L. Eliel and S. H. Wilen, in "Stereochemistry of Organic Compound", John Wiley & Sons, Inc, 1999, 297–464 and references therein.)

It will be appreciated that in any of the above mentioned reactions any reactive group in the substrate molecule may be protected, according to conventional chemical practice. Suitable protecting groups in any of the above mentioned reactions are those used conventionally in the art. The methods of formation and removal in such protecting groups are those conventional methods appropriate to the molecule being protected. T. W. Greene and P. G. M. Wuts "Protective groups in Organic Synthesis", John Wiley & Sons, Inc, 1999, $3^{rd}$ Ed., 201–245 along with references therein.

It will be appreciated that the above-mentioned preparation of the compounds of Formula (I), or a pharmaceutically acceptable salt thereof, and/or pharmaceutically acceptable solvate thereof is a stereoselective procedure and that the compound of formula (I) is a single stereoisomer. Favorably, a compound of formula (I) is present in admixture with less than 50% w/w of its racemic isomer, suitably 80–100% and preferably 90–100% pure, such as 90–95%, most preferably 95–100%, for example 95%, 96%, 97%, 98%, 99% and 99.99% optically pure.

Preferably the compounds of Formula (I), or a pharmaceutically acceptable salt thereof, and/or pharmaceutically acceptable solvate thereof is in optically pure form.

The absolute stereochemistry of the compounds may be determined using conventional methods, such as X-ray crystallography.

The pharmaceutically acceptable salts forming a part of this invention may be prepared by treating the compound of formula (I) with 1–6 equivalents of a base such as sodium hydride, sodium methoxide, sodium ethoxide, sodium hydroxide, potassium tert-butoxide, calcium hydroxide, calcium acetate, calcium chloride, magnesium hydroxide, magnesium chloride, magnesium alkoxide and the like. Solvents such as water, acetone, ether, THF, methanol, ethanol, t-butanol, 2-butanone, dioxane, propanol, butanol, isopropanol, diisopropyl ether, tert-butyl ether or mixtures thereof may be used. Organic bases such as lysine, arginine, methyl benzylamine, ethanolamine, diethanolamine, tromethamine, choline, guanidine and their derivatives may be used. Acid addition salts, wherever applicable may be prepared by treatment with acids such as tartaric acid, mandelic acid, fumaric acid, malic acid, lactic acid, maleic acid, salicylic acid, citric acid, ascorbic acid, benzene sulfonic acid, p-toluene sulfonic acid, hydroxynaphthoic acid, methane sulfonic acid, acetic acid, benzoic acid, succinic acid, palmitic acid, hydrochloric acid, hydrobromic acid, sulfuric acid, nitric acid and the like in solvents such as water, alcohols, ethers, ethyl acetate, dioxane, THF, acetonitrile, DMF or a lower alkyl ketone such as acetone, or mixtures thereof.

Another aspect of the present invention comprises a pharmaceutical composition, containing at least one of the compounds of the general formula (I), their derivatives, their analogs, their tautomeric forms, their stereoisomers, their pharmaceutically acceptable salts, their pharmaceutically acceptable solvates thereof as an active ingredient, together with pharmaceutically employed carriers diluents and the like.

Pharmaceutical compositions containing a compound of the present invention may be prepared by conventional techniques, e.g. as described in Remington: the Science and Practice of Pharmacy, $19^{th}$ Ed., 1995. The compositions may be in the conventional forms, such as capsules, tablets, powders, solutions, suspensions, syrups, aerosols or topical applications. They may contain suitable solid or liquid carriers or in suitable sterile media to form injectable solutions or suspensions. The compositions may contain 0.5 to 20%, preferably 0.5 to 10% by weight of the active compound, the remaining being pharmaceutically acceptable carriers, excipients, diluents, solvents and the like.

Typical compositions containing a compound of formula (I) or a pharmaceutically acceptable acid addition salt thereof, associated with a pharmaceutically acceptable excipients which may be a carrier or a diluent or be diluted by a carrier, or enclosed within a carrier which can be in the form of a capsule, sachet, paper or other container. When the carrier serves as a diluent, it may be a solid, semi-solid, or liquid material, which acts as a vehicle, excipients or medium for the active compound. The active compound can be absorbed on a granular solid container for example in a sachet. Some of suitable carriers are water, salt solutions, alcohols, polyethylene glycols, polyhydroxyethoxylated castor oil, peanut oil, olive oil, gelatin, lactose, terra alba, sucrose, cyclodextrin, amylose, magnesium sterate, talc, gelatin, agar, pectin, acacia, stearic acid or lower alkyl ethers of cellulose, silicic acid, fatty acids, fatty acid amines, fatty acids monoglycerides and diglycerides, pentaerythritol fatty acids esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preservatives, sweetening agents or flavoring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, buffers and/or coloring substances and the like, which do not deleteriously react with the active compounds.

The route of administration may be any route, which effectively transports the active drug to the appropriate or desired site of action effectively, such as oral, nasal, transdermal, pulmonary or parental e.g. rectal, depot, subcutaneous, intravenous, intraurethral, intramuscular, intranasal, ophthalmic solution or an ointment, preferably through oral route.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula (I) dissolved or suspended in a liquid carrier, in particular an aqueous carrier, for aerosol application. The carrier may contain additives such as solubilizing agent, e.g. propylene glycol, surfactants, absorption enhancers such as lecithin (phosphatidylcholine) or cyclodextrin, or preservatives such as parabens.

For parental application, particularly suitable are injectable solutions or suspensions, preferably aqueous solutions with the active compound dissolved in polyhydroxylated castor oil.

Tablet, dragees or capsules having talc and/or a carbohydrate carrier or binder or the like are particularly suitable for oral application. Preferably, carriers for tablets, dragees or capsules include lactose, corn starch and/or potato starch. A syrup or elixir can be used in cases where a sweetened vehicle can be employed.

A typical tablet which may be prepared by conventional tabletting techniques may contain:

| | |
|---|---|
| Active compound (as free compound or salt thereof) | 5.0 mg |
| Colloidal silicon dioxide | 1.5 mg |
| Cellulose, microcrytalline | 70.0 mg |
| Modified cellulose gum | 7.5 mg |
| Magnesium sterate | ad. |
| Coating: | |
| HPMC approx | 9.0 mg |
| *Mywacett 9–40 T approx. | 0.9 mg |

*Acylated monoglyceride used as plasticizer for film coating.

The compounds of general formula (I) or the compositions thereof are useful for the treatment and/or prophylaxis of disease caused by metabolic disorders such as hyperlipidemia, insulin resistance, Leptin resistance, hyperglycemia, obesity, or inflammation.

These compounds are useful for the treatment of hypercholesteremia, familial hypercholesteremia, hypertriglyceridemia, type 2 diabetes, dyslipidemia, disorders related to syndrome X such as hypertension, obesity, insulin resistance, coronary heart disease, atherosclerosis, xanthoma, stroke, peripheral vascular diseases and related disorders, diabetic complications, certain renal diseases such as glomerulonephritis, glomerulosclerosis, nephrotic syndrome, hypertensive nephrosclerosis, retinopathy, nephropathy, psoriasis, polycystic ovarian syndrome, osteoporosis, inflammatory bowel diseases, myotonic dystrophy, arteriosclerosis, Xanthoma, pancreatitis and for the treatment of cancer.

The compounds of the invention may be administered to a mammal, especially, a human in need of such treatment, prevention, elimination, alleviation or amelioration of diseases mentioned above.

The compounds of the present invention are effective over a wide dosage range, however, the exact dosage, mode of administration and form of composition depends upon the subject to be treated and is determined by the physician or veterinarian responsible for treating the subject. Generally, dosages from about 0.025 to about 200 mg preferably from about 0.1 to about 100 mg, per day may be used. Generally, the unit dosage form comprises about 0.01 to 100 mg of the compound of formula (I), as an active ingredient together with a pharmaceutically acceptable carrier. Usually suitable dosage forms for nasal, oral, transdermal or pulmonary administration comprises from about 0.001 mg to about 100 mg, preferably from 0.01 mg to about 50 mg of the active ingredient mixed with a pharmaceutically acceptable carrier or diluent.

In another aspect of the present invention, method of treatment and/or prevention of the diseases mentioned above are provided.

In a further aspect of the present invention, use of one or more compounds of the general formula (I) or pharmaceutically acceptable salts, for the preparation of a medicament thereof for the treatment and/or prevention of diseases mentioned in this document is provided.

In still further aspect of the present invention use of the compounds of the present invention alone or in combination with statins, glitazones, biguanides, angiotensin II inhibitors, aspirin, insulin secretagogue, β-sitosterol inhibitor, sulfonylureas, insulin, fibric acid derivatives, nicotinic acid, cholestyramine, cholestipol or probucol, α-glycosidase inhibitors or antioxidants, which may be administered together or within such a period as to act synergistically together.

The invention is explained in detail by the examples given below, which are provided by way of illustration only and therefore should not be construed to limit the scope of the invention.

(1H NMR spectral data given in the tables (vide infra) are recorded using a 300 MHz spectrometer (Bruker AVANCE-300) and reported in δ scale. Until and otherwise mentioned, the solvent used for NMR is $CDCl_3$ using Tetramethyl silane as the internal standard.)

PREPARATION 1

Preparation of 1-(2-hydroxyethyl)-5-ethyl-2phenyl-1H-pyrrole (Compound No. 17)

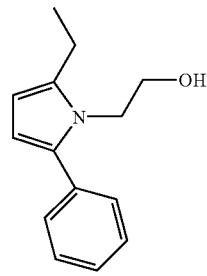

(Compound No. 17)

A mixture of 1-phenyl-hexane-1,4-dione (5 g), ethanol amine (1.6 g) and pivalic acid (2.15 g) in a solvent mixture containing n-heptane:tetrahydrofuran:toluene (4:1:1, 50 mL) was refluxed with stirring at 110–120° C. Water formed during the reaction was removed azeotropically during 3 to 4 hrs. The reaction mixture was cooled and the solvent was removed. The residue obtained was dissolved in dichloromethane (50 mL), washed with saturated sodium bicarbonate solution (50 mL), water (50 mL), and then with brine (50 mL), dried ($Na_2SO_4$) and the solvent was evaporated. The crude compound obtained as an oily mass. The crude substance was used in the next step without purification.

In the like manner to that described in Preparation 1, the following compounds of general formula (1e) were prepared from the appropriately substituted diketones as mentioned in Table 1. The latter can be synthesized by using various routes found in literature.

TABLE 1

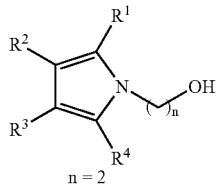

(1e)

n = 2

| Comp. No. | Substituents on the pyrrole ring in (1e) | | | | | |
|---|---|---|---|---|---|---|
| | $R^1$ | $R^2$ | $R^3$ | $R^4$ | | |
| 1. | $CH_3$ | H | H | $CH_2CH_3$ | Mol. Wt. = 153 | Yield = 53% |
| | $^1$H: 1.26(3H, t, J=7.4 Hz); 2.22(3H, s); 2.56(2H, q, J=7.4 Hz); 3.71(2H, t, J=5.86 Hz); 3.88(2H, t, J=5.89 Hz); 5.79–5.81(2H, m). | | | | | |
| 2. | $CH_3$ | H | H | $(CH_2)_2CH_3$ | Mol. Wt. = 167 | Yield = 36% |
| | $^1$H: 1.02(3H, t, J=7 Hz); 1.65(2H, m); 2.25(3H, s); 2.5(2H, t, J=7.7 Hz); 4.1(2H, t, J=5.9 Hz); 4.35(2H, t, J=5.9 Hz); 5.8–5.82(2H, m). | | | | | |
| 3. | $CH_3$ | H | H | $(CH_2)_3CH_3$ | Mol. Wt. = 181 | Yield = 58% |
| | $^1$H: 0.94(3H, t, J=7.2 Hz); 1.36–1.4(2H, m); 1.58–1.67(2H, m); 2.22(3H, s); 2.53(2H, t, J=7.7 Hz); 3.7(2H, t, J=5.8 Hz); 3.89(2H, t, J=5.8 Hz); 5.7–5.8(2H, m). | | | | | |
| 4. | $CH_3$ | H | H | phenyl | Mol. Wt. = 201 | Yield = 62% |
| | $^1$H: 2.33(3H, s); 3.5–3.6(2H, t, J=5.9 Hz); 4.05–4.09(2H, t, J=6.0 Hz); 5.95(1H, d, J=3.3 Hz); 6.09(1H, d, J=3.3 Hz); 7.25–7.29(1H, m); 7.30–7.38(4H, m). | | | | | |
| 5. | $CH_3$ | H | H | 4-methylphenyl | Mol. Wt. = 215 | Yield = 55% |
| | $^1$H: 2.32(3H, s); 2.37(3H, s); 3.59(2H, t, J=6.9 Hz); 4.10(2H, t, J=6.9 Hz); 5.94(1H, d, J=3.36 Hz); 6.0(1H, d, J=3.36 Hz); 7.2(2H, d, J=8.5 Hz); 7.25(2H, d, J=8.5 Hz) | | | | | |
| 6. | $CH_3$ | H | H | 3-methylphenyl | Mol. Wt. = 215 | Yield = 60% |
| | $^1$H: 2.32(3H, s); 2.36(3H, s); 3.57(2H, t, J=6 Hz); 4.08(2H, t, J=6.06 Hz); 5.94(1H, d, J=2.28 Hz); 6.1(1H, d, J=3.39 Hz); 7.09–7.3(4H, m). | | | | | |
| 7. | $CH_3$ | H | H | 2-methylphenyl | Mol. Wt. = 215 | Yield = 60% |
| | $^1$H: 2.32(3H, s); 2.36(3H, s); 3.58(2H, t, J=6 Hz); 4.07(2H, t, J=6.06 Hz); 5.94(1H, d, J=2.28 Hz); 6.07(1H, d, J=3.39 Hz); 7.09–7.15(2H, m); 7.24–7.29(2H, m). | | | | | |
| 8. | $CH_3$ | H | H | 4-methoxyphenyl | Mol. Wt. = 231 | Yield = 45% |
| | $^1$H: 2.3(3H, s); 3.53(2H, t, J=6.9 Hz); 3.84(3H, s); 4.0(2H, t, J=6.9 Hz); 5.9(1H, d, J=3.36 Hz); 6.0(1H, d, J=3.36 Hz); 6.95(2H, d, J=6.78 Hz); 7.2(2H, d, J=6.78 Hz). | | | | | |
| 9. | $CH_3$ | H | H | 4-bromophenyl | Mol. Wt. = 280 | Yield = 55% |

TABLE 1-continued

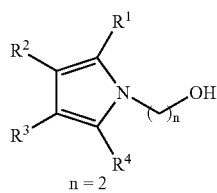

(1e)

n = 2

| Comp. No. | Substituents on the pyrrole ring in (1e) | | | | | |
|---|---|---|---|---|---|---|
| | R¹ | R² | R³ | R⁴ | | |

$^1$H: 2.32(3H, s); 3.61–3.63(2H, m) 4.05(2H, t, J = 6.2 Hz); 5.95(1H, dd); 6.1(1H, d, J=3.4 Hz); 7.25–7.3(2H, m); 7.47–7.52(2H, m).

| 10. | CH₃ | H | H | 4-F-C₆H₄ | Mol. Wt. = 219 | Yield = 32% |

$^1$H: 2.3(3H, s); 3.6(2H, t, J=6.0 Hz); 4.05(2H, t, J=6.0 Hz); 5.9(1H, d, J=2.8); 6.0(1H, d, J=3.3 Hz); 7.04–7.1(2H, m); 7.26–7.37(2H, m)

| 11. | CH₃ | H | H | 4-Cl-C₆H₄ | Mol. Wt. = 235.5 | Yield = 61% |

$^1$H: 2.3(3H, s); 3.6(2H, t, J=5.9 Hz); 4.12(2H, t, J=5.9 Hz); 5.97(1H, d, J=3.2 Hz); 6.10(1H, d, J=3.2 Hz); 7.09–7.37(4H, m).

| 12. | CH₃ | H | C₆H₅ | C₆H₅ | Mol. Wt. = 277 | Yield = 90% |

$^1$H: 2.37(3H, s); 3.5(2H, t, J=6 Hz); 3.95(2H, t, J=6.0 Hz); 6.2(1H, d, J=2.8); 7.1–7.4(10H, m).

| 13. | i-Pr | H | H | i-Pr | Mol. Wt. = 195 | Yield = 93% |

$^1$H: 1.21–1.24(12H, d, J=6.7 Hz); 2.91–2.98(2H, m); 3.77(2H, t, J=6.2 Hz); 4.01(2H, t, J=6.2 Hz); 5.8(2H, s).

| 14. | i-Pr | H | H | C₆H₅ | Mol. Wt. = 229 | Yield = 86% |

$^1$H: 1.29(6H, d, J=6.78 Hz); 3.0–3.05(1H, m); 3.51(2H, t, J=6.21 Hz); 4.12(2H, t, J =6.25 Hz); 6.0(1H, d, J=3.54 Hz); 6.125(1H, d, J=3.54 Hz); 7.27–7.31(3H, m) 7.37(2H, m)

| 15. | i-Pr | C₆H₅NHCO | H | 4-F-C₆H₄ | Mol. Wt. = 366 | Yield = 45% |

$^1$H: 1.43–1.45(6H, d, J=7.2 Hz); 3.3–3.4(1H, m); 4.09–4.1(2H, m); 3.80–3.85(2H, m); 6.85(1H, s); 7.0–7.5(9H, m).

| 16. | —C₂H₅ | H | H | —C₂H₅ | Mol. Wt. = 167 | Yield = 82% |

$^1$H: 1.26(6H, t, J=7.4 Hz); 2.59(4H, q, J=7.4 Hz); 3.76(2H, t, J=5.8 Hz); 3.93(2H, t, J=5.9 Hz); 5.86(2H, s)

| 17. | —C₂H₅ | H | H | C₆H₅ | Mol. Wt. = 215 | Yield = 82% |

$^1$H: 1.32(3H, t, J=7.3 Hz); 2.68(2H, q, J=7.6 Hz); 3.57(2H, t, J=5.9 Hz); 4.09(2H, t, J=5.9 Hz); (1H, d, J=3.4 Hz); 6.1(1H, d, J=3.4 Hz); 7.28–7.39(5H, m)

TABLE 1-continued

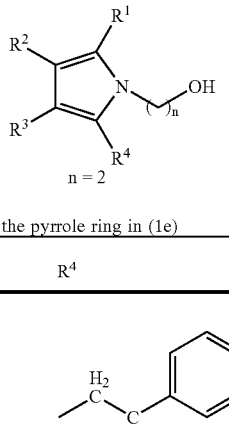

(1e)

n = 2

| Comp. No. | Substituents on the pyrrole ring in (1e) | | | | | |
|---|---|---|---|---|---|---|
| | R¹ | R² | R³ | R⁴ | | |
| 18. | —CH₃ | H | H | 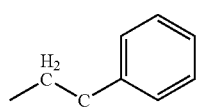 | Mol. Wt. = 229 | Yield = 76% |

¹H: 2.23(3H, s); 2.8–2.9(2H, m); 2.91–2.99(2H, m); 3.69(2H, t, J=5.8 Hz);
3.86(2H, t, J=5.8 Hz); 5.83(1H, d, J=3.3 Hz); 5.88(1H, d, J=3.6 Hz); 7.17–7.31(5H, m)

| 19. | —CH₃ | H | H | 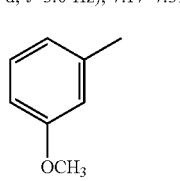 | Mol. Wt. = 231 | Yield = 80% |

¹H: 2.33(3H, s); 3.64(2H, t, J=6 Hz); 3.82(3H, s); 4.11(2H, t, J=6 Hz);
5.9(1H, d, J=3.3 Hz); 6.12(1H, d, J=3.3 Hz); 6.8–7.32(4H, m)

| 20. | —CH₃ | H | H | 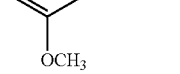 | Mol. Wt. = 207 | Yield = 82% |

¹H: 1.24–1.81(10H, m); 2.23(3H, s); 2.47–2.52(1H, m); 3.76–3.78(2H, m);
3.94(2H, t, J=6 Hz); 5.79–5.83(2H, m)

| 21. | —CH₃ | H | H | 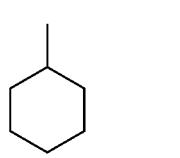 | Mol. Wt. = 277 | Yield = 76% |

¹H: 2.32(3H, s); 3.6(2H, t, J=6 Hz); 4.09(2H, t, J=6 Hz); (1H, d, J=2.94 Hz);
6.15(1H, d, 3.39 Hz); 7.2–7.6(9H, m)

| 22. | —CH₃ | H | H | 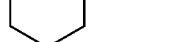 | Mol. Wt. = 191 | Yield = 70% |

¹H: 2.3(3H, s); 3.81–3.83(2H, m); 4.17(2H, t, J=5.8 Hz); 5.93(1H, d, J=3.5 Hz);
6.33(2H, dd, J=3.3 Hz, J₂=3.4 Hz); 6.43(1H, dd, J=1.87 Hz, 1.88 Hz); 7.402–7.407(1H, m)

| 23. | —CH₃ | H | H | 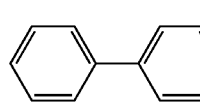 | Mol. Wt. = 205 | Yield = 80% |

¹H: 2.30(3H, s); 2.32(3H, s); 3.85(2H, t, J=5.77 Hz); 4.15(2H, t, J=5.8 Hz);
5.9(1H, d, J=3.5 Hz); 6.0(1H, d, J=3.43 Hz); 6.22(1H, d, J=3.09 Hz); 6.27(1H, d, J=3.54 Hz)

TABLE 1-continued

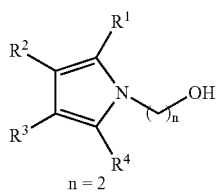

(1e)

n = 2

| Comp. No. | Substituents on the pyrrole ring in (1e) | | | | | |
|---|---|---|---|---|---|---|
| | R¹ | R² | R³ | R⁴ | | |
| 24. | —CH₃ | H | H | 4-(methylthio)phenyl | Mol. Wt. = 247 | Yield = 100% |

¹H: 2.3(3H, s); 2.49(3H, s); 3.58(2H, t, J=6.03 Hz); 4.0(2H, t, J=6.0 Hz);
5.93–5.94(1H, dd, J₁=0.738 Hz, J₂=0.665 Hz); 6.0(1H, d, J=3.4 Hz); 7.22–7.32(4H, m)

| 25. | —CH₃ | H | H | 4-cyanophenyl | Mol. Wt. = 226 | Yield = 70% |

¹H: 2.34(3H, s); 3.67(2H, t, J=5.9 Hz); 4.14(2H, t, J=6 Hz); 6.011(1H, d, J=3.4 Hz);
6.23(1H, d, J=3.5 Hz); 7.5(2H, d, J=8.5 Hz); 7.65(2H, d, J=8.5 Hz)

| 26. | —CH₃ | H | H | 4-phenoxy-3-methylphenyl | Mol. Wt. = 293 | Yield = 76% |

¹H: 2.33(3H, s); 3.65(2H, t, J=6 Hz); 4.09(2H, t, J=6 Hz); 5.9(1H, d, J=3.31 Hz);
6.08(1H, d, J=3.38 Hz); 6.99–7.38(9H, m)

| 27. | —CH₃ | H | H | N-(p-tolylsulfonyl)-2-methylpyrrol-5-yl | Mol. Wt. = 344 | Yield = 85% |

¹H: 2.8(3H, s); 2.4(3H, s); 3.59(2H, t, J=5.7 Hz); 3.74(2H, t, J=5.7 Hz);
5.63(1H, d, J=3.4 Hz); 5.86(1H, d, J=3.4 Hz); 6.25–6.26(1H, m); 6.31(1H, t, J=3.3 Hz);
7.23(2H, d, J=8.3 Hz); 7.43–7.48(3H, m)

| 28. | —CH₃ | H | H | 3,4-dimethoxyphenyl | Mol. Wt. = 261 | Yield = 100% |

¹H: 2.3(3H, s); 3.65(2H, t, J=5.9 Hz); 3.88(3H, s); 3.9(3H, s); 4.06(2H, t, J=6.0 Hz);
5.94–5.95(1H, m) 6.0(1H, d, J=3.1 Hz); 6.87–7.26(3H, m)

| 29. | —CH₃ | H | H | 4-(acetamido)phenyl | Mol. Wt. = 258 | Yield = 78% |

¹H: 2.12(3H, s); 2.3(3H, s); 3.61(2H, t, J=6.03 Hz); 4.15(2H, t, J=6.0 Hz);
5.9(1H, d, J=2.7 Hz); 6.02(1H, d, J=3.3 Hz); 6.7(2H, d, J=8.5 Hz); 7.16(2H, d, J=8.5 Hz)

TABLE 1-continued (1e)

Structure: pyrrole ring with substituents R¹, R², R³, R⁴ and N-(CH₂)ₙ-OH where n = 2

| Comp. No. | R¹ | R² | R³ | R⁴ | | |
|---|---|---|---|---|---|---|
| 30. | —CH₃ | H | H | 4-methylphenyl-O-CH₂CH₂-N(piperidine) | Mol. Wt. = 328 | Yield = 92% |

¹H: 1.4–1.63(6H, m); 2.3(3H, s); 2.48–2.5(4H, m); 2.75(2H, t, J=6.03 Hz); 3.5(2H, t, J=6.2 Hz); 4.0(2H, t, J=6.3 Hz); 4.1(2H, t, J=6.0 Hz); 5.91-5.92(1H, m); 6.0(1H, d, J=3.3 Hz); 6.889(2H, d, J=8.5 Hz); 7.2(2H, d, J=8.5 Hz)

| 31. | —CH₃ | H | H | 4-methylphenyl-O-allyl | Mol. Wt. = 257 | Yield = 83% |

¹H: 2.3(3H, s); 3.6(2H, t, J=6 Hz); 4.03(2H, t, J=6.1 Hz); 4.55(2H, d, J=5.3 Hz); 5.28–5.32(2H, dd, J=1.35 Hz J₂= 1.35 Hz); 5.40–5.46(1H, dd, J=1.56 Hz, J₂=1.5 Hz); 5.93(1H, d, J=3.36 Hz); 6.04(1H, d, J=3.42 Hz); 6.93(2H, d, J=8.5 Hz), 7.28(2H, d, J=8.5 Hz)

| 32. | —CH₃ | H | H | 4-methylphenyl-S-phenyl | Mol. Wt. = 309 | Yield = 79% |

¹H: 2.3(3H, s); 3.64(2H, t, J=6 Hz); 4.08(2H, t, J=6.09 Hz); 5.96(1H, d, J=3.36 Hz); 6.11(1H, d, J=3.45 Hz); 7.25–7.42(9H, m)

| 33. | —CH₃ | H | H | 4-methylphenyl-SO₂-CH₃ | Mol. Wt. = 279 | Yield = 80% |

¹H: 2.35(3H, s); 2.08(3H, s) 3.68(2H, t, J=5.7 Hz); 4.17(2H, t, J=5.8 Hz); 6.02(1H, d, J=3.5 Hz); 5.7(1H, d, J=3.5 Hz); 7.6(2H, d, J=8.5 Hz); 7.94(2H, d, J=8.5 Hz)

| 34. | —CH₃ | H | H | 4-methylphenyl-O-CH₂-cyclohexyl | Mol. Wt. = 313 | Yield = 89% |

¹H: 1.03–1.69(11H, m) 2.3(3H, s); 3.6(2H, t, J=6.0 Hz); 3.7(2H, d, J=6.2 Hz);

TABLE 1-continued

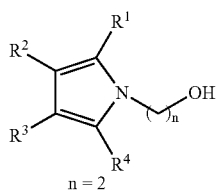

(1e)

n = 2

| Comp. No. | Substituents on the pyrrole ring in (1e) | | | | | |
|---|---|---|---|---|---|---|
| | R¹ | R² | R³ | R⁴ | | |

4.04(2H, t, J=6 Hz) 5.9(1H, d, J=3.3 Hz); 6.0(1H, d, J=3.3 Hz); 6.88(2H, d, J=8.5 Hz); 7.29(2H, d, J=8.5 Hz)

| 35. | —CH₃ | H | H | 2-thienyl | Mol. Wt. = 207 | Yield = 55% |

¹H: 2.3(3H, s), 3.74(2H, t, J=3.4 Hz); 4.13(2H, t, J=6 Hz) 5.9(1H, d, J=3.4 Hz); 6.2(1H, d, J=3.4 Hz); 7.03–7.05(2H, m); 7.25–7.27(1H, m)

| 36. | —CH₃ | H | H | 4-OBn-phenyl | Mol. Wt. = 307 | Yield = 98% |

¹H: 2.3(3H, s), 3.58(2H, t, J=6.0 Hz); 4.0(2H, t, J=6.0 Hz); 5.0(2H, s); 5.91(1H, d, J=3.3 Hz); 6.0(1H, d, J=3.3 Hz); 6.96–6.99(2H, m); 7.27–7.45(7H, m)

| 37. | H | H | H | phenyl | Mol. Wt. = 187 | Yield = 99% |

¹H: 3.7(2H, t, J=5.4 Hz); 4.1(2H, t, J=5.4 Hz); 6.23(2H, m); 6.8(1H, m); 7.4–7.8(5H, m)

| 38. | —CH₃ | H | H | cyclopropyl | Mol. Wt. = 165 | Yield = 61% |

¹H: 0.58–0.61(2H, m); 0.79–0.85(2H, m); 1.66–1.7(1H, m); 2.24(3H, s); 3.87(2H, t, J=5.87) Hz; 4.11(2H, t, J=5.89 Hz); 5.69(1H, d, J=3.26 Hz); 5.76(1H, d, J=3.2 Hz)

| 39. | —CH₃ | H | H | 2-benzofuryl | Mol. Wt. = 241 | Yield = 47% |

¹H: 2.36(3H, s); 3.93(2H, t, J=5.77 Hz); 4.32(2H, t, J=5.76 Hz); 6.0(1H, d, J=3.63 Hz); 6.57(1H, d, J=3.63 Hz); 6.69(1H, s); 7.54–7.2(4H, m)

| 40. | —CH₃ | COOCH₃ | H | phenyl | Mol. Wt. = 259 | Yield = 92% |

TABLE 1-continued

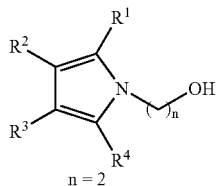

(1e)

n = 2

| Comp. No. | Substituents on the pyrrole ring in (1e) | | | | | |
|---|---|---|---|---|---|---|
| | R¹ | R² | R³ | R⁴ | | |

¹H: 2.63(3H, s); 3.61–3.63; (2H, m); 3.79(3H, s); 4.07–4.15(2H, m); 6.54(1H, s); 7.34–7.43(5H, m)

| 41. | —CH₃ | H | H | 2-(5-chlorothiophenyl) | Mol. Wt. = 241 | Yield = 58% |

¹H: 2.3(3H, s); 3.74(2H, t, J=5.7 Hz); 4.13(2H, t, J=5.9 Hz); 5.9(1H, d, J=3.0 Hz); 6.1(1H, d, J=3.5 Hz); 6.8(1H, d, J=3.8 Hz); 6.84(1H, d, J=3.8 Hz)

| 42. | —CH₃ | H | H | 4-ethoxyphenyl | Mol. Wt. = 245 | Yield = 99% |

¹H: 1.43(3H, t, J=6.97 Hz); 2.33(3H, s); 3.6(2H, t, J=5.99 Hz); 4.02(4H, m); 5.94(1H, d, J=3.28 Hz); 6.04(1H, d, J=3.35 Hz); 6.91(2H, d, J=8.69 Hz); 7.28(2H, d, J=8.6.9 Hz)

| 43. | —CH₃ | H | H | 5-methylthiophen-2-yl | Mol. Wt. = 221 | Yield = 93% |

¹H: 2.3(3H, s); 2.4(3H, s); 3.74(2H, t, J=6.0) Hz; 4.13(2H, t, J=6 Hz); 5.9(1H, d, J=3.4 Hz); 6.17(1H, d, J=3.4 Hz); 6.67(1H, d, J=3.4 Hz); 6.8(1H, d, J=3.4 Hz)

| 44. | —CH₃ | CH₃ | H | C₆H₅ | Mol. Wt. = 215 | Yield = 50% |

¹H: 2.06(3H, s); 2.2(3H, s); 3.62(2H, t, J=6); 4.07(2H, t, J=6); 6.0(1H, s); 7.25(1H, m); 7.3–7.4(4H, m)

| 45. | —CH₃ | H | H | benzo[d][1,3]dioxol-5-yl | Mol. Wt. = 245 | Yield = 100% |

¹H: 2.32(3H, s); 3.62(2H, t, J=6.03 Hz); 4.05(2H, t, J=6.04 Hz); 5.92(1H, d, J=3.27 Hz); 5.98(2H, s); 6.03(1H, d, J=3.36 Hz); 6.84(2H, d, J=8.46 Hz); 7.16(1H, s)

| 46. | —CH₃ | H | H | 1-naphthyl | Mol. Wt. = 251 | Yield = 36% |

¹H: 2.37(3H, s); 3.42(2H, t, J=5.85 Hz); 3.5–3.8(2H, m); 6.02(1H, d, J=3.27 Hz);

TABLE 1-continued

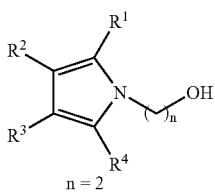

(1e)

n = 2

| Comp. No. | R¹ | R² | R³ | R⁴ | | |
|---|---|---|---|---|---|---|
| | 6.15(1H, d, J=3.36 Hz); 7.43–7.89(7H, m) | | | | | |
| 47. | —CH₃ | H | H | 3-OBn-phenyl | Mol. Wt. = 307 | Yield = 100% |
| | ¹H: 2.31(3H, s); 3.56(2H, t, J=6.03 Hz); 4.03(2H, t, J=6.03 Hz); 5.08(2H, s); 5.94(1H, d, J=3.36 Hz); 6.1(1H, d, J=3.39 Hz); 6.93–7.44(9H, m) | | | | | |
| 48. | —CH₃ | H | H | 5-bromo-2-methylthiophene | Mol. Wt. = 286 | Yield = 30% |
| | ¹H: 2.31(3H, s); 3.76(2H, t, J=5.9 Hz); 4.1(2H, t, J=5.9 Hz); 5.9(1H, d, J=3.48 Hz); 6.95(1H, d, J=3.54 Hz); 6.7(1H, d, J=3.78 Hz); 6.9(1H, d, J=3.78 Hz). | | | | | |
| 49. | —CH₃ | H | H | 4-isopropoxyphenyl | Mol. Wt. = 259 | Yield = 100% |
| | ¹H: 1.33(6H, d, J=5.13 Hz); 2.94(3H, s); 3.60(2H, t, J=6.07 Hz); 4.03(2H, t, J=6.07 Hz); 4.52–4.60(1H, m); 5.92(1H, d, J=2.82 Hz); 6.03(1H, d, J=3.36 Hz); 6.88(2H, d, J=8.7 Hz); 7.27(2H, d, J=8.67 Hz) | | | | | |
| 50. | —CH₃ | H | CH₃ | phenyl | Mol. Wt. = 215 | Yield = 57% |
| | ¹H: 1.97(3H, s); 2.29(3H, s); 3.51(2H, t, J=6 Hz); 3.95(2H, t, J=6 Hz); 5.83(1H, s); 7.25–7.43(5H, m) | | | | | |
| 51. | H | H | H | H | Mol. Wt. = 111 | Yield = 98% |
| 52. | CH₃ | H | H | CH₃ | Mol. Wt. = 139 | Yield = 65% |
| | ¹H: 2.21(6H, s); 3.70–3.72(2H, m); 3.89(2H, t, J=5.8 Hz); 5.76(2H, s). | | | | | |
| 53. | i-Pr | phenyl | H | i-Pr | Mol. Wt. = 271 | Yield = 42% |
| | ¹H: 1.25(12H, d, J=6.5 Hz); 2.97(1H, sept, J=6.7 Hz); 3.24(1H, sep, J=6.7 Hz); 3.85(2H, m); 4.1(2H, t, J=7 Hz); 5.87(1H, s); 7.19–7.32(5H, m) | | | | | |

TABLE 1-continued (1e)

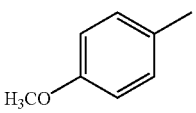

n = 2

| Comp. No. | Substituents on the pyrrole ring in (1e) | | | | | |
|---|---|---|---|---|---|---|
| | $R^1$ | $R^2$ | $R^3$ | $R^4$ | | |
| 54. | i-Pr | H | H | 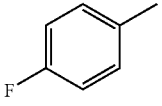 | Mol. Wt. = 259 | Yield = 84% |

$^1$H: 1.27(6H, d, J=6.5 Hz); 2.99–3.04(1H, m); 3.53(2H, t, J=6.15 Hz); 3.82(3H, s); 4.09(2H, t, J=6.2 Hz); 5.96(1H, d, J=3.5 Hz); 6.67(1H, d, J=3.48 Hz); 6.91(2H, d, J=8.9 Hz); 7.29(2H, d, J=8.6 Hz)

| 55. | i-Pr | H | H | 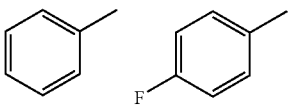 | Mol. Wt. = 247 | — |

$^1$H: 1.27(6H, d, J=6.0 Hz); 2.97–3.06(1H, m); 3.53(2H, t, J=6.0 Hz); 4.08(2H, t, J=6.0 Hz); 5.99(1H, d, J=3.60 Hz); 6.10(1H, d, J=3.3 Hz); 7.05–7.1(2H, t, J=8.8 Hz); 7.34–7.37(2H, m)

| 56. | i-Pr | H | 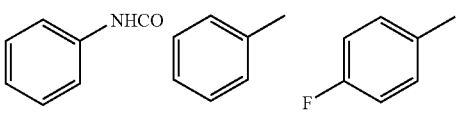 | | Mol. Wt. = 323.2 | Yield = 55% |

$^1$H: 1.34(6H, d, J=7 Hz); 3.09(1H, sep, J=7 Hz); 3.57(2H, t, J=4.5 Hz); 4.02(2H, t, J=4.5 Hz); 6.22(1H, s); 7.03–7.30(9H, m);

| 57. | i-Pr | 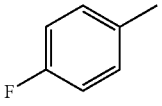 | | | Mol. Wt. = 442 | Yield = 52% |

$^1$H: 1.47(6H, d, J=7.2 Hz); 3.5–3.6(1H, m); 3.59(2H, t, J=6.2 Hz); 3.99(2H, t, J=6.6 Hz); 6.79(1H, s); 6.91–7.0(3H, m); 7.08–7.19(10H, m).

| 58. | 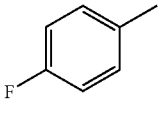 | —H | H | | Mol. Wt. = 281 | 79 |

$^1$H: 1.55(1H, s); 3.3(2H, dd, J=6.0 Hz); 4.2(2H, t, J=6.0 Hz); 6.25(2H, dd, J=3.6 Hz); 7.1(2H, t, J=7.0 Hz); 7.4(1H, m, J=9.0 Hz); 7.42–7.47(6H, m)

| 59. | | —COOEt | H | | Mol. Wt. = 353 | 55 |

$^1$H: 1.10(3H, t, J=7.0 Hz); 1.60(1H, s, OH); 3.35(2H, t, J=6.0 Hz); 4.00(2H, t, J=6.0 Hz); 4.10(2H, t, J=Hz); 6.69(1H, s); 7.10(2H, t, J=9.9 Hz); 7.39–7.46(7H, m)

| 60. | i-Pr | H | H | CH$_3$ | Mol. Wt. = 167 | 68 |

$^1$H: 1.2(6H, d, J=8 Hz); 2.2(3H, s); 2.94(1H, septet); 3.77(2H, t, J=6.9 Hz); 3.97(2H, t, J=6.9 Hz); 5.8(2H, s).

PREPARATION 2

1-(2-hydroxyethyl)-2-ethyl-1H-pyrrole (compound no. 61)

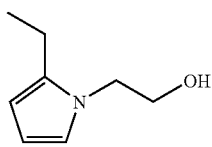

A mixture containing 1-(2-bromoethyl)-2-acetyl-1H-pyrrole (8.2 g), ethylene glycol (45 mL), 85% potassium hydroxide pellets (8.91 g) and 80% hydrazine hydrate (6.76 mL) was stirred at 200° C. for about 1.5 hr along with simultaneous distillation of volatile materials. The product obtained was extracted with ethyl acetate (2×100 mL). The ethyl acetate layer was washed with water (100 mL), dried over sodium sulfate, filtered and evaporated. The crude product obtained was purified by column chromatography (silica gel 100–200), using ethyl acetate:pet. ether (8:2) as an eluent to obtain 2.2 g of the title compound.

TABLE 2

| Comp. No. | Substituents on the pyrrole ring in (1e) | | | | | |
|---|---|---|---|---|---|---|
| | $R^1$ | $R^2$ | $R^3$ | $R^4$ | | |
| 61. | $C_2H_5$ | H | H | H | Mol. Wt. = 139 | Yield = 42% |
| | $^1$H: 1.26(3H, t, J=6.0Hz); 2.59(2H, q, $J_1$=7.62Hz, $J_2$=7.44Hz); 3.84(2H, t, J=5.4Hz); 3.98(2H, t, J=5.35Hz); 5.92–5.93(1H, m); 6.11(1H, t, J=3.12Hz); 6.65(1H, t, J=2.22Hz). | | | | | |

PREPARATION 3

1-(2-Bromoethyl)-1H-pyrrole-2-carbaldehyde (compound no. 62)

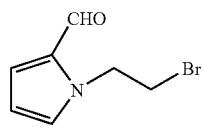

(Compound No. 62)

A mixture of 2-formylpyrrole (1 g), potassium hydroxide (2.3 g) and dry DMSO (20 mL) was stirred under nitrogen atmosphere. 1,2-dibromoethane (7.9 g) was added dropwise at 20–25° C. and stirred till the reaction is complete. Water (50 mL) was added and the reaction mixture was extracted with diethyl ether (3×50 mL). The combined organic layer was washed with water (30 mL), followed by brine (30 mL) and was dried over $Na_2SO_4$. The solvent was evaporated and the compound obtained was purified by column chromatography (silica gel 100–200) using ethyl acetate: hexane (2:8) as an eluent to obtain the title compound.

In like manner to that described in Preparation 3, following compounds of the formula (1c) (Given in Table 3) were prepared from the appropriately substituted pyrrole derivatives. The latter can be synthesized by using various routes found in literature.

TABLE 3

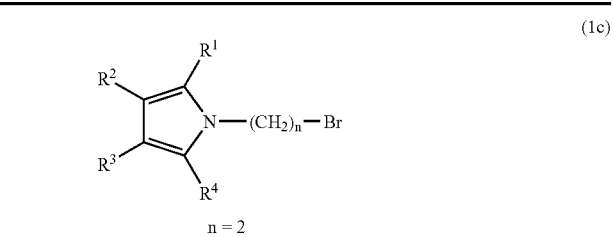

(1c)

n = 2

| Comp. No. | Substituents on the pyrrole ring in (1c) | | | | | |
|---|---|---|---|---|---|---|
| | $R^1$ | $R^2$ | $R^3$ | $R^4$ | | |
| 62. | CHO | H | H | H | Mol. Wt. = 202 | Yield = 47% |
| | $^1$H: 3.65(2H, t, J=6 Hz); 4.65(2H, t, J=6 Hz); 6.33(1H, m); 6.95–7.05(2H, m); 9.5(1H, m). | | | | | |
| 63. | $COCH_3$ | H | H | H | Mol. Wt. = 216 | Yield = 32% |
| | $^1$H: 2.44(3H, s); 3.67(2H, t, J=6 Hz); 4.65(2H, t, J=6 Hz); 6.16–6.18(1H, m); 6.94(1H, t, J=6 Hz); 7.01–7.03(1H, m). | | | | | |
| 64. | —COPh | H | H | H | Mol. Wt. = 277 | Yield = 66% |
| | $^1$H: 3.79(2H, t, J=6.08 Hz); 4.75(2H, t, J=6.12 Hz); 6.22(1H, dd, J=2.57 Hz, $J_2$=2.53 Hz); 6.825(1H, dd, $J_1$=1.64 Hz, $J_2$=1.67 Hz); 7.06–7.08(1H, m); 7.45–7.80(5H, 1m) | | | | | |

PREPARATION 4

Preparation of 1-(2-hydroxyethyl)-2-methylthio-1H-pyrrole (compound no. 65)

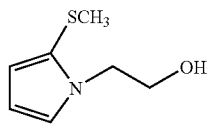
(Compound No. 65)

To a mixture of potassium hydroxide (7.9 g) and dry DMSO (90 mL), 2-thiomethylpyrrole (4 g) was added dropwise at 20–25° C., with stirring under nitrogen atmosphere. Stirring was continued for 1 hr at 20–25° C. Ethyl bromoacetate (11.85 g) was added dropwise at 20–25° C. and stirring was continued for 2 hr. In the reaction mixture (100 mL) DM water was added and pH was made acidic (pH=3) with 20% HCl (30 mL). The reaction mixture was extracted with diethyl ether (2×50 mL). The combined organic extract was washed with DM water (50 mL), saturated brine (50 mL) and dried over $Na_2SO_4$. The solvent was evaporated to obtain 2-thiomethylpyrrol-1-yl-acetic acid (4.5 g).

To a suspension of sodium borohydride (1.77 g) in tetrahydrofuran (50 mL), 2-thiomethylpyrrol-1-yl-acetic acid (4 g) dissolved in THF (50 mL) was added dropwise at 20° C.–25° C. within 10–15 min under nitrogen atmosphere. When the evolution of hydrogen gas ceases, the reaction mixture was cooled to 5–10° C. and iodine (5.94 g) dissolved in THF (20 mL) was added dropwise at 5° C.–10° C. and was stirred further for 2 hrs at 20° C.–25° C. The reaction mixture poured in mixture of ice-cold KOH solution (10 mL) and DM water (50 mL). The solution was extracted with ethyl acetate (2×50 mL). The organic extract was washed with water (30 mL), brine (30 mL) and dried over $Na_2SO_4$. The solvent was evaporated under reduced pressure, to obtain the title compound.

In like manner to that described in Preparation 4, following compounds of the formula (1e) (Given in Table 4) were prepared from the appropriately substituted pyrrole. The latter can be synthesized by using various routes found in literature.

TABLE 4

(1e)

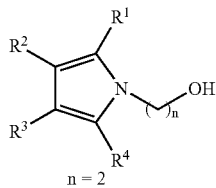

n = 2

| Comp. No. | $R^1$ | $R^2$ | $R^3$ | $R^4$ | | |
|---|---|---|---|---|---|---|
| 65. | $SCH_3$ | H | H | H | Mol. Wt. = 157 | Yield = 90% |
| | $^1$H: 2.2(3H, s); 3.85(2H, t, J=6.0 Hz); 4.1(2H, t, J=5.5 Hz); 6.14(1H, dd); 6.38(1H, dd); 6.85(1H, dd) | | | | | |
| 66. | C₆H₅ | H | $CH_3$ | H | Mol. Wt. = 201 | Yield = 13% |
| | $^1$H: 2.05(3H, s); 3.75(2H, t, J=6 Hz); 4.03(2H, t, J=5.5 Hz); 6.07(1H, s); 6.62(1H, s); 7.27–7.42(5H, m). | | | | | |
| 67. | $CH_3$ | H | C₆H₅ | H | Mol. Wt. = 201 | Yield = 57% |
| | $^1$H: 2.24(3H, s); 3.82–4.01(4H, m); 6.19(1H, s); 6.9(1H, s); 7.1–7.4(5H, m). | | | | | |
| 68. | $CH_3$ | H | $CH_3$ | H | Mol. Wt. = 139 | Yield = 40.4% |
| | $^1$H: 2.02(3H, s); 2.19(3H, s); 3.7–3.9(4H, m); 5.73(1H, s); 6.38(1H, s). | | | | | |

PREPARATION 5

Preparation of Methyl 2-(5-ethyl-2-phenyl-1H-pyrrol-1-yl)ethane sulfonate (Compound No. 90)

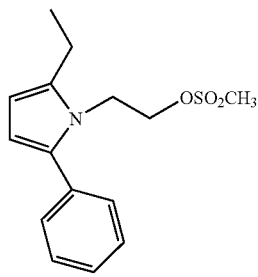

To a solution of compound 17 (4.0 g in 30 mL dichloromethane) obtained in preparation 1, triethylamine (2.75 mL) was added followed by addition of methanesulfonyl chloride (2.1 g) at 0° C. The reaction mixture was stirred at 0° C. for 1 h under nitrogen atmosphere. The mixture was warmed to temperature of about 20 to 25° C. and was stirred at that temperature for about 2 h (TLC). After the completion of the reaction, water (30 mL) was added and the organic layer was separated. The mixture was washed with saturated sodium bicarbonate solution (20 mL), water (20 mL) and then with brine (20 mL) and dried over $Na_2SO_4$. The organic layer was concentrated under reduced pressure. The crude substance was used in the next step without purification.

In like manner to that described in Preparation 5 following compounds of the formula (1c) (given in Table 5) were prepared from the appropriately substituted pyrrole derivatives (1e) described earlier.

TABLE 5

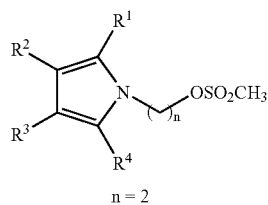

(1e)

n = 2

| Comp. No. | $R^1$ | $R^2$ | $R^3$ | $R^4$ | | |
|---|---|---|---|---|---|---|
| 69. | $CH_3$ | H | $CH_3$ | H | Mol. Wt. = 217 | Yield = 98% |
| 70. | $C_2H_5$ | H | H | H | Mol. Wt. = 217 | Yield = 90% |

$^1$H: 1.29(3H, t, J=2.64 Hz); 2.58(2H, q, J=7.32 Hz); 2.71(3H, s); 4.15(2H, t, J=5.52 Hz); 4.41(2H, t, J=5.5 Hz); 5.92(1H, m); 6.11(1H, t, J=3.16 Hz); 6.63(1H, t, J=2.26 Hz).

| | | | | | | |
|---|---|---|---|---|---|---|
| 71. | $CH_3$ | H | H | $CH_2CH_3$ | Mol. Wt. = 231 | Yield = 56% |

$^1$H: 1.26(3H, t, J=7.4 Hz); 2.25(3H, m) 2.57(2H, q, J=7.42 Hz); 2.69(3H, s); 4.12(2H, t, J=5.9 Hz); 4.34(2H, t, J=5.9 Hz); 5.8–5.83(2H, m).

| | | | | | | |
|---|---|---|---|---|---|---|
| 72. | $CH_3$ | H | H | $(CH_2)_2CH_3$ | Mol. Wt. = 246 | Yield = 45% |

$^1$H: 1.02(3H, t, J=7 Hz); 1.65(2H, m); 2.25(3H, s); 2.5(2H, t, J=7.7 Hz); 2.69(3H, s); 4.1(2H, t, J=5.9 Hz); 4.35(2H, t, J=5.9 Hz); 5.8–5.83(2H, m)

| | | | | | | |
|---|---|---|---|---|---|---|
| 73. | $CH_3$ | H | H | $(CH_2)_3CH_3$ | Mol. Wt. = 259 | Yield = 72% |

$^1$H: 0.95(3H, t, J=7.2 Hz); 1.44–1.46(2H, m); 1.58–1.62(2H, m); 2.25(3H, s); 2.5(2H, t, J=5.9 Hz); 2.7(3H, s); 4.1(2H, t, J=5.9 Hz); 4.39(2H, t, J=5.9 Hz); 5.8(2H, s).

| | | | | | | |
|---|---|---|---|---|---|---|
| 74. | $CH_3$ | H | H | phenyl | Mol. Wt. 279 | Yield = 98% |

$^1$H: 2.34(3H, s); 2.83(3H, s); 4.11(2H, t, J=5.7 Hz); 4.27(2H, t, J=5.7 Hz); 5.96(1H, d, J=3.4 Hz); 6.10(1H, d, J=3.4 Hz); 7.27–7.43(5H, m).

| | | | | | | |
|---|---|---|---|---|---|---|
| 75. | $CH_3$ | H | phenyl | H | Mol. Wt. = 279 | Yield = 86% |

$^1$H: 2.28(3H, s); 2.73(3H, m); 4.16(2H, d, J=5.4 Hz); 4.4(2H, d, J=5.4 Hz); 6.2(1H, s); 6.9(1H, s); 7.17(1H, d, J=6.75 Hz); 7.3(2H, d, J=7.0 Hz); 7.46(2H, d, J=7.0 Hz).

TABLE 5-continued

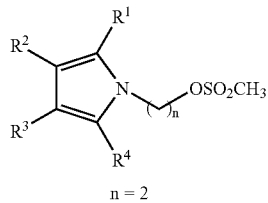

(1e)

n = 2

| Comp. No. | Substituents on the pyrrole ring in (1c) | | | | | |
|---|---|---|---|---|---|---|
| | $R^1$ | $R^2$ | $R^3$ | $R^4$ | | |
| 76. | $CH_3$ | H | H | 4-methylphenyl ($H_3C$—C$_6H_4$—) | Mol. Wt. = 293 | Yield = 68% |

$^1$H: 2.33(3H, s); 2.38(3H, s); 2.65(3H, s); 4.12(2H, t, J=6.3 Hz); 4.25(2H, t, J=6.3 Hz); 5.95(1H, d, J=3.4 Hz); 6.10(1H, d, J=3.4 Hz); 7.19–7.25(4H, m).

| 77. | $CH_3$ | H | H | 3-methylphenyl | Mol. Wt. = 293 | Yield = 95% |

$^1$H: 2.33(3H, s); 2.38(3H, s); 2.66(3H, s); 4.12(2H, t, J=5.8 Hz); 4.27(2H, t, J=5.7 Hz); 5.95(1H, d, J=3.37 Hz); 6.09(1H, d, J=3.42 Hz); 7.12–7.16(2H, m); 7.25–7.31(2H, m).

| 78. | $CH_3$ | H | H | 2-methylphenyl | Mol. Wt. = 293 | Yield = 55% |

$^1$H: 2.34(3H, s); 2.38(3H, s); 2.67(3H, s); 4.13(2H, t, J=5.8 Hz); 4.27(2H, t, J=5.7 Hz); 5.96(1H, d, J=3.36 Hz); 6.1(1H, d, J=3.39 Hz); 7.13–7.29(4H, m).

| 79. | $CH_3$ | H | H | 4-methoxyphenyl | Mol. Wt. = 309 | Yield = 62% |

$^1$H: 2.3(3H, s); 2.67(3H, s); 3.8(3H, s); 4.12(2H, t, J=5.45 Hz); 4.24(2H, t, J=5.45 Hz); 5.9(1H, d, J=3.39 Hz); 6.0(1H, d, J=3.39 Hz); 6.95(2H, d, J=6.78 Hz); 7.26(2H, d, J=6.78 Hz).

| 80. | $CH_3$ | H | H | 4-bromophenyl | Mol. Wt. = 358 | Yield = 70% |

$^1$H: 2.33(3H, s); 2.7(3H, s); 4.13–4.15(2H, m); 4.2–4.25(2H, m); 5.97(1H, d, J=3.4 Hz); 6.12(1H, d, J=3.4 Hz); 7.21–7.26(2H, m); 7.52–7.55(2H, m).

| 81. | $CH_3$ | H | H | 4-fluorophenyl | Mol. Wt. = 297 | Yield = 90% |

$^1$H: 2.3(3H, s); 2.7(3H, s); 3.6(2H, t, J=6.0 Hz); 4.1(2H, d, J=5.6 Hz); 4.22(2H, d, J=5.4 Hz); 5.9(1H, d, J=3.4 Hz); 6.0(1H, d, J=3.4 Hz); 7.04–7.1(2H, m); 7.2–7.3(2H, m).

| 82. | $CH_3$ | H | H | 4-chlorophenyl | Mol. Wt. = 313.5 | Yield = 82% |

TABLE 5-continued

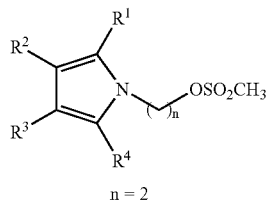

(1e)

n = 2

| Comp. No. | Substituents on the pyrrole ring in (1c) | | | | | |
|---|---|---|---|---|---|---|
| | R¹ | R² | R³ | R⁴ | | |
| | ¹H: 2.3(3H, s); 2.69(3H, s); 4.15(2H, d, J=6.3 Hz); 4.25(2H, d, J=6.3 Hz); 5.96–5.97(1H, dd); 6.1(1H, d, J=3.4 Hz); 7.27–7.4(4H, m). | | | | | |
| 83. | Ph | H | CH₃ | H | Mol. Wt. = 279 | Yield = 90% |
| | ¹H: 2.13(3H, s); 2.73(3H, m); 4.2–4.28(4H, m); 6.05(1H, s); 6.59(1H, s); 7.29–7.43(5H, m). | | | | | |
| 84. | CH₃ | H | Ph | Ph | Mol. Wt. = 355 | Yield = 90% |
| | ¹H: 2.3(3H, s); 2.73(3H, s); 4.09–4.14(4H, m); 6.2(1H, s); 7.0–7.4(10H, m). | | | | | |
| 85. | i-Pr | H | H | i-Pr | Mol. Wt. = 272 | Yield = 37% |
| | ¹H: 1.23–1.25(12H, d, J=6.7 Hz); 2.76(3H, s); 2.82–2.99(2H, m); 4.18(2H, m); 4.33(2H, m); 5.86(2H, s) | | | | | |
| 86. | i-Pr | H | H | Ph | Mol. Wt. = 307 | Yield = 100% |
| | ¹H: 1.30(6H, t, J=6.78 Hz); 2.65(3H, m); 2.96–3.00(1H, m); 4.04(2H, t, J=6 Hz); 4.32(2H, t, J=6 Hz); 6.0(1H, d, J=3.54 Hz); 6.12(1H, d, J=3.54 Hz); 7.32–7.43(5H, m). | | | | | |
| 87. | i-Pr | Ph-NHCO | H | 4-F-C₆H₄ | Mol. Wt. = 444 | Yield = 15% |
| | ¹H: 1.5–1.52(6H, d, J=7.1 Hz); 2.84(3H, s); 3.44–3.52(1H, m); 4.12–4.15(2H, t, J=6.4 Hz); 4.3–4.34(2H, t, J=6.4 Hz); 6.32(1H, s); 7.12–7.18(3H, t, J=8.5 Hz); 7.3–7.4(4H, m); 7.56–7.59(2H, d, J=7.6 Hz). | | | | | |
| 88. | SCH₃ | H | H | H | Mol. Wt. = 235 | Yield = 95% |
| | ¹H: 2.29(3H, s); 2.77(3H, s); 4.35–4.48(4H, m); 6.17(1H, dd); 6.4(1H, dd); 6.85(1H, dd). | | | | | |
| 89. | C₂H₅ | H | H | C₂H₅ | Mol. Wt. = 245 | Yield = 82% |
| | ¹H: 1.27(6H, t, 7.3 Hz); 2.58(4H, q, J=7.4 Hz); 2.7(3H, s); 4.11(2H, t, J=6.04 Hz); 4.34(2H, t, J=6.2 Hz); 5.8(2H, s) | | | | | |
| 90. | C₂H₅ | H | H | Ph | Mol. Wt. = 293 | Yield = 92% |
| | ¹H: 1.33(3H, t, J=7.3 Hz); 2.6–2.7(5H, m); 4.1(2H, t, J=5.9 Hz); 4.28(2H, t, J=5.9 Hz); 5.9(1H, d, J=3.59 Hz); 6.1(1H, d, J=3.48 Hz); 7.3–7.43(5H, m) | | | | | |

TABLE 5-continued

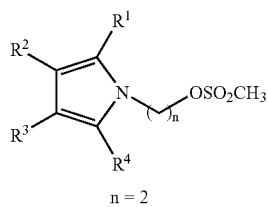

(1e)

n = 2

| Comp. No. | Substituents on the pyrrole ring in (1c) | | | | | |
|---|---|---|---|---|---|---|
| | R[1] | R[2] | R[3] | R[4] | | |
| 91. | CH$_3$ | H | H | H$_2$C–CH$_2$–C$_6$H$_5$ (phenethyl) | Mol. Wt. = 307 | Yield = 96% |

[1]H: 2.24(3H, s); 2.65(3H, s); 2.8–2.85(2H, m); 2.94–2.99(2H, m); 4.03(2H, t, J=5.8 Hz); 4.28(2H, t, J=5.8 Hz); 5.84(1H, d, J=3.39 Hz); 5.9(1H, d, J=3.39 Hz); 7.18–7.23(3H, m), 7.31–7.32(2H, m)

| 92. | CH$_3$ | H | H | 3-methoxyphenyl | Mol. Wt. = 309 | Yield = 75% |

[1]H: 2.34(3H, s); 2.68(3H, s); 3.83(3H, s); 4.16(2H, t, J=5.6 Hz); 4.29(2H, t, J=5.9 Hz); 5.96(1H, d, J=3.36 Hz); 6.12(1H, d, J=3.42 Hz); 6.94–7.34(4H, m)

| 93. | CH$_3$ | H | H | cyclohexyl | Mol. Wt. = 285 | Yield = 84% |

[1]H: 1.21–1.88(10H, m); 2.24(3H, s) 2.24–2.45(1H, m); 2.7(3H, s); 4.12(2H, t, J=5.94 Hz); 4.34(2H, t, J=6 Hz); 5.79–5.83(2H, m)

| 94. | CH$_3$ | H | H | 4-biphenyl | Mol. Wt. = 355 | Yield = 74% |

[1]H: 2.35(3H, s); 2.68(3H, s); 4.17(2H, t, J=5.59 Hz); 4.33(2H, t, J=5.55 Hz); 5.99(1H, d, J=2.49 Hz); 6.12(1H, d, J=3.18 Hz); 7.2–7.65(9H, m)

| 95. | CH$_3$ | H | H | 2-furyl | Mol. Wt. = 269 | Yield = 84% |

[1]H: 2.31(3H, s), 2.69(3H, s); 4.35(2H, t, J=5.2 Hz); 4.43(2H, J=4.9 Hz); 5.91–5.92(1H, dd, J1=0.68 Hz, J2=0.73 Hz); 6.3(2H, d, J=3.5 Hz); 6.35(1H, d, J=2.8 Hz); 7.41–7.42(1H, dd, J1=0.7 Hz, J2=0.65 Hz)

| 96. | CH$_3$ | H | H | 5-methyl-2-furyl | Mol. Wt. = 283 | Yield = 90% |

TABLE 5-continued

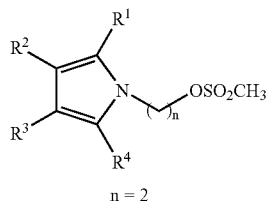

(1e)

n = 2

| Comp. No. | Substituents on the pyrrole ring in (1c) | | | |
|---|---|---|---|---|
| | $R^1$ | $R^2$ | $R^3$ | $R^4$ |

$^1$H: 2.30(3H, s); 2.32(3H, s); 2.68(3H, s), 3.88(2H, t, J=5.2 Hz);
4.20(2H, t, J=4.9 Hz); 5.93(1H, d, J=3.5 Hz); 6.33(1H, d, J=3.5 Hz);
6.22(1H, d, J=3.09 Hz); 6.27(1H, d, J=3.54 Hz)

97. $CH_3$  H  H  [4-methylthiophenyl group]  Mol. Wt. = 325  Yield = 80%

$^1$H: 2.33(3H, s); 2.5(3H, s); 2.68(3H, s); 4.14(2H, t, J=5.82 Hz);
4.25(2H, t, J=5.64 Hz); 5.96(1H, d, J=3.33 Hz); 6.0(1H, d, J=3.4 Hz); 7.25–7.27(4H, m)

98. $CH_3$  H  H  [4-cyanophenyl group]  Mol. Wt. = 304  Yield = 90%

$^1$H: 2.36(3H, s); 2.73(3H, s); 4.16(2H, t, J=5.6 Hz); 4.32(2H, t, J=5.8 Hz),
6.03(1H, d, J=3.5 Hz); 6,238(1H, d, J=3.54 Hz); 7.45(2H, d, J=8.5 Hz); 7.69(2H, d, J=8.5 Hz)

99. $CH_3$  H  H  [4-phenoxyphenyl group]  Mol. Wt. = 371  Yield = 85%

$^1$H: 2.33(3H, s); 2.69(3H, s); 4.15(2H, t, J=5.5 Hz); 4.26(2H, t, J=5.7 Hz);
5.96(1H, d, J=3.29 Hz); 6.09(1H, d, J=3.4 Hz); 7.0–7.39(9H, m)

100. $CH_3$  H  H  [N-(p-tolylsulfonyl)-2-methylpyrrolyl group]  Mol. Wt. = 422  Yield = 93%

$^1$H: 2.3(3H, s); 2.4(3H, s); 2.75(3H, s); 3.96(2H, t, J=5.8 Hz);
4.18(2H, t, J=5.98 Hz); 5.68(1H, d, J=3.47 Hz); 5.86(1H, d, J=3.38 Hz);
6.27–6.28(1H, dd, J1=1.72 Hz, J2=1.75 Hz); 6.32(1H, t, J=3.3 Hz);
7.18(2H, d, J=8.3 Hz); 7.41(2H, d, J=8.3 Hz); 7.46–7.47(1H, dd, J1=1.7 Hz, J2=1.72 Hz)

101. $CH_3$  H  H  [2,5-dimethoxy-4-methylphenyl group]  Mol. Wt. = 339  Yield = 78%

$^1$H: 2.26(3H, s); 2.7(3H, s); 3.89(3H, s); 3.92(3H, s); 4.15–4.25(4H, m);
5.95(1H, d, J=3.0 Hz); 6.0(1H, d, J=3.1 Hz); 6.87–7.26(3H, m)

TABLE 5-continued

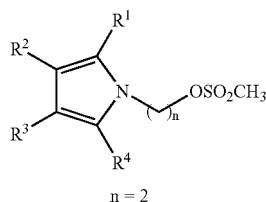

(1e)

n = 2

| Comp. No. | Substituents on the pyrrole ring in (1c) | | | | | |
|---|---|---|---|---|---|---|
| | $R^1$ | $R^2$ | $R^3$ | $R^4$ | | |
| 102. | $CH_3$ | H | H | ―⟨C6H4⟩―NHCOCH$_3$ | Mol. Wt. = 336 | Yield = 90% |

$^1$H: 2.1(3H, s); 2.29(3H, s); 2.69(3H, s); 4.11(2H, t, J=5.35 Hz);
4.27(2H, t, J=5.6 Hz); 7.29(2H, d, J=8.5 Hz); 7.58(2H, d, J=8.5 Hz)(no peak of py. proton)

| 103. | $CH_3$ | H | H | ―⟨C6H4⟩―O―CH$_2$CH$_2$―N(piperidine) | Mol. Wt. = 406 | Yield = 93% |

$^1$H: 1.45–1.65(6H, m); 2.32(3H, s); 2.51–2.52(4H, m); 2.67(3H, s);
2.8(2H, t, J=6 Hz); 4.1–4.15(4H, m); 4.2(2H, t, J=5.5 Hz); 5.9(1H, d, J=3.33 Hz);
6.0(1H, d, J=3.4 Hz); 6.96(2H, d, J=8.5 Hz); 7.26(2H, d, J=8.5 Hz)

| 104. | $CH_3$ | H | H | ―⟨C6H4⟩―O―CH$_2$CH=CH$_2$ | Mol. Wt. = 335 | Yield = 73% |

$^1$H: 2.32(3H, s); 2.67(3H, s); 4.14(2H, t, J=5.3 Hz); 4.23(2H, t, J=5.5 Hz);
4.57(2H, d, J=5.3 Hz) Hz); 5.32–5.47(1H, dd, J$_1$=1.35 Hz, J$_2$=1.53 Hz);
5.4–5.48(1H, dd, J=1.5 Hz, 1.5 Hz); 5.9(1H, d, J=3.36 Hz); 6.05(1H, d, J=3.42 Hz);
6.08–6.14(1H, m); 6.94(2H, d, J=8.5 Hz); 6.728(2H, d, J=8.5 Hz)

| 105. | $CH_3$ | H | H | ―⟨C6H4⟩―S(=O)$_2$―CH$_3$ | Mol. Wt. = 357 | Yield = 93% |

$^1$H: 2.36(3H, s); 2.74(3H, s); 3.1(3H, s); 4.15(2H, t, J=5.86 Hz);
4.34(2H, t, J=5.83 Hz); 6.03(1H, d, J=3.5 Hz); 6.25(1H, d, J=3.54 Hz);
7.5(2H, d, J=8.5 Hz); 7.97(2H, d, J=8.5 Hz)

| 106. | $CH_3$ | H | H | ―⟨C6H4⟩―O―CH$_2$―cyclohexyl | Mol. Wt. = 391 | Yield = 90% |

$^1$H: 1.03–1.69(11H, m); 2.3(3H, s); 2.67(3H, s); 3.7(2H, t, J=6.24 Hz);
4.11(2H, t, J=3.3 Hz); 4.2(2H, t, J=3.3 Hz); 5.9(1H, d, J=3.39 Hz);
6.04(1H, d, J=3.39 Hz); 6.91(2H, d, J=8.5 Hz); 7.24(2H, d, J=8.5 Hz)

| 107. | $CH_3$ | H | H | 2-thienyl | Mol. Wt. = 285 | Yield = 94% |

$^1$H: 2.3(3H, s); 2.6(3H, s); 4.29(4H, m); 5.9(1H, d, J=3.4 Hz);
6.2(1H, d, J=3.4 Hz); 6.9–7.01(1H, m); 7.05–7.06(1H, m); 7.29(1H, m)

TABLE 5-continued

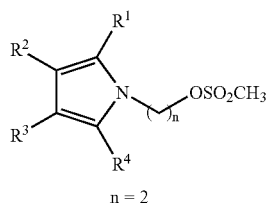

(1e)

n = 2

| Comp. No. | Substituents on the pyrrole ring in (1c) | | | | | |
|---|---|---|---|---|---|---|
| | $R^1$ | $R^2$ | $R^3$ | $R^4$ | | |
| 108. | $CH_3$ | H | H | 4-OBn-C$_6$H$_4$ | Mol. Wt. = 385 | |

$^1$H: 2.3(3H, s); 2.7(3H, s); 4.13(2H, t, J=5.3 Hz); 4.2(2H, t, J=5.3 Hz);
5.09(2H, s); 5.9(1H, d, J=3.3 Hz); 6.0(1H, d, J=3.3 Hz); 7.0(2H, d, J=8.7 Hz);
7.25–7.46; (7H, m)

| 109. | H | H | H | $C_6H_5$ | Mol. Wt. = 265 | Yield = 40% |

$^1$H: 2.7(3H, s); 4.12(4H, m); 6.22(2H, m); 6.8(1H, m); 7.3–7.9(5H, m)

| 110. | $CH_3$ | H | H | 5-Cl-thiophen-2-yl | Mol. Wt. = 320 | Yield = 98% |

$^1$H: 2.3(3H, s); 2.75(3H, s); 4.29(4H, m); 5.9(1H, d, J=3.4 Hz);
6.2(1H, d, J=3.5 Hz); 6.78(1H, d, J=3.78 Hz); 6.88(1H, d, J=3.4 Hz)

| 111. | $CH_3$ | H | H | 4-OEt-C$_6$H$_4$ | Mol. Wt. = 323 | Yield = 99% |

$^1$H: 1.44(3H, t, J=6.98 Hz); 2.33(3H, s); 2.67(3H, s); 4.05(2H, t, J=6.98 Hz);
4.09(2H, t, J=5.0 Hz); 4.22(2H, m); 5.94(1H, d, J=3.24 Hz); 6.04(1H, d, J=3.34 Hz);
6.93(2H, d, J=9.43 Hz); 7.26(2H d, J=8.63 Hz)

| 112. | $CH_3$ | H | H | 5-Br-thiophen-2-yl | Mol. Wt. = 299 | 96% |

$^1$H: 2.3(3H, s); 2.4(3H, s); 2.69(3H, s); 4.29(4H, s); 5.9(1H, d, J=3.4 Hz);
6.17(1H, d, J=3.5 Hz); 6.7(1H, d, J=3.4 Hz); 6.77(1H, d, J=3.4 Hz)

| 113. | $CH_3$ | $CH_3$ | H | $C_6H_5$ | Mol. Wt. = 293 | Yield = 92% |

$^1$H: 2.04(3H, s); 2.24(3H, s); 2.67(3H, s); 4.12(2H, t, J=5.6 Hz);
4.24(2H, t, J=5.6 Hz); 6.01(1H, s); 7.2–7.4(5H, m)

| 114. | $CH_3$ | H | H | cyclopropyl | Mol. Wt. = 243 | Yield = 95% |

$^1$H: 0.59–0.62(2H, m); 0.82–0.87(2H, m); 1.5–1.6(1H, m); 2.24(3H, s); 2.69(3H, s);
4.27(2H, t, J=5.9 Hz); 4.45(2H, t, J=5.8 Hz); 5.68(1H, d, J=3.3 Hz); 5.75(1H, d, J=3.34 Hz)

TABLE 5-continued

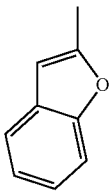

(1e)

n = 2

| Comp. No. | Substituents on the pyrrole ring in (1c) | | | |
|---|---|---|---|---|
| | R¹ | R² | R³ | R⁴ |

115. CH₃    H    H    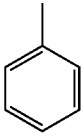    Mol. Wt. = 319    Yield = 81%

¹H: 2.36(3H, s); 2.73(3H, s); 3.93(2H, t, J=5.77 Hz); 4.32(2H, t, J=5.76 Hz);
6.0(1H, d, J=3.63 Hz); 6.57(1H, d, J=3.63 Hz); 6.69(1H, s); 7.54–7.72(4H, m)

116. CH₃    COOCH₃    H    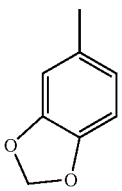    Mol. Wt. = 337    Yield = 84%

¹H: 2.64(3H, s); 2.73(3H, s); 3.81(3H, s); 4.11(2H, t, J=5.76 Hz);
4.29(2H, t, J=5.76 Hz); 6.56(1H, s); 7.26–7.45(5H, m).

117. CH₃    H    H    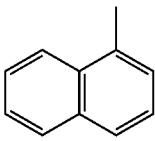    Mol. Wt. = 323    Yield = 85%

¹H: 2.32(3H, s); 2.7(3H, s); 4.14(2H, t, J=5.37 Hz), 4.23(2H, t, J=5.47 Hz);
5.92(1H, d, J=2.85 Hz); 6.0(2H, s); 6.03(1H, d, J=3.39 Hz); 6.74–6.86(3H, m)

118. CH₃    H    H    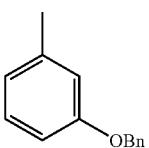    Mol. Wt. = 329    Yield = 97%

¹H: 2.39(3H, s); 2.59(3H, s); 3.91–3.98(2H, m); 4.1–4.16(2H, m);
6.07(1H, d, J=3.33 Hz); 6.17(1H, d, J=3.36 Hz); 7.43–7.90(7H, m)

119. CH₃    H    H        Mol. Wt. = 385    Yield = 100%

¹H: 2.31(3H, s); 2.62(3H, s); 4.06(2H, t, J=5.56 Hz); 4.18(2H, t, J=5.65 Hz);
5.1(2H, s); 5.94(1H, d, J=3.03 Hz); 6.1(1H, d, J=3.42 Hz); 6.92–7.44(9H, m)

TABLE 5-continued

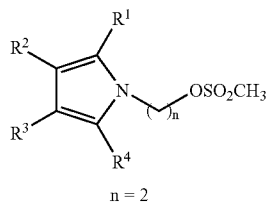

(1e)

n = 2

| Comp. No. | Substituents on the pyrrole ring in (1c) | | | | | |
|---|---|---|---|---|---|---|
| | $R^1$ | $R^2$ | $R^3$ | $R^4$ | | |
| 120. | $CH_3$ | H | H | 5-bromo-2-thienyl | Mol. Wt. = 364 | Yield = 96% |

$^1$H: 2.32(3H, s); 2.73(3H, s); 4.28(4H, s); 5.9(1H, d, J=3.5 Hz);
6.2(1H, d, J=3.54 Hz); 6.7(1H, d, J=3.75 Hz); 7.02(1H, d, J=3.81 Hz)

| 121. | $CH_3$ | H | H | 4-isopropoxyphenyl | Mol. Wt. = 337 | Yield = 100% |

$^1$H: 1.36(6H, d, J=6.03 Hz); 2.32(3H, s); 2.66(3H, s); 4.13(2H, t, J=5.29 Hz);
4.22(2H, t, J=5.53 Hz); 4.53–4.61(1H, m); 5.92(1H, d, J=3.36 Hz); 6.03(1H, d, J=3.39 Hz);
6.90(2H, d, J=8.7 Hz); 7.24(2H, d, J=8.1 Hz)

| 122. | $CH_3$ | H | $CH_3$ | phenyl | Mol. Wt. = 293 | Yield = 95% |

$^1$H: 1.88(3H, s); 2.29(3H, s); 2.68(3H, s); 4.03(2H, t, J=5.26 Hz);
4.13(2H, t, J=5.61 Hz); 5.83(1H, s); 7.26–7.45(5H, m)

| 123. | H | H | H | H | Mol. Wt. = 189 | Yield = 26% |

$^1$H: 2.7(3H, s); 4.19(2H, t, J=5.2 Hz); 4.43(2H, t, J=5.2 Hz);
6.17(2H, t, J=2.1 Hz); 6.7(2H, t, J=2.1 Hz);

| 124. | $CH_3$ | H | H | $CH_3$ | Mol. Wt. = 217 | Yield = 64% |

$^1$H: 2.23(6H, s); 2.68(3H, s); 4.08(2H, t, J=5.8 Hz);
4.34(2H, t, J=5.8 Hz); 5.78(2H, s)

| 125. | i-Pr | phenyl | H | i-Pr | Mol. Wt. = 349 | Yield = 97% |

—

| 126. | i-Pr | H | H | 4-methoxyphenyl | Mol. Wt. = 337 | Yield = 99% |

—

TABLE 5-continued

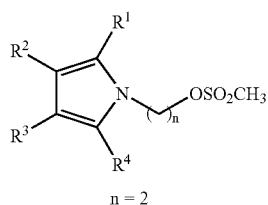

(1e)

n = 2

| Comp. No. | Substituents on the pyrrole ring in (1c) | | | | | |
|---|---|---|---|---|---|---|
| | R¹ | R² | R³ | R⁴ | | |
| 127. | i-Pr | H | H | 4-F-C₆H₄ | Mol. Wt. = 325 | Yield = 72% |

¹H: 1.29(6H, d, J=6.0 Hz); 2.69(3H, s); 2.92–2.99(1H, m);
4.05(2H, t, J=6.0 Hz); 4.27(2H, t, J=6.0 Hz); 6.00(1H, d, J=3.4 Hz);
6.1(1H, d, J=3.4 Hz); 7.07–7.1(2H, t, J=6.0 Hz); 7.30–7.35(2H, m)

| 128. | i-Pr | H | C₆H₅ | 4-F-C₆H₄ | Mol. Wt. = 369 | Yield = 61% |

¹H: 1.35(6H, d, J=7 Hz); 2.76(3H, s); 3.0–3.05(1H, m);
4.05(2H, t, J=6.2 Hz); 4.15(2H, t, J=6 Hz); 6.22(1H, s); 7.07–7.30(9H, m)

| 129. | i-Pr | C₆H₅NHCO | C₆H₅ | 4-F-C₆H₄ | Mol. Wt. = 520 | Yield = 85% |

—

| 130. | i-Pr | C₆H₅NHCO | C₆H₅ | 4-F-C₆H₄ | Mol. Wt. = 534 | Yield = 100% |

—

| 131. | C₆H₅ | H | H | 4-F-C₆H₄ | Mol. Wt. = 359 | Yield = 98% |

—

| 132. | C₆H₅ | —COOEt | H | 4-F-C₆H₄ | Mol. Wt. = 431 | Yield = 98.3% |

| 133. | i-Pr | H | H | CH₃ | Mol. Wt. = 245 | Yield = 97.1% |

¹H: 1.28(6H, d, J=7.7 Hz); 2.25(3H, s); 2.7(3H, s); 2.83–2.92(1H, m);
4.14(2H, t, J=6.9 Hz); 4.34(2H, t, J=6.9 Hz); 5.83(2H, s).

PREPARATION 6

4-[2-(5-Methyl-2-phenylpyrrol-1-yl)ethoxy]benzaldehyde (compound No. 134)

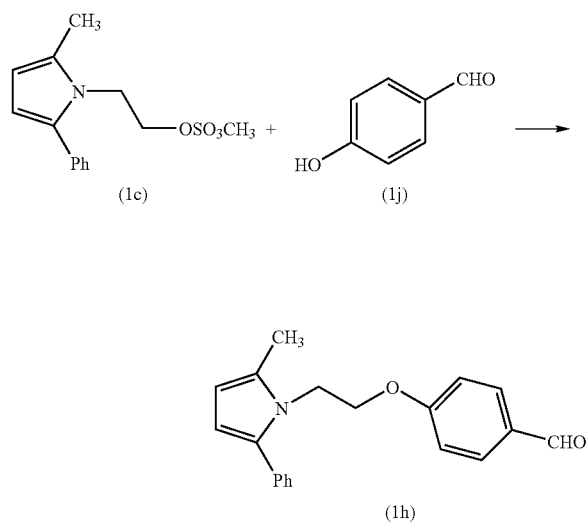

To a suspension of potassium carbonate (16.43 g) in dimethyl formamide (50 mL), 4-hydroxy benzaldehyde (4.37 g) was added and warmed to 90° C. to 95° C. To the solution, methyl 1-[5-methyl-2-phenyl-1H-pyrrol-1yl] ethane sulfonate (10 g) (compound no. 74 dissolved in dimethyl formamide (50 mL) was added within 30 min and the reaction was continued for further 4 hours. The reaction mixture was diluted with water (100 mL) and was extracted with ethyl acetate (3×100 mL), washed with water (3×100 mL), brine (200 mL), and was dried over sodium sulfate. The solvent was evaporated under reduced pressure, to yield the title compound.

PREPARATION 7

(S)-Ethyl 3-{4-[2-(2-ethyl-5-methyl pyrrol-1-yl)ethoxy]phenyl}-2-ethoxypropanoate (Example 5)

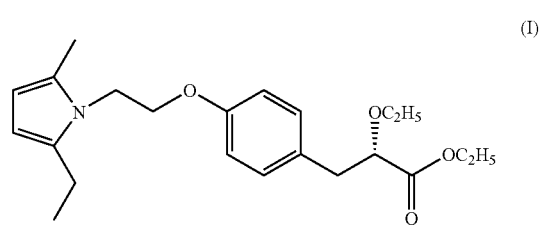

A mixture of (S)-ethyl 3-(4-hydroxyphenyl)-2-ethoxypropionate (2.24 g) and dry potassium carbonate (3.7 g) in dimethyl formamide (30 mL) was stirred at 80° C. for 30 min. Compound. No. 71(Table 5) (2.27 g) was added at 40° C. and stirring was continued at 80° C. for 24 h. The reaction mixture was cooled to 20° C.–25° C. and 20 mL water was added. The reaction mixture was extracted with ethyl acetate (2×40 mL), washed with water (2×40 mL), brine (40 mL) and was dried over sodium sulfate. The organic layer was evaporated under reduced pressure to obtain an oily product. The crude oily product was chromatographed over silica gel (100–200 mesh) using ethyl acetate: petroleum ether (1:9) as an eluent to afford the title compound as a yellow oil (1.654 g, 45%).

PREPARATION 8

(S)-Ethyl 3-{4-[2-(2-formylpyrrol-1-yl)ethoxy]phenyl}-2-ethoxypropanoate (Example 3)

A mixture of (S)-ethyl 3-(4-hydroxyphenyl)-2-ethoxypropionate (1.12 g) and dry potassium carbonate (2.37 g) in dimethyl formamide (20 mL) was stirred at 80° C. for 30 min. 1-(2-bromoethyl)2-carbaldehyde pyrrole (1.0 g, Compound. No. 62) was added at 40° C. and stirring was continued at 80° C. for 24 h. The reaction mixture was cooled to 20° C.–25° C. and 20 mL water was added. The reaction mixture was extracted with ethyl acetate (2×25 mL), washed with water (2×20 mL), brine (25 mL) and was dried over sodium sulfate. The organic layer was evaporated

TABLE 6

| Comp. No. | R¹ | R² | R³ | R⁴ | | |
|---|---|---|---|---|---|---|
| 134. | $CH_3$ | H | H | Phenyl | Mol. Wt. = 306 | Yield = 99% |
| $^1$H: 2.39(3H, s); 4.0(2H, t, J=6.3 Hz); 4.35(2H, t, J=6.3 Hz); 5.98(1H, d, J=3.4 Hz); 6.12(1H, t, J=3.4 Hz); 6.74(2H, d, J=8.7); 7.38–7.42(5H, m); 7.73–7.75(2H, d, J=8.8 Hz); 9.85(1H, s). | | | | | | | under reduced pressure to obtain an oily product. The crude oily product was chromatographed over silica gel (100–200 mesh) using ethyl acetate:petroleum ether (1:9) as an eluent to afford the title compound as a yellow oil (0.4 g, 22%).

PREPARATION 9

(S)-Ethyl 3-{4-[2-(5-ethyl-2-phenyl)pyrrol-1-yl) ethoxy]phenyl}-2-ethoxypropanoate (Example 24)

A mixture of (S)-ethyl 3-(4-hydroxyphenyl)-2-ethoxypropionate (2.3 g), and dry potassium carbonate (2.6 g) in toluene (15 mL) was heated to reflux for 45 min with continuous removal of water using a Dean-Stark water separation. The mixture was cooled to 50° C. and mesylate compound No. 90 (Table 5) (2.9 g) was added. The reaction mixture was continued to reflux for 24 hrs. Later it was cooled to 20° C.–25° C. and toluene was distilled at reduced pressure. To the residue, DM water (30 mL) was added and the crude product was extracted with ethyl acetate (2×25 mL), washed with water (2×20 mL), brine (25 mL) and was dried over sodium sulfate. The solvent was evaporated under reduced pressure to obtain an oily product. The crude oily product was chromatographed over silica gel using ethyl acetate:petroleum ether (60–80) (1:9) as an eluent to afford the title product as a yellow oil (73%).

In like manner to that described in preparation 7–9, the following compounds of the formula (I) (given in Table 7) were prepared from appropriately substituted pyrrole derivatives. described in either Table 5 or obtained from other methods described herein.

TABLE 7

(I)

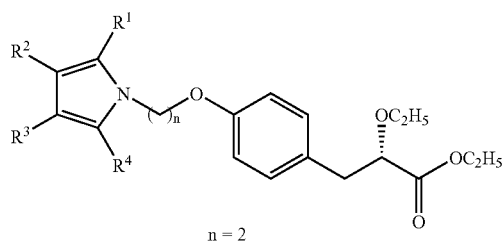

n = 2

| Ex. No. | Substituents on the pyrrole ring in (I) | | | | | |
|---|---|---|---|---|---|---|
| | $R^1$ | $R^2$ | $R^3$ | $R^4$ | | |
| 1. | $CH_3$ | H | $CH_3$ | H | Mol. Wt. = 359 | Yield = 18% |
| | $^1$H: 1.15(3H, t, J=7 Hz); 1.26(3H, t, J=7 Hz); 2.04(3H, s); 2.23(3H, s); 2.91–2.94(2H, m); 3.3–3.39(1H, m); 3.5–3.62(1H, m); 3.92(1H, dd, J=6.0 Hz); 4.12–4.2(6H, m); 5.7(1H, s); 6.4(1H, s); 6.77(2H, d, J=8.6 Hz); 7.15(2H, d, J=8.6 Hz). | | | | | |
| 2. | $C_2H_5$ | H | H | H | Mol. Wt. = 359 | Yield = 18% |
| | $^1$H: 1.15(3H, t, J=7.02 Hz); 1.22(3H, t, J=5.74 Hz); 1.26(3H, t, J=6.03 Hz); 2.62(2H, q); 2.93(2H, d, J=5.7 Hz); 3.3–3.4(1H, m); 3.5–3.6(1H, m); 3.94(2H, t, J=6.0 Hz); 4.12–4.20(5H, m); 5.91(1H, m); 6.10(1H, t, J=3.12 Hz); 6.69–6.75(1H, m); 6.76(2H, d, J=6.7 Hz); 7.13(2H, d, J=8.61 Hz). | | | | | |
| 3. | CHO | H | H | H | Mol. Wt. = 359 | Yield = 22% |
| | $^1$H: 1.1(3H, t, J=6.9 Hz); 1.26(3H, t, J=6.9 Hz); 2.94–4.08(5H, m); 4.08–4.1(2H, m); 4.22(2H, t, J=4.9 Hz); 4.7(2H, t, J=4.9 Hz); 6.23(1H, d); 6.7(2H, d, J=8.5 Hz); 6.97(1H, dd); 7.1(1H, dd); 7.4(2H, d, J=8.5 Hz); 9.5(1H, s). | | | | | |
| 4. | $COCH_3$ | H | H | H | Mol. Wt. = 137 | Yield = 10% |
| | $^1$H: 1.15(3H, t, J=3.48 Hz); 1.2(3H, t, J=5.1 Hz); 2.44(3H, s); 2.93(2H, dd, J=5.55 Hz); 3.0–3.35(2H, m); 3.94(2H, t, J=3.58 Hz); 4.16(2H, q, $J_1$=1.44 Hz, $J_2$=1.41 Hz); 4.21(1H, t, J=5.04 Hz); 4.69(2H, t, J=4.99 Hz); 6.14–6.15(1H, m); 6.75(2H, d, J=8.37 Hz); 6.99–7.01(2H, m) 7.11(2H, d, J=8.64 Hz). | | | | | |
| 5. | $CH_3$ | H | H | $CH_2CH_3$ | Mol. Wt. = 373 | Yield = 45% |
| | $^1$H: 1.15(3H, t, J=7 Hz); 1.22(3H, t, J=7 Hz); 1.27(3H, t, J=7 Hz); 2.28(3H, m); 2.63(2H, q, J=7.4 Hz); 2.9–2.96(2H, m); 3.3–3.6(2H, m); 3.92–4.19(7H, m); 5.8–5.83(2H, m); 6.75(2H, d, J=6.78 Hz); 7.14(2H, d, J=6.78 Hz). | | | | | |
| 6. | $CH_3$ | H | H | $(CH_2)_2CH_3$ | Mol. Wt. = 389 | Yield = 41% |
| | $^1$H: 1.02(3H, t, J=6.9 Hz); 1.15(3H, t, J=6.9 Hz); 1.23(3H, t, J=7.14 Hz); 1.65–1.7(2H, m); 2.28(3H, s); 2.5(2H, t, J=7.75 Hz); 2.9–2.92(2H, m); 3.25–3.5(2H, m); 3.94(1H, t, J=3.66 Hz); 4.0–4.2(6H, m) 5.8–5.83(2H, m); 6.75(2H, d, J=8.5 Hz); 7.15(2H, d, J=8.5 Hz). | | | | | |
| 7. | $CH_3$ | H | H | $(CH_2)_3CH_3$ | Mol. Wt. = 401 | Yield = 46% |
| | $^1$H: 0.95(3H, t, J=7.2 Hz); 1.15(3H, t, J=7 Hz); 1.23(3H, t, J=7 Hz); 1.4–1.47(2H, m); 1.6–1.7(2H, m); 2.28(3H, s); 2.5(2H, t, J=7.7 Hz); 2.9–2.97(2H, m); 3.3–3.39(1H, m); 3.55–3.63(1H, m); 4.04–4.22(7H, m); 5.8–5.83(2H, m); 6.7(2H, d, J=8.5 Hz); 7.15(2H, d, J=8.5 Hz). | | | | | |
| 8. | $CH_3$ | H | H | 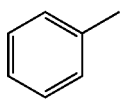 | Mol. Wt. = 421 | Yield = 85% |
| | $^1$H: 1.15(3H, t, J=6.9 Hz); 1.22(3H, t, J=7.1 Hz); 2.37(3H, s); 2.9–2.92(2H, dd); | | | | | |

TABLE 7-continued

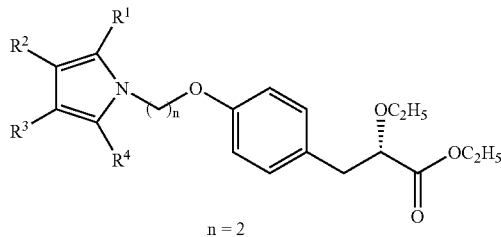

n = 2

| Ex. No. | Substituents on the pyrrole ring in (I) | | | |
|---|---|---|---|---|
| | R¹ | R² | R³ | R⁴ |

3.32–3.35(1H, m); 3.5–3.58(1H, m); 3.9–3.92(3H, m); 4.12–4.19(2H, q); 4.28(2H, t, J=6.5 Hz);
5.96–5.97(1H, d, J=3.1 Hz); 6.1–6.11(1H, d, J=3.11 Hz); 6.6(2H, d, J=8.5 Hz);
7.06–7.09(2H, d, J=8.5 Hz); 7.3–7.4(5H, m).

| 9. | CH₃ | H | 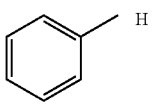 | H | Mol. Wt. = 421 | Yield = 63% |

$^1$H: 1.15(3H, t, J=6.9 Hz); 1.22(3H, t, J=7.1 Hz); 2.37(3H, s); 2.9–2.92(2H, m);
3.3–3.4(1H, m); 3.53–3.62(1H, m); 3.9(1H, t, J=6.6 Hz); 4.1–4.22(6H, m); 6.2(1H, s);
6.8(2H, d, J=8.5 Hz); 6.98(1H, s); 7.15(2H, d, J=8.5 Hz); 7.23–7.33(3H, m); 7.4(2H, t, J=7.1 Hz).

| 10. | CH₃ | H | H | 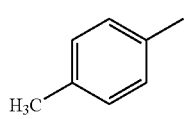 | Mol. Wt. = 435 | Yield = 34% |

$^1$H: 1.16(3H, t, J=6.9 Hz); 1.22(3H, t, J=6.9 Hz); 2.37(3H, s); 2.39(3H, s);
2.9–2.92(2H, m); 3.3–3.37(1H, m); 3.56–3.62(1H, m); 3.91–4.2(5H, m); 4.27(2H, m);
5.95(1H, d, J=3.36 Hz); 6.10(1H, d, J=3.36 Hz); 6.6(2H, d, J=8.5 Hz);
7.0(2H, d, J=6.78 Hz); 7.19(2H, d, J=8.5 Hz); 7.28(2H, d, J=6.78 Hz).

| 11. | CH₃ | H | H | 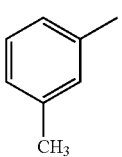 | Mol. Wt. = 435 | Yield = 37% |

$^1$H: 1.15(3H, t, J=6.9 Hz); 1.22(3H, t, J=7.13 Hz); 2.37(6H, s);
2.91(2H, d, J=5.94 Hz); 3.89–3.95(5H, m); 4.15(2H, q, J₁=7.11 Hz, J₂=7.11 Hz);
4.28(2H, t, J=6.63 Hz); 5.95(1H, d, J=3.39 Hz); 6.07(1H, d, J=3.39 Hz); 6.59(2H, d, J=7.62 Hz);
7.07(2H, d, J=8.64 Hz); 7.15–7.28(4H, m).

| 12. | CH₃ | H | H | 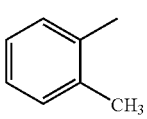 | Mol. Wt. = 435 | Yield = 53% |

$^1$H: 1.15(3H, t, J=6.9 Hz); 1.22(3H, t, J=7.13 Hz); 2.37(6H, s); 2.9–2.92(2H, m);
3.3–3.58(2H, m); 3.89–3.95(3H, m); 4.15(2H, t, J=6 Hz); 4.28(2H, t, J=6 Hz);
5.95(1H, d, J=3.2 Hz); 6.0(1H, d, J=3.2 Hz); 6.6(2H, d, J=7.62 Hz); 7.0(2H, d, J=8.64 Hz);
7.12–7.28(4H, m).

| 13. | CH₃ | H | H | 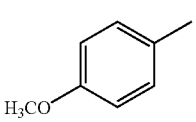 | Mol. Wt. = 451 | Yield = 41% |

$^1$H: 1.1(3H, t, J=7 Hz); 1.22(3H, t, J=7 Hz); 2.36(3H, s); 2.9–2.92(2H, dd);
3.3–3.32(1H, m); 3.52–3.62(1H, m); 3.84(3H, m); 3.9–3.94(3H, m); 4.14(2H, t, J=6.68 Hz);
4.22(2H, t, J=6.68 Hz); 5.9(1H, d, J=3.36 Hz); 6.0(1H, d, J=3.36 Hz); 6.64(2H, d, J=8.58 Hz);
6.95(2H, d, J=6.78 Hz); 7.10(2H, d, J=8.5 Hz); 7.31(2H, d, J=6.78 Hz).

TABLE 7-continued

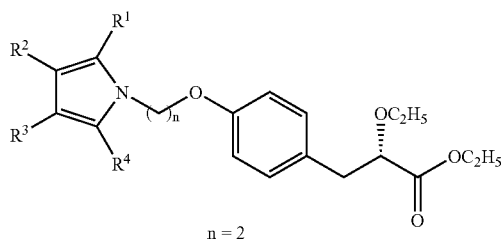

n = 2

| Ex. No. | Substituents on the pyrrole ring in (I) | | | | | |
|---|---|---|---|---|---|---|
| | R¹ | R² | R³ | R⁴ | | |
| 14. | CH₃ | H | H | 4-Br-C₆H₄ | Mol. Wt. = 500 | Yield = 40% |

¹H: 1.15(3H, t, J=7 Hz); 1.2(3H, t, J=7 Hz); 2.37(3H, s); 2.95(2H, dd);
3.29–3.38(1H, m); 3.55–3.63(1H, m); 3.9–3.95(3H, m); 4.17(2H, t, J=6.3 Hz);
4.28(2H, t, J=6.3 Hz); 5.9(1H, d, J=3.42 Hz); 6.1(1H, d, J=3.42 Hz);
6.6(2H, d, J=8.5 Hz); 7.21(2H, d, J=8.5 Hz); 7.29(2H, d, J=8.5 Hz); 7.5(2H, d, J=8.5 Hz).

| 15. | CH₃ | H | H | 4-F-C₆H₄ | Mol. Wt. = 439 | Yield = 30% |

¹H: 1.15(3H, t, J=6.99 Hz); 1.23(3H, t, J=6.99 Hz); 1.58(3H, s); 2.9–2.93(2H, dd);
3.3–3.4(1H, m); 3.55–3.65(1H, m); 3.85–4.0(3H, m); 4.1–4.2(2H, m);
4.24(2H, t, J=6.4 Hz); 5.9(1H, d, J=3.3); 6.0(1H, d, J=3.4 Hz); 6.6(2H, t, J=8.6 Hz);
7.0–7.1(4H, m); 7.26–7.38(2H, m).

| 16. | CH₃ | H | H | 4-Cl-C₆H₄ | Mol. Wt. = 455.5 | Yield = 62% |

¹H: 1.15(3H, t, J=7 Hz); 1.23(3H, t, J=7 Hz); 2.36(3H, s); 2.9–2.95(2H, dd);
3.33–3.4(1H, m); 3.53–3.62(1H, m); 3.9–4.13(3H, m); 4.18(2H, t, J=6.3 Hz);
4.26(2H, t, J=6.3 Hz); 5.97(1H, d, J=3.27 Hz); 6.1(1H, d, J=3.4 Hz); 6.6(2H, d, J=8.4 Hz);
7.1(2H, d, J=8.4 Hz); 7.25–7.38(2H, m); 7.4(2H, d, J=8.5 Hz).

| 17. | C₆H₅ | H | CH₃ | H | Mol. Wt. = 421 | Yield = 13% |

¹H: 1.15(3H, t, J=6.9 Hz); 1.23(3H, t, J=7.2 Hz); 2.13(3H, s); 2.92(2H, d);
3.33(1H, m); 3.59(1H, m); 3.94(3H, m); 4.07–4.26(4H, m); 6.05(1H, s); 6.67–6.72(3H, m);
7.12(2H, m); 7.3–7.43(5H, m).

| 18. | CH₃ | H | C₆H₅ | C₆H₅ | Mol. Wt. = 497 | Yield = 32% |

¹H: 1.153(3H, t, J=7.0 Hz); 1.24(3H, t, J=7 Hz); 2.4(3H, s); 2.9–2.92(2H, m);
3.33–3.36(1H, m); 3.53–3.63(1H, m); 3.85–3.95(3H, m); 4.1–4.2(4H, m); 6.2(1H, s);
6.5–7.4(14H, m).

| 19. | i-Pr | H | H | i-Pr | Mol. Wt. = 415 | Yield = 36% |

¹H: 1.15(3H, t, J=6.9 Hz); 1.23(3H, t, J=7.0 Hz); 1.24–1.26(12H, d, J=6.7 Hz);
2.9(4H, m); 3.35 1(H); 3.6(1H, m); 3.95(1H, m); 4.05(2H, t); 4.1–4.2(2H, q, J₁=6.8 Hz,
J₂=7.1 Hz); 4.23(2H, t, J=6.6 Hz); 5.87(2H, s); 6.75–6.76(2H, d, J=8.6 H);
7.12–7.15(2H, d, J=8.6 Hz)

| 20. | i-Pr | H | H | C₆H₅ | Mol. Wt. = 449 | Yield = 31% |

TABLE 7-continued

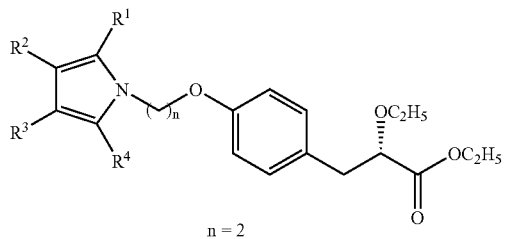

(I)

n = 2

| Ex. No. | Substituents on the pyrrole ring in (I) | | | |
|---|---|---|---|---|
| | R¹ | R² | R³ | R⁴ |

¹H: 1.14(3H, t, J=6.99 Hz); 1.21(3H, t, J=5.55 Hz); 1.31(6H, d, J=6.15 Hz);
2.90(2H, d, J=6.15 Hz); 3.1(1H, m); 3.32–3.57(2H, m); 3.84(2H, t, J=6.75 Hz);
3.91(1H, t, J=3.55 Hz); 4.12–4.19(2H, q, J₁=7.14 Hz, J₂=7.14 Hz);
4.33(2H, t, J=6.8 Hz); 6.00(1H, d, J=3.51 Hz); 6.12(1H, d, J=3.51 Hz); 6.53(2H, d, J=8.64 Hz);
7.05(2H, d, J=8.61 Hz); 7.31 7.40(5H, m).

| 21. | i-Pr | ⌬—NHCO | H | ⌬—F (4-F-phenyl) | Mol. Wt. = 586 | Yield = 20% |

¹H: 1.15(3H, t, J=6.9 Hz); 1.23(3H, t, J=7.1 Hz); 1.51–1.53(6H, d, J=7.1 Hz);
2.92(2H, dd, J=7.11 Hz); 3.33–3.4(1H, m); 3.5–3.6(2H, Complex); 3.9–4.0(3H, m);
4.1–4.2(2H, q, J=7.11 Hz); 4.3–4.4(2H, t, J=6.3 Hz); 6.31(1H, s);
6.58–6.61(2H, d, J=8.5 Hz); 7.0–7.2(4H, m); 7.3–7.4(4H, m); 7.5(1H, s);
7.6(2H, d, J=7.6 Hz)

| 22. | SCH₃ | H | H | H | Mol. Wt. = 377 | Yield = 20% |

¹H: 1.14(3H, t, J=7.0 Hz); 1.24(3H, t, J=7.0 Hz); 2.29(3H, s);
2.90–2.94(2H, m); 3.30–3.40(1H, m); 3.54–3.62(1H, m); 3.95(1H, t, J=3.6 Hz);
4.13–4.22(4H, m); 4.40(2H, t, J=5.6 Hz); 6.15(2H, d, J=3.2 Hz); 6.37(1H, dd);
6.80(2H, d, J=8.5 Hz); 6.94(1H, m); 7.15(2H, d, J=8.5 Hz).

| 23. | C₂H₅ | H | H | C₂H₅ | Mol. Wt. = 387 | Yield = 73% |

¹H: 1.15(3H, t, J=7 Hz); 1.25(3H, t, J=7 Hz); 1.28(6H, t, J=7.3 Hz);
2.64(4H, t, J=7.4 Hz); 2.92–2.94(2H, m); 3.29–3.38(1H, m); 3.53–3.61(1H, m);
3.94(1H, t, J=1.38 Hz); 4.07(2H, t, J=5.97 Hz); 4.12–4.21(4H, m); 5.8(2H, s);
6.7(2H, d, J=8.6 Hz); 7.15(2H, d, J=8.6 Hz)

| 24. | C₂H₅ | H | H | C₆H₅ | Mol. Wt. = 435 | Yield = 73% |

¹H: 1.15(3H, t, J=6.9 Hz); 1.22(3H, t, J=7.1 Hz); 1.24(3H, t, J=7.3 Hz);
2.73(2H, q, 2≈7.4 Hz); 2.9–3.1(2H, m); 3.28–3.38(1H, m); 3.53–3.61(1H, m); 3.88–3.95(3H, m);
4.19(2H, t, J=7.1 Hz); 4.29(2H, t, J=7.2 Hz); 6.0(1H, d, J=3.42 Hz); 6.15(1H, d, J=3.45 Hz);
6.59(2H, d, J=8.5 Hz); 7.0(2H, d, J=8.5 Hz); 7.3–7.4(5H, m)

| 25. | CH₃ | H | H | 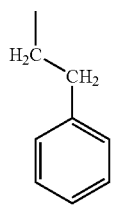 | Mol. Wt. = 449 | Yield = 72% |

¹H: 1.15(3H, t, J=6.9 Hz); 1.25(3H, t, J=7 Hz); 2.29(3H, s); 2.9–2.97(6H, m);
3.29–3.37(1H, m); 3.53–3.62(1H, m); 3.9–4.2(7H, m); 5.85(1H, d, J=3.1 Hz);
5.9(1H, d, J=3.37 Hz); 6.73(2H, d, J=8.6 Hz); 7.13(2H, d, J=8.6 Hz); 7.21–7.3(5H, m)

| 26. | CH₃ | H | H | 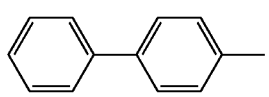 | Mol. Wt. = 497 | Yield = 60% |

¹H: 1.14(3H, t, J=6.9 Hz); 1.23(3H, t, J=7.1 Hz); 2.39(3H, s);
2.9(2H, d, J=6.1 Hz); 3.28–3.38(1H, m); 3.53–3.61(1H, m); 3.92–4.2(5H, m);
4.34(2H, t, J=6.5 Hz); 5.9(1H, d, J=3.3 Hz); 6.17(1H, d, J=3.4 Hz);
6.6(2H, d, J=8.5 Hz); 7.0(2H, d, J=8.5 Hz); 7.43–7.5(5H, m); 7.6–7.68(4H, m)

TABLE 7-continued

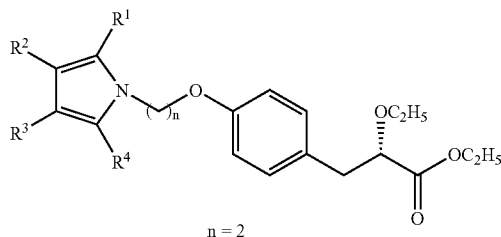

(I)

n = 2

| Ex. No. | Substituents on the pyrrole ring in (I) | | | | | |
|---|---|---|---|---|---|---|
| | $R^1$ | $R^2$ | $R^3$ | $R^4$ | | |
| 27. | CH$_3$ | H | H | (2-methylfuran) | Mol. Wt. = 411 | Yield = 60% |

$^1$H: 1.15(3H, t, J=6.9 Hz); 1.22(3H, t, J=7 Hz); 2.35(3H, s); 2.91–2.94(2H, m); 3.29–3.38(1H, m); 3.53–3.63(1H, m); 3.9(1H, t, J=6.0 Hz); 4.12–4.2(4H, m); 4.4(2H, t, J=6.4 Hz); 5.91–5.92(1H, m); 6.31–6.38(2H, m); 6.42–6.45(1H, m); 6.7(2H, d, J=8.6 Hz); 7.13(2H, d, J=8.5 Hz); 7.41–7.42(1H, m)

| 28. | CH$_3$ | H | H | (4-methylthiophenyl-Me) | Mol. Wt. = 467 | Yield = 80% |

$^1$H: 1.15(3H, t, J=6.9 Hz); 1.22(3H, t, J=7.1 Hz); 2.29(3H, s); 2.3(3H, s); 2.92(2H, d, J=7.26 Hz); 3.28–3.38(1H, m); 3.53–3.61(1H, m); 3.89–3.97(3H, m); 4.19(2H, t, J=7 Hz); 4.29(2H, t, J=6.55 Hz); 5.96(1H, d, J=3.36 Hz); 6.0(1H, d, J=3.39 Hz); 6.6(2H, d, J=8.5 Hz); 7.0(2H, d, J=8.5 Hz); 7.22–7.33,(4H, m)

| 29. | CH$_3$ | H | H | (2,5-dimethylfuran) | Mol. Wt. = 425 | Yield = 60% |

$^1$H: 1.15(3H, t, J=6.9 Hz); 1.22(3H, t, J=7.1 Hz); 2.29(3H, s); 2.3(3H, s); 2.94(2H, d, J=7.26 Hz); 3.3–3.38(1H, m); 3.54–3.63(1H, m); 3.94(1H, t, J=6.0 Hz); 4.12–4.19(4H, m); 4.36(2H, t, J=6.4 Hz); 5.91(1H, d, J=3.4 Hz); 5.9–6.0(1H, m); 6.22(1H, d, J=3.06 Hz); 6.26(1H, d, J=3.5 Hz); 6.7(2H, d, J=8.6 Hz), 7.13–(2H, d, J=8.58 Hz)

| 30. | CH$_3$ | H | H | (4-cyanophenyl-CN) | Mol. Wt. = 446 | Yield = 70% |

$^1$H: 1.15(3H, t, J=6.69 Hz); 1.23(3H, t, J=7 Hz); 2.38(3H, s); 2.91–2.95(2H, m); 3.3–3.40(1H, m); 3.54–3.64(1H, m); 3.9–3.98(3H, m); 4.16(2H, q, J=7.1 Hz); 4.34(2H, t, J=6.18 Hz); 6.0(1H, d, J=3.48 Hz); 6.2(1H, d, J=3.54 Hz); 6.62(2H, d, J=8.6 Hz); 6.75(2H, d, J=8.49 Hz); 7.5(2H, d, J=8.37 Hz); 7.67(2H, d, J=8.3 Hz)

| 31. | CH$_3$ | H | H | (4-phenoxyphenyl) | Mol. Wt. = 513 | Yield = 60% |

$^1$H: 1.15(3H, t, J=7 Hz); 1.22(3H, t, J=6.9 Hz); 2.37(3H, s); 2.93(2H, d, J=7 Hz); 3.29–3.38(1H, m); 3.54–3.62(1H, m); 3.94(3H, t, J=6.2 Hz); 4.17(2H, q, J=7 Hz); 4.28(2H, t, J=6.3 Hz); 5.96(1H, d, J=3.3 Hz); 6.08(1H, d, J=3.39 Hz); 6.64(2H, d, J=8.6 Hz); 7.0–7.4(11H, m)

| 32. | CH$_3$ | H | H | (N-(4-methoxyphenylsulfonyl)-2-methylpyrrole) | Mol. Wt. = 564 | Yield = 30% |

TABLE 7-continued

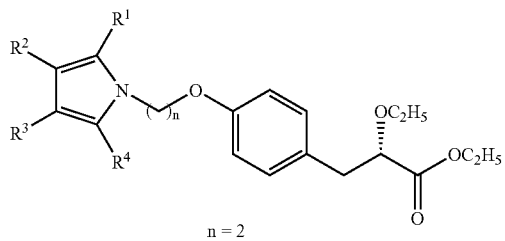

(I)

n = 2

| Ex. No. | Substituents on the pyrrole ring in (I) | | | | | |
|---|---|---|---|---|---|---|
| | R¹ | R² | R³ | R⁴ | | |

¹H: 1.15(3H, t, J=6.9 Hz); 1.22(3H, t, J=7.1 Hz); 2.28(3H, s); 2.3(3H, s);
2.95(2H, d, J=6.5 Hz); 3.3–3.38(1H, m); 3.54–3.62(1H, m); 3.86–4.2(7H, m);
5.7(1H, d, J=3.48 Hz); 5.88–7.8(1H, m)

| 33. | CH₃ | H | H | 3,4-dimethoxyphenyl (OMe, OMe) | Mol. Wt. = 481 | Yield = 64% |

¹H: 1.15,(3H, t, J=6.9 Hz); 1.22(3H, t, J=9 Hz); 2.37(3H, s);
2.9–2.92(2H, m); 3.28–3.35(1H, m); 3.55–3.62(1H, m); 3.86(3H, s); 3.91(3H, s);
3.9–3.95(3H, m); 4.17(2H, q, J=7.1 Hz); 4.27(2H, t, J=6.6 Hz);
5.96(1H, d, J=3.39 Hz); 6.0(1H, d, J=3.39 Hz); 6.64(2H, d, J=8.5 Hz);
6.91–6.94(3H, m); 7.1(2H, d, J=8.5 Hz)

| 34. | CH₃ | H | H | 4-(SOCH₃)phenyl | Mol. Wt. = 483 | Yield = 90% |

¹H: 1.15,(3H, t, J=6.9 Hz); 1.22(3H, t, J=9 Hz); 2.38(3H, s);
2.90–2.93(2H, m); 2.77(3H, s); 3.28–3.38(1H, m); 3.54–3.62(1H, m); 3.9–3.99(3H, m);
4.17(2H, q, J=7.1 Hz); 4.34(2H, t, J=6.3 Hz); 5.9(1H, d, J=3.48 Hz);
6.18(1H, d, J=3.48 Hz); 6.64(2H, d, J=8.6 Hz); 7.11(2H, d, J=8.6 Hz);
7.58(2H, d, J=8.4 Hz); 7.66(2H, d, J=8.4 Hz)

| 35. | CH₃ | H | H | 4-(NHCOCH₃)phenyl | Mol. Wt. = 464 | Yield = 40% |

¹H: 1.15(3H, t, J=7.0 Hz); 1.22(3H, t, J=6.9 Hz); 2.32(3H, s);
2.8–2.9(2H, m); 3.23–3.4(1H, m); 3.48–3.59(1H, m); 3.64(3H, s); 3.9(2H, t, J=6.0 Hz);
3.9–4.0(3H, m); 4.28(2H, t, J=6.0 Hz); 5.85(1H, d, J=3.28 Hz); 5.96(1H, d, J=3.4 Hz);
6.58(2H, d, J=8.6 Hz); 7.02(2H, d, J=8.5 Hz); 7.32(2H, d, J=8.5 Hz); 7.57(2H, d, J=8.5 Hz)

| 36. | CH₃ | H | H | 4-(2-piperidinoethoxy)phenyl | Mol. Wt. = 548 | Yield = 60% |

¹H: 1.15(3H, t, J=6.9 Hz); 1.22(3H, t, J=6.9 Hz); 1.4–1.7(6H, m);
2.36(3H, s); 2.5–2.55(4H, m); 2.79(2H, t, J=6.06 Hz); 2.9–2.95(2H, m); 3.3–3.41(1H, m);
3.53–3.62(1H, m); 3.88–3.98(3H, m); 4.1–4.2(4H, m); 4.26(2H, t, J=6 Hz);
5.94(1H, d, J=3.1 Hz); 6.0(1H, d, J=3.1 Hz); 6.6(2H, d, J=8.5 Hz); 6.94(2H, d, J=8.5 Hz);
7.1(2H, d, J=8.5 Hz); 7.31(2H, d, J=8.6 Hz)

| 37. | CH₃ | H | H | 4-(allyloxy)phenyl | Mol. Wt. = 477 | Yield = 50% |

¹H: 1.15(3H, t, J=6.9 Hz); 1.22(3H, t, J=7.1 Hz); 2.36(3H, s);
2.9(2H, d, J=7.1 Hz); 3.28–3.99(1H, m); 3.53–3.63(1H, m); 3.91(3H, t, J=6.6 Hz); 4.15(2H, q, J=7.1 Hz);
4.25(2H, t, J=6.6 Hz); 4.56(2H, d, J=3.9 Hz); 5.29–5.34(1H, dd); 5.4–5.5(1H, dd);
5.94(1H, d, J=2.9 Hz); 6.05(1H, d, J=3.48 Hz); 6.08–6.13(1H, m); 6.63(2H, d, J=8.6 Hz);
6.95(2H, d, J=8.7 Hz); 7.09(2H, d, J=8.5 Hz); 7.3(2H, d, J=8.69 Hz);

TABLE 7-continued

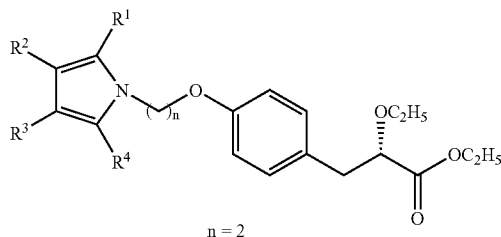

n = 2

| Ex. No. | Substituents on the pyrrole ring in (I) | | | | | |
|---|---|---|---|---|---|---|
| | R¹ | R² | R³ | R⁴ | | |
| 38. | CH₃ | H | H | 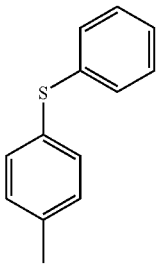 | Mol. Wt. = 529 | Yield = 50% |

¹H: 1.15(3H, t, J=7 Hz); 1.22(3H, t, J=7 Hz); 2.36(3H, s); 2.90–2.91(2H, m);
3.29–3.38(1H, m); 3.53–3.61(1H, m); 3.94(3H, t, J=6.25 Hz); 4.19(2H, q, J=7 Hz);
4.3(2H, t, J=6.3 Hz); 5.9(1H, d, 3.3 Hz); 6.11(1H, d, J=3.4 Hz); 6.6(2H, d, J=8.67 Hz);
7.1(2H, d, J=8.6 Hz); 7.26–7.42(9H, m)

| 39. | CH₃ | H | H | 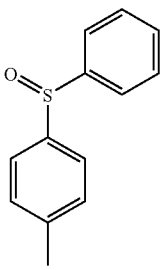 | Mol. Wt. = 545 | Yield = 80% |

¹H: 1.15(3H, t, J=7 Hz); 1.22(3H, t, J=7 Hz); 2.36(3H, s);
2.9–2.93(2H, m); 3.3–3.39(1H, m); 3.52–3.64(1H, m); 3.91–3.94(3H, m);
4.26(2H, t, J=6.0 Hz); 4.3(2H, t, J=6.0 Hz); 5.97(1H, d, J=3.6 Hz);
6.14(1H, d, J=3.48 Hz); 6.6(2H, d, J=8.6 Hz); 7.09(2H, d, J=8.5 Hz);
7.46–7.7(9H, m)

| 40. | CH₃ | H | H | 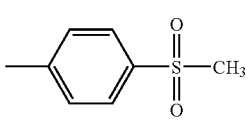 | Mol. Wt. = 499 | Yield = 75% |

¹H: 1.15(3H, t, J=7 Hz); 1.22(3H, t, J=7 Hz); 2.39(3H, s); 2.9–3.0(2H, m); 3.09(3H, s);
3.4–3.62(2H, m); 3.91–3.94(3H, m); 4.26(2H, t, J=6.0 Hz); 4.3(2H, t, J=6 Hz);
6.02(1H, d, J=3.3 Hz); 6.2(1H, d, J=3.5 Hz); 6.6(2H, d, J=8.58 Hz);
7.11(2H, d, J=8.5 Hz); 7.6(2H, d, J=8.4 Hz); 7.9(2H, d, J=8.4 Hz)

| 41. | CH₃ | H | H | 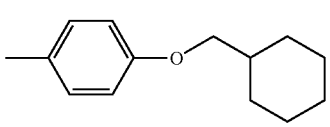 | Mol. Wt. = 533 | Yield = 64% |

¹H: 1.12–1.29(6H, m); 1.15(3H, t, J=7 Hz); 1.22(3H, t, J=7 Hz); 1.56–1.86(5H, m);
2.35(3H, s); 2.9(2H, d, J=7.05 Hz); 3.3–3.38(1H, m); 3.53–3.62(1H, m);
3.78(2H, d, J=6.18 Hz); 3.89–3.97(3H, m); 4.17(2H, t, J=7.1 Hz);
4.23(2H, t, J=7 Hz); 5.9(1H, d, J=3.3 Hz); 6.04(1H, d, J=3.36 Hz);
6.62(2H, d, J=8.6 Hz); 6.92(2H, d, J=8.7 Hz); 7.09(2H, d, J=8.58 Hz);

TABLE 7-continued

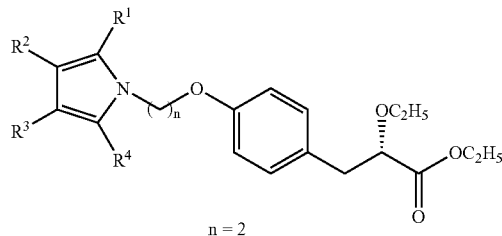

(I)

n = 2

| Ex. No. | Substituents on the pyrrole ring in (I) | | | | | |
|---|---|---|---|---|---|---|
| | $R^1$ | $R^2$ | $R^3$ | $R^4$ | | |
| | 7.3(2H, d, J=8.7 Hz) | | | | | |
| 42. | COPh | H | H | H | Mol. Wt. = 435 | Yield = 45% |
| | $^1$H: 1.15(3H, t, J=6.9 Hz); 1.22(3H, t, J=7.1 Hz); 2.95(2H, d, J=6.6 Hz); 3.3–3.4(1H, m); 3.51–3.62(1H, m); 3.95–4.2(7H, m); 5.66–6.15(2H, m); 6.72–6.75(1H, m); 6.74(2H, d, J=8.5 Hz); 6.8–7.96(7H, m) | | | | | |
| 43. | CH₃ | H | H | cyclopropyl | Mol. Wt. = 385 | Yield = 60% |
| | $^1$H: 0.6–0.62(2H, m); 0.81–0.84(2H, m); 1.15(3H, t, J=6.99 Hz); 1.23(3H, t, J=7.1 Hz); 1.7(1H, m); 2.27(3H, s); 2.94(2H, d, J=5.64 Hz); 3.3–3.9(2H, m); 3.95–3.96(1H, m); 4.12–4.2(4H, m); 4.32(2H, t, J=6.43 Hz); 5.7(1H, d, J=3.3 Hz); 5.76(1H, d, J=3.3 Hz); 6.76(2H, d, J=8.61 Hz); 7.14(2H, d, J=8.58 Hz) | | | | | |
| 44. | CH₃ | H | H | benzofuran-2-yl | Mol. Wt. = 461 | Yield = 41.5% |
| | $^1$H: 1.14(3H, t, J=6.98 Hz); 1.21(3H, t, J=6.04 Hz); 2.39(3H, s); 2.92(2H, d, J=6 Hz); 3.57–3.32(2H, m); 3.92(1H, t, J=3.56 Hz); 4.15(2H, q, J₁=7.13 Hz, J₂= 7.12 Hz); 4.23(2H, t, J=6.06 Hz); 4.53(2H, t, J=6.05 Hz); 5.99(1H, d, J=3.5 Hz); 6.56(1H, d, J=3.6 Hz); 6.69(1H, s); 6.73(2H, d, J=8.59 Hz); 7.1(2H, d, J=8.56 Hz); 7.54–8.2(4H, m) | | | | | |
| 45. | CH₃ | COOCH₃ | H | p-tolyl | Mol. Wt. = 479 | Yield = 33% |
| | $^1$H: 1.12–1.28(6H, m); 2.69(3H, s); 2.91(2H, d, J=5.8 Hz); 3.32(2H, m); 3.8(3H, s); 3.8–3.93(3H, m); 4.11–4.19(2H, m); 4.3(2H, t, J=6.18 Hz); 6.54–6.61(3H, m); 7.07(2H, d, J=8.58 Hz); 7.36–7.44(5H, m) | | | | | |
| 46. | CH₃ | H | H | benzo[d][1,3]dioxol-5-yl | Mol. Wt. = 465 | Yield = 28% |
| | $^1$H: 1.15(3H, t, J=6.99 Hz); 1.22(3H, t, J=7.12 Hz); 2.35(3H, s); 2.92(2H, d, J=5.91 Hz); 3.0–3.8(2H, m); 3.89–3.95(3H, m); 4.12–4.17(2H, q, J₁=7.11 Hz, J₂= 7.11 Hz); 4.25(2H, t, J=6.72 Hz); 5.93(1H, d, J=3.33 Hz); 5.99(2H, s); 6.03(1H, d, J=3.39 Hz); 6.62(2H, d, J=8.67 Hz); 6.84–6.88(3H, m); 7(2H, d, J=8.64 Hz) | | | | | |

TABLE 7-continued

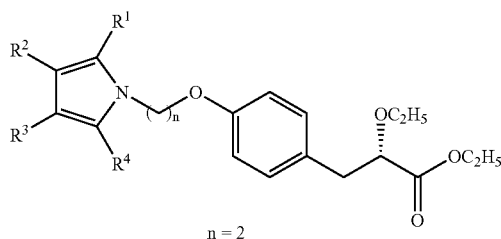

(I)

n = 2

| Ex. No. | Substituents on the pyrrole ring in (I) | | | | | |
|---|---|---|---|---|---|---|
| | $R^1$ | $R^2$ | $R^3$ | $R^4$ | | |
| 47. | $CH_3$ | H | H | 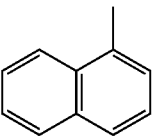 | Mol. Wt. = 417 | Yield = 56% |

$^1$H: 1.16(3H, t, J=6.16 Hz); 1.23(3H, t, J=7.81 Hz); 2.43(3H, s);
2.87(2H, d, J=6.84 Hz); 2.9–3.3(2H, m); 3.74(2H, t, J=6.48 Hz); 3.89(2H, t, J=6.64 Hz);
4.1–4.18(3H, m); 6.06(1H, d, J=3.33 Hz); 6.15(1H, d, J=3.36 Hz); 6.38(2H, d, J=8.61 Hz);
6.98(2H, d, J=8.58 Hz); 7.41–7.9(7H, m)

| 48. | $CH_3$ | H | H | 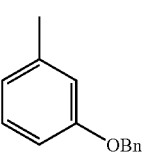 | Mol. Wt. = 527 | Yield = 42% |

$^1$H: 1.14(3H, t, J=6.99 Hz); 1.22(3H, t, J=7.14 Hz); 2.36(3H, s);
2.89–2.92(2H, m); 3.0–3.85(2H, m); 3.86–3.92(3H, m); 4.15(2H, q, $J_1$=7.14 Hz,
$J_2$=7.10 Hz); 4.23(2H, t, J=6.42 Hz); 5.08(2H, s); 5.94(1H, d, J=3.27);
6.1(1H, d, J=3.39 Hz); 6.6(2H, d, J=8.61 Hz); 6.98–7.05(3H, m); 7.08(2H, d, J=8.58 Hz);
7.3–7.4(6H, m)

| 49. | $CH_3$ | H | H | 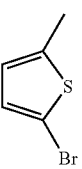 | Mol. Wt. = 506 | Yield = 50% |

$^1$H: 1.15(3H, t, J=6.99 Hz); 1.123(3H, t, J=7.14 Hz); 2.35(3H, s); 2.92(2H, m);
3.33–3.59(2H, m); 3.94(1H, t, J=6.7 Hz); 4.04(2H, t, J=6.22 Hz);
4.13–4.2(2H, q, $J_1$=7.11 Hz, $J_2$=7.11 Hz); 4.31(2H, t, J=6.24 Hz);
5.92(1H, d, J=3.48 Hz); 6.2(1H, d, J=3.51 Hz); 6.7(2H, d, J=8.61 Hz);
6.78(1H, d, J=3.78 Hz); 6.99(1H, d, J=3.75 Hz); 7.12(2H, d, J=8.58 Hz)

| 50. | $CH_3$ | H | H | 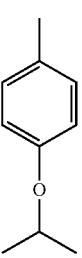 | Mol. Wt. = 479 | Yield = 60% |

$^1$H: 1.15(3H, t, J=6 Hz); 1.22(3H, t, J=6 Hz); 1.36(6H, d, J=6.06 Hz); 2.36(3H, s);
2.91(2H, d, J=7.11 Hz); 3.33–3.58(2H, m); 3.89–3.95(3H, m); 4.12–4.26(4H, m);
4.3–4.57(1H, m); 5.93(1H, d, J=3.33 Hz); 6.04(1H, d, J=3.39 Hz); 6.62(2H, d, J=8.61 Hz);
6.90(2H, d, J=8.67 Hz); 7.07(2H, d, J=8.55 Hz); 7.26(2H, d, J=8.28 Hz)

TABLE 7-continued (I)

Structure: Pyrrole ring with substituents $R^1$, $R^2$, $R^3$, $R^4$; N-linked to $-(CH_2)_n-O-$ connected to a para-substituted phenyl group bearing $-CH_2-CH(OC_2H_5)-C(=O)-OC_2H_5$ (with defined stereochemistry).

n = 2

| Ex. No. | R¹ | R² | R³ | R⁴ | | |
|---|---|---|---|---|---|---|
| 51. | CH₃ | H | CH₃ | phenyl (C₆H₅) | Mol. Wt. = 435 | Yield = 49% |

¹H: 1.15(3H, t, J=6.9 Hz); 1.21(3H, t, J=7.1 Hz); 1.91(3H, s); 2.33(3H, s); 2.90(2H, d, J=7.02 Hz) 3.32–3.58(2H, m); 3.83(2H, t, J=6.67 Hz); 3.90–3.95(1H, m); 4.10–4.19(4H, m); 5.84(1H, s); 6.54(2H, d, J=8.64 Hz); 7.05(2H, d, J=8.61 Hz); 7.30–7.42(5H, m)

| 52. | Me | H | H | 2-thienyl | Mol. Wt. = 427 | Yield = 42% |
|---|---|---|---|---|---|---|

¹H: 1.15(3H, t, J=6.9 Hz), 1.23(3H, t, J=7 Hz), 2.36(3H, s); 2.9(2H, m), 3.3(1H, m); 3.6(1H, m); 3.9(1H, m); 4.05(2H, t, J=6.4 Hz), 4.12–4.2(2H, q, J₁=J₂=7 Hz); 4.3(2H, t, J=6.4 Hz); 5.9(1H, d, J=3.5 Hz); 6.2(1H, d, J=3.5 Hz); 6.6(2H, d, J=8.6 Hz); 7.0–7.1(2H, m), 7.12–7.15(2H, m); 7.25–7.27(1H, m)

| 53. | CH₃ | H | H | 4-(OBn)-phenyl | Mol. Wt. = 527 | Yield = 52% |
|---|---|---|---|---|---|---|

¹H: 1.15(3H, t, J=6.9 Hz); 1.23(3H, t, J=6.9); 2.3(3H, s); 2.90–2.93(2H, m); 3.3(1H, m); 3.55(1H, m); 3.9(2H, m) 4.1–4.15(3H, m); 4.2(2H, m); 5.1(2H, s); 5.9(1H, d, J=3.3 Hz); 6.0(1H, d, J=3.3 Hz); 6.6(2H, d, J=8.5 Hz); 6.99(2H, d, J=8.5 Hz); 7.1(2H, d, J=8.5 Hz); 7.3–7.47(7H, m)

| 54. | CH₃ | H | H | 4-(OH)-phenyl | Mol. Wt. = 437 | Yield = 50% |
|---|---|---|---|---|---|---|

¹H: 1.17(3H, t, J=6.9 Hz); 1.23(3H, t, J=7 Hz); 2.3(3H, s); 2.9(2H, m); 3.3(1H, m); 3.6(1H, m); 3.9–4.0(3H, m); 4.1–4.2(4H, m); 5.9(1H, d, J=3.3 Hz); 6.0(1H, d, J=3.3 Hz); 6.5(2H, d, J=8.6 Hz); 6.8(2H, d, J=8.6 Hz); 7.0(2H, d, J=8.6 Hz); 7.2(2H, d, J=8.6 Hz)

| 55. | H | H | H | C₆H₅ | Mol. Wt. = 407 | Yield = 99% |
|---|---|---|---|---|---|---|

¹H: 1.15(3H, t, J=6.9 Hz); 1.22(3H, t, J=7.11 Hz); 2.9(2H, m); 3.3–3.4(1H, m); 3.55–3.6(1H, m); 3.9(1H, m); 4.08(2H, t, J=6.1 Hz); 4.12–4.17(2H, q, J₁=J₂=7.1 Hz); 4.3(2H, t, J=5 Hz); 6.0(2H, m); 6.6(2H, d, J=8.6 Hz); 6.9(1H, m); 7.0(2H, d, J=8.6 Hz); 7.1–7.4(5H, m)

TABLE 7-continued

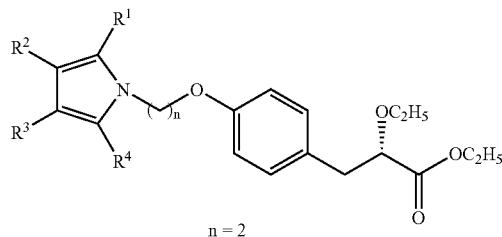

(I)

n = 2

| Ex. No. | Substituents on the pyrrole ring in (I) | | | | | |
|---|---|---|---|---|---|---|
| | R¹ | R² | R³ | R⁴ | | |
| 56. | CH₃ | H | H | 5-chloro-2-methylthiophene | Mol. Wt. = 461.5 | Yield = 60% |

$^1$H: 1.1(3H, t, J=6.9 Hz); 1.23(3H, t, J=7 Hz); 2.36(3H, s); 2.9(2H, m); 3.3(1H, m); 3.6(1H, m); 3.9(1H, t, J=5.9 Hz); 4.05(2H, t, J=6.1 Hz); 4.16(2H, q, J=7 Hz); 4.3(2H, t, J=6.3 Hz), 5.9(1H, d, J=3.5 Hz); 6.2(1H, d, J=3.5 Hz); 6.6(2H, d, J=8.6 Hz); 6.8(1H, d, J=3.8); 6.86(1H, d, J=3.8 Hz) 7.12(2H, d, J=8.58 Hz)

| 57. | CH₃ | H | H | 4-ethoxyphenyl | Mol. Wt. = 465 | Yield = 56% |

$^1$H: 1.15(3H, t, J=7.14 Hz); 1.2(3H, t, J=7.14 Hz); 1.45(3H, t, J=6.99 Hz); 2.36(3H, s); 2.9(2H, d, J=5.97 Hz); 3.35(1H, m); 3.6(1H, m); 3.91(3H, m); 4.15(4H, m); 4.23(2H, m); 5.94(1H, d, J=3.30 Hz); 6.05(1H, d, J=3.33 Hz); 6.62(2H, d, J=8.64 Hz); 6.92(2H, d, J=6.78 Hz); 7.08(2H, d, J=8.64 Hz); 7.3(2H, d, J=6.69 Hz)

| 58. | CH₃ | H | H | 2,5-dimethylthiophene | Mol. Wt. = 441 | Yield = 53% |

$^1$H: 1.15(3H, t, J=6.99 Hz); 1.23(3H, t, J=7 Hz); 2.36(3H, s); 2.48(3H, s); 2.93(2H, d, J=6.17 Hz); 3.33–3.59(2H, m); 3.9(1H, t, J=6.6 Hz); 4.05(2H, t, J=6.4 Hz); 4.15(2H, t, J₁=6.4 Hz, J₂=7 Hz); 4.32(2H, t, J=6.4 Hz); 5.91(1H, d, J=3.38 Hz); 6.17(1H, d, J=3.4 Hz); 6.68–6.71(3H, m); 6.8(1H, d); 7.1(2H, d, J=8.2 Hz)

| 59. | CH₃ | CH₃ | H | C₆H₅ | Mol. Wt. = 435 | Yield = 51% |

$^1$H: 1.15(3H, t, J=7 Hz); 1.22(3H, t, J=7 Hz); 2.05(3H, s); 2.27(3H, s); 2.9(2H, m); 3.3(1H, m); 3.5(1H, m); 3.9(3H, m); 4.1(2H, m); 4.26(2H, t, J=6.6 Hz); 6.0(1H, S); 6.6(2H, d, J=8.6 Hz); 7.05(2H, d, J=8.5 Hz); 7.26(1H, m); 7.29–7.35(4H, m)

| 60. | CH₃ | H | H | 3-methoxyphenyl | Mol. Wt. = 451 | Yield = 70% |

$^1$H: 1.15(3H, t, J=6.9 Hz); 1.22(3H, t, J=7 Hz); 2.37(3H, s); 2.9–2.95(2H, m); 3.29–3.38(1H, m); 3.55–3.63(1H, m); 3.8(3H, s); 3.94(3H, t, J=6.24 Hz); 4.17(2H, q, J=7.1 Hz); 4.3(2H, t, J=6.6 Hz); 5.96(1H, d, J=2.8 Hz); 6.12(1H, d, J=3.39 Hz); 6.69(2H, d, J=8.6 Hz); 6.88–7.0(2H, m); 7.09(2H, d, J=8.6 Hz); 7.26–7.31(2H, m)

TABLE 7-continued

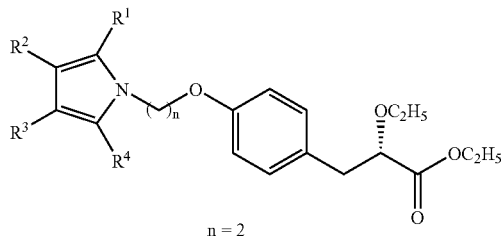

(I)

n = 2

| Ex. No. | Substituents on the pyrrole ring in (I) | | | | | |
|---|---|---|---|---|---|---|
| | $R^1$ | $R^2$ | $R^3$ | $R^4$ | | |
| 61. | $CH_3$ | H | H | cyclohexyl | Mol. Wt. = 427 | Yield = 54% |

$^1$H: 1.16(3H, t, J=6.9 Hz); 1.23(3H, t, J=7 Hz); 1.3–1.88(10H, m); 2.27(3H, s); 2.51–2.53(1H, m); 2.92–2.95(2H, m); 3.3–3.4(1H, m); 3.53–3.63(1H, m); 3.95(1H, t, J=5.9 Hz); 4.0–4.1(2H, m); 4.1–4.22(4H, m); 5.8(1H, d, J=3.4 Hz); 5.84(1H, d, J=3.3 Hz); 6.7(2H, d, J=8.6 Hz); 7.13(2H, d, J=8.5 Hz)

| 62. | H | H | H | H | Mol. Wt. = 331 | Yield = 37% |

$^1$H: 1.15(3H, t, J=6.9 Hz); 1.22(3H, t, J=6.9 Hz); 2.94(2H, dd); 3.33–3.38(1H, m); 3.54–3.65(1H, m); 3.95(1H, dd); 4.12–4.26(6H, m); 6.16(2H, t, J=2.1 Hz); 6.7(2H, t, J=2.1 Hz); 6.8(2H, d, J=8.5 Hz); 7.15(2H, d, J=8.5 Hz).

| 63. | $CH_3$ | H | H | $CH_3$ | Mol. Wt. = 359 | Yield = 57% |

$^1$H: 1.15(3H, t, J=6.9 Hz); 1.25(3H, t, J=6.9 Hz); 2.27(6H, s); 2.91–2.94(2H, m); 3.32–3.60(2H, m); 3.97–4.2(7H, m); 5.78(2H, s); 6.78(2H, d, J=8.5 Hz); 7.15(2H, d, J=8.5 Hz).

| 64. | i-Pr | phenyl | H | i-Pr | Mol. Wt. = 491 | Yield = 35% |

$^1$H: 1.16(3H, t, J=6.9 Hz); 1.2–1.3(15H, m); 2.94–2.96(3H, m); 3.31–3.34(2H, m); 3.96(2H, t, J=6.9 Hz); 4.1–4.2(4H, m); 4.3(2H, t, J=6.9); 5.89(1H, s); 6.8(2H, d, J=8.5 Hz); 7.15(2H, d, J=8.5 Hz); 7.2–7.33(5H, m)

| 65. | i-Pr | H | H | 4-methoxyphenyl | Mol. Wt. = 479 | Yield = 33% |

$^1$H: 1.1(3H, t, J=7 Hz); 1.2(3H, t, J=7 Hz); 1.31(6H, d, J=6 Hz); 3.0–3.1(1H, m); 2.90(2H, dd); 3.33(2H, m); 3.8(3H, s); 3.85(2H, t,); 3.92(1H, t); 4.12–4.16(2H, q, J=7.14 Hz); 4.28(2H, t, J=6.8 Hz); 5.98(1H, d, J=3.4 Hz); 6.07(1H, d, J=3.5 Hz); 6.56(2H, d, J=8.6 Hz); 6.93(2H, d, J=8.7 Hz); 7.32(2H, d, J=8.5 Hz); 7.05(2H, d, J=8.5 Hz);

| 66. | i-Pr | H | H | 4-fluorophenyl | Mol. Wt. = 467 | Yield = 51% |

$^1$H: 1.15(3H, t, J=6.9 Hz); 1.22(3H, t, J=7.1 Hz); 1.31(6H, d, J=6 Hz); 2.90(2H, dd); 3.33–3.35(1H, m); 3.84(2H, t, J=6.6 Hz); 3.33–3.58(2H, m); 3.91–3.95(1H, dd); 4.12–4.19(2H, q, J=7.0 Hz); 4.29(2H, t, J=6.6 Hz); 6.55(2H, d, J=8.6 Hz); 6.10(1H, d, J=3.5 Hz); 5.98(1H, d, J=3.4 Hz); 7.0–7.1(4H, m); 7.3–7.38(2H, m)

TABLE 7-continued

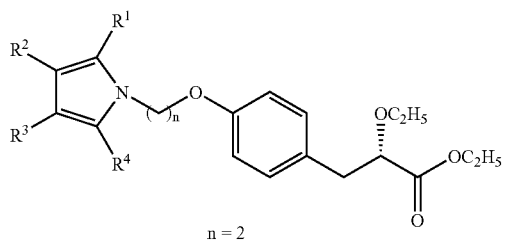

(I)

n = 2

| Ex. No. | Substituents on the pyrrole ring in (I) | | | | | |
|---|---|---|---|---|---|---|
| | $R^1$ | $R^2$ | $R^3$ | $R^4$ | | |
| 67. | i-Pr | H | phenyl | 4-F-phenyl | Mol. Wt. = 543 | Yield = 48% |

$^1$H: 1.1(3H, t, J=6.99 Hz); 1.2(3H, t, J=7.1 Hz); 1.36(6H, d, J=7 Hz); 2.9(2H, d, J=6.29 Hz); 3.0–3.1(1H, m); 3.3–3.58(2H, m); 3.8(2H, t, J=6.8 Hz); 3.9(2H, t, J=7 Hz); 4.1–4.2(3H, m); 6.2(1H, s); 6.5–7.3(13H, m).

| 68. | i-Pr | phenyl-NHCO | phenyl | 4-F-phenyl | Mol. Wt. = 662 | Yield = 44% |

$^1$H: 1.08(3H, t, J=7.0 Hz); 1.16(3H, t, J=7.0 Hz); 1.49(6H d, J=7 Hz); 2.85(2H, dd); 3.26(1H, m); 3.5(2H, m), 3.87(2H, t); 3.9(1H, t); 4.09(2H, q); 4.19(2H, t); 6.53(2H, d, J=8.5 Hz) 6.79(1H, s); 6.90–7.18(15H, m)

| 69. | phenyl | H | H | 4-F-phenyl | Mol. Wt. = 501 | Yield = 15% |

$^1$H: 1.12(3H, t, J=7.0 Hz); 1.21(3H, t, J=7.0 Hz); 2.88(2H, d, J=6.0 Hz); 3.3(1H, m); 3.6(1H, m); 3.61(2H, t); 3.9(1H, m); 4.1(2H, t, J=7.9 Hz); 4.37(2H, t, J=6.0 Hz); 6.26(2H, dd, J=3.3 Hz); 6.9(2H, d, J=9.0 Hz); 7.1(2H, m); 7.41–7.49(9H, m).

| 70. | phenyl | —COOEt | H | 4-F-phenyl | Mol. Wt. = 573 | Yield = 13.5% |

$^1$H: 1.1–1.25(9H, m); 2.8(2H, d, J=6.3 Hz); 3.3(1H, m); 3.6(1H, m); 3.61(2H, m); 3.9(1H, t); 4.1–4.21(6H, m); 6.3(1H, s); 6.9(2H, d, J=9.0 Hz); 7.1(2H, m); 7.42–7.47(9H, m)

| 71. | i-Pr | H | H | CH$_3$ | Mol. Wt. = 387 | Yield = 32.4% |

$^1$H: 1.15(3H, t, J=6.9 Hz); 1.2(3H, t, J=6.9 Hz); 1.25(6H, d, J=6.7 Hz); 2.27(3H, s); 2.9–3.0(3H, m); 3.3–3.63(2H, m); 3.96(1H, dd, ); 4.06(2H, t, J=6.9 Hz); 4.14–4.24(4H, m); 5.83(2H, s); 6.73(2H, d, J=8.5 Hz); 7.15(2H, d, J=8.5 Hz).

PREPARATION 10

(S)-Ethyl[3-{4-[2-(5-methyl-2-quinolinyl)pyrrole-1-yl)ethoxy]phenyl}-2-ethoxypropanoate (Example 72)

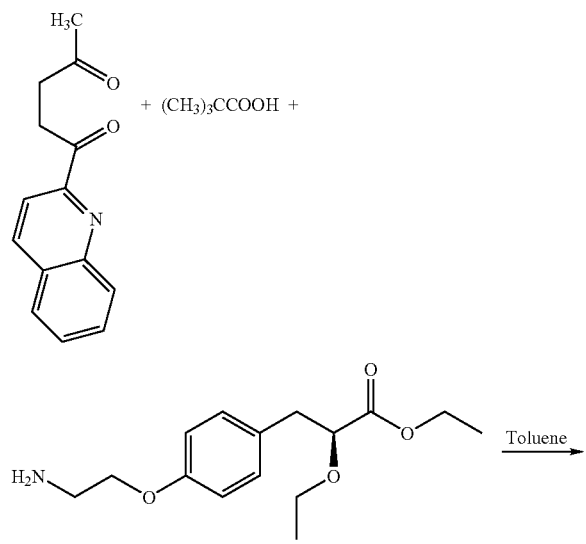

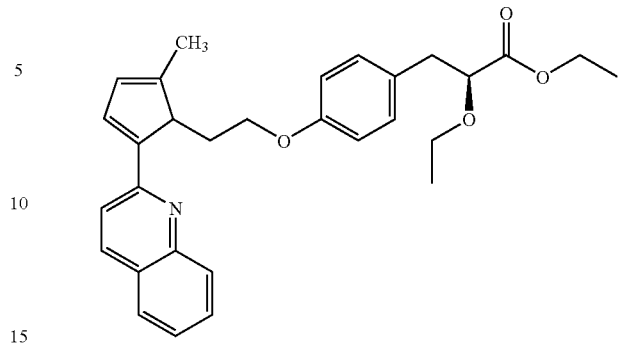

A mixture of diketo compound (0.8 g), pivalic acid (0.06 g), amino ester (0.4 g) in toluene(20 ml.) was heated to reflux for 3 hours with continuous removal of water using a Dean-Stark apparatus. Later it was cooled to 20–25° C. and toluene was distilled at reduced pressure. To the residue was added D.M. water (20 ml) and crude product was extracted with ethylacetate (2×30 ml), washed with water (2×30 ml) and saturated brine solution (30 ml.). Organic layer was dried over $Na_2SO_4$ to obtain brown thick oil (0.32 g). The crude product was purified by column chromatography using sillica gel (100–200) and ethyl acetate:PET ether(1:9) as an eluent to afford yellowish thick oil (0.1 g).

In like manner to that described in preparation 10, the following compounds of general formula (I) were prepared.

TABLE 8

| Ex. No. | Substituents on the pyrrole ring in (I) | | | | |
|---|---|---|---|---|---|
| | $R_1$ | $R_2$ | $R_3$ | $R_4$ | |
| 72. | $CH_3$ | H | H |  | Mol. Wt. = 472  Yield = 35% |

$^1$H: 1.14(3H, t, J=6.99Hz); 1.23(3H, t, J=7.14Hz); 2.4(3H, s); 2.89–2.92(2H, m); 3.28–3.38(1H, m); 3.52–3.6(1H, m); 3.9–3.95(1H, m); 4.14(2H, q, J$_1$=7.08Hz, J$_2$=7.08 Hz); 4.45(2H, t, J=5.76Hz); 5.02(2H, t, J=5.79Hz); 6.02(1H, d, J=3.72Hz); 6.75–6.78(3H, m); 7.10(2H, d, J=8.6Hz); 7.4–7.7(4H, m); 7.89(1H, d, J=8.3Hz); 8.0(1H, d, J=8.7Hz)

| 73. | $CH_3$ | H | H |  | Mol. Wt. = 422  Yield = 23% |

$^1$H: 1.15(3H, t, J=6.99Hz); 1.23(3H, t, J=7.14Hz); 2.39(3H, s); 2.91(2H, d, J=7.44 Hz); 3.58–3.80(2H, m); 3.93(1H, t, J=6.63Hz); 3.99(2H, t, J=6.12Hz); 4.12–4.20(2H, q, J$_1$=7.11Hz, J$_2$=7.11Hz); 4.38(2H, t, J=6.12Hz); 6.01(1H, d, J=3.45Hz); 6.30(1H, d, J=3.54Hz); 6.63(2H, d, J=8.61Hz); 7.10(2H, d, J=8.55Hz); 7.33(2H, d, J=6Hz); 8.58(2H, d, J=5.89Hz)

| 74. | $CH_3$ | H | H |  | Mol. Wt. = 422  Yield = 21% |

$^1$H: 1.15(3H, t, J=7Hz); 1.22(3H, t, J=6.9Hz); 2.39(3H, s); 2.91(2H, d, J=7.02Hz); 3.32–3.57(2H, m); 3.94(1H, t, J=6.63Hz); 4.15(2H, q, J$_1$=7.14Hz, J$_2$=7.11Hz); 4.25 (2H, t, J=6.06Hz); 4.81(2H, t, J=6.07Hz); 5.95(1H, d, J=3.21Hz); 6.53(1H, d, J=

TABLE 8-continued 3.63Hz); 6.75(2H, d, J=8.49Hz); 7.02–7.08(1H, m); 7.10(2H, d, J=8.64); 7.51(1H, d, J=8.07Hz); 7.5–7.6(1H, m); 8.49–8.50(1H, m)

| 75. | CH₃ | H | H | 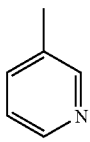 | Mol. Wt. = 422 | 24% |

¹H: 1.15(3H, t, J=7Hz); 1.23(3H, t, J=7.11Hz); 2.38(3H, s); 2.91(2H, t, J=3.78Hz); 3.32–3.58(2H, m); 3.9–3.97(3H, m); 4.16(2H, q, J₁=7.11Hz, J₂=7.11Hz); 4.29(2H, t, J=6.15Hz); 6.0(1H, d, J=3.45Hz); 6.17(1H, d, J=3.48Hz); 6.62(2H, d, J=8.64Hz); 7.09(2H, d, J=8.58Hz); 7.32–7.34(1H, m); 7.71–7.74(1H, m); 8.53–8.55(1H, m); 8.68–8.69(1H, m)

PREPARATION 11

(R/S) Methyl-2-ethoxy-3[6-[2-[2-(4-methoxyphenyl)-5-methyl-pyrrol-1-yl]ethoxy]napthalen-2yl] propanoate (Example 76)

A mixture of (R/S)-ethyl 3-(4-hydroxynapthyl)-2-ethoxypropionate (1 g) and dry potassium carbonate (0.7 g) in dimethyl formamide (20 mL) was stirred at 80° C. for 30 min. Compound. No. 79 (Table 5) (1.2 g) was added at 40° C. and stirring was continued at 80° C. for 24 h. The reaction mixture was to 20° C.–25° C. and 20 mL water was added. The reaction mixture was extracted with ethyl acetate (2×30 mL), washed with water (2×30 mL), brine (30 mL) and was dried over sodium sulfate. The organic layer was evaporated under reduced pressure to obtain an oily product. The crude oily product was chromatographed over silica gel (100–200 mesh) using ethyl acetate: petroleum ether (1:9) as an eluent to afford the title compound as a yellow oil (0.6 g, 31%).

TABLE 9

| Ex. No. | Substituents on the pyrrole ring in (I) | | | | | |
|---|---|---|---|---|---|---|
|  | R¹ | R² | R³ | R⁴ | | |
| 76. | CH₃ | H | H | 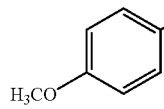 | Mol. Wt. = 487 | Yield = 31% |

¹H: 1.14(3H, t, J=7Hz)Hz; 2.4(3H, s); 3.1–3.16(2H, m); 3.3–3.8(1H, m); 3.55–3.64(1H, m); 3.68(3H, s); 3.84(3H, s); 4.03–4.41(3H, m); 4.32(2H, t, J=6.6Hz); 5.96(1H, d, J=3.36Hz); 6.0(1H, d, J=3.39Hz); 6.8(1H, d, J=2.37Hz); 6.9–7.0(3H, m); 7.33–7.38(3H, m); 7.52–7.64(3H, m)

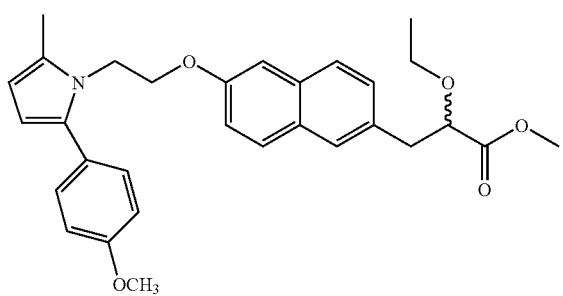

(I)

PREPARATION 12

(S)-Methyl 3-{4-[2-(2-phenyl-5-methyl pyrrol-1-yl)ethoxy]phenyl}-2-methoxypropanoate (Example 77)

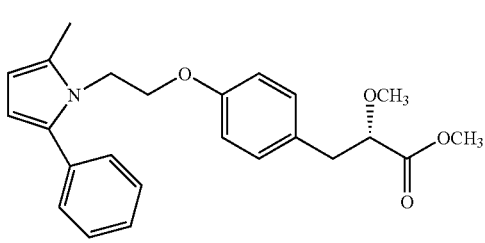

(I)

Using a similar procedure to that described in preparation 7, (S)-methyl 3-(4-hydroxyphenyl)-2-methoxypropanoate (3.3 g), and mesylate (compound no. 74, table 5), (4.38 g), gave the titled compound (1.2 g,20%).

In the like manner to that described in above example, the corresponding propoxy derivative (Example no. 78) was prepared using (S)-Propyl 3-(4-hydroxyphenyl)-2-propoxy propionate and mesylate (given in the Table 5).

TABLE 10

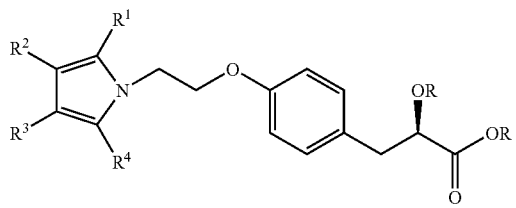

(I)

| Ex. No. | Substituents on the pyrrole ring in (I) | | | | | | |
|---|---|---|---|---|---|---|---|
| | $R^1$ | $R^2$ | $R^3$ | $R^4$ | | | |
| 77. | $CH_3$ | H | H | Phenyl | R = $CH_3$ | Mol. Wt. = 393 | Yield = 20% |

$^1$H: 2.37(3H; s); 2.9–3.0(2H, m); 3.33(3H, s); 3.71(3H, m); 3.92(3H, t, J=6.96Hz); 4.29 (2H, t, J=6.6Hz); 5.97(1H, d, J=3.36Hz); 6.11(1H, d, J=3.39Hz); 6.6(2H, d, J=8.67 Hz); 7.05(2H, d, J=8.64Hz); 7.30–7.40(5H, m).

| 78. | $CH_3$ | H | H | Phenyl | R = $C_3H_7$ | Mol. Wt. = 449 | Yield = 20% |

$^1$H: 0.83(3H, t, J= 7.4Hz); 0.89(3H, t, J=7.4Hz); 1.53–1.63(4H, m); 2.37(3H, s)2.91(2H, d, J=5.54 Hz); 3.20–3.48(2H, m); 3.92(3H, t, J=6.59Hz); 4.06(2H, t, J=6.67Hz); 4.28(2H, t, J= 7.4Hz); 5.97(1H, d, J=3.39Hz); 6.11(1H, d, J=3.4Hz); 6.59(2H, d, J=8.64Hz); 7.07(2H, d, J=8.63Hz); 7.25–7.4(5H, m).

PREPARATION NO. 13

Ethyl (E/Z) 2-ethoxy-3-[4-[2-(5-methyl-2-phenylpyrrol-1-yl)ethoxy]phenyl]prop-2-enoate (Example 79)

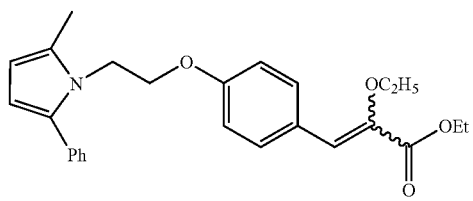

To a solution of triethyl 2-ethoxyphosphonoacetate (12.5 g) in dry THF (60 mL) was added slowly to a well-stirred ice-cold suspension of NaH (1.8 g, 60% dispersion in oil) in dry THF (60 mL) under $N_2$ atmosphere. The reaction mixture was stirred at 0° C. for 30 min. and 4-[2-(5-methyl-2-phenylpyrrol-1-yl) ethoxy]benzaldehyde (compound no. 134, table 6) (10.8 g) in dry THF (80 mL) was added. The mixture was allowed to warm up to 20° C. to 25° C. and stirred for 3.5 hrs. The solvent was evaporated and the residue was diluted with water (150 mL) further the product was extracted with ethyl acetate (2×150 mL). The combined extract was washed with water (150 mL), brine (50 mL), and was dried over sodium sulfate. The solvent was evaporated under reduced pressure to afford crude product. The crude product was chromatographed over silica gel using pet. ether:ether (9:1) as an eluent to afford E and Z isomers, which were isolated by removing the of solvents.

TABLE 11

| Ex. No. | Substituents on the pyrrole ring | | | | | |
|---|---|---|---|---|---|---|
| | $R^1$ | $R^2$ | $R^3$ | $R^4$ | | |
| 79. | $CH_3$ | H | H | Phenyl | Mol. Wt. = 419 | Yield = 40% E/Z-isomer |
| 80. | $CH_3$ | H | H | Phenyl | Mol. Wt. = 419 | Yield = 15% E-isomer |

$^1$H: 1.13(3H, t, J=7.14Hz); 1.4(3H, t, J=6.9Hz); 2.3(3H, s); 3.86–3.95(4H, m); 4.13(2H, q, J=7.1Hz); 4.27–4.31 (2H, t, J=6.6Hz); 5.96(1H, d, J=3.3Hz); 6.03(1H, s); 6.11(1H, d, J=3.3Hz); 6.5–6.6(2H, d, J=8.7Hz); 7.03–7.06 (2H, d, J=8.5Hz) 7.32–7.34(1H, m); 7.35–7.41(4H, m).

| 81. | $CH_3$ | H | H | Phenyl | Mol. Wt. = 419 | Yield = 15% Z-isomer |

$^1$H: 1.33–1.38(6H, t, J=7.0Hz); 2.38(3H, s); 3.92–3.99(4H, m); 4.24–4.33(4H, m); 5.98(1H, d, J=3.3Hz); 6.11(1H, d, J=3.3Hz); 6.63–6.6(2H, d, J=8.9Hz); 6.92(1H, s); 7.33(1H, m); 7.36–7.41(4H, m); 7.64–7.67(2H, d, J=8.8Hz).

PREPARATION 14

(R/S) Methyl 2-ethoxy-3[4-[2-[2-methyl-5-phenyl-1H-pyrrol-1-yl]ethoxy]phenyl]propanoate (Example 82)

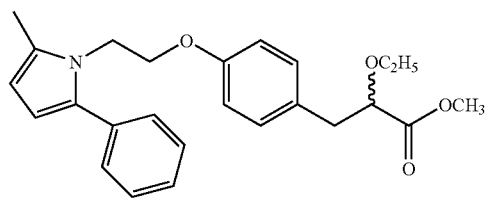

Mixture of E/Z compounds (Example no. 80 and 81) obtained in preparation 13 (7.1 g, 0.016 mole) and magnesium turnings (7.3 g, 0.3 mole) in dry methanol (70 mL) was stirred at 25° C. for 3.5 hrs. $H_2O$ (150 mL) was added and pH of the reaction mixture was adjusted to 2–3 with 35% hydrochloric acid. The product was extracted in ethyl acetate (2×100 mL) combined extract was washed with $H_2O$ (2×100 mL) brine (100 mL) and dried over $Na_2SO_4$. The extract was concentrated under reduced pressure. The crude product was chromatographed over silica gel using pet. ether:ether (9:1) as an eluent. The product obtained was racemic mixture but ethyl ester was converted to methyl ester.

Alternatively, the E and Z compound mixture is hydrogenated in the presence of 10% Pd/C catalyst at 60 psi pressure to obtain the title compound.

TABLE 12

| Ex. No. | Substituents on the pyrrole ring | | | | |
|---|---|---|---|---|---|
| | $R^1$ | $R^2$ | $R^3$ | $R^4$ | |
| 82. | $CH_3$ | H | H | Phenyl | Mol. Wt. = 407  Yield = 50% |
| | $^1H$: 1.15(3H, t, J=7.0Hz); 2.37(3H, s); 2.90–2.92(2H, m); 3.32–3.34(1H, m); 3.55–3.57(1H, m); 3.69(3H, s); | | | | |

TABLE 12-continued

| Ex. No. | Substituents on the pyrrole ring | | | |
|---|---|---|---|---|
| | $R^1$ | $R^2$ | $R^3$ | $R^4$ |
| | 3.90–3.97(2H, m); 4.29(2H, t, J=6.5Hz); 5.9(1H, d, J=3.41Hz); 6.1(1H, d, J=3.4Hz); 6.59(2H, d, J=8.6Hz); 7.05(2H, d, J=8.5Hz); 7.26–7.41 5H, m). | | | |

PREPARATION 15

(S)-3-{4-[2-(5-ethyl-2-phenylpyrrol-1-yl)ethoxy]phenyl}-2-ethoxypropanoic acid (Example 96)

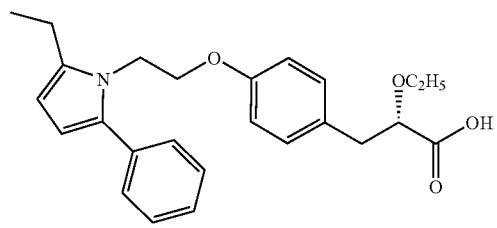

A mixture of substituted ester (prepared in example 24) (1.3 g), sodium hydroxide (0.24 g in 5 mL D.M. water) in methanol (10 mL) was stirred at 20° C. to 25° C. for 10 h. Methanol was evaporated under reduced pressure. The residue was diluted with water (10 mL) and was acidified with dilute hydrochloric acid. The product was extracted with ethyl acetate (3×20 mL) and washed with water (2×30 mL), brine (30 mL) and was dried over sodium sulfate to obtain an oily product (1.17 g, 96%). The crude product (3 g) was used in next step without purification.

In like manner to that described in Preparation 15 above following compounds of the formula (I) (given in Table 13) were prepared from the appropriately substituted pyrrole derivatives described elsewhere:

TABLE 13

(I)

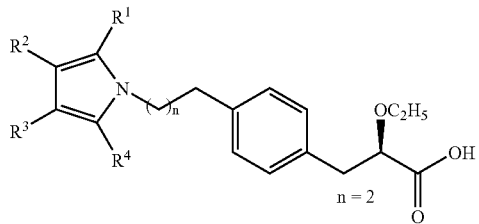

n = 2

| Ex. No. | Substituents on the pyrrole ring in (I) | | | | |
|---|---|---|---|---|---|
| | $R^1$ | $R^2$ | $R^3$ | $R^4$ | |
| 83. | $CH_3$ | H | $CH_3$ | H | Mol. Wt. = 331  Yield = 88% |
| | $^1H$: 0.96(3H, t, J=6.76Hz); 1.9(3H, s); 2.13(3H, s); 2.78(2H, m); 3.3–3.6(2H, m); 4.05 (5H, m); 5.53(1H, s); 6.43(1H, s) 6.75(2H, d, J=9.0Hz); 7.07(2H, d, J=9.0Hz). | | | | |
| 84. | $C_2H_5$ | H | H | H | Mol. Wt. = 331  Yield = 10% |
| | $^1H$: 1.16(3H, t, J=6.9Hz); 1.27(3H, t, J=3.51Hz); 2.51(2H, m); 2.62(2H, q); 3.44–3.46 (2H, m); 4.03(1H, dd, $J_1$=4.23Hz, $J_2$=4.5Hz); 4.13(2H, t, J=5.2Hz); 4.18(2H, t, J=3.76Hz); 5.91–5.92(1H, m) 6.10(1H, t, J=3.12Hz); 6.70(1H, d, J=2.01Hz); 6.77(2H, d, J=8.7Hz); 7.135(2H, d, J=8.64Hz). | | | | |

TABLE 13-continued

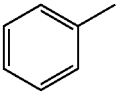

(I)

| | R¹ | R² | R³ | R⁴ | | |
|---|---|---|---|---|---|---|
| 85. | CHO | H | H | H | Mol. Wt. = 331 | Yield = 75% |

¹H: 1.10(3H, t, J=7Hz); 2.8–4.0(5H, m); 4.16(2H, t, J=4.9Hz); 4.65(2H, t, J=4.9Hz); 6.22(1H, dd); 6.7(2H, d, J=8.5Hz); 6.97(1H, dd); 7.1–7.4(1H, m); 7.1(2H, d, J=8.5Hz); 9.49(1H, s).

| 86. | COCH₃ | H | H | H | Mol. Wt. = 345 | Yield = 10% |

¹H: 0.87(3H, t, J=6.87Hz); 2.39(3H, s); 2.66(2H, dd, J=11.55Hz); 2.95–3.06(2H, m); 3.73(1H, t, J=4.5Hz); 4.09(2H, t, J=4.74Hz); 4.60(2H, t, J=4.89Hz); 6.08(1H, dd, J₁=2.64Hz, J₂=2.64Hz); 6.58(2H, d, J=8.37Hz); 6.92–6.99(2H, m); 7.00(2H, d, J=8.34 Hz).

| 87. | CH₃ | H | H | CH₂CH₃ | Mol. Wt. = 345 | Yield = 54% |

¹H: 1.16(3H, t, J=7Hz); 1.28(3H, t, J=7Hz); 2.28(3H, m); 2.55(2H, t, J=7.4Hz); 3.06 (2H, dd); 3.4–3.62(2H, m); 4.0–4.16(5H, m); 5.8–5.84(2H, m); 6.75(2H, d, J=6.78Hz); 7.14(2H, d, J=6.78Hz).

| 88. | CH₃ | H | H | (CH₂)₂CH₃ | Mol. Wt. = 423 | Yield = 66% |

¹H: 1.02(3H, t, J=6.9Hz); 1.17(3H, t, J=6.9Hz); 1.7(2H, sextet); 2.28(3H, s); 2.55(2H, t, J=7.7Hz); 2.94(1H, dd); 3.4(1H, dd); 3.4–3.62(2H, m); 4.0–4.2(5H, m); 5.8–5.84 (2H, m); 6.75(2H, d, J=8.5Hz); 7.14(2H, d, J=8.5Hz).

| 89. | CH₃ | H | H | (CH₂)₃CH₃ | Mol. Wt. = 373 | Yield = 76% |

¹H: 0.95(3H, t, J=7.2Hz); 1.17(3H, t, J=7.0Hz); 1.4–1.5(2H, m); 1.6–1.7(2H, m); 2.28(3H, s); 2.57(2H, t, J=7.7Hz); 2.95(1H, dd); 3.07(1H, dd); 3.4–3.5(1H, m); 3.53–3.62(1H, m); 4.0–4.2(5H, m); 5.8–5.83(2H, m); 6.77(2H, d, J=8.5Hz); 7.15(2H, d, J=8.5Hz).

| 90. | CH₃ | H | H | 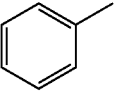 | Mol. Wt. = 393 | Yield = 96% |

¹H: 1.16(3H, t, J=6.9Hz); 2.37(3H, s); 2.92–3.02(2H, dd, J₁=7Hz, J₂=4.2Hz); 3.41–3.58(2H, m); 3.92(2H, t); 3.98–4.01(1H, m); 4.1–4.3(2H, t, J=6.5Hz); 5.96(1H, d, J=3.3Hz); 6.1(1H, d, J=3.3Hz); 6.6(2H, d, J=8.5Hz); 7.0(2H, d, J=8.5Hz); 7.06–7.09 (2H, d, J=8.6Hz); 7.2–7.4(5H, m).

| 91. | CH₃ | H | 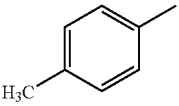 | H | Mol. Wt. = 393 | Yield = 96% |

¹H: 1.12(3H, t, J=6.9Hz); 2.37(3H, s); 2.92–3.02(2H, dd, J₁=7Hz, J₂=4.2Hz); 3.41–3.58(2H, m); 3.92(2H, t); 3.98–4.01(1H, m); 4.1–4.3(2H, t, J=6.5Hz); 5.96(1H, d, J=3.3Hz); 6.1(1H, d, J=3.3Hz); 6.6(2H, d, J=8.5Hz); 7.0(2H, d, J=8.5Hz); 7.2–7.4 (5H, m).

| 92. | CH₃ | H | H | 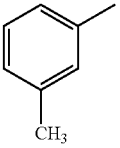 | Mol. Wt. = 407 | Yield = 75% |

¹H: 1.02(3H, t, J=6.9Hz); 2.34(3H, s); 2.36(3H, s); 2.74(1H, dd); 3.0(1H, dd); 3.19–3.22(1H, m); 3.4–3.45(1H, m); 3.78–3.79(1H, m); 3.8(2H, t, J=6.4Hz); 4.25(2H, t, J=6.4Hz); 5.96(1H, d, J=3.36Hz); 6.07(1H, d, J=3.3Hz); 6.1(1H, d, J=8.5Hz); 7.09(2H, d, J=8.5Hz); 7.19(2H, d, J=8.5Hz); 7.28(2H, d, J=8.5Hz).

| 93. | CH₃ | H | H |  | Mol. Wt. = 407 | Yield = 100% |

¹H: 1.08(3H, t, J=6.99Hz); 2.33(3H, s); 2.35(3H, s); 2.62(2H, m); 3.28–3.31(2H, m); 3.71(1h, m); 3.90(2H, t, J=6.05Hz); 4.3(2H, t, J=6.05Hz); 5.86(1H, d, J=3.36Hz); 5.96(1H, d, J=3.4Hz); 6.57(2H, d, J=8.6Hz); 7.09(2H, d, J=8.6Hz); 7.13–7.29(4H, m).

TABLE 13-continued (I)

| # | R¹ | R² | R³ | R⁴ | | |
|---|---|---|---|---|---|---|
| 94. | CH₃ | H | H | 2-methylphenyl | Mol. Wt. = 407 | Yield = 85% |
| 95. | CH₃ | H | H | 4-methoxyphenyl (H₃CO-C₆H₄-) | Mol. Wt. = 423 | Yield = 62% |

¹H: 1.077(3H, t, J=7Hz); 2.368(3H, s); 2.93(3H, s); 2.94(1H, m); 3.35–3.5(2H, m); 3.78(1H, t, J=7.1Hz); 3.8(3H, m); 3.9(2H, t J=7Hz); 4.25(2H, t, J=7Hz); 5.9(1H, d, J=3.36Hz); 6.0(1H, d, J=3.36Hz); 6.64(2H, d, J=8.5Hz); 7.1(2H, d, J=8.5Hz); 7.31 (2H, d, J=6.78Hz).

| 96. | CH₃ | H | H | 4-bromophenyl | Mol. Wt. = 472 | Yield = 84% |

¹H: 1.02(3H, t, J=6.9Hz); 2.353(3H, s); 2.74(1H, dd); 2.95(1H, dd); 3.19–3.28(1H, m); 3.4–3.45(1H, m); 3.8(1H, dd); 3.9(2H, t, J=6.21Hz); 4.26(2H, t, J=6.2Hz); 5.9(1H, d, J=3Hz); 6.1(1H, d, J=3.4Hz); 6.6(2H, d, J=8.5Hz); 7.1(2H, d, J=8.5Hz); 7.29(2H, d, J=8.5Hz); 7.5(2H, d, J=8.5Hz).

| 97. | CH₃ | H | H | 4-fluorophenyl | Mol. Wt. = 419 | Yield = 77% |

¹H: 1.02(3H, t, J=6.9Hz); 2.3(3H, s); 2.7–2.8(1H, m); 2.96(1H, m); 3.1–3.2(1H, m); 3.4–3.5(1H, m); 3.86–3.91(2H, t, J=6.3Hz); 4.2–4.24(2H, t, J=6.3Hz); 5.9(1H, d, J=3.3Hz); 6.05(1H, d, J=3.3Hz); 6.56–6.59(2H, d, J=8.6Hz); 7.05–7.09(4H, m); 7.28–7.37 (2H, m).

| 98. | CH₃ | H | H | 4-chlorophenyl | Mol. Wt. = 427.5 | Yield = 37% |
| 99. | phenyl | H | CH₃ | H | Mol. Wt. = 393 | Yield = 41% |
| 100. | CH₃ | H | phenyl | phenyl | Mol. Wt. = 469 | Yield = 83% |

¹H: 1.16(3H, t, J=7Hz); 2.41(3H, s); 2.9(1H, dd); 3.05(1H, dd); 3.4–3.6(2H, m); 3.9 (2H, t, J=6.5Hz); 4.03(1H, dd); 4.16(2H, t, J=6.5Hz); 6.2(1H, s); 6.5–7.4(14H, m).

| 101. | i-Pr | H | H | i-Pr | Mol. Wt. = 387 | Yield = 50% |

¹H: 1.19(3H, t, J=6.8Hz); 1.24–1.26(12H, d, J=6.7Hz); 2.92–2.99(4H, complex); 3.40

TABLE 13-continued

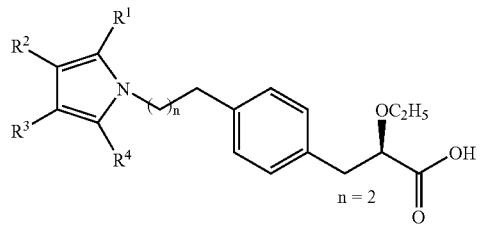

(I)

(1H, m); 3.6(1H, m); 4.03(3H, complex); 4.24(2H, t, J=Hz); 5.87(2H, s); 6.75–6.76(2H, d, J=8.8Hz); 7.13–7.15(2H, d, J=8.6Hz).

102. i-Pr     H     H     (phenyl)     Mol. Wt. = 443     Yield = 87%

$^1$H: 0.94(3H, t, J=7.29Hz); 1.22(6H, d, J=7.29Hz); 2.49–2.51(2H, dd, J=6.75Hz); 3.03–3.08(2H, m); 3.45–3.53(2H, m); 3.82(2H, t, J=5.91Hz); 4.29(2H, t, J=5.92Hz); 5.85 (1H, d, J=3.51Hz); 5.95(1H, d, J=3Hz); 6.52(2H, d, J=8.58Hz); 7.01(2H, d, J=8.52 Hz); 7.29–7.40(5H, m).

103. i-Pr     (Ph-NHCO)     H     (4-F-phenyl)     Mol. Wt. = 558     Yield = 50%

$^1$H: 1.18(3H, t, J=6.9Hz); 1.51–1.53(6H, d, J=7Hz); 2.9–3.1(2H, m); 3.5–3.6(3H, Complex); 3.92(2H, t, J=6.2Hz); 4.05(1H, m); 4.3(2H, t, J=6.2Hz); 6.31(1H, s); 6.58–6.60(2H, d, J=6.7Hz); 7.1(4H, m); 7.30–7.38(4H, m); 7.5(1H, s); 7.58–7.59(2H, d)

104. SCH$_3$     H     H         Mol. Wt. = 349     Yield = 93%

$^1$H: 1.18(3H, t, J=7Hz); 2.29(3H, s); 2.5(2H, m); 2.9–3.1(2H, m); 3.4–3.6(2H, m); 4.0–4.04(1H, m); 4.2(2H, t, J=5.6Hz); 4.42(2H, t, J=5.6Hz); 6.1(1H, t, J=3.2Hz); 6.38 (1H, dd); 6.8(2H, d, J=8.5Hz); 6.95(1H, dd); 7.15(2H, d, J=8.5Hz).

105. C$_2$H$_5$     H     H     C$_2$H$_5$     Mol. Wt. = 359     Yield = 99%

$^1$H: 1.16(3H, t, J=6.8Hz); 1.29(6H, t, J=7.4Hz); 2.65(4H, q, J=7.4Hz); 2.94–3.05(2H, m); 3.39–3.49(1H, m); 3.51–3.6(1H, m); 4.01–4.07(3H, m); 4.15(2H, t, J=5.8Hz); 5.86 (2H, s); 6.7(2H, d, J=8.5Hz); 7.15(2H, d, J=8.5Hz)

106. C$_2$H$_5$     H     H     C$_6$H$_5$     Mol. Wt. = 407     Yield = 90%

$^1$H: 1.16(3H, t, J=6.99Hz); 1.34(3H, t, J=7.4Hz); 2.73–2.78(2H, q, J=7.5Hz,); 2.9–3.9 (2H, m); 3.4–3.48(1H, m); 3.52–3.6(1H, m); 3.9(2H, t, J=6.63Hz); 4.0–4.05(1H, m); 4.3 (2H, t, 6.75Hz); 6.0(1H, d, J=3.48Hz); 6.15(1H, d, J=3.5Hz); 6.6(2H, d, J=8.5Hz); 7.08 (2H, d, J=8.6Hz); 7.3–7.4(5H, m)

107. CH$_3$     H     H     (CH(CH$_2$)CH$_2$-Ph)     Mol. Wt. = 421     Yield = 98%

$^1$H: 1.16(3H, t, J=6.9Hz); 2.29(3H, s); 2.88–3.04(6H, m); 3.38–3.48(1H, m); 3.53–3.62 (1H, m); 3.99–4.07(3H, m); 4.15(2H, t, J=7Hz); 5.85(1H, d, J=3.3Hz); 5.9(1H, d, J=3.3 Hz); 6.7(2H, d, J=8.6Hz); 7.14(2H, d, J=8.6Hz); 7.2–7.3(5H, m)

108. CH$_3$     H     H     (3-OCH$_3$-phenyl)     Mol. Wt. = 423     Yield = 90%

$^1$H: 1.15(3H, t, J=6.9Hz); 2.24(3H, s); 2.89–2.95(2H, m); 3.3–3.58(2H, m); 3.67(3H, s); 3.78–4.17(3H, m); 4.28(2H, t, J=6Hz); 5.89(1H, d, J=3.1Hz); 6.06(1H, d, J=3Hz); 6.49–7.21(8H, m)

TABLE 13-continued

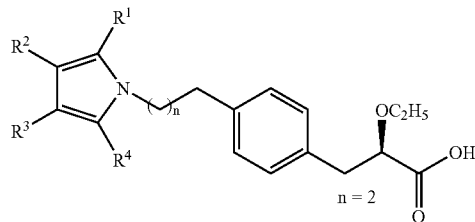

(I)

| 109. | CH₃ | H | H | 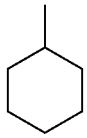 | Mol. Wt. = 399 | Yield = 92% |

¹H: 1.17(3H, t, J=6.9Hz); 1.3–1.4(6H, m); 1.75–2.5(5H, m); 2.27(3H, s); 2.9–3.08(2H, m); 3.38–3.45(1H, m); 3.57–3.65(1H, m); 3.98–4.15(3H, m); 4.2(2H, t, J=7.2Hz); 5.8(1H, d, J=3.4Hz); 5.84(1H, d, J=3.3Hz); 6.78(2H, d, J=8.5Hz); 7.17(2H, d, J=8.5Hz)

| 110. | CH₃ | H | H | 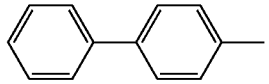 | Mol. Wt. = 469 | Yield = 85% |

¹H: 1.16(3H, t, J=6.9Hz); 2.33(3H, s); 2.9–3.0(2H, m); 3.38–3.48(1H, m); 3.55–3.66(1H, m); 3.88–3.94(1H, m); 3.99(2H, t, J=5.8Hz); 4.3(2H, t, J=6.3Hz); 5.91(1H, d, J=3.3Hz); 6.07(1H, d, J=3.4Hz); 6.63(2H, d, J=8.5Hz); 7.1(2H, d, J=8.5Hz); 7.3–7.5(5H, m); 7.68 (4H, d, J=8.2Hz)

| 111. | CH₃ | H | H | 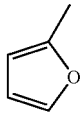 | Mol. Wt. = 383 | Yield = 92% |

¹H: 1.16(3H, t, J=6.99Hz); 2.32(3H, s); 2.9–3.0(2H, m); 3.38–3.48(1H, m); 3.55–3.64 (1H, m); 4.00–4.04(1H, dd, J=4.2Hz); 4.15(2H, t, J=5.98Hz); 4.38(2H, t, J=6.1Hz); 5.9 (1H, d, J=3.48Hz); 6.32(1H, d, J=3.55Hz); 6.35(1H, d, J=3.5Hz); 6.42–6.43(1H, m); 6.7 (2H, d, J=8.5Hz); 7.14(2H, d, J=8.5Hz); 7.4–7.41(1H, m)

| 112. | CH₃ | H | H | 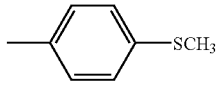 | Mol. Wt. = 439 | Yield = 99% |

¹H: 1.14(3H, t, J=6.9Hz); 2.37(3H, s); 2.48(3H, s); 2.92–3.06(2H, m); 3.32–3.42(1H, m); 3.57–3.64(1H, m); 3.9(2H, t, J=6.36Hz); 4.0(1H, dd); 4.28(2H, t, J=6.z); 5.9(1H, d, J=3.3 Hz); 6.08(1H, d, J=3.38Hz); z); 6.6(2H, d, J=8.5, Hz); 7.1(2H, d, J=8.5Hz); 7.26(2H, d, J= 8.4Hz); 7.3(2H, d, J=8.34Hz)

| 113. | CH₃ | H | H | 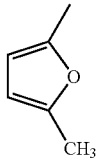 | Mol. Wt. = 397 | Yield = 95% |

¹H: 1.07(3H, t, J=6.97Hz); 2.27(3H, s); 2.3(3H, s); 2.7–2.8(1H, m); 2.89–2.96(1H, m); 3.2–3.3(1H, m); 3.5–3.6(1H, m); 3.76–3.8(1H, m); 4.12(2H, t, J=5.8Hz); 4.35(2H, t, J=5.9 Hz); 5.79–5.81(1H, dd, J=0.69Hz, J=0.69Hz); 6.01–6.02(1H, dd, J=1, 1Hz); 6.15(1H, d, J=3.5Hz); 6.2(1H, d, J=3.1Hz); 6.7(2H, d, 8.6)Hz); 7.14(2H, d, J=8.6Hz)
(solvent used is CD₃OD)

| 114. | CH₃ | H | H | 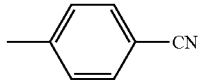 | Mol. Wt. = 418 | Yield = 85% |

¹H: 1.069(3H, t, J=6.9Hz); 2.34(3H, s); 2.74–2.8(2H, m); 3.2–3.25(1H, m); 3.5–3.58(1H, m); 3.76–3.8(1H, dd); 3.93(2H, t, J=5.58Hz); 4.37(2H, t, J=5.56Hz); 5.9(1H, d, J=3.3 Hz); 6.16(1H, d, J=3.5Hz); 6.57(2H, d, J=8.5Hz); 7.1(2H, d, J=8.5Hz); 7.56(2H, d,

TABLE 13-continued

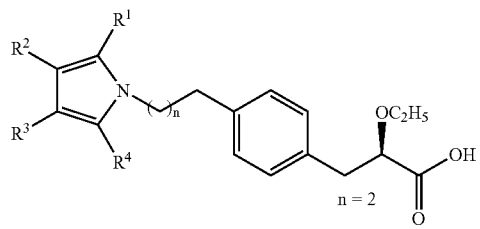

(I)

| | | | | | | |
|---|---|---|---|---|---|---|
| | | | | | | J=8.57Hz); 7.68(2H, d, J=8.59Hz) (solvent used is CD₃OD) |

| | | | | | | |
|---|---|---|---|---|---|---|
| 115. | CH₃ | H | H |  | Mol. Wt. = 485 | Yield = 92% |

¹H: 1.07(3H, t, J=6.96Hz); 2.33(3H, s); 2.7–2.95(2H, m); 3.2–3.35(1H, m); 3.5–3.6(1H, m); 3.76–3.8(1H, m); 3.94(2H, t, J=5.9Hz); 4.28(2H, t, J=5.9Hz); 5.86(1H, d, J=3.1Hz); 5.96(1H, d, J=3.4Hz); 6.6(2H, d, J=8.5Hz); 7.08–7.37(11H, m) (solvent used is CD₃OD)

| 116. | CH₃ | H | H |  | Mol. Wt. = 535 | Yield = 80% |

¹H: 1.07(3H, t, J=6.96Hz); 2.26(3H, s); 2.37(3H, s); 2.7–2.95(2H, m); 3.17–3.3(1H, m); 3.5–3.6(1H, m); 3.6–3.8(5H, m); 5.7(1H, d, J=3.48Hz); 5.8(1H, d, J=2.79Hz); 6.25–6.27 (1H, m); 6.34(1H, t, J=3.36Hz); 6.6(2H, d, J=8.5Hz); 7.12(2H, d, J=8.5Hz); 7.25(2H, d, J=8.1Hz); 7.35(2H, d, J=8.4Hz); 7.5–7.51(1H, m) (solvent used is CD₃OD)

| 117. | CH₃ | H | H |  | Mol. Wt. = 453 | Yield = 88% |

¹H: 1.07(3H, t, J=6.9Hz); 2.32(3H, s); 2.7–2.93(2H, m); 3.2–3.3(1H, m); 3.5–3.6(1H, m); 3.78(3H, s); 3.84(3H, s); 3.9(2H, t, J=6Hz); 3.93–3.95(1H, m); 4.2(2H, t, J=6Hz); 5.84 (1H, d, J=3.1Hz); 6.0(1H, d, J=3.1Hz); 6.59(2H, d, J=8.5Hz); 6.92–7.0(3H, m); 7.07(2H, d, J=8.57Hz) (solvent used is CD₃OD)

| 118. | CH₃ | H | H |  | Mol. Wt. = 455 | Yield = 88% |

¹H: 1.19(3H, t, J=6.9Hz); 2.38(3H, s); 2.8(3H, s); 2.9–3.06(2H, m); 3.43–3.52(1H, m); 3.62–3.72(1H, m); 4.0–4.12(3H, m); 4.23(2H, t, J=3.8Hz); 6.0(1H, d, J=3.2Hz); 6.18(1H, d, J=3.2Hz); 6.52–6.55(2H, dd, J=6.4Hz); 7.02–7.07(2H, dd, J=6.3Hz); 7.49–7.5(2H, dd, J=3.2Hz); 7.6–7.63(2H, dd, J=3.69Hz)

| 119. | CH₃ | H | H |  | Mol. Wt. = 450 | Yield = 99% |

¹H: 1.09(3H, t, J=6.99Hz); 2.13(3H, s); 2.32(3H, s); 2.77–2.98(2H, m); 3.25–3.36(1H, m); 3.5–3.6(1H, m); 3.90(2H, t, J=6.18Hz); 3.92–3.94(1H, m); 4.27(2H, t, J=6.0Hz); 5.85(1H, d, J=3.0Hz); 5.96(1H, d, J=3.3Hz); 6.58(2H, d, J=8.6Hz); 7.06(2H, d, J=8.6 Hz); 7.3(2H, d, J=8.6Hz); 7.57(2H, d, J=8.6Hz)

| 120. | CH₃ | H | H | | Mol. Wt. = 520 | Yield = 80% |

TABLE 13-continued

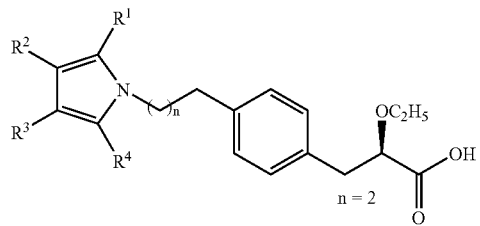

(I)

¹H: 1.15(3H, s, J=6.9Hz); 1.25–2.1(6H, m); 2.3(3H, s); 2.9–3.03(2H, m); 3.2–3.33(1H, m); 3.22–3.6(5H, m); 3.58–3.66(1H, m); 3.9(2H, t, J=6.9Hz); 3.98(2H, t, J=6.9Hz); 4.15 (2H, t, J=6Hz); 4.57(2H, t, J=4.87Hz); 5.9(1H, d, J=3.1Hz); 6.0(1H, d, J=3.3Hz); 6.45(2H, d, J=8.5Hz); 6.96(2H, d, J=8.6Hz); 7.0(2H, d, J=8.5Hz); 7.3(2H, d, J=8.5Hz)

121.  CH₃   H   H   [4-allyloxyphenyl group]   Mol. Wt. = 449   Yield = 97%

¹H: 1.07(3H, t, J=6.9Hz); 2.3(3H, s); 2.9–3.2(2H, m); 3.2–3.8(3H, m); 3.9(2H, t, J=6.03 Hz); 4.2(2H, t, J=6.2Hz); 4.55(2H, d, J=1.5Hz); 5.12–5.3(1H, dd); 5.43–5.44(1H, dd, J=1.67Hz); 5.83(1H, d, J=3.3Hz); 5.9(1H, d, J=3.2Hz); 6.0–6.12(1H, m); 6.58(2H, d, J=8.5Hz); 6.96(2H, d, J=8.6Hz); 7.1(2H, d, J=8.5Hz); 7.28(2H, d, J=8.7Hz)
(solvent used is CD₃OD)

122.  CH₃   H   H   [phenyl-S-(4-methylphenyl)]   Mol. Wt. = 501   Yield = 94%

¹H: 1.07(3H, t, J=6.97Hz); 2.3(3H, s); 2.7–2.8(1H, m) 2.88–2.95(1H, m); 3.2–3.33(1H, m); 3.5–3.6(1H, m); 3.73–3.8(1H, m); 3.92(2H, t, J=5.8Hz); 4.3(2H, t, J=5.9Hz); 5.87 (1H, d, J=3.4Hz); 6.0(1H, d, J=3.4Hz); 6.57(2H, d, J=8.5Hz); 7.1(2H, d, J=8.6Hz); 7.26–7.35(9H, m) (solvent used is CD₃OD)

123.  CH₃   H   H   [phenyl-S(O)-(4-methylphenyl)]   Mol. Wt. = 517   Yield = 90%

¹H: 1.07(3H, t, J=6.98Hz); 2.3(3H, s); 2.7–2.94(2H, m); 3.2–3.34(1H, m); 3.5–3.6(1H, m); 3.74–3.8(1H, m); 3.9(2H, t, J=5.87Hz); 4.30(2H, t, J=5.87Hz); 5.87(1H, d, J=3.45 Hz); 6.1(1H, d, J=3.45Hz); 6.56(2H, d, J=8.56Hz); 7.17(2H, d, J=8.54Hz); 7.51–7.56 (5H, m); 7.65–7.77(4H, m) (solvent used is CD₃OD)

124.  CH₃   H   H   [4-(methylsulfonyl)phenyl-(4-methylphenyl)]   Mol. Wt. = 471   Yield = 80%

¹H: 1.26(3H, t, J=6.2Hz); 2.39(3H, s); 2.97–3.09(2H, m); 3.09(3H, s); 3.4–3.5(1H, m); 3.55–3.64(1H, m); 4.0(2H, t, 6.0Hz); 4.02–4.06(1H, m); 4.33(2H, t, J=6.12Hz); 6.02(1H, d, J=3.3Hz); 6.24(1H, d, J=3.5Hz); 6.6(2H, d, J=8.58Hz); 7.11(2H, d, J=8.58Hz); 7.6 (2H, d, J=8.4)Hz; 7.93(2H, d, J=8.4Hz)

TABLE 13-continued

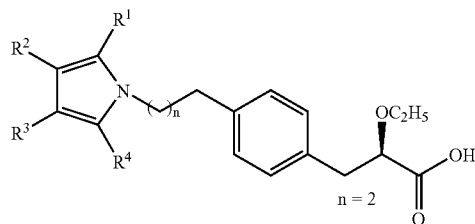
(I)

n = 2

| | $R^1$ | $R^2$ | $R^3$ | $R^4$ | | |
|---|---|---|---|---|---|---|
| 125. | CH$_3$ | H | H | 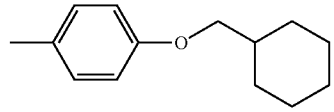 | Mol. Wt. = 505 | Yield = 94% |

$^1$H: 0.88–1.86(14H, m); 2.29(3H, s); 2.52–3.4(4H, m); 3.75(2H, d, J=3.39Hz); 3.76–4.18 (5H, m); 5.9(1H, d, J=2.97Hz); 6.01(1H, d, 3.3Hz); 6.5(2H, d, J=8.0Hz); 6.8(2H, d, J=8.6 Hz); 7.0(2H, d, J=8.0Hz); 7.26(2H, d, J=8.5Hz)

| 126. | COPh | H | H | H | Mol. Wt. = 407.2 | Yield = 76% |

$^1$H: 1.15(3H, t, J=6.96Hz); 2.84–2.95(2H, m); 3.33–3.42(1H, m); 3.48–3.58(1H, m); 3.98–4.13(5H, m); 5.64–5.66(1H, dd, J$_1$=1.5Hz, J$_2$=1.5Hz); 6.17(1H, , d, J=3.4Hz); 6.64–6.72 (1H, dd, J$_1$=1.65Hz, J$_2$=1.65Hz); 6.7–7.9(9H, m)

| 127. | CH$_3$ | H | H | 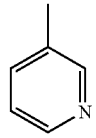 | Mol. Wt. = 394 | Yield = 36% |

$^1$H: 1.07(3H, t, J=6.99Hz); 2.35(3H, s); 2.75–2.89(2H, m); 3.22–3.28(1H, m); 3.57–3.76 (2H, m); 3.96(2H, t, J=5.5Hz); 4.32(2H, t, J=5.5Hz); 5.9(1H, d, J=3.45Hz); 6.12(1H, d, J=3.49Hz); 6.55(2H, d, J=8.6Hz); 7.08(2H, d, J=8.6Hz); 7.42–7.45(1H, m); 7.85–7.88 (1H, m); 8.4–8.42(1H, m); 8.55(1H, s)

| 128. | CH$_3$ | H | H |  | Mol. Wt. = 357 | Yield = 58% |

$^1$H: 0.6–0.62(2H, m); 0.81–0.84(2H, m); 1.3(3H, t, J=6.99Hz); 1.3–1.8(1H, m); 2.28(3H, s); 2.97–3.04(2H, m); 3.4–3.6(2H, m); 4.02–4.03(1H, m); 4.15(2H, t, J=7.9Hz); 4.33(2H, t, J=6.38Hz); 5.7(1H, d, J=3.3Hz); 5.76(1H, d, J=3.28Hz); 6.78(2H, d, J=8.6Hz); 7.15(2H, d, J=8.57Hz)

| 129. | CH$_3$ | H | H | 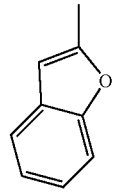 | Mol. Wt. = 433 | Yield = 29% |

$^1$H: 1.06(3H, t, J=6.99Hz); 2.37(3H, s); 2.60–2.68(2H, m); 3.2–3.6(2H, m); 3.7–3.8(1H, m); 4.22(2H, t, J=5.5Hz); 4.55(2H, t, J=5.63Hz); 5.93(1H, d, J=3.63Hz); 6.52(1H, d, J=3.62Hz); 6.69(2H, d, J=8.57Hz); 6.76(1H, s); 7.1(2H, d, J=8.55Hz); 7.18–7.54 (4H, m)

| 130. | CH$_3$ | COOCH$_3$ | H | 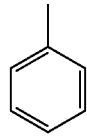 | Mol. Wt. = 451 | Yield = 46% |

$^1$H: 1.08(3H, t, J=6.98Hz); 2.66(3H, s); 2.88–2.89(2H, m); 3.22–3.31(3H, m); 3.77(3H, s); 3.93(2H, t, J=5.64Hz); 4.37(2H, t, J=5.64Hz); 6.45(1H, s); 6.59(2H, d, J=8.6Hz); 7.11(2H, d, J=8.58v); 7.36–7.45(5H, m)

TABLE 13-continued

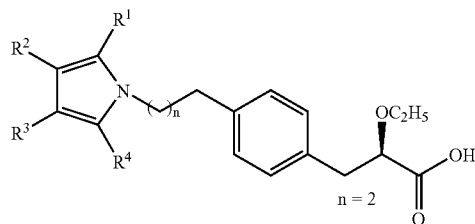

(I)

| | | | | | |
|---|---|---|---|---|---|
| 131. | CH₃ | COOH | H | 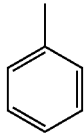 | Mol. Wt. = 437  Yield = 58% |

¹H: 1.2(3H, t, J=6.99Hz); 2.68(3H, s); 2.93–3.03(2H, m); 3.43–3.49(2H, m); 3.89(2H, t, J=5.74Hz); 4.04(1H, t, J=5.88Hz); 4.31(2H, t, J=5.75Hz); 6.58–6.61(3H, m); 7.09 (2H, d, J=8.58Hz); 7.37–7.45(5H, m)

| | | | | | |
|---|---|---|---|---|---|
| 132. | CH₃ | H | H | 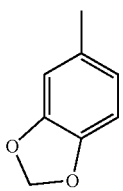 | Mol. Wt. = 437  Yield = 82% |

¹H: 1.07(3H, t, J=6.99Hz); 2.32(3H, s); 2.6–2.63(2H, m); 3.23–3.31(2H, m); 3.32–3.8 (1H, m); 3.92(2H, t, J=5.98Hz); 4.26(2H, t, J=5.97Hz); 5.83(1H, d, J=3.36Hz); 5.91 (1H, d, J=3.39Hz); 5.98(2H, s); 6.6(2H, d, J=8.64Hz); 6.84–6.88(3H, m); 7.11(2H, d, J= 8.58Hz)

| | | | | | |
|---|---|---|---|---|---|
| 133. | CH₃ | H | H | 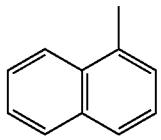 | Mol. Wt. = 443  Yield = 82% |

¹H: 1.06(3H, t, J=6.97Hz); 2.4(3H, s); 2.6–2.62(2H, m); 3.21–3.31(2H, m); 3.71(2H, t, J= 6.04Hz); 3.8–4.0(3H, m); 5.99(1H, d, J=3.35Hz); 6.03(1H, d, J=3.36Hz); 6.35(2H, d, J=8.64Hz); 6.99(2H, d, J=8.61Hz); 7.4–7.92(7H, m)

| | | | | | |
|---|---|---|---|---|---|
| 134. | CH₃ | H | H | 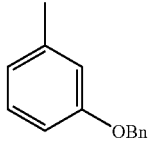 | Mol. Wt. = 499  Yield = 93% |

¹H: 1.07(3H, t, J=6.97Hz); 2.33(3H, s); 2.64–3.2(2H, m); 3.28–3.33(3H, m); 3.9(2H, t, J= 5.88Hz); 4.25(2H, t, J=5.88Hz); 5.11(2H, s); 5.86(1H, d, J=3.78Hz); 6.01(1H, d, J= 3.39Hz); 6.58(2H, d, J=8.61Hz); 6.69–7.01(3H, m); 7.1(2H, d, J=8.58Hz); 7.28–7.43 (6H, m)

| | | | | | |
|---|---|---|---|---|---|
| 135. | CH₃ | H | H | 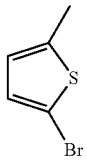 | Mol. Wt. = 478  Yield = 79% |

¹H: 1.08(3H, t, J=6.97Hz); 2.33(3H, s); 2.6–2.62(2H, m); 3.26–4(3H, m); 4.06(2H, t, J= 5.73Hz); 4.34(2H, t, J=5.7Hz); 5.86(1H, d, J=3.51Hz); 6.12(1H, d, J=3.54Hz); 6.67(2H, d, J=8.64Hz); 6.86(1H, d, J=3.81Hz); 7.05(1H, d, J=3.87Hz); 7.13(2H, d, J= 8.58Hz)

TABLE 13-continued

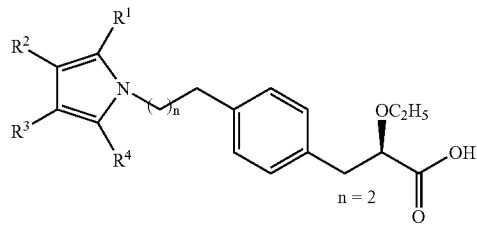

(I)

| 136. | CH$_3$ | H | H | 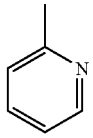 | Mol. Wt. = 394 | Yield = 20% |

$^1$H: 1.08(3H, t, J=6.91Hz); 2.37(3H, s); 2.7–3.1(2H, m); 3.23–4.0(3H, m); 4.17(2H, t, J= 5.64Hz); 4.71–4.78(2H, m); 5.92(1H, d, J=3.66Hz); 6.49(1H, d, J=3.69Hz); 6.67 (2H, d, J=8.52Hz); 7.10–7.14(3H, m); 7.58(1H, d, J=8.1Hz); 7.69–7.72(1H, m); 8.47– 8.49(1H, m)

| 137. | CH$_3$ | H | H | 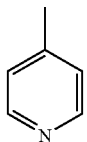 | Mol. Wt. = 394 | Yield = 20% |

$^1$H: (3H, t, J=6Hz); 2.38(3H, s); 3.01(2H, m); 3.51–3.67(2H, m); 4.02–4.13(3H, m); 4.37 (2H, t, J=6Hz); 6.05(1H, d, J=3.45Hz); 6.34(1H, d, J=3.57Hz); 6.49(2H, d, J=8.55 Hz); 7.04(2H, d, J=8.55Hz); 7.30(2H, d, J=6.27Hz); 8.44(2H, d, J=6.12Hz)

| 138. | CH$_3$ | H | H | 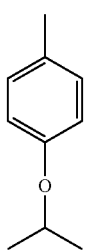 | Mol. Wt. = 451 | Yield = 87% |

$^1$H: 1.07(3H, t, J=6.67Hz); 1.32(6H, d, J=6Hz); 2.32(3H, s); 2.61–2.62(2H, m); 3.28– 3.32(1H, m); 3.33–3.83(2H, m); 3.91(2H, t, J=6.03Hz); 4.25(2H, t, J=6.03Hz); 4.62 (1H, t, J=6.06Hz); 5.83(1H, d, J=3.39Hz); 5.91(1H, d, J=3.39Hz); 6.59(2H, d, J= 8.37Hz); 6.92(2H, d, J=8.7Hz); 7.10(2H, d, J=8.43Hz); 7.27(2H, d, J=8.73Hz)

| 139. | CH$_3$ | H | CH$_3$ | 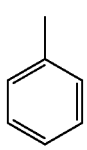 | Mol. Wt. = 407 | Yield = 87% |

$^1$H: 1.1(3H, t, J=6.29Hz); 2.2(3H, s); 2.61(3H, s); 2.87(2H, d, d, 2H); 3.22–3.28(2H, m); 3.75–3.82(1H, m); 3.8(2H, t, J=6.16Hz); 4.14(2H, t, J=6.16Hz); 5.73(1H, s); 6.5 (2H, d, J=8.5Hz); 7.08(2H, d, J=8.5Hz); 7.26–7.44(5H, m)

| 140. | CH$_3$ | H | H | 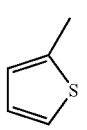 | Mol. Wt. = 399 | Yield = 55% |

$^1$H: 1.08(3H, t, J=6.9Hz); 2.3(3H, s); 2.88(2H, m); 3.22–3.6(2H, m); 3.8(1H, m); 4.02 (2H, t, J=6.0Hz); 4.3(2H, t, J=6.0Hz); 5.8(1H, d, J=3.5Hz); 6.1(1H, d, J=3.5Hz); 6.6(2H, d, J=8.6Hz); 7.04–7.1(2H, m); 7.13–7.15(2H, m); 7.32–7.34(1H, m)
(solvent used is CD$_3$OD)

TABLE 13-continued

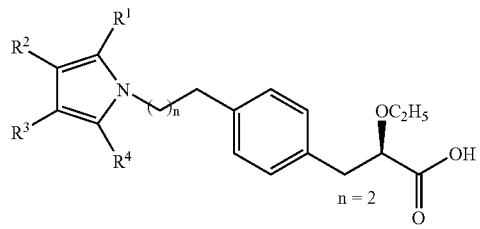

(I)

| | R¹ | R² | R³ | R⁴ | | |
|---|---|---|---|---|---|---|
| 141. | CH₃ | H | H |  | Mol. Wt. = 499 | Yield = 78% |

¹H: 1.07(3H, t, J=6.9Hz); 2.3(3H, s); 2.7–2.9(2H, m); 3.4–3.5(2H, m); 3.7–3.8(1H, m); 3.9(2H, m); 4.2(2H, m); 5.0(2H, s), 5.8(1H, d, J=3.4Hz); 5.9(1H, d, J=3.3Hz); 6.5(2H, d, J=8.7Hz); 7.0(2H, d, J=8.5Hz); 7.2(2H, d, J=8.8Hz); 7.35–7.44(7H, m) (solvent used is CD₃OD)

| 142. | CH₃ | H | H | 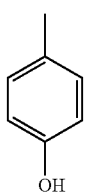 | Mol. Wt. = 409 | Yield = 88% |
|---|---|---|---|---|---|---|

¹H: 1.2(3H, t, J=7Hz); 2.3(3H, s); 3.0(2H, m); 3.5(2H, m); 3.9(2H, m); 4.1(1H, m); 4.2 (2H, m); 5.9(1H, d, J=3.3Hz); 6.0(1H, d, J=3.3Hz); 6.5(2H, d, J=8.6Hz); 6.86(2H, d, J=8.6Hz); 7.0(2H, d, J=8.7Hz); 7.22–7.26(2H, m)

| 143. | H | H | H | Ph | Mol. Wt. = 379 | Yield = 73% |
|---|---|---|---|---|---|---|

¹H: 1.08(3H, t, J=6.99Hz); 2.7–2.9(2H, m); 3.1–3.2(1H, m); 3.4–3.5(1H, m); 3.7(1H, m); 4.06(2H, t, J=5.6Hz); 4.29(2H, t, J=5.6Hz); 6.08(2H, m); 6.6(2H, d, J=8.6Hz); 6.8(1H, m); 7.1(2H, d, J=8.6Hz); 7.38–7.39(5H, m) (solvent used is CD₃OD)

| 144. | CH₃ | H | H | 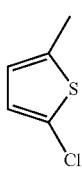 | Mol. Wt. = 433 | Yield = 90% |
|---|---|---|---|---|---|---|

¹H: 1.08(3H, t, J=6.9Hz); 2.3(3H, s); 2.75–3.0(2H, m); 3.2–3.3(1H, m); 3.5–3.6(1H, m); 3.8(1H, m); 4.05(2H, t, J=5.6Hz); 4.31(2H, t, J=5.6Hz); 5.8(1H, d, J=3.4Hz); 6.1 (1H, d, J=3.5Hz); 6.6(2H, d, J=8.6Hz); 6.8(1H, d, J=3.8Hz); 6.9(1H, d, J=3.8Hz); 7.1(2H, d, J=8.6Hz) (solvent used is CD₃OD)

| 145. | CH₃ | H | H |  | Mol. Wt. = 437 | Yield = 77% |
|---|---|---|---|---|---|---|

¹H: 1.07(3H, t, J=6.98Hz); 1.39(3H, t, J=6.96Hz); 2.31(3H, s); 2.88(2H, m); 3.29(1H, m); 3.6(1H, m); 3.78(1H, m); 3.88(2H, t, J=6.03Hz); 4.04(2H, q, J=6.97Hz); 4.23 (2H, t, J=6.12Hz); 5.82(1H, d, J=3.36Hz); 5.9(1H, d, J=3.37Hz); 6.7(2H, d, J=8.61 Hz); 6.91(2H, d, J=6.93Hz); 7.8(2H, d, J=8.58)Hz); 7.25(2H, d, J=6.67Hz)

TABLE 13-continued

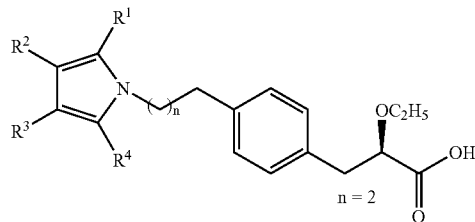

(I)

| | | | | | |
|---|---|---|---|---|---|
| 146. | CH₃ | H | H | 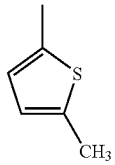 | Mol. Wt. = 399  Yield = 97% |

¹H: 1.08(3H, t, J=6.9Hz), 2.3(3H, s); 2.45(3H, s); 2.89(2H, m); 3.23–3.57(2H, m); 3.6–3.9(1H, m); 4.0(2H, t, J=6Hz); 4.3(2H, t, J=6Hz); 5.8(1H, d, J=3.3Hz); 6.0(1H, d, J=3.47Hz); 6.65(2H, d, J=8.6Hz); 6.69–6.71(1H, m); 6.79(1H, d, J=3.44); 7.11(2H, d, J=8.6Hz) (solvent used is CD₃OD)

| 147. | CH₃ | CH₃ | H | C₆H₅ | Mol. Wt. = 407  Yield = 50% |
|---|---|---|---|---|---|

¹H: 1.0(3H, t, J=7Hz); 2.1(3H, s); 2.23(3H, s); 2.7–2.9(2H, m); 3.55(1H, m); 3.56(1H, m), 3.75(1H, m); 3.9(2H, t, J=6.1Hz); 4.2(2H, t,); 5.87(1H, s); 6.5(2H, d, J=8.5Hz); 7.0(2H, d, J=8.5Hz); 7.2–7.3(3H, m); 7.3–7.36(2H, m) (solvent used is CD₃OD)

| 148. | CH₃ | H | H | 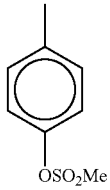 | Mol. Wt. = 487  Yield = 50% |
|---|---|---|---|---|---|

¹H: 0.9(3H, t, J=6.9Hz); 2.6(3H, s); 2.7–2.8(1H, m), 2.9–3.0(1H, m); 3.0–3.1(4H, m); 3.3–3.4(1H, m); 3.7–3.8(1H, m); 3.8–3.9(2H, m); 4.1–4.2(2H, m); 5.9(1H, d, J=3.3Hz); 6.0(1H, d, J=3.4Hz); 6.4(2H, d, J=8.4Hz); 6.9(2H, d, J=8.47Hz); 7.2–7.3(2H, m); 7.38(2H, d, J=8.6Hz)

| 149. | H | H | H | H | Mol. Wt. = 303  Yield = 79% |
|---|---|---|---|---|---|

¹H: 1.16(3H, t, J=6.9Hz); 2.97(1H, dd); 3.0(1H, dd); 3.36–3.6(2H, m); 4.01(1H, dd); 4.17–4.28(4H, m) 6.16(2H, t, J=2.1Hz); 6.75–6.80(4H, m); 6.7(2H, t, J=2.1Hz); 6.8 (2H, d, J=8.5Hz); 7.15(2H, d, J=8.5Hz).

| 150. | CH₃ | H | H | CH₃ | Mol. Wt. = 331.2  Yield = 59% |
|---|---|---|---|---|---|

¹H: 1.18(3H, t, J=7Hz); 2.28(6H, s); 2.93–3.08(2H, m); 3.45–3.59(2H, m); 4.03–4.18 (5H, m); 5.79(1H, s); 6.0(1H, s); 6.78(2H, d, J=8.5Hz); 7.15(2H, d, J=8.5Hz).

| 151. | i-Pr | 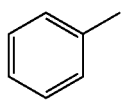 | H | i-Pr | Mol. Wt. = 463  Yield = 48% |
|---|---|---|---|---|---|

¹H: 1.12(3H, t, J=6.9Hz); 1.2–1.3(12H, m); 2.96–3.76(7H, m); 4.03–4.05(2H, m); 4.30 (2H, t, J=6.9Hz); 5.89(1H, s); 6.80(2H, d, J=8.5Hz); 7.15(2H, d, J=8.5Hz); 7.2–7.33 (5H, m).

| 152. | i-Pr | H | H | 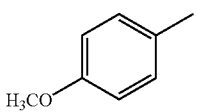 | Mol. Wt. = 451  Yield = 84% |
|---|---|---|---|---|---|

¹H: 1.2(3H, t, J=7Hz); 1.29(6H, d, J=6Hz); 2.90(2H, dd); 3.04–3.06(1H, m); 3.33–3.59(2H, m); 3.8(3H, s); 4.0(1H, t); 3.84(2H, t, J=6Hz); 4.28(2H, t, J=6.7Hz); 5.98 (1H, d, J=3.4Hz); 6.56(2H, d, J=8.6Hz); 6.08(1H, d, J=3.5Hz); 6.93(2H, d, J=8.7Hz); 7.03(2H, t, J=8.5Hz); 7.32(2H, d, J=8.5Hz).

| 153. | i-Pr | H | H | 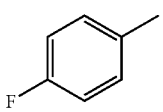 | Mol. Wt. = 439  Yield = 36% |
|---|---|---|---|---|---|

TABLE 13-continued

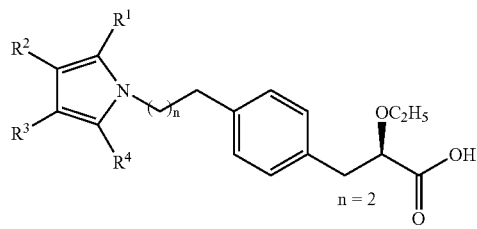

(I)

¹H: 1.17(3H, t, J=6.9Hz); 1.31(6H, d, J=6.9Hz); 2.93(2H, dd); 3.03–3.1(1H, m); 3.33–3.58(2H, m); 3.84(2H, t, J=6.5Hz); 4.0(1H, m); 4.29(2H, t, J=6.6Hz); 6.56(2H, d, J=8.6Hz); 6.10(1H, d, J=3.5Hz); 6.00(1H, d, J=3.5Hz); 7.0–7.1(4H, m); 7.3–7.38(2H, m).

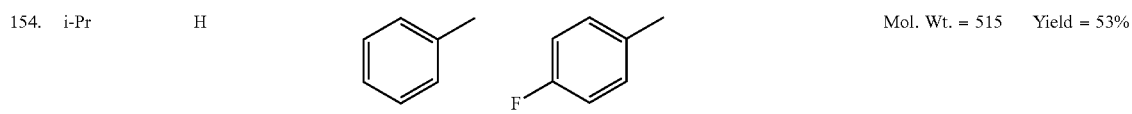

154. i-Pr    H    (phenyl)    (4-F-phenyl)    Mol. Wt. = 515    Yield = 53%

¹H: 1.19(3H, t, J=6.9Hz); 1.36(6H, d, J=7Hz); 2.95(2H, dd, J=7.1Hz); 3.0–3.1(1H, m); 3.45–3.57(2H, m); 3.83(2H, t, J=6.5Hz); 4.0–4.04(1H, m); 4.2(2H, t, J=6.7Hz); 6.2 (1H, s); 6.5–7.28(13H, m).

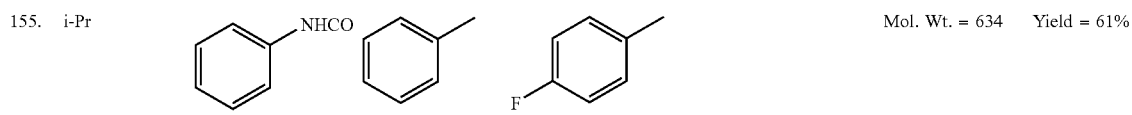

155. i-Pr    (PhNHCO-)    (phenyl)    (4-F-phenyl)    Mol. Wt. = 634    Yield = 61%

¹H: 0.91(3H, t, J=6.7Hz); 1.45(6H, d, J=6.8Hz); 2.91(2H, dd); 3.13(1H, m); 3.32–3.49 (2H, m); 3.80(3H, m) 4.15(2H, t, J=6.5Hz); 6.46(2H, d); 6.78(1H, s); 6.86–7.18(15H, m).

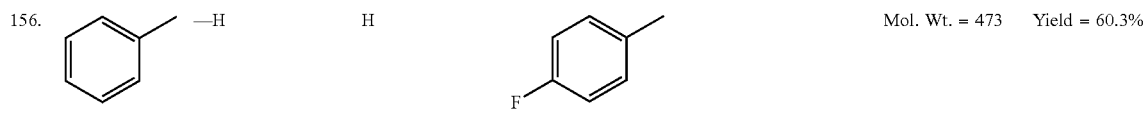

156. (phenyl)    —H    H    (4-F-phenyl)    Mol. Wt. = 473    Yield = 60.3%

¹H: 0.9(3H, t); 2.6(1H, t); 2.9(2H, d); 3.2(1H, m); 3.5(2H, t); 3.6(1H, m); 6.21(2H, dd, J=3Hz); 6.9(2H, d); 7.0(2H, t, J=9.0Hz); 7.31–7.6(9H, m).

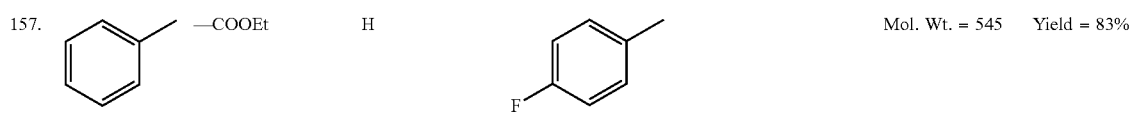

157. (phenyl)    —COOEt    H    (4-F-phenyl)    Mol. Wt. = 545    Yield = 83%

¹H: 0.9(3H, t); 2.6(1H, t); 2.9(2H, d); 3.2(1H, m); 3.5(2H, t); 3.6(1H, m); 6.7(1H, s); 6.9 (2H, d); 7.1(2H, t); 7.29–7.6(9H, m).

158. i-Pr    H    H    CH₃    Mol. Wt. = 359    Yield = 20%

¹H: 1.17(3H, t, J=6.9Hz); 1.26(6H, d, J=6.7Hz); 2.27(3H, s); 2.9–3.0(1H, m); 3.07 (2H, dd); 3.42–3.58(2H, m); 4.02–4.08(3H, m); 4.2(2H, t, J=6.3Hz); 5.83(2H, s); 6.7 (2H, d, J=8Hz); 7.15(2H, d, J=8Hz).

PREPARATION 16

(R/S) 2-ethoxy-3[6-[2-[2-(4-methoxyphenyl)-5-methyl-pyrrol-1-yl]ethoxy]napthalen-2yl] propanoic acid In a like manner to the procedure given in Preparation 15, the esters described in examples 76 can be converted to a corresponding acid.

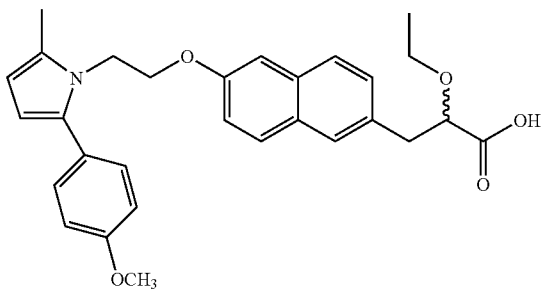

(I)

TABLE 14

| Ex. No. | Substituents on the pyrrole ring in (I) | | | |
|---|---|---|---|---|
| | R¹ | R² | R³ | R⁴ |
| 159. | CH₃ | H | H | 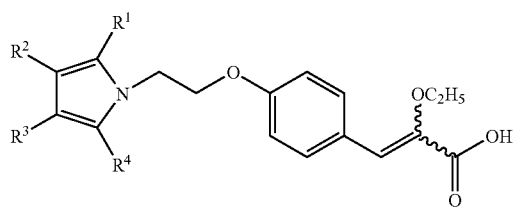 Mol. Wt. = 473  Yield = 82% |

¹H: 1.15(3H, t, J=7Hz); 2.4(3H, s); 3.1–3.16(2H, m); 3.4–3.62(2H, m); 3.57(3H, s); 4.07 (2H, t, J=6.6Hz); 4.13–4.18(1H, dd, J=3.48Hz); 4.32(2H, t, J=6.6Hz); 5.96(1H, d, J= 3.36Hz); 6.0(1H, d, J=3.39Hz); 6.8(1H, d, J=2.37Hz); 6.9–7.0(3H, m); 7.33–7.38(3H, m); 7.52–7.64(3H, m)

PREPARATION 17

(E/Z) 3-{4-[2-(5-methyl-2-phenylpyrrol-1-yl)ethoxy]phenyl}-2-ethoxypropen-2-oic acid (Example 161)

In a like manner to the procedure given in Preparation 15, the esters described in examples 79, 80, 81 can be converted to a corresponding acid.

TABLE 15

| Ex. No. | Substituents on the pyrrole ring in (1 h) | | | | | | |
|---|---|---|---|---|---|---|---|
| | R¹ | R² | R³ | R⁴ | | | |
| 160. | CH₃ | H | H | Phenyl | Mol. Wt. = 391 | Yield = 59% | |
| 161. | CH₃ | H | H | Phenyl | Mol. Wt. = 391 | Yield = 25% | |
| E-isomer | | | | | | | |
| ¹H: 1.35(3H, t, J=6.8Hz); 2.36(3H, s); 3.8–3.9(4H, m); 4.28(2H, t, J=6.4Hz); 5.5(1H, s); 5.9(1H, d, J=3.3Hz); 6.0(1H, d, J=3.3Hz); 6.5(2H, d, J=8.7Hz); 7.1(2H, d, J= 8.6Hz); 7.3–7.4(5H, m). | | | | | | | |
| 162. | CH₃ | H | H | Phenyl | Mol. Wt. = 391 | Yield = 25% | |
| Z-isomer | | | | | | | |
| ¹H: 1.37(3H, t, J=7.0Hz); 2.3(3H, s); 3.9–4.02(4H, m); 4.3(2H, t, J=6.4Hz); 5.9(1H, d, J=3.2Hz); 6.1(1H, d, J=3.2Hz); 6.6(2H, d, J=8.8Hz); 7.0(1H, s); 7.26–7.42(5H, m); 7.6(2H, d, J=8.8Hz). | | | | | | | |

PREPARATION 18

(R/S) 3-{4-[2-(5-methyl-2-phenylpyrrol-1-yl)ethoxy]phenyl}-2-ethoxypropanoic acid (Example 163)

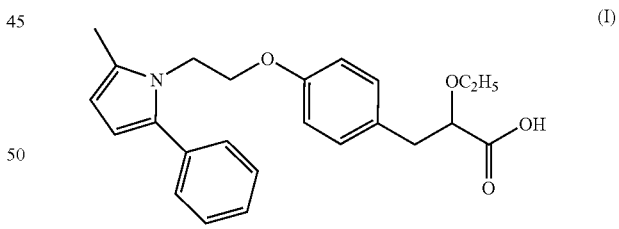

(I)

Using the procedure similar to that described in Preparation 15, the racemic ester (Example 72) was hydrolysed to its corresponding acid.

TABLE 16

| Ex. No. | Substituents on the pyrrole ring | | | |
|---|---|---|---|---|
| | R¹ | R² | R³ | R⁴ |
| 163. | CH₃ | H | H | Phenyl  Mol. Wt. = 393  Yield = 50% |

¹H: 1.06(3H, t, J=6.9Hz); 2.3(3H, s); 2.75–2.84(2H, m); 3.15–3.25(1H, m); 3.5–3.6(1H, m); 3.7(1H, m); 3.88(2H, t, J=6.0Hz); 4.29(2H, t, J=6.0Hz); 5.8(1H, d, J=3.3Hz);

TABLE 16-continued

| Ex. No. | Substituents on the pyrrole ring |     |     |     |
|---------|-----|-----|-----|-----|
|         | R¹  | R²  | R³  | R⁴  |
| | 5.9(1H, d, J=3.3Hz); 6.53–6.56(2H, d, J=8.6Hz); 7.1(2H, d, J=8.6Hz); 7.28–7.38(5H, m). | | | |

PREPARATION 19

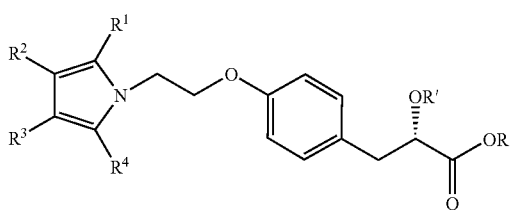

(I)

Using the procedure similar to that described in Preparation 15, the methoxy and propoxy ester (Example 77 and 78) was hydrolysed to its corresponding acid.

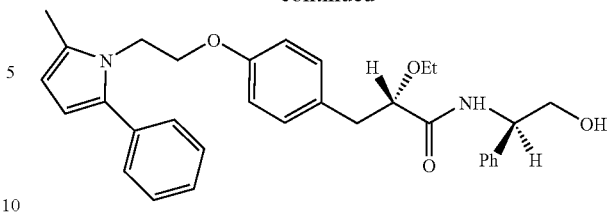

To a well-stirred solution of (±) 2-ethoxy 3-{4-[2-(5-Methyl-2-(4-methylphenyl)pyrrol-1-yl)ethoxy]phenyl}-propanoic acid (1 g, 2 mmole) (prepared as in Example no. 164) in dry dichloromethane (10 mL), triethylamine (0.674 mL, 0.485 g, 4 mmole) was added at 0° C., followed by ethylchloroformate (0.311 g, 0.275 mL, 2 mmole) and stirred for 3.5 hr at same temperature. To this reaction, solution containing of (S)-phenyl glycinol (0.329 g, 2 mmole) in dichloromethane (5 mL) and triethylamine (0.674 mL, 0.485 g, 4 mmole) was added at 0° C. to 5° C. After stirring for 3 hrs at 0 to 10° C., the reaction was warmed to 20–25° C. and stirred for 16 hrs. The reaction mixture was diluted with dichloromethane (20 mL) and washed with H₂O (20 mL), brine (20 mL), dried over anhy. Na₂SO₄ and evaporated.

TABLE 17

| Ex. No. | Substituents on the pyrrole ring | | | | | | |
|---------|-----|-----|-----|-----|-----|-----|-----|
|         | R¹  | R²  | R³  | R⁴  | R'  |     |     |
| 164. | CH₃ | H | H | (phenyl) | CH₃ | Mol. Wt. = 379 | Yield = 20% |
| 165. | CH₃ | H | H | (phenyl) | C₃H₇ | Mol. Wt. = 408 | Yield = 22% |

PREPARATION 20

[2R, N(1S)]/[2S, N(1S)] 2-Ethoxy-N-(2-hydroxy-1-phenylethyl)-3-{4-[2-(5-methyl-2-phenyl pyrrol-1-yl)ethoxy]phenyl}propanamide

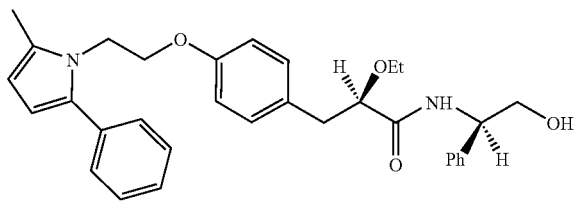

The residue was chromatographed over silica gel using a gradient of 10–50% of ethyl acetate:pet. ether as an eluent to afford firstly diastereomer assigned as [(2R)-N(1S)]-2-Ethoxy-3-{4-[2-(5-methyl-2-phenylpyrrol-1-yl)ethoxy]phenyl}-N-(2-hydroxy-1-phenylethyl)propanamide and [(2S)-N(1S)]-2-Ethoxy-3-{4-[2-(5-methyl-2-phenylpyrrol-1-yl)ethoxy]phenyl}-N-(2-hydroxy-1-phenylethyl)propanamide.

TABLE 18

| Ex. No. | Substituents on the pyrrole ring | | | | | |
|---------|-----|-----|-----|-----|-----|-----|
|         | R¹  | R²  | R³  | R⁴  |     |     |
| 166. (2R) diastereomer | CH₃ | H | H | Phenyl | Mol. Wt. = 407 | Yield = 50% |
| ¹H: 1.12(3H, t, J=6.9Hz); 2.30(3H, s); 2.80–3.1(2H, dd); 3.5(2H, m); 3.91–3.95(5H, m); 4.30(2H, t, J=6.5Hz); 5.00(1H, m); 5.90(1H, d, J=3.3Hz); 6.10(1H, d, J=3.3Hz); | | | | | | |

TABLE 18-continued

| Ex. No. | Substituents on the pyrrole ring | | | | |
|---|---|---|---|---|---|
| | $R^1$ | $R^2$ | $R^3$ | $R^4$ | |
| | 6.60(2H, d, J=8.4Hz); 6.9–7.1(4H, m); 7.2–7.3(3H, m); 7.32–7.4(5H, m). | | | | |
| 167. | $CH_3$ | H | H | Phenyl | Mol. Wt. = 407  Yield = 50% |
| | (2S) diastereomer | | | | |
| | $^1$H: 1.18(3H, t, J=7.0Hz); 2.39(3H, s); 2.80–3.1(2H, dd); 3.5–3.55(2H, m); 3.84–3.97(5H, m); 4.30(2H, t, J=6.7Hz); 5.00(1H, m); 5.90(1H, d, J=3.3Hz); 6.10(1H, d, J=3.3Hz); 6.55(2H, d, J=8.6Hz); 6.9–7.1(4H, d, J=8.5Hz); 7.22–7.26(3H, m) 7.41(5H, m). | | | | |

PREPARATION 21

(R)-3-{4-[2-(5-methyl-2-phenylpyrrol-1-yl)ethoxy]phenyl}-2-ethoxypropanoic acid from the corresponding diastereomer (Example No. 168)

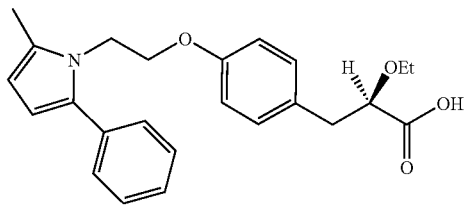

A solution of [(2R)-N(1S)]-2-Ethoxy-3-{4-[2-(5-methyl-2-phenylpyrrol-1-yl)ethoxy]phenyl}-N-(2-hydroxy-1-phenylethyl)propanamide (Example no. 167)(280 mg, 0.546 mmole) in a mixture of 1M. sulfuric acid (7 mL) and dioxane: $H_2O$:HCl (1:1:56 mL) was heated for at 100° C. for 24 hrs. The reaction mixture was cooled to 20° C. to 30° C. Product was extracted in ethyl acetate (2×30 mL). Combined extract was washed with $H_2O$ (3×30 mL), brine (30 mL) and dried over anhy. $Na_2SO_4$. Ethyl acetate was evaporated under reduced pressure to afford (252 mg) product.

PREPARATION 22

(S)-3-{4-[2-(5-methyl-2-phenylpyrrol-1-yl)ethoxy]phenyl}-2-ethoxypropanoic acid from the corresponding diastereomer(Example No. 169)

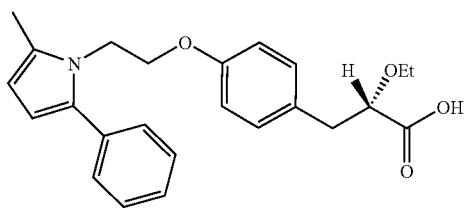

A solution of [(2S)-N(1S)]-2-Ethoxy-3-{4-[2-(5-methyl-2-phenylpyrrol-1-yl)ethoxy]phenyl}-N-(2-hydroxy-1-phenylethyl) propanamide (Example no. 168) was treated same as in preparation 20 to obtain the corresponding optically active acid. This was found identical to that obtained in (Example no. 90).

PREPARATION 23

3-{4-[2-(5-Methyl-2-phenylpyrrol-1-yl)ethoxy]phenyl}-2-ethoxypropanoic acid sodium salt (Example 170)

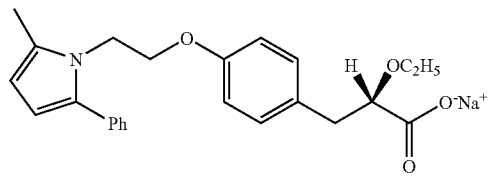

The acid prepared in example 90 (2.6 g) was dissolved in methanol (30 mL), sodium hydroxide (0.264 g) was added and stirred for 1 hour at 20° C. to 25° C. Afterwards, methanol was distilled at reduced pressure, to obtain an oily product. It was stirred with diisopropyl ether (50 mL) at 20–30° C. Solid sodium salt obtained was carefully filtered (2.3 g).

PREPARATION 24

3-{4-[2-(5-Methyl-2-phenylpyrrol-1-yl)ethoxy]phenyl}-2-ethoxy propanoic acid calcium salt (Example 171)

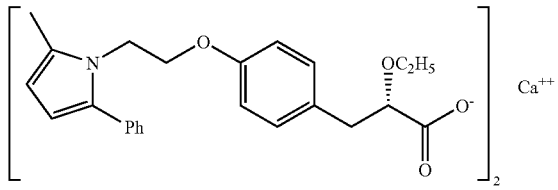

The sodium salt of example 170 (0.200 g), was dissolved in methanol (10 mL) and treated with calcium acetate (0.090 g) at 20° C.–25° C. Further, 50 mL of water was added when the calcium salt of the acid precipitates out. The precipitate was filtered, washed with water and then with di-isopropyl ether (2×20 mL) to afford the title compound.

Using the above procedure for Example 170 and Example 171 following salts are prepared using the appropriate acids/bases or according to the methods known in literature.

TABLE 19

$$\text{(I)}$$

Structure: Pyrrole ring with substituents R¹, R², R³, R⁴ on positions, N-linked to -(CH₂)ₙ-O-phenyl-CH₂-CH(OC₂H₅)-C(=O)-O⁻M⁺

| | Substituents on the pyrrole ring in (I) | | | | M | |
|---|---|---|---|---|---|---|
| | | | | | Na⁺ salts | Ca⁺⁺ salts Example |
| R¹ | R² | R³ | R⁴ | n | Example no. | no. |
| CH₃ | H | CH₃ | H | 2 | 172. | 173. |
| C₂H₅ | H | H | H | 2 | 174. | 175. |
| CHO | H | H | H | 2 | 176. | 177. |
| COCH₃ | H | H | H | 2 | 178. | 179. |
| CH₃ | H | H | CH₂CH₃ | 2 | 180. | 181. |
| CH₃ | H | H | (CH₂)₂CH₃ | 2 | 182. | 183. |
| CH₃ | H | H | (CH₂)₃CH₃ | 2 | 184. | 185. |
| CH₃ | H | H | phenyl | 2 | 186. | 187. |
| CH₃ | H | H | 4-methylphenyl | 2 | 188. | 189. |
| CH₃ | H | H | 3-methylphenyl | 2 | 190. | 191. |
| CH₃ | H | H | 4-methoxyphenyl | 2 | 192. | 193. |
| CH₃ | H | H | 4-bromophenyl | 2 | 194. | 195. |
| CH₃ | H | H | 4-fluorophenyl | 2 | 196. | 197. |
| CH₃ | H | phenyl | H | 2 | 198. | 199. |
| CH₃ | H | phenyl | phenyl | 2 | 200. | 201. |
| i-Pr | H | H | i-Pr | 2 | 202. | 203. |

TABLE 19-continued
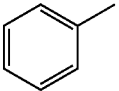
(I)
| | Substituents on the pyrrole ring in (I) | | | | M | |
|---|---|---|---|---|---|---|
| | | | | | Na⁺ salts | Ca⁺⁺ salts Example |
| R¹ | R² | R³ | R⁴ | n | Example no. | no. |
| i-Pr | H | H | 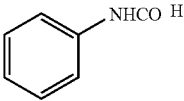 | 2 | 204. | 205. |
| i-Pr | 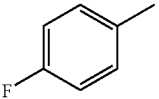 NHCO | H | 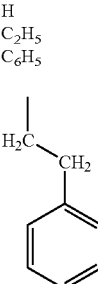 F | 2 | 206. | 207. |
| SCH₃ | H | H | H | 2 | 208. | 209. |
| C₂H₅ | H | H | C₂H₅ | 2 | 210. | 211. |
| C₂H₅ | H | H | C₆H₅ | 2 | 212. | 213. |
| CH₃ | H | H | 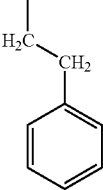 | 2 | 214. | 215. |
| CH₃ | H | H | 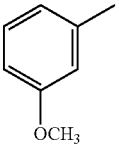 OCH₃ | 2 | 216. | 217. |
| CH₃ | H | H | 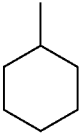 | 2 | 218. | 219. |
| CH₃ | H | H | 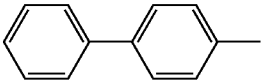 | 2 | 220. | 221. |
| CH₃ | H | H | 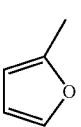 | 2 | 222. | 223. |
| CH₃ | H | H | 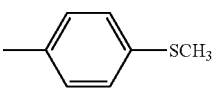 SCH₃ | 2 | 224. | 225. |

TABLE 19-continued
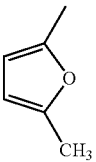
(I)
| | | Substituents on the pyrrole ring in (I) | | | M | |
|---|---|---|---|---|---|---|
| | | | | | Na⁺ salts | Ca⁺⁺ salts Example |
| R¹ | R² | R³ | R⁴ | n | Example no. | no. |
| CH₃ | H | H | 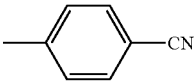 | 2 | 226. | 227. |
| CH₃ | H | H | 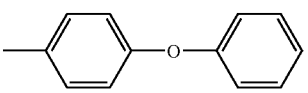 | 2 | 228. | 229. |
| CH₃ | H | H | 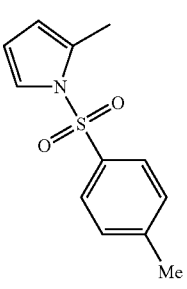 | 2 | 230. | 231. |
| CH₃ | H | H | 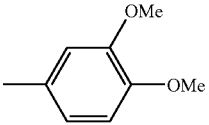 | 2 | 232. | 233. |
| CH₃ | H | H | 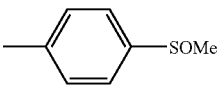 | 2 | 234. | 235. |
| CH₃ | H | H | 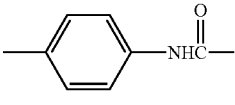 | 2 | 236. | 237. |
| CH₃ | H | H | 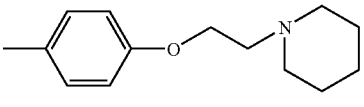 | 2 | 238. | 239. |
| CH₃ | H | H |  | 2 | 240. | 241. |

TABLE 19-continued

Structure (I): Pyrrole ring with substituents R¹, R², R³, R⁴ on positions, N-linked via (CH₂)ₙ-O to para-substituted phenyl-CH₂-CH(OC₂H₅)-C(=O)-O⁻M⁺

| Substituents on the pyrrole ring in (I) | | | | | M | |
|---|---|---|---|---|---|---|
| | | | | | Na⁺ salts | Ca⁺⁺ salts Example |
| R¹ | R² | R³ | R⁴ | n | Example no. | no. |
| CH₃ | H | H | –C₆H₄–O–CH₂–CH=CH₂ (4-allyloxyphenyl) | 2 | 242. | 243. |
| CH₃ | H | H | –C₆H₄–S–C₆H₄–CH₃ (4-(phenylthio)-4'-methylphenyl) | 2 | 244. | 245. |
| CH₃ | H | H | –C₆H₄–S(=O)–C₆H₄–CH₃ (sulfinyl) | 2 | 246. | 247. |
| CH₃ | H | H | –C₆H₄–S(=O)₂–CH₃ (methylsulfonyl-tolyl) | 2 | 248. | 249. |
| CH₃ | H | H | –C₆H₄–O–CH₂–cyclohexyl | 2 | 250. | 251. |
| COPh | H | H | H | 2 | 252. | 253. |
| CH₃ | H | H | 3-pyridyl | 2 | 254. | 255. |
| CH₃ | H | H | cyclopropyl | 2 | 256. | 257. |

TABLE 19-continued (I)

Substituents on the pyrrole ring in (I)

| R¹ | R² | R³ | R⁴ | n | Na⁺ salts Example no. | Ca⁺⁺ salts Example no. |
|---|---|---|---|---|---|---|
| $CH_3$ | H | H | 2-benzofuranyl | 2 | 258. | 259. |
| $CH_3$ | $COOCH_3$ | H | phenyl | 2 | 260. | 261. |
| $CH_3$ | COOH | H | phenyl | 2 | 262. | 263. |
| $CH_3$ | H | H | benzo[1,3]dioxol-5-yl | 2 | 264. | 265. |
| $CH_3$ | H | H | 1-naphthyl | 2 | 266. | 267. |
| $CH_3$ | H | H | 3-(OBn)phenyl | 3 | 268. | 269. |
| $CH_3$ | H | H | 5-bromothien-2-yl | 2 | 270. | 271. |

TABLE 19-continued
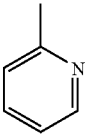
(I)
| | Substituents on the pyrrole ring in (I) | | | | M | |
|---|---|---|---|---|---|---|
| | | | | | Na⁺ salts | Ca⁺⁺ salts Example |
| R¹ | R² | R³ | R⁴ | n | Example no. | no. |
| CH₃ | H | H | 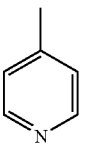 | 2 | 272. | 273. |
| CH₃ | H | H | 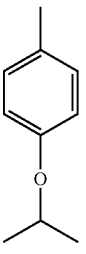 | 2 | 274. | 275. |
| CH₃ | H | H | 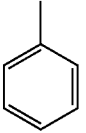 | 2 | 276. | 277. |
| CH₃ | H | CH₃ | 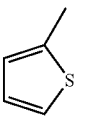 | | 278. | 279. |
| CH₃ | H | H |  | 2 | 280. | 281. |
| CH₃ | H | H |  | 2 | 282. | 283. |

TABLE 19-continued
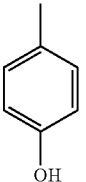
(I)
| | | Substituents on the pyrrole ring in (I) | | | M | |
|---|---|---|---|---|---|---|
| | | | | | Na⁺ salts | Ca⁺⁺ salts Example |
| R¹ | R² | R³ | R⁴ | n | Example no. | no. |
| CH₃ | H | H | 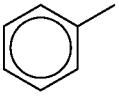 | 2 | 284. | 285. |
| H | H | H | 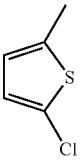 | 2 | 286. | 287. |
| CH₃ | H | H |  | 2 | 288. | 289. |
| CH₃ | H | H | 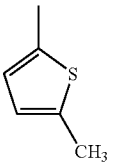 | 2 | 290. | 291. |
| CH₃ | H | H | 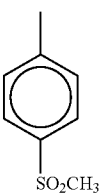 | 2 | 292. | 293. |
| CH₃ | CH₃ | H | C₆H₅ | 2 | 294. | 295. |
| CH₃ | H | H | (4-SO₂CH₃-C₆H₄) | 2 | 296. | 297. |
| H | H | H | H | 2 | 298. | 299. |
| CH₃ | H | H | CH₃ | 2 | 300. | 301. |

TABLE 19-continued

Structure (I):

Pyrrole ring with substituents R¹, R², R³, R⁴ on ring positions; N-(CH₂)ₙ-O-C₆H₄-CH₂-C*H(OC₂H₅)-C(=O)-O⁻M⁺ (with S-configuration indicated)

| | Substituents on the pyrrole ring in (I) | | | | M | |
|---|---|---|---|---|---|---|
| | | | | | Na⁺ salts | Ca⁺⁺ salts Example |
| R¹ | R² | R³ | R⁴ | n | Example no. | no. |
| i-Pr | phenyl | H | i-Pr | 2 | 302. | 303. |
| i-Pr | H | H | 4-methoxyphenyl (H₃CO-C₆H₄-) | 2 | 304. | 305. |
| i-Pr | H | H | 4-fluorophenyl (F-C₆H₄-) | 2 | 306. | 307. |
| i-Pr | H | phenyl | 4-fluorophenyl | 2 | 308. | 309. |
| i-Pr | phenyl-NHCO | phenyl | 4-fluorophenyl | 2 | 310. | 311. |
| phenyl | —H | H | 4-fluorophenyl | 2 | 312. | 313. |
| phenyl | —COOEt | H | 4-fluorophenyl | 2 | 314. | 315. |
| i-Pr | H | H | CH₃ | 2 | 316. | 317. |

TABLE 20

(I)

[Structure: pyrrole ring with R1, R2, R3, R4 substituents, N-(CH2)n-O-phenyl-CH=C(OC2H5)-C(=O)-O-M+]

| Substituents on the pyrrole ring in (I) | | | | | M | |
|---|---|---|---|---|---|---|
| | | | | | Na+ salts | Ca++ salts |
| R1 | R2 | R3 | R4 | N | Example no. | Example no. |
| CH3 | H | H | 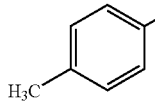 | 2 E-isomer | 318. | 319. |
| CH3 | H | H | 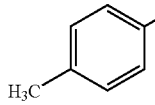 | 2 Z-isomer | 320. | 321. |

TABLE 21

(I)

[Structure: pyrrole ring with R1, R2, R3, R4 substituents, N-(CH2)n-O-phenyl-CH2-CH(OR')-C(=O)-O-M+]

| Ex. No. | Substituents on the pyrrole ring | | | | R' | M | |
|---|---|---|---|---|---|---|---|
| | R1 | R2 | R3 | R4 | | | |
| 322. | CH3 | H | H | 4-CH3-C6H4-CH2- | CH3 | Na | Mol. Wt. = 401 Yield = 100% |

1H: 2.37(3H, s); 2.93–3.03(2H, m); 3.37(3H, s); 3.90–3.96(3H, m); 4.28(2H, t, J=6.57 Hz); 5.96(1H, d, J=3.33Hz); 6.10(1H, d, J=3.36Hz); 6.61(2H, d, J=8.58Hz); 7.08 (2H, d, J=8.55Hz); 7.26–7.41(5H, m).

| 323. | CH3 | H | H | 4-CH3-C6H4-CH2- | CH3 | Ca | Mol. Wt. = 796 Yield = 44% |

1H: 0.83(3H, t, J=7.4Hz); 0.89(3H, t, J=7.4Hz); 1.53–1.63(4H, m); 2.37(3H, s); 2.91(2H, d, J=5.54Hz); 3.20–3.48(2H, m); 3.92(6H, s); 4.06(2H, t, J= 6.67Hz); 4.28(2H, t, J=6.61Hz)5.97(1H, d, J=3.33Hz); 6.11(1H, d, J=3.40Hz); 6.59 (2H, d, J=8.64Hz); 7.07(2H, d, J=8.63Hz); 7.25–7.40(5H, m).

| 324. | CH3 | H | H | 4-CH3-C6H4-CH2- | C3H7 | Ca | Mol. Wt. = 852 Yield = 42% |

TABLE 21-continued

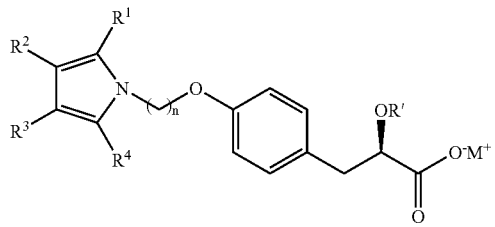

$^1$H: 0.77(3H, t, J=7.41Hz); 1.47–1.49(4H, m); 2.34(3H, s); 2.60–2.63(2H, s) 3.07–3.38(2H, m); 3.90(2H, t, J=6.01Hz); 4.31(2H, t, J=6.61Hz)5.87(1H, d, J=3.36Hz); 5.99(1H, d, J=3.39Hz); 6.58(2H, d, J=8.52Hz); 7.10(2H, d, J=8.52Hz); 7.29–7.40 (5H, m).

The compounds of the present invention lowered triglyceride, total cholesterol, LDL, VLDL and increased HDL and lowered serum glucose levels. This was demonstrated by in vivo animal experiments.

A) Demonstration of in Vitro Efficacy of Compounds:

i) Determination of hPPARα Activity:

A chimeric expression vectors constructs containing the translational sequences of PPAR and amino acid sequences of DNA binding domains were fused and inserted into PGL3 basic vector. The expression and sequence were verified through immunobloting and sequence analysis (ABI DNA analyzer). These chimeric vectors containing ligand binding as well as DNA binding domain and a reporter plasmid containing the luciferase gene driven by SV40 promoter were transfected into CV-1 cell using the transfectin (Gibco BRL, USA). A control reporter plasmid was also transfected to monitor the transfection efficiency. After 48 hrs of transfection, The test compound was added in various concentration and incubated overnight. The luciferase activity was analyzed as a function of compound binding/activation capacity of PPARα, by luciferase assay system (promega, USA).

ii) Determination of hPPARγ Activity:

A chimeric expression vectors constructs containing the translational sequences of PPARγ and amino acid sequences of DNA binding domains were fused and inserted into PGL3 basic vector. The expression and sequence were verified through immunobloting and sequence analysis (ABI DNA analyzer). These chimeric vectors containing ligand binding as well as DNA binding domain and a reporter plasmid containing the luciferase gene driven by SV40 promoter were transfected into CV-1 cell using the transfectin (Gibco BRL, USA). A control reporter plasmid was also transfected to monitor the transfection efficiency. After 48 hrs of transfection, The test compound was added in various concentration and incubated overnight. The luciferase activity was analyzed as a function of compound binding/activation capacity of PPARγ, by luciferase assay system (promega, USA).

B) Demonstration of in Vivo Efficacy of Compounds:

i) Serum Triglyceride and Total Cholesterol Lowering Activity in Swiss Albino Mice:

Male Swiss albino mice (SAM) were bred in Zydus animal house. All these animals were maintained under 12 hour light and dark cycle at 25±1° C. Animals were given standard laboratory chow (NIN, Hyderabad, India) and water ad libitum. SAM of 20–30 g body weight range were used.

The test compounds were administered orally to Swiss albino mice at 0.001 to 50 mg/kg/day dose for 6 days. The compound was administered after suspending it in 0.25% CMC or dissolving it in water, when compound is water-soluble. Control mice were treated with vehicle (0.25% of Carboxymethylcellulose; dose 10 ml/kg).

The blood samples were collected on $0^{th}$ day and in fed state 1 hour after drug administration on $6^{th}$ day of the treatment. The blood was collected in non heparinised capillary and the serum was analyzed for triglyceride and total cholesterol (Wieland, O. Methods of Enzymatic analysis. Bergermeyer, H., O., Ed., 1963. 211–214; Trinder, P. Ann. Clin. Biochem. 1969. 6:24–27). Measurement of serum triglyceride and total cholesterol was done using commercial kits (Zydus-Cadila, Pathline, Ahmedabad, India).

Formula for Calculation:

Percentage reduction in triglycerides/total cholesterol were calculated according to the formula:

$$\text{Percentage reduction } (\%) = 1 - \left[ \frac{TT/OT}{TC/OC} \right] \times 100$$

OC=Zero day control group value OT=Zero day treated group value
TC=Test day control group TT=Test day treated group

TABLE 1

Triglyceride lowering activity in Swiss albino mice:

| Example No. | Dose (mg/kg/day) | % Triglyceride lowering |
|---|---|---|
| 76 | 3 | 26 |
| 287 | 3 | 54 |
| 257 | 3 | 55 |
| 231 | 3 | 57 | ii) Cholesterol Lowering Activity in Hypercholesterolemic Rat Models

Male Sprague Dawley rats stock bred in Zydus animal house were maintained under 12 hour light and dark cycle at 25±1° C. Rats of 100–150 g body weight range were used for the experiment. Animals were made hypercholesterolemic by feeding 1% cholesterol and 0.5% sodium cholate mixed with standard laboratory chow (NIN, Hyderabad, India) and water ad libitum for 5 days. The animals were maintained on the same diet throughout the experiment [Petit D., Bonnefis M. T., Rey C and Infante R., Effects of ciprofibrate on liver lipids and lipoprotein synthesis in normal and hyperlipidemic rats, *Atherosclerosis*, 74, 215–225(1988)].

The test compounds were administered orally at a dose 0.03 to 50 mg/kg/day for 4 days, after suspending it in 0.25% CMC or dissolving it in water when compound is water-soluble. Control group was treated with vehicle alone (0.25% of Carboxymethylcellulose; dose 10 ml/kg).

The blood samples were collected in fed state on $0^{th}$ and 1 hour after drug administration on $6^{th}$ day of the treatment. The blood was collected from the retro-orbital sinus through non-heparinised capillary and the serum samples were analyzed for triglyceride and total cholesterol using commercial kits (Zydus-Cadila, Pathline, Ahmedabad, India). LDL and HDL by commercial kits (Point Scientific, USA). LDL and VLDL cholesterol were calculated from the data obtained for total cholesterol, HDL and triglyceride.

The reduction in VLDL cholesterol is calculated according to the formula.

VLDL cholesterol in mg/dl=Total cholesterol−HDL cholesterol−LDL cholesterol

TABLE 2

| Example No. | Dose (mg/kg/day) | Total cholesterol reduction (%) |
|---|---|---|
| 227 | 3 | 59 |
| 118 | 3 | 53 |
| 277 | 3 | 62 | iii) Serum Glucose Lowering Activity in db/db Mice Models

Homozygous animal $C_{57}BL/KsJ$-db/db mice are obese, hyperglycemic, hyperinsulinemic and insulin resistant (J. Clin. Invest., 85, 962–967, 1990), whereas heterozygous are lean and normoglycemic. The homozygous animals very closely mimic the human type II diabetes when blood sugar levels are not sufficiently controlled. Since this type of model resembles human type II diabetes mellitus, the compounds of the invention were tested for their antidiabetic activity in this model.

The compounds of the present invention showed serum glucose and triglycerides lowering activities. Male $C_{57}$ BL/KsJ-db/db mice of 8 to 14 weeks age, having body weight range of 40 to 60 grams, procured from the Jackson Laboratory, USA, were used in the experiment.

Test compounds were suspended on 0.25% carboxymethyl cellulose or dissolved in water when the compound is water soluble and administered to test group containing 6 animals at a dose of 0.001 mg to 50 mg/kg through oral gavage daily for 6 days. The control group received vehicle (dose 10 ml/kg). On the $6^{th}$ day, one hour after the drug dosing, blood was collected from retro-orbital sinus and the serum was analyzed for glucose and triglycerides were measured using commercial kits (Zydus-Cadila, Pathline, Ahmedabad, India). The serum glucose and triglyceride lowering activities of the test compound was calculated according of the formula:

$$\text{Serum glucose lowering activity (\%)} = 1 - \left[\frac{TT/OT}{TC/OC}\right] \times 100$$

| Example No. | Dose (mg/kg/day) | Serum Glucose reduction (%) | Plasma TG reduction (%) |
|---|---|---|---|
| 259 | 1 | 62 | 11 |
| 283 | 1 | 67 | 27 |

OC = Zero day control group value
OT = Zero day treated group value
TC = Test day control group
TT = Test day control group iv) Serum Triglyceride/Cholesterol/Body Weight Lowering Effect in Golden Syrian Hamsters:

Male Golden Syrian hamsters were fed with a standard diet mixed with 1% cholesterol and 0.5% sodium cholate for 5 days. On $6^{th}$ day test compounds in dose ranging from 1 mg to 10 mg/kg/day were administered as CMC suspension, and the same diet was maintained for the next 15 days. On the $15^{th}$ day the blood samples were collected in fed state, one hour after drug administration from retro-orbital sinus and the serum was analyzed for triglyceride and cholesterol using commercial kits (Zydus-Cadila, Pathline, Ahmedabad, India). The body weight was measured with respect to untreated group on hypercholesteremic diet. The compounds of the present invention reduced triglycerides, cholesterol and body weight in this animal model.

No adverse effects were observed for any of the mentioned compounds of invention. The compounds of the present invention showed good serum glucose, lipid and cholesterol lowering activity in the experimental animals used. These compounds are useful for the testing/prophylaxis of diseases caused by hyperlipidemia, hypercholesterolemia, hyperinsulinemia, hyperglycemia such as NIDDM, cardiovascular diseases, stroke, hypertension, obesity since such diseases are interlinked to each other.

We claim:
1. The compound of formula (Ih),

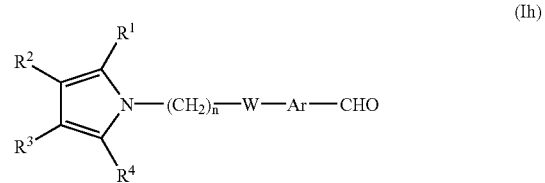

(Ih)

wherein one or more groups $R^1$, $R^2$, $R^3$, $R^4$ may be same or different, and represent hydrogen, halogen, haloalkyl, perhaloalkyl, haloalkoxy, perhaloalkoxy, hydroxy, thio, amino, nitro, cyano, formyl, amidino, guanidino, or substituted or unsubstituted groups selected from linear or branched $(C_1–C_{12})$alkyl, linear or branched $(C_1–C_{12})$alkenyl, linear or branched $(C_1–C_{12})$alkynyl, $(C_3–C_7)$cycloalkyl, $(C_3–C_7)$cycloalkenyl, bicycloalkyl, bicycloalkenyl, $(C_1–C_{12})$alkoxy, $(C_1–C_{12})$alkenoxy, cyclo$(C_3–C_7)$alkoxy, aryl, aryloxy, aralkyl, ar$(C_1–C_{12})$alkoxy, heterocyclyl, heteroaryl, heterocyclyl$(C_1–C_{12})$alkyl, heteroar$(C_1–C_{12})$alkyl, heteroaryloxy, heteroar$(C_1–C_{12})$alkoxy, heterocycloxy, heterocyclylalkyloxy, acyl, acyloxy, acylamino, mono-substituted or di-substituted amino, arylamino, aralkylamino, carboxylic acid and its derivatives such as esters and amides, hydroxyalkyl, aminoalkyl, mono-substituted or di-substituted aminoalkyl, alkoxyalkyl, aryloxyalkyl, aralkoxyalkyl, ($C_1$–$C_{12}$)alkylthio, thio($C_1$–$C_{12}$)alkyl, arylthio, ($C_1$–$C_{12}$)alkoxycarbonylamino, aryloxycarbonylamino, aralkyloxycarbonylamino, aminocarbonylamino, alkylaminocarbonylamino, alkylamidino, alkylguanidino, dialkylguanidino, hydrazino, alkyl hydrazino, alkoxyamino, hydroxyl amino, derivatives of sulfenyl and sulfonyl groups, sulfonic acid and its derivatives, phosphonic acid and its derivatives; n represents an integer varying from 1 to 8; W represents O, S or $NR^9$, where R9 represents hydrogen, ($C_1$–$C_{12}$)alkyl or aryl groups; Ar represents a substituted or unsubstituted divalent single or fused aromatic, heteroaromatic or a heterocyclic group.

2. A process for the preparation of compound of formula (Ih), as claimed in claim 1,

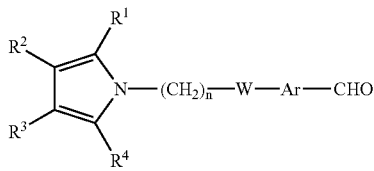

wherein one or more groups $R^1$, $R^2$, $R^3$, $R^4$ may be same or different, and represent hydrogen, halogen, haloalkyl, perhaloalkyl, haloalkoxy, perhaloalkoxy, hydroxy, thio, amino, nitro, cyano, formyl, amidino, guanidino, or substituted or unsubstituted groups selected from linear or branched ($C_1$–$C_{12}$)alkyl, linear or branched ($C_1$–$C_{12}$)alkenyl, linear or branched ($C_1$–$C_{12}$)alkynyl, ($C_3$–$C_7$)cycloalkyl, ($C_3$–$C_7$)cycloalkenyl, bicycloalkyl, bicycloalketlyl, ($C_1$–$C_{12}$)alkoxy, ($C_1$–$C_{12}$)alkenoxy, cyclo($C_3$–$C_7$)alkOxY, aryl, aryloxy, aralkyl, ar($C_1$–$C_{12}$)alkoxy, heterocyclyl, heteroaryl, heterocyclyl($C_1$–$C_{12}$)alkyl, heteroar(Cl—$C_1$2)alkyl, heteroaryloxy, heteroar(Cl—$C_{12}$)alkoxy, heterocycloxy, heterocyclylalkyloxy, acyl, acyloxy, acylamino, mono-substituted or di-substituted amino, arylamino, aralkylamino, carboxylic acid and its derivatives such as esters and amides, hydroxyalkyl, aminoalkyl, mono-substituted or di-substituted aminoalkyl, alkoxyalkyl, aryloxyalkyl, aralkoxyalkyl, ($C_1$–$C_{12}$) alkylthio, thio($C_1$–$C_{12}$)alkyl, arylthio, ($C_1$–$C_{12}$) alkoxycarbonylamino, aryloxycarbonylamino, aralkyloxycarboflylamiflo, aminocarbonylamino, alkylaminocarbonylamino, alkylamidino, alkylguanidino, dialkylguanidino, hydrazino, alkyl hydrazino, alkoxyamiflo, hydroxyl amino, derivatives of sulfenyl and sulfonyl groups, sulfonic acid and its derivatives, phosphonic acid and its derivatives; n represents an integer varying from 1 to 8; W represents O, S or $NR^9$, where R represents hydrogen, ($C_1$–$C_{12}$)alkyl or aryl groups; Ar represents a substituted or unsubstituted divalent single or fused aromatic, heteroaromatic or a heterocyclic group, which comprises, a. reacting a compound of the general formula (Ic)

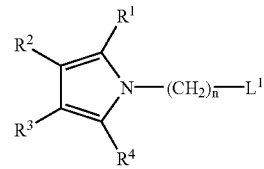

wherein one or more groups $R^1$, $R^2$, $R^3$, $R^4$ may be same or different, and represent hydrogen, halogen, haloalkyl, perhaloalkyl, haloalkoxy, perhaloalkoxy, hydroxy, thio, amino, nitro, cyano, formyl, amidino, guanidino, or substituted or unsubstituted groups selected from linear or branched ($C_1$–$C_{12}$)alkyl, linear or branched ($C_1$–$C_{12}$)alkenyl, linear or branched ($C_1$–$C_{12}$)alkynyl, ($C_3$–$C_7$)cycloalkyl, ($C_3$–$C_7$)cycloalkenyl, bicycloalkyl, bicycloalkenyl, ($C_1$–$C_{12}$)alkoxy, ($C_1$–$C_{12}$)alkenoxy, cyclo($C_3$–$C_7$)alkoxy, aryl, aryloxy, aralkyl, ar($C_1$–$C_{12}$)alkoxy, heterocyclyl, heteroaryl, heterocyclyl($C_1$–$C_{12}$)alkyl, heteroar($C_1$–$C_{12}$)alkyl, heteroaryloxy, heteroar($C_1$–$C_{12}$)alkoxy, heterocycloxy, heterocyclylalkyl oxy, acyl, acyloxy, acylamino, mono-substituted or di-substituted amino, arylamino, aralkylamino, carboxylic acid and its derivatives such as esters and amides, hydroxyalkyl, aminoalkyl, mono-substituted or di-substituted aminoalkyl, alkoxyalkyl, aryloxyalkyl, aralkoxyalkyl, ($C_1$–$C_{12}$)alkylthio, thio($C_1$–$C_{12}$)alkyl, arylthio, ($C_1$–$C_{12}$)alkoxycarbonylamino, aryloxycarbonylamino, aralkyloxycarbonylamino, aminocarbonylamino, alkylaminocarbonylamino, alkylamidino, alkylguanidino, dialkylguanidino, hydrazino, alkyl hydrazino, alkoxyamino, hydroxyl amino, derivatives of sulfenyl and sulfonyl groups, sulfonic acid and its derivatives, phosphonic acid and its derivatives; n represents an integer varying from 1 to 8; and $L^1$ is either a halogen atom such as chlorine, bromine or iodine or a leaving group such as methanesulfonate, trifluoromethanesulfonate and p-toluenesulfonate groups, with a compound of general formula (Ij), where Ar is as defined earlier;

HO—Ar—CHO (Ij)

b. reacting a compound of the formula (Ie), with compound of the formula (Ik), where $L^2$ is a halogen atom such as fluorine, chlorine, bromine or iodine and Ar is as defined earlier,

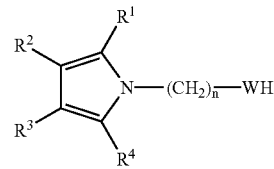

$L^2$—Ar—CHO (Ik)

wherein one or more groups $R^1$, $R^2$, $R^3$, $R^4$ may be same or different, and represent hydrogen, halogen, haloalkyl, perhaloalkyl, haloalkoxy, perhaloalkoxy, hydroxy, thio, amino, nitro, cyano, formyl, amidino, guanidino, or substituted or unsubstituted groups selected from linear or branched ($C_1$–$C_{12}$)alkyl, linear or branched ($C_1$–$C_{12}$)alkenyl, linear or branched ($C_1$–$C_{12}$)alkynyl, ($C_3$–$C_7$)cycloalkyl, ($C_3$–$C_7$)cycloalkenyl, bicycloalkyl, bicycloalkenyl, ($C_1$–$C_{12}$)alkoxy, ($C_1$–$C_{12}$)alkenoxy, cyclo($C_3$–$C_7$)alkoxy, aryl, aryloxy, aralkyl, ar($C_1$–$C_{12}$)alkoxy, heterocyclyl, heteroaryl, heterocyclyl($C_1$–$C_{12}$)alkyl, heteroar($C_1$–$C_{12}$)alkyl, heteroaryloxy, heteroar($C_1$–$C_{12}$)alkoxy, heterocycloxy, heterocyclylalkyloxy, acyl, acyloxy, acylamino, mono-substituted or di-substituted amino, arylamino, aralkylamino, carboxylic acid and its derivatives such as esters and amides, hydroxyalkyl, aminoalkyl, mono-substituted or di-substituted aminoalkyl, alkoxyalkyl, aryloxyalkyl, aralkoxyalkyl, ($C_1$–$C_{12}$)alkylthio, thio($C_1$–$C_{12}$)alkyl, arylthio, ($C_1$–$C_{12}$)alkoxycarbonylamino, aryloxycarbonylamino, aralkyloxycarbonylamino, aminocarbonylamino, alkylaminocarbonylamino, alkylamidino, alkylguanidino, dialkylguanidino, hydrazino, alkyl hydrazino, alkoxyamino, hydroxyl amino, derivatives of sulfenyl and sulfonyl groups, sulfonic acid and its derivatives, phosphonic acid and its derivatives; n represents an integer varying from 1 to 8; W represents O, S or NR1, where R1 represents hydrogen, ($C_1$–$C_{12}$)alkyl or aryl groups; with the proviso that:

i. $R^1$, $R^2$ it$^3$, it' all does not represent hydrogen atom at the same time, irrespective of what n is;

ii. $R^4$ does not represent $SO_2CH_3$, when R1=H or $COCH_3$; $R^2$ and $R^3$=H; and n=2;

iii. $R^4$ does not represent CHO, when $R^1$, $R^2$ and $R^3$=H; and n=2;

iv. $R^1$ does not represent $NO_2$, when $R^2$ and $R^3$ H; $R^4$=acyl; and n=2;

v. $R^2$ and $R^3$ does not represent hydrogen, when $R^1$ and $R^4$ both are methyl; and n=2 to 5;

vi. $R^2$ and $R^3$ does not represent hydrogen, when R' is methyl; $R^4$ is nonaryl; and n=1 and 2;

vii. $R^2$ and $R^3$ does not represent hydrogen, when R1 and $R^4$ are same or different substituents selected the group such as $NO_2$, $SO_2$, CN, OMe, Halogen, COOH, COOR, $SO_2R$, SO(OR), SOR, PO(OR)$_2$, SR and n=1 to 8;

viii. $R^4$ does not represent $CH_2COOCH_3$, when $R^1$=H; $R^2$ is either of hydrogen, lower alkyl [$C_1$–$C_4$, straight chain] or halide; $R^3$ is either of hydrogen or $COOCH_3$ and n=2 to 4;

ix. $R^1$, $R^3$ and $R^4$ does not represent hydrogen at a time when $R^2$ is unsubstituted phenyl or phenyl substituted with halogen, methyl, trifluoromethyl, OMe, SMe; and n=1;

x. $R^1$ and $R^4$ does not represent hydrogen at a time, when $R^2$ is unsubstituted phenyl or phenyl substituted with halogen, methyl trifluoromethyl, OMe, SMe; $R^3$ is CN, and n=1 to 9;

xi. $R^1$ and $R^3$ does not represent hydrogen at a time, when $R^2$ is halogen; $R^3$ is $C(O)CO_2Et$, $CH(OH)CO_2Et$ and $CH_2OOH_3$, and n=2;

xii. $R^1$, $R^2$ and $R^3$ does not represent hydrogen at a time, when $R^3$ is either of $CH_2CN$ or $CH_2NCH_3$, and n=2;

xiii. $R^2$ does not represent hydrogen, when $R^1$ is phenyl or 3,4-dimethoxyphenyl, and $R^3$ is either hydrogen, COOH or COOEt, and $R^4$ is methyl; and n=2 or 3;

xiv. $R^3$ and $R^4$ does not represent hydrogen, when $R^1$ is hydrogen; $R^2$ is unsubstituted benzyl or monofluorobenzyl; and n=1; and $R^2$ and $R^3$ does not represent hydrogen, when $R^3$ and $R^4$ are both alkyl; and n=1.

* * * * *